(12) United States Patent
Wu et al.

(10) Patent No.: US 12,161,672 B2
(45) Date of Patent: *Dec. 10, 2024

(54) CHIMERIC ANTIGEN RECEPTOR AND METHODS OF USE THEREOF

(71) Applicant: The Regents of the University of California, Oakland, CA (US)

(72) Inventors: Chia-Yung Wu, San Francisco, CA (US); James Onuffer, Alameda, CA (US); Wendell A. Lim, San Francisco, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 58 days.

This patent is subject to a terminal disclaimer.

(21) Appl. No.: 17/932,259

(22) Filed: Sep. 14, 2022

(65) Prior Publication Data

US 2023/0051989 A1 Feb. 16, 2023

Related U.S. Application Data

(63) Continuation of application No. 16/824,434, filed on Mar. 19, 2020, now Pat. No. 11,478,510, which is a continuation of application No. 15/669,707, filed on Aug. 4, 2017, now Pat. No. 10,632,152, which is a continuation of application No. 14/766,105, filed as application No. PCT/US2014/016527 on Feb. 14, 2014, now abandoned.

(60) Provisional application No. 61/765,585, filed on Feb. 15, 2013.

(51) Int. Cl.
| | |
|---|---|
| *A61K 35/17* | (2015.01) |
| *A61K 47/68* | (2017.01) |
| *C07K 14/705* | (2006.01) |
| *C07K 14/725* | (2006.01) |
| *C07K 16/18* | (2006.01) |
| *C07K 16/28* | (2006.01) |
| *C12N 5/0783* | (2010.01) |
| *C12N 9/14* | (2006.01) |
| *C12N 9/90* | (2006.01) |
| *A61K 39/00* | (2006.01) |

(52) U.S. Cl.
CPC .......... *A61K 35/17* (2013.01); *A61K 47/6891* (2017.08); *C07K 14/705* (2013.01); *C07K 14/7051* (2013.01); *C07K 14/70521* (2013.01); *C07K 14/70575* (2013.01); *C07K 14/70578* (2013.01); *C07K 16/18* (2013.01); *C07K 16/2803* (2013.01); *C07K 16/2866* (2013.01); *C12N 5/0636* (2013.01); *C12N 9/14* (2013.01); *C12N 9/90* (2013.01); *C12Y 502/01008* (2013.01); *A61K 2039/505* (2013.01); *C07K 2317/622* (2013.01); *C07K 2319/00* (2013.01); *C07K 2319/03* (2013.01); *C07K 2319/20* (2013.01); *C07K 2319/33* (2013.01); *C07K 2319/74* (2013.01); *C12N 2510/00* (2013.01)

(58) Field of Classification Search
CPC ...................................................... A61K 35/17
USPC ...................................................... 424/134.1
See application file for complete search history.

(56) References Cited

U.S. PATENT DOCUMENTS

| | | | |
|---|---|---|---|
| 5,359,046 | A | 10/1994 | Capon et al. |
| 5,712,149 | A | 1/1998 | Roberts |
| 5,830,462 | A | 11/1998 | Crabtree et al. |
| 5,834,266 | A | 11/1998 | Crabtree et al. |
| 5,869,337 | A | 2/1999 | Crabtree et al. |
| 5,871,753 | A | 2/1999 | Crabtree et al. |
| 5,906,936 | A | 5/1999 | Eshhar et al. |
| 5,912,172 | A | 6/1999 | Eshhar et al. |
| 6,133,456 | A | 10/2000 | Holt et al. |
| 6,150,527 | A | 11/2000 | Holt et al. |
| 6,165,787 | A | 12/2000 | Crabtree et al. |
| 6,410,319 | B1 | 6/2002 | Raubitschek et al. |
| 6,649,595 | B2 | 11/2003 | Clackson et al. |
| 7,404,950 | B2 | 7/2008 | Spencer et al. |
| 7,446,179 | B2 | 11/2008 | Jensen et al. |
| 7,446,190 | B2 | 11/2008 | Sadelain et al. |
| 7,741,465 | B1 | 6/2010 | Eshhar et al. |
| 8,106,191 | B2 | 1/2012 | Holt et al. |
| 8,399,645 | B2 | 3/2013 | Campana et al. |
| 8,492,122 | B2 | 7/2013 | Ostermeier |
| 8,771,671 | B2 | 7/2014 | Spencer et al. |
| 8,911,993 | B2 | 12/2014 | June et al. |
| 8,999,949 | B2 | 4/2015 | Spencer et al. |
| 9,587,020 | B2 | 3/2017 | Wu et al. |
| 9,745,368 | B2 | 8/2017 | Milone et al. |

(Continued)

FOREIGN PATENT DOCUMENTS

| | | |
|---|---|---|
| EP | 481673 | 4/1992 |
| FR | 2968013 | 6/2012 |

(Continued)

OTHER PUBLICATIONS

Bayle et al (Chemistry & Biology, 2006, 13: 99-107).*
Abate-Daga, et a.; "CAR models: next-generation CAR modifications for enhanced T-cell function"; Molecular Therapy-Oncolytics; vol. 3, 7 pages (2016).
Baitsch, et al.; "Extended Co-Expression of Inhibitory Receptors by Human CD8 T-Cells Depending on Differentiation, Antigen-Specificity and Anatomical Localization"; PLoS One; vol. 7, No. 2, 10 pages (Feb. 2012).

(Continued)

Primary Examiner — Sean E Aeder
(74) Attorney, Agent, or Firm — James S. Keddie; Bozicevic, Field & Francis LLP

(57) ABSTRACT

The present disclosure provides a heterodimeric, conditionally active chimeric antigen receptor (CAR), and a nucleic acid comprising a nucleotide sequence encoding the CAR. The present disclosure provides cells genetically modified to produce the CAR. A CAR of the present disclosure can be used in various methods, which are also provided.

18 Claims, 64 Drawing Sheets

Specification includes a Sequence Listing.

(56) References Cited

U.S. PATENT DOCUMENTS

| | | |
|---|---|---|
| 9,821,012 B2 | 11/2017 | Wu et al. |
| 10,105,391 B2 | 10/2018 | Wu et al. |
| 10,287,354 B2 | 5/2019 | Brogdon et al. |
| 10,632,152 B2 | 4/2020 | Wu et al. |
| 2003/0077249 A1 | 4/2003 | Bebbington et al. |
| 2004/0038886 A1 | 2/2004 | Finney et al. |
| 2005/0113564 A1 | 5/2005 | Campana et al. |
| 2008/0057515 A1 | 3/2008 | Paszty et al. |
| 2011/0286980 A1 | 11/2011 | Brenner |
| 2012/0029063 A1 | 2/2012 | Zhang et al. |
| 2012/0108455 A1 | 5/2012 | Kodandapani et al. |
| 2012/0277286 A1 | 11/2012 | Youle et al. |
| 2013/0040836 A1 | 2/2013 | Himmler et al. |
| 2013/0095097 A1 | 4/2013 | Blankenship et al. |
| 2013/0195800 A1 | 8/2013 | Roeth et al. |
| 2014/0050708 A1 | 2/2014 | Powell et al. |
| 2014/0099309 A1 | 4/2014 | Powell et al. |
| 2014/0134142 A1 | 5/2014 | Smith et al. |
| 2014/0286987 A1 | 9/2014 | Spencer et al. |
| 2014/0308746 A1 | 10/2014 | Rossi et al. |
| 2015/0368342 A1 | 12/2015 | Wu et al. |
| 2017/0292118 A1 | 10/2017 | Duchateau et al. |
| 2017/0306303 A1 | 10/2017 | Taunton et al. |
| 2017/0340672 A1 | 11/2017 | Wu et al. |

FOREIGN PATENT DOCUMENTS

| | | |
|---|---|---|
| WO | WO 2001/032866 | 5/2001 |
| WO | WO 2002/070559 | 9/2002 |
| WO | WO 2011/119773 A1 | 9/2011 |
| WO | WO 2012/079000 | 6/2012 |
| WO | WO 2012/099973 A2 | 7/2012 |
| WO | WO 2014/039513 A1 | 3/2014 |
| WO | WO 2014/127261 | 8/2014 |
| WO | WO 2015/057852 | 4/2015 |
| WO | WO 2015/090229 | 6/2015 |
| WO | WO 2015/123527 A1 | 8/2015 |
| WO | WO 2015/142661 | 9/2015 |
| WO | WO 2015/150771 | 10/2015 |
| WO | WO 2016/055551 | 4/2016 |
| WO | WO 2017/087723 | 5/2017 |
| WO | WO 2017/120546 | 7/2017 |

OTHER PUBLICATIONS

Barnea, et al.; "The genetic design of signaling cascades to record receptor activation"; PNAS; vol. 105, No. 1, pp. 64-69 (Jan. 8, 2008).

Chaudhry et al., "Energetics of glutamate receptor ligand binding domain dimer assembly are modulated by allosteric ions", PNAS, 2009, 106(30): 12329-12334.

Chen et al., "Overexpression of a glutamate receptor (GluR2) ligand binding domain in *Escherichia coli*: Application of a novel protein folding screen", Proc. Natl. Acad. Sci., 1997, 94: 13431-13436.

Co-pending U.S. Appl. No. 15/835,329, filed Dec. 7, 2017.

Camacho-Soto, et al.; "Ligand-Gated Split-Kinases"; Journal of the American Chemical Society; vol. 136, pp. 3995-4002 (2014).

Camacho-Soto, et al.; "Small Molecule Gated Split-Tyrosine Phosphatases and Orthogonal Split-Tyrosine Kinases"; Journal of the American Chemical Society; vol. 136, No. 49, 9 pages (2014).

Cartellieri, et al.; "Chimeric Antigen Receptor-Engineered T Cells for Immunotherapy of Cancer"; J. Biomed. Biotechnol.; vol. 2010, 13 pages (2010).

Chelur, et al.; "Targeted cell killing by reconstituted caspases"; PNAS; vol. 105, No. 2, pp. 2283-2288 (Feb. 13, 2007).

Curran, et al.; "Chimeric Antigen Receptors for T cell Immunotherapy: Current Understanding and Future Direction"; J. Gene. Med.; vol. 14, No. 6, pp. 405-445 (Jun. 2012).

Dasgupta, et al.; "Nuclear Receptor Coactivators: Master Regulators of Human Health and Disease"; Annu. Rev. Med.; vol. 65, pp. 279-292 (2014).

Davila, et al.; "How do CARs work ?: Early insights from recent clinical studies targeting CD19"; Oncoimmunology; vol. 1, No. 9, pp. 1577-1583 (Dec. 1, 2012).

Derose, et al.; "Manipulating signaling at will: chemically-inducible dimerization (CID) techniques resolve problems in cell biology"; Pflugers Arch; vol. 465, No. 3, pp. 409-417 (Jan. 9, 2013).

Di Stasi, et al.; "Inducible apoptosis as a safety switch for adoptive cell therapy"; N Engl J Med; vol. 365, No. 18, pp. 1673-1683 (Nov. 3, 2011).

Di Stasi et al., "T lymphocytes coexpressing CCR4 and a chimeric antigen receptor targeting CD30 have improved homing and anti-tumor activity in a Hodgkin tumor model", Blood, 2009; 113 (25): 6392-6402.

Dotti, et al.; "Design and development of therapies using chimeric antigen receptor-expressing T cells"; Immunological Reviews; vol. 257, pp. 107-126 (2014).

Duttagupta, et al.; "Costimulation Signals for Memory CD8+T Cells During Viral Infections"; Crit. Rev. Immunol.; vol. 29, No. 6, pp. 469-486 (2009).

Fegan, et al.; "Chemically controlled protein assembly: techniques and applications"; Chem Rev; vol. 110, No. 6, pp. 3315-3336 (Jun. 9, 2010).

Fridy, et al.; "A robust pipeline for rapid production of versatile nanobody repertoires"; Nat. Methods; vol. 11, No. 12, pp. 1253-1260 (Dec. 2014).

Fridy, et al.; "A robust pipeline for rapid production of versatile nanobody repertoires"; Nat. Methods; vol. 11, No. 12, pp. 1253-1260 (Dec. 2014)—Supplemental Materials.

Garfall, et al.; "Immunotherapy with Chimeric Antigen Receptors for Multiple Myeloma"; Discovery Medicine; vol. 17, No. 91, pp. 37-46 (Jan. 2014).

Gizinski, et al.; "Costimulation and T cells as therapeutic targets"; Best Pract. Res. Clin. Rheumatol.; vol. 24, No. 4, pp. 463-477 (Aug. 2010).

Gooz; "ADAM-17: The Enzyme That Does It All"; Crit. Rev. Biochem. Mol. Biol.; vol. 45, No. 2, pp. 146-169, 146-169 (Apr. 2010).

Gordon, et al.; "Effects of S1 cleavage on the structure, surface export, and signaling activity of human Notch1 and Notch2"; PLoS One; vol. 4, No. 8, 12 pages (Aug. 2009).

Graef, et al.; "Proximity and orientation underlie signaling by the non-receptor tyrosine kinase ZAP70"; EMBO J; vol. 16, No. 18, pp. 5618-5628 (Sep. 15, 1997).

Gurevich, et al.; "Corepressors of agonist-bound nuclear receptors"; Toxicology and Applied Pharmacology; vol. 223, pp. 288-298 (2007).

Heldin, et al.; "Dimerization of Cell Surface Receptors in Signal Transduction"; Cell; vol. 80, pp. 213-223 (Jan. 27, 1995).

Hultman, et al.; "The Ligand-Dependent Interaction of Mineralocorticoid Receptor with Coactivator and Corepressor Peptides Suggests Multiple Activation Mechanisms"; Molecular Endocrinology; vol. 19, No. 6, pp. 1460-1473 (Jun. 2005).

Isakov; "Immunoreceptor tyrosine-based activation motif (ITAM), a unique module linking antigen and Fc receptors to their signaling cascades"; J. Leukoc . Biol.; vol. 61, No. 1, pp. 6-16 (Jan. 1997).

James, et al.; "Biophysical mechanism of T-cell receptor triggering in a reconstituted system"; Nature; vol. 487, pp. 64-69 (Jul. 5, 2012).

Juillerat, et al.; "Design of chimeric antigen receptors with integrated controllable transient functions"; Scientific Reports; doi: 10.1038/srep18950; 7 pages (Jan. 11, 2016).

Kalos, et al.; "T Cells with Chimeric Antigen Receptors Have Potent Antitumor Effects and Can Establish Memory in Patients with Advanced Leukemia"; Sci Transl Med.; vol. 3, No. 95, 12 pages (Aug. 10, 2011).

Kawahara, et al.; "Engineering cytokine receptors to control cellular functions"; Biochemical Engineering Journal; vol. 48, pp. 283-294 (2010).

Kimchi-Sarfaty, et al.; "A 'Silent' Polymorphism in the MDR1 Gene Changes Substrate Specificity"; Science; vol. 315, pp. 525-528 (Jan. 26, 2007).

Klemm et al., "Dimerization as a Regulatory Mechanism in Signal Transduction", Annu. Rev. Immunol., 1998, 16: 569-592.

(56) References Cited

OTHER PUBLICATIONS

Kloss, et al.; "Combinatorial antigen recognition with balanced signaling promotes selective tumor eradication by engineered T cells"; Nat Biotechnol; vol. 31, pp. 71-75 (Dec. 16, 2012).
Kopan, et al.; "The Canonical Notch Signaling Pathway: Unfolding the Activation Mechanism"; Cell; vol. 137, pp. 216-233 (Apr. 17, 2009).
Lanitis et al., "Redirected Antitumor Activity of Primary Human Lymphocytes Transduced With a Fully Human Anti-mesothelin Chimeric Receptor", Molecular Therapy, Mar. 2012, 20(3): 633-643.
Lecourtois, et al.; "Indirect evidence for Delta-dependent intracellular processing of notch in *Drosophila* embryos"; Curr. Biol.; vol. 8, No. 13, pp. 771-774 (Jun. 1998).
Lemmon et al., "Cell signaling by receptor-tyrosine kinases", Cell, 2010, 141(7): 1117-1134.
Li et al., "Receptor tyrosine kinase transmembrane domains", Cell Adhesion & Migration, 2010, 4:2, 249-254.
Liu, et al.; "Construction of a fluorescein-responsive chimeric receptor with strict ligand dependency"; Biotechnol Bioeng. Dec. 1, 2008;101(5):975-84. doi: 10.1002/bit.21961.
Maus, et al.; "Antibody-modified T cells: CARs take the front seat for hematologic malignancies"; Blood; vol. 123, No. 17, pp. 2625-2635 (Apr. 24, 2014).
Matsuda, et al.; "Synthetic Signal Propagation Through Direct Cell-Cell Interaction"; Sci. Signal; vol. 5, No. 220, 9 pages (Apr. 17, 2012).
Maus et al., "Antibody-modified T cells: CARs take the front seat for hematologic malignancies", BLOOD, Apr. 24, 2014, 123(17): 2625-2635.
Mumm, et al.; "A ligand-induced extracellular cleavage regulates gamma-secretase-like proteolytic activation of Notch1"; Mol. Cell; vol. 5, No. 2, pp. 197-206 (Feb. 2000).
Nagy, et al.; "Mechanism of the nuclear receptor molecular switch"; TRENDS in Biochemical Sciences; vol. 29, No. 6, pp. 317-324 (Jun. 2004).
Ngo, et al.; "Computational Complexity, Protein Structure Prediction, and the Levinthal Paradox"; The Protein Folding Problem and Tertiary Structure Prediction; pp. 433 and 492-495 (1994).
Odorizzi, et al.; "Inhibitory Receptors on Lymphocytes: Insights from Infections"; J. Immunol.; vol. 188, No. 7, pp. 2957-2965 (Apr. 1, 2012).
Ogawa, et al.; "Construction of Unnatural Heterodimeric Receptors Based on IL-2 and IL-6 Receptor Subunits"; Biotechnol. Prog.; vol. 29, No. 6, pp. 1512-1518 (2013).
Olefsky, et al.; "Minireview Prologue: Nuclear Receptor Minireview Series"; J. Biol. Chem.; vol. 276, pp. 36863-36864 (2001).
Ott et al., "Integral membrane protein biosynthesis: why topology is hard to predict", Journal of Cell Science, 2002, 115: 2003-2009.
Porter, et al.; "Chimeric antigen receptor-modified T cells in chronic lymphoid leukemia"; Engl J Med; vol. 365, No. 8, pp. 725-733 (Aug. 25, 2011).
RAULET; "Roles of the NKG2D Immunoreceptor and Its Ligands"; Nature Reviews Immunology; vol. 3, pp. 781-790 (Oct. 2003).
Robyr, et al.; "Nuclear Hormone Receptor Coregulators In Action: Diversity For Shared Tasks"; Molecular Endocrinology; vol. 14, No. 3, pp. 329-347 (2000).
Rosenberg; "Raising the bar: the curative potential of human cancer immunotherapy"; Science Translational Medicine; vol. 4, Issue 127, pp. 127ps8 (Mar. 23, 2012).
Sadelain, et al.; "The Basic Principles of Chimeric Antigen Receptor Design"; Cancer Discovery; vol. 3, No. 4, pp. 388-398 (Apr. 2013).
Sadelain, et al.; "The promise and potential pitfalls of chimeric antigen receptors"; Current Opinion in Immunology; vol. 21, No. 2, pp. 215-223 (Apr. 1, 2009).
Sanchez-Irizarry, et al.; "Notch Subunit Heterodimerization and Prevention of Ligand-Independent Proteolytic Activation Depend, Respectively, on a Novel Domain and the LNR Repeats"; Molecular and Cellular Biology; vol. 24, No. 21, 9265-9273 (Nov. 2004).
Schreiber; "Chemical Genetics Resulting from a Passion for Synthetic Organic Chemistry"; Bioorganic & Medicinal Chemistry; vol. 6, pp. 1127-1152 (1998).
Song, et al.; "In vivo persistence, tumor localization and anti-tumor activity of CAR engineered T cells is enhanced by costimulatory signaling through CD137 (4-1BB)"; Cancer Res.; vol. 71, No. 13, pp. 4617-4627 (Jul. 1, 2011).
Spencer et al., "Controlling Signal Transduction with Synthetic Ligands", Science, Nov. 12, 1993, 262: 1019-1024.
Springael et al., "Dimerization of chemokine receptors and its functional consequences", Cytokine & Growth Factor Reviews, 2005, 16: 611-623.
Stashi, et al.; "Steroid Receptor Coactivators: Servants and Masters for Control of Systems Metabolism"; Trends Endocrinol. Metab.; vol. 25, No. 7, pp. 337-347 (Jul. 2014).
Stroud et al., "Mechanistic Diversity of Cytokine Receptor Signaling Across Cell Membranes", Science's STKE., 2004: re7.
Struhl, et al.; "Nuclear access and action of notch in vivo"; Cell; vol. 93, No. 4, pp. 649-660 (May 15, 1998).
Stuhlmann-Laeisz, et al.; "Forced dimerization of gp130 leads to constitutive STAT3 activation, cytokine-independent growth, and blockade of differentiation of embryonic stem cells"; Mol Biol Cell. Jul. 2006; 17(7):2986-95. Epub Apr. 19, 2006.
Tal, et al.; "An NCR1-based chimeric receptor endows T-cells with multiple anti-tumor specificities"; Oncotarget; vol. 5, No. 21, pp. 10949-10958 (Apr. 24, 2014).
Tetel; "Nuclear receptor coactivators: Essential players in steroid hormone action in brain and behavior"; J. Neuroendocrinol; vol. 21, No. 4, pp. 229-237 (Mar. 2009).
Tone, et al.; "Cell Fate Conversion by Conditionally Switching the Signal-Transducing Domain of Signalobodies"; Biotechnology and Bioengineering; vol. 110, No. 12, pp. 3219-3226 (Dec. 2013).
Voet, et al.; Biochemistry; pp. 126-128 (1990).
Vooijs, et al.; "Mapping the consequence of Notch1 proteolysis in vivo with NIP-CRE"; Development; vol. 132, No. 3, pp. 535-544 (Feb. 2007).
Wang et al., "Structural Biology of Shared Cytokine Receptors", Annu Rev Immunol., 2009, 27: 29-60.
Weissman, et al.; "Molecular cloning and chromosomal localization of the human T-cell receptor zeta chain: distinction from the molecular CD3 complex"; PNAS; vol. 85, No. 24, pp. 9709-9713 (Dec. 1988).
Wu, et al.; "Remote control of therapeutic T cells through a small molecule-gated chimeric receptor"; Sciencexpress; sciencemag.org/content/early/recent; doi: 10.1126/science.aab4077; 15 pages (Sep. 24, 2015).
Yang et al., "Activation of Growth Hormone Receptors by Growth Hormone and Growth Hormone Antagonist Dimers: Insights into Receptor Triggering", Molecular Endocrinology, 2008, 22(4): 978-988.
Zhang et al., "LAT: The ZAP-70 Tyrosine Kinase Substrate that Links T Cell Receptor to Cellular Activation", Cell, Jan. 9, 1998, 92: 83-92.
Zhao, et al.; "Multiple injections of electroporated autologous T cells expressing a chimeric antigen receptor mediate regression of human disseminated tumor"; Cancer Res.; vol. 70, No. 22, pp. 9053-9061 (Nov. 15, 2010).

* cited by examiner

Figures 1A and 1B. Construct #122, encoding a polypeptide comprising "anti-CD19 scFv – CD8 alpha hinge and transmembrane domain – FKBP"

Figure 1A
Signal peptide:
ATGGCCTTACCAGTGACCGCCTTGCTCCTGCCGCTGGCCTTGCTGCTCCACGCCGCCAGGCCG (SEQ ID NO:1)
MALPVTALLLPLALLLHAARP (SEQ ID NO:2)
Myc epitope tag:
GAGCAGAAGCTGATCAGCGAGGAGGACCTG (SEQ ID NO:3)
EQKLISEEDL (SEQ ID NO:4)

Anti-human CD19 scFv:
GACATCCAGATGACACAGACTACATCCTCCCTGTCTGCCTCTCTGGGAGACAGAGTCACCATCAGTTGCA
GGGCAAGTCAGGACATTAGTAAATATTTAAATTGGTATCAGCAGAAACCAGATGGAACTGTTAAACTCCT
GATCTACCATACATCAAGATTACACTCAGGAGTCCCATCAAGGTTCAGTGGCAGTGGGTCTGGAACAGAT
TATTCTCTCACCATTAGCAACCTGGAGCAAGAAGATATTGCCACTTACTTTTGCCAACAGGGTAATACGC
TTCCGTACACGTTCGGAGGGGGGACCAAGCTGGAGATCACAGGTGGCGGTGGCTCGGGCGGTGGTGGGTC
GGGTGGCGGCGGATCTGAGGTGAAACTGCAGGAGTCAGGACCTGGCCTGGTGGCGCCCTCACAGAGCCTG
TCCGTCACATGCACTGTCTCAGGGGTCTCATTACCCGACTATGGTGTAAGCTGGATTCGCCAGCCTCCAC
GAAAGGGTCTGGAGTGGCTGGGAGTAATATGGGGTAGTGAAACCACATACTATAATTCAGCTCTCAAATC
CAGACTGACCATCATCAAGGACAACTCCAAGAGCCAAGTTTTCTTAAAAATGAACAGTCTGCAAACTGAT
GACACAGCCATTTACTACTGTGCCAAACATTATTACTACGGTGGTAGCTATGCTATGGACTACTGGGGCC
AAGGAACCTCAGTCACCGTCTCCTCA (SEQ ID NO:5)

DIQMTQTTSSLSASLGDRVTISCRASQDISKYLNWYQQKPDGTVKLLIYHTSRLHSGVPSRFSGSGSGTD
YSLTISNLEQEDIATYFCQQGNTLPYTFGGGTKLEITGGGSGGGGSGGGGSEVKLQESGPGLVAPSQSL
SVTCTVSGVSLPDYGVSWIRQPPRKGLEWLGVIWGSETTYYNSALKSRLTIIKDNSKSQVFLKMNSLQTD
DTAIYYCAKHYYYGGSYAMDYWGQGTSVTVSS (SEQ ID NO:6)

Figure 1B
Human CD8 alpha extracellular spacer/hinge and transmembrane domain:
ACCACGACGCCAGCGCCGCGACCACCAACACCGGCGCCCACCATCGCGTCGCAGCCCCTGTCCCTGCGCC
CAGAGGCGTGCCGGCCAGCGGCGGGGGGCGCAGTGCACACGAGGGGGCTGGACTTCGCCTGTGATATCTA
CATCTGGGCGCCCTTGGCCGGGACTTGTGGGGTCCTTCTCCTGTCACTGGTTATCACCCTTTACTGC
(SEQ ID NO:7)

TTTPAPRPPTPAPTIASQPLSLRPEACRPAAGGAVHTRGLDFACDIYIWAPLAGTCGVLL
LSLVITLYC (SEQ ID NO:8)

Linker:
TCCCTAGGAAGCGGGTCCGGTAGCGGATCT (SEQ ID NO:9)
SLGSGSGSGS (SEQ ID NO:10)

FKBP:
ATGGGAGTcCAGGTGGAAACCATCTCCCCAGGAGACGGGCGCACCTTCCCCAAGCGCGGCCAGACCTGCG
TGGTGCACTACACCGGGATGCTTGAAGATGGAAAGAAATTTGATTCCTCCCGGGACAGAAACAAGCCCTT
TAAGTTTATGCTAGGCAAGCAGGAGGTGATCCGAGGCTGGGAAGAAGGGGTTGCCCAGATGAGTGTGGGT
CAGAGAGCCAAACTGACTATATCTCCAGATTATGCCTATGGTGCCACTGGGCACCCAGGCATCATCCCAC
CACATGCCACTCTCGTCTTCGATGTGGAGCTTCTAAAACTGGAA (SEQ ID NO:11)

MGVQVETISPGDGRTFPKRGQTCVVHYTGMLEDGKKFDSSRDRNKPFKFMLGKQEVIRGWEEGVAQMSVG
QRAKLTISPDYAYGATGHPGIIPPHATLVFDVELLKLE (SEQ ID NO:12)

Figures 2A and 2B. Construct #123, encoding a polypeptide comprising "FRB - CD3 zeta intracellular chain - mCherry"

Figure 2A

FRB:
ATGATCCTCTGGCATGAGATGTGGCATGAAGGCCTGGAAGAGGCATCTCGTTTGTACTTTGGGGAAAGGA
ACGTGAAAGGCATGTTTGAGGTGCTGGAGCCCTTGCATGCTATGATGGAACGGGGCCCCCAGACTCTGAA
GGAAACATCCTTTAATCAGGCCTATGGTCGAGATTTAATGGAGGCCCAAGAGTGGTGCAGGAAGTACATG
AAATCAGGGAATGTCAAGGACCTCCTCCAAGCCTGGGACCTCTATTATCATGTGTTCCGACGAATCTCAA
AG (SEQ ID NO:13)

MILWHEMWHEGLEEASRLYFGERNVKGMFEVLEPLHAMMERGPQTLKETSFNQAYGRDLMEAQEWCRKYM
KSGNVKDLLQAWDLYYHVFRRISK (SEQ ID NO:14)

Linker:
GGAAGCGGGTCCGGTAGCGGATCTTCCCTA (SEQ ID NO:15)
GSGSGSGSSL (SEQ ID NO:16)

Human CD3 zeta intracellular chain:
AGAGTGAAGTTCAGCAGGAGCGCAGACGCCCCCGCGTACCAGCAGGGCCAGAACCAGCTCTATAACGAGC
TCAATCTAGGACGAAGAGAGGAGTACGATGTTTTGGACAAGAGACGTGGCCGGGACCCTGAGATGGGGGG
AAAGCCGAGAAGGAAGAACCCTCAGGAAGGCCTGTACAATGAACTGCAGAAAGATAAGATGGCGGAGGCC
TACAGTGAGATTGGGATGAAAGGCGAGCGCCGGAGGGGCAAGGGGCACGATGGCCTTTACCAGGGTCTCA
GTACAGCCACCAAGGACACCTACGACGCCCTTCACATGCAGGCCCTGCCCCCTCGC (SEQ ID
NO:17)

RVKFSRSADAPAYQQGQNQLYNELNLGRREEYDVLDKRRGRDPEMGGKPRRKNPQEGLYNELQKDKMAEA
YSEIGMKGERRRGKGHDGLYQGLSTATKDTYDALHMQALPPR (SEQ ID NO:18)

Linker:
TCGCGAGGAAGCGGGTCCGGTAGCGGATCT (SEQ ID NO:19)

SRGSGSGSGS (SEQ ID NO:20)

Figure 2B
mCherry:
ATGGTGAGCAAGGGCGAGGAGGATAACATGGCCATCATCAAGGAGTTCATGCGCTTCAAGGTGCACATGG
AGGGCTCCGTGAACGGCCACGAGTTCGAGATCGAGGGCGAGGGCGAGGGCCGCCCCTACGAGGGCACCCA
GACCGCCAAGCTGAAGGTGACCAAGGGTGGCCCCCTGCCCTTCGCCTGGGACATCCTGTCCCCTCAGTTC
ATGTACGGCTCCAAGGCCTACGTGAAGCACCCCGCCGACATCCCCGACTACTTGAAGCTGTCCTTCCCCG
AGGGCTTCAAGTGGGAGCGCGTGATGAACTTCGAGGACGGCGGCGTGGTGACCGTGACCCAGGACTCCTC
CCTGCAGGACGGCGAGTTCATCTACAAGGTGAAGCTGCGCGGCACCAACTTCCCCTCCGACGGCCCCGTA
ATGCAGAAGAAGACCATGGGCTGGGAGGCCTCCTCCGAGCGGATGTACCCCGAGGACGGCGCCCTGAAGG
GCGAGATCAAGCAGAGGCTGAAGCTGAAGGACGGCGGCCACTACGACGCTGAGGTCAAGACCACCTACAA
GGCCAAGAAGCCCGTGCAGCTGCCCGGCGCCTACAACGTCAACATCAAGTTGGACATCACCTCCCACAAC
GAGGACTACACCATCGTGGAACAGTACGAACGCGCCGAGGGCCGCCACTCCACCGGCGGCATGGACGAGC
TGTACAAG (SEQ ID NO:21)

MVSKGEEDNMAIIKEFMRFKVHMEGSVNGHEFEIEGEGEGRPYEGTQTAKLKVTKGGPLPFAWDILSPQF
MYGSKAYVKHPADIPDYLKLSFPEGFKWERVMNFEDGGVVTVTQDSSLQDGEFIYKVKLRGTNFPSDGPV
MQKKTMGWEASSERMYPEDGALKGEIKQRLKLKDGGHYDAEVKTTYKAKKPVQLPGAYNVNIKLDITSHN
EDYTIVEQYERAEGRHSTGG
MDELYK (SEQ ID NO:22)

Figures 3A and 3B. Construct #125, encoding a conventional CAR comprising "anti-CD19 scFv – CD8 alpha hinge and transmembrane domain – 4-1BB & CD3 zeta intracellular chains"

Figure 3A

Signal peptide:
ATGGCCTTACCAGTGACCGCCTTGCTCCTGCCGCTGGCCTTGCTGCTCCACGCCGCCAGGCCG (SEQ ID NO:1)
MALPVTALLLPLALLLHAARP (SEQ ID NO:2)

Myc epitope tag:
GAGCAGAAGCTGATCAGCGAGGAGGACCTG (SEQ ID NO:3)
EQKLISEEDL (SEQ ID NO:4)

Anti-human CD19 scFv:
GACATCCAGATGACACAGACTACATCCTCCCTGTCTGCCTCTCTGGGAGACAGAGTCACCATCAGTTGCA
GGGCAAGTCAGGACATTAGTAAATATTTAAATTGGTATCAGCAGAAACCAGATGGAACTGTTAAACTCCT
GATCTACCATACATCAAGATTACACTCAGGAGTCCCATCAAGGTTCAGTGGCAGTGGGTCTGGAACAGAT
TATTCTCTCACCATTAGCAACCTGGAGCAAGAAGATATTGCCACTTACTTTTGCCAACAGGGTAATACGC
TTCCGTACACGTTCGGAGGGGGGACCAAGCTGGAGATCACAGGTGGCGGTGGCTCGGGCGGTGGTGGGTC
GGGTGGCGGCGGATCTGAGGTGAAACTGCAGGAGTCAGGACCTGGCCTGGTGGCGCCCTCACAGAGCCTG
TCCGTCACATGCACTGTCTCAGGGGTCTCATTACCCGACTATGGTGTAAGCTGGATTCGCCAGCCTCCAC
GAAAGGGTCTGGAGTGGCTGGGAGTAATATGGGGTAGTGAAACCACATACTATAATTCAGCTCTCAAATC
CAGACTGACCATCATCAAGGACAACTCCAAGAGCCAAGTTTTCTTAAAAATGAACAGTCTGCAAACTGAT
GACACAGCCATTTACTACTGTGCCAAACATTATTACTACGGTGGTAGCTATGCTATGGACTACTGGGGCC
AAGGAACCTCAGTCACCGTCTCCTCA (SEQ ID NO:5)

DIQMTQTTSSLSASLGDRVTISCRASQDISKYLNWYQQKPDGTVKLLIYHTSRLHSGVPSRFSGSGSGTD
YSLTISNLEQEDIATYFCQQGNTLPYTFGGGTKLEITGGGSGGGGSGGGGSEVKLQESGPGLVAPSQSL
SVTCTVSGVSLPDYGVSWIRQPPRKGLEWLGVIWGSETTYYNSALKSRLTIIKDNSKSQVFLKMNSLQTD
DTAIYYCAKHYYYGGSYAMDYWGQGTSVTVSS (SEQ ID NO:6)

Figure 3B
Human CD8 alpha extracellular spacer/hinge and transmembrane domain:
ACCACGACGCCAGCGCCGCGACCACCAACACCGGCGCCCACCATCGCGTCGCAGCCCCTGTCCCTGCGCC
CAGAGGCGTGCCGGCCAGCGGCGGGGGGCGCAGTGCACACGAGGGGGCTGGACTTCGCCTGTGATATCTA
CATCTGGGCGCCCTTGGCCGGGACTTGTGGGGTCCTTCTCCTGTCACTGGTTATCACCCTTTACTGC
(SEQ ID NO:7)

TTTPAPRPPTPAPTIASQPLSLRPEACRPAAGGAVHTRGLDFACDIYIWAPLAGTCGVLLLSLVITLYC
(SEQ ID NO:8)

Linker:
TCCCTA
SerLeu

Human 4-1BB intracellular chain:
AAACGGGGCAGAAAGAAACTCCTGTATATATTCAAACAACCATTTATGAGACCAGTACAAACTACTCAAG
AGGAAGATGGCTGTAGCTGCCGATTTCCAGAAGAAGAAGAAGGAGGATGTGAACTG (SEQ ID
NO:23)

KRGRKKLLYIFKQPFMRPVQTTQEEDGCSCRFPEEEEGGCEL (SEQ ID NO:24)

Human CD3 zeta intracellular chain:
AGAGTGAAGTTCAGCAGGAGCGCAGACGCCCCCGCGTACAAGCAGGGCCAGAACCAGCTCTATAACGAGC
TCAATCTAGGACGAAGAGAGGAGTACGATGTTTTGGACAAGAGACGTGGCCGGGACCCTGAGATGGGGGG
AAAGCCGAGAAGGAAGAACCCTCAGGAAGGCCTGTACAATGAACTGCAGAAAGATAAGATGGCGGAGGCC
TACAGTGAGATTGGGATGAAAGGCGAGCGCCGGAGGGGCAAGGGGCACGATGGCCTTTACCAGGGTCTCA
GTACAGCCACCAAGGACACCTACGACGCCCTTCACATGCAGGCCCTGCCtCCTCGC (SEQ ID
NO:25)

RVKFSRSADAPAYKQGQNQLYNELNLGRREEYDVLDKRRGRDPEMGGKPRRKNPQEGLYNELQKDKMAEA
YSEIGMKGERRRGKGHDGLYQGLSTATKDTYDALHMQALPPR (SEQ ID NO:26)

Figure 4
Construct #126, encoding the fusion protein "FRB - mCherry"

FRB:
ATGATCCTCTGGCATGAGATGTGGCATGAAGGCCTGGAAGAGGCATCTCGTTTGTACTTTGGGGAAAGGA
ACGTGAAAGGCATGTTTGAGGTGCTGGAGCCCTTGCATGCTATGATGGAACGGGGCCCCCAGACTCTGAA
GGAAACATCCTTTAATCAGGCCTATGGTCGAGATTTAATGGAGGCCCAAGAGTGGTGCAGGAAGTACATG
AAATCAGGGAATGTCAAGGACCTCCTCCAAGCCTGGGACCTCTATTATCATGTGTTCCGACGAATCTCAA
AG (SEQ ID NO:13)

MILWHEMWHEGLEEASRLYFGERNVKGMFEVLEPLHAMMERGPQTLKETSFNQAYGRDLMEAQEWCRKYM
KSGNVKDLLQAWDLYYHVFRRISK (SEQ ID NO:14)

Linker:
GGAAGCGGGTCCGGTAGCGGATCTTCCCTA (SEQ ID NO:15)
GSGSGSGSSL (SEQ ID NO:16)

mCherry:
ATGGTGAGCAAGGGCGAGGAGGATAACATGGCCATCATCAAGGAGTTCATGCGCTTCAAGGTGCACATGG
AGGGCTCCGTGAACGGCCACGAGTTCGAGATCGAGGGCGAGGGCGAGGGCCGCCCCTACGAGGGCACCCA
GACCGCCAAGCTGAAGGTGACCAAGGGTGGCCCCCTGCCCTTCGCCTGGGACATCCTGTCCCCTCAGTTC
ATGTACGGCTCCAAGGCCTACGTGAAGCACCCCGCCGACATCCCCGACTACTTGAAGCTGTCCTTCCCCG
AGGGCTTCAAGTGGGAGCGCGTGATGAACTTCGAGGACGGCGGCGTGGTGACCGTGACCCAGGACTCCTC
CCTGCAGGACGGCGAGTTCATCTACAAGGTGAAGCTGCGCGGCACCAACTTCCCCTCCGACGGCCCCGTA
ATGCAGAAGAAGACCATGGGCTGGGAGGCCTCCTCCGAGCGGATGTACCCCGAGGACGGCGCCCTGAAGG
GCGAGATCAAGCAGAGGCTGAAGCTGAAGGACGGCGGCCACTACGACGCTGAGGTCAAGACCACCTACAA
GGCCAAGAAGCCCGTGCAGCTGCCCGGCGCCTACAACGTCAACATCAAGTTGGACATCACCTCCCACAAC
GAGGACTACACCATCGTGGAACAGTACGAACGCGCCGAGGGCCGCCACTCCACCGGCGGCATGGACGAGC
TGTACAAG (SEQ ID NO:21)

MVSKGEEDNMAIIKEFMRFKVHMEGSVNGHEFEIEGEGEGRPYEGTQTAKLKVTKGGPLPFAWDILSPQF
MYGSKAYVKHPADIPDYLKLSFPEGFKWERVMNFEDGGVVTVTQDSSLQDGEFIYKVKLRGTNFPSDGPV
MQKKTMGWEASSERMYPEDGALKGEIKQRLKLKDGGHYDAEVKTTYKAKKPVQLPGAYNVNIKLDITSHN
EDYTIVEQYERAEGRHSTGGMDELYK (SEQ ID NO:22)

Figures 5A and 5B. Construct #168, encoding a polypeptide comprising "DAP10 extracellular domain – CD8 alpha transmembrane domain – FRB – CD3 zeta intracellular chain – mCherry"

Figure 5A

Human DAP10 signal sequence and extracellular domain:
Atgatccatctgggtcacatcctcttcctgcttttgctcccagtggctgcagctcagacgactccaggag
agagatcatcactccctgcctttaccctggcacttcaggctcttgttccggatgtgggtccctctctct
gccg (SEQ ID NO:27)
MIHLGHILFLLLLPVAAAQTTPGERSSLPAFYPGTSGSCSGCGSLSLP (SEQ ID NO:28)

Human CD8alpha transmembrane domain:
ATCTACATCTGGGCGCCCTTGGCCGGGACTTGTGGGGTCCTTCTCCTGTCACTGGTTATCACCCTTTACT
GC (SEQ ID NO:29)
IYIWAPLAGTCGVLLLSLVITLYC (SEQ ID NO:30)

Linker:
GGtTCCGGcAGCGGaTCTGGtAGcGGAAGCGGGTCCGGTAGCGGATCT (SEQ ID NO:31)
GSGSGSGSGSGSGSGS (SEQ ID NO:32)

FRB:
ATCCTCTGGCATGAGATGTGGCATGAAGGCCTGGAAGAGGCATCTCGTTTGTACTTTGGGGAAAGGAACG
TGAAAGGCATGTTTGAGGTGCTGGAGCCCTTGCATGCTATGATGGAACGGGGCCCCCAGACTCTGAAGGA
AACATCCTTTAATCAGGCCTATGGTCGAGATTTAATGGAGGCCCAAGAGTGGTGCAGGAAGTACATGAAA
TCAGGGAATGTCAAGGACCTCCTCCAAGCCTGGGACCTCTATTATCATGTGTTCCGACGAATCTCAAAG
(SEQ ID NO:33)

ILWHEMWHEGLEEASRLYFGERNVKGMFEVLEPLHAMMERGPQTLKETSFNQAYGRDLMEAQEWCRKYMK
SGNVKDLLQAWDLYYHVFRRISK (SEQ ID NO:34)

Linker:
GGAAGCGGGTCCGGTAGCGGATCTTCCCTA (SEQ ID NO:15)
GSGSGSGSSL (SEQ ID NO:16)

Figure 5B
Human CD3 zeta intracellular chain:
AGAGTGAAGTTCAGCAGGAGCGCAGACGCCCCGCGTACCAGCAGGGCCAGAACCAGCTCTATAACGAGC
TCAATCTAGGACGAAGAGAGGAGTACGATGTTTTGGACAAGAGACGTGGCCGGGACCCTGAGATGGGGGG
AAAGCCGAGAAGGAAGAACCCTCAGGAAGGCCTGTACAATGAACTGCAGAAAGATAAGATGGCGGAGGCC
TACAGTGAGATTGGGATGAAAGGCGAGCGCCGGAGGGGCAAGGGGCACGATGGCCTTTACCAGGGTCTCA
GTACAGCCACCAAGGACACCTACGACGCCCTTCACATGCAGGCCCTGCCCCCTCGC (SEQ ID
NO:17)

RVKFSRSADAPAYQQGQNQLYNELNLGRREEYDVLDKRRGRDPEMGGKPRRKNPQEGLYNELQKDKMAEA
YSEIGMKGERRRGKGHDGLYQGLSTATKDTYDALHMQALPPR (SEQ ID NO:18)

Linker:

TCGCGAGGAAGCGGGTCCGGTAGCGGATCT (SEQ ID NO:19)

SRGSGSGSGS (SEQ ID NO:20)

mCherry:
ATGGTGAGCAAGGGCGAGGAGGATAACATGGCCATCATCAAGGAGTTCATGCGCTTCAAGGTGCACATGG
AGGGCTCCGTGAACGGCCACGAGTTCGAGATCGAGGGCGAGGGCGAGGGCCGCCCCTACGAGGGCACCCA
GACCGCCAAGCTGAAGGTGACCAAGGGTGGCCCCCTGCCCTTCGCCTGGGACATCCTGTCCCCTCAGTTC
ATGTACGGCTCCAAGGCCTACGTGAAGCACCCCGCCGACATCCCCGACTACTTGAAGCTGTCCTTCCCCG
AGGGCTTCAAGTGGGAGCGCGTGATGAACTTCGAGGACGGCGGCGTGGTGACCGTGACCCAGGACTCCTC
CCTGCAGGACGGCGAGTTCATCTACAAGGTGAAGCTGCGCGGCACCAACTTCCCCTCCGACGGCCCCGTA
ATGCAGAAGAAGACCATGGGCTGGGAGGCCTCCTCCGAGCGGATGTACCCCGAGGACGGCGCCCTGAAGG
GCGAGATCAAGCAGAGGCTGAAGCTGAAGGACGGCGGCCACTACGACGCTGAGGTCAAGACCACCTACAA
GGCCAAGAAGCCCGTGCAGCTGCCCGGCGCCTACAACGTCAACATCAAGTTGGACATCACCTCCCACAAC
GAGGACTACACCATCGTGGAACAGTACGAACGCGCCGAGGGCCGCCACTCCACCGGCGGCATGGACGAGC
TGTACAAG (SEQ ID NO:21)

MVSKGEEDNMAIIKEFMRFKVHMEGSVNGHEFEIEGEGEGRPYEGTQTAKLKVTKGGPLPFAWDILSPQF
MYGSKAYVKHPADIPDYLKLSFPEGFKWERVMNFEDGGVVTVTQDSSLQDGEFIYKVKLRGTNFPSDGPV
MQKKTMGWEASSERMYPEDGALKGEIKQRLKLKDGGHYDAEVKTTYKAKKPVQLPGAYNVNIKLDITSHN
EDYTIVEQYERAEGRHSTGGMDELYK (SEQ ID NO:22)

Figures 6A-6C. Construct #169, encoding a polypeptide comprising "DAP10 extracellular domain - CD8 alpha transmembrane domain - FRB - 4-1BB & CD3 zeta intracellular chains - mCherry"

Figure 6A

Human DAP10 signal sequence and extracellular domain:
Atgatccatctgggtcacatcctcttcctgcttttgctcccagtggctgcagctcagacgactccaggag
agagatcatcactccctgccttttaccctggcacttcaggctcttgttccggatgtgggtccctctctct
gccg (SEQ ID NO:27)
MIHLGHILFLLLLPVAAAQTTPGERSSLPAFYPGTSGSCSGCGSLSLP (SEQ ID NO:28)

Human CD8alpha transmembrane domain:
ATCTACATCTGGGCGCCCTTGGCCGGGACTTGTGGGGTCCTTCTCCTGTCACTGGTTATCACCCTTTACT
GC (SEQ ID NO:29)
IYIWAPLAGTCGVLLLSLVITLYC (SEQ ID NO:30)

Linker:
GGtTCCGGcAGCGGaTCTGGtAGcGGAAGCGGGTCCGGTAGCGGATCT (SEQ ID NO:31)
GSGSGSGSGSGSGSGS (SEQ ID NO:32)

FRB:
ATCCTCTGGCATGAGATGTGGCATGAAGGCCTGGAAGAGGCATCTCGTTTGTACTTTGGGGAAAGGAACG
TGAAAGGCATGTTTGAGGTGCTGGAGCCCTTGCATGCTATGATGGAACGGGGCCCCCAGACTCTGAAGGA
AACATCCTTTAATCAGGCCTATGGTCGAGATTTAATGGAGGCCCAAGAGTGGTGCAGGAAGTACATGAAA
TCAGGGAATGTCAAGGACCTCCTCCAAGCCTGGGACCTCTATTATCATGTGTTCCGACGAATCTCAAAG
(SEQ ID NO:33)

ILWHEMWHEGLEEASRLYFGERNVKGMFEVLEPLHAMMERGPQTLKETSFNQAYGRDLMEAQEWCRKYMK
SGNVKDLLQAWDLYYHVFRRISK (SEQ ID NO:34)

Linker:
GGAAGCGGGTCCGGTAGCGGATCTTCCCTA (SEQ ID NO:15)
GSGSGSGSSL (SEQ ID NO:16)

Figure 6B
Human 4-1BB intracellular chain:
AAACGGGGCAGAAAGAAACTCCTGTATATATTCAAACAACCATTTATGAGACCAGTACAAACTACTCAAG
AGGAAGATGGCTGTAGCTGCCGATTTCCAGAAGAAGAAGAAGGAGGATGTGAACTG (SEQ ID
NO:23)

KRGRKKLLYIFKQPFMRPVQTTQEEDGCSCRFPEEEEGGCEL (SEQ ID NO:24)

Human CD3 zeta intracellular chain:
AGAGTGAAGTTCAGCAGGAGCGCAGACGCCCCCGCGTACCAGCAGGGCCAGAACCAGCTCTATAACGAGC
TCAATCTAGGACGAAGAGAGGAGTACGATGTTTTGGACAAGAGACGTGGCCGGGACCCTGAGATGGGGGG
AAAGCCGAGAAGGAAGAACCCTCAGGAAGGCCTGTACAATGAACTGCAGAAAGATAAGATGGCGGAGGCC
TACAGTGAGATTGGGATGAAAGGCGAGCGCCGGAGGGGCAAGGGGCACGATGGCCTTTACCAGGGTCTCA
GTACAGCCACCAAGGACACCTACGACGCCCTTCACATGCAGGCCCTGCCCCCTCGC (SEQ ID
NO:17)

RVKFSRSADAPAYQQGQNQLYNELNLGRREEYDVLDKRRGRDPEMGGKPRRKNPQEGLYNELQKDKMAEA
YSEIGMKGERRRGKGHDGLYQGLSTATKDTYDALHMQALPPR (SEQ ID NO:18)

Linker:

TCGCGAGGAAGCGGGTCCGGTAGCGGATCT (SEQ ID NO:19)

SRGSGSGSGS (SEQ ID NO:20)

Figure 6C
mCherry:
ATGGTGAGCAAGGGCGAGGAGGATAACATGGCCATCATCAAGGAGTTCATGCGCTTCAAGGTGCACATGG
AGGGCTCCGTGAACGGCCACGAGTTCGAGATCGAGGGCGAGGGCGAGGGCCGCCCCTACGAGGGCACCCA
GACCGCCAAGCTGAAGGTGACCAAGGGTGGCCCCCTGCCCTTCGCCTGGGACATCCTGTCCCCTCAGTTC
ATGTACGGCTCCAAGGCCTACGTGAAGCACCCCGCCGACATCCCCGACTACTTGAAGCTGTCCTTCCCCG
AGGGCTTCAAGTGGGAGCGCGTGATGAACTTCGAGGACGGCGGCGTGGTGACCGTGACCCAGGACTCCTC
CCTGCAGGACGGCGAGTTCATCTACAAGGTGAAGCTGCGCGGCACCAACTTCCCCTCCGACGGCCCCGTA
ATGCAGAAGAAGACCATGGGCTGGGAGGCCTCCTCCGAGCGGATGTACCCCGAGGACGGCGCCCTGAAGG
GCGAGATCAAGCAGAGGCTGAAGCTGAAGGACGGCGGCCACTACGACGCTGAGGTCAAGACCACCTACAA
GGCCAAGAAGCCCGTGCAGCTGCCCGGCGCCTACAACGTCAACATCAAGTTGGACATCACCTCCCACAAC
GAGGACTACACCATCGTGGAACAGTACGAACGCGCCGAGGGCCGCCACTCCACCGGCGGCATGGACGAGC
TGTACAAG (SEQ ID NO:21)

MVSKGEEDNMAIIKEFMRFKVHMEGSVNGHEFEIEGEGEGRPYEGTQTAKLKVTKGGPLPFAWDILSPQF
MYGSKAYVKHPADIPDYLKLSFPEGFKWERVMNFEDGGVVTVTQDSSLQDGEFIYKVKLRGTNFPSDGPV
MQKKTMGWEASSERMYPEDGALKGEIKQRLKLKDGGHYDAEVKTTYKAKKPVQLPGAYNVNIKLDITSHN
EDYTIVEQYERAEGRHSTGGMDELYK (SEQ ID NO:22)

Figures 7A and 7B. Construct #170, encoding a polypeptide comprising "DAP10 extracellular domain – CD8 alpha transmembrane domain – FRB – mCherry"

Figure 7A

Human DAP10 signal sequence and extracellular domain:
Atgatccatctgggtcacatcctcttcctgcttttgctcccagtggctgcagctcagacgactccaggag agagatcatcactccctgccttttaccctggcacttcaggctcttgttccggatgtgggtccctctctct gccg (SEQ ID NO:27)
MIHLGHILFLLLLPVAAAQTTPGERSSLPAFYPGTSGSCSGCGSLSLP (SEQ ID NO:28)

Human CD8alpha transmembrane domain:
ATCTACATCTGGGCGCCCTTGGCCGGGACTTGTGGGGTCCTTCTCCTGTCACTGGTTATCACCCTTTACT GC (SEQ ID NO:29)
IYIWAPLAGTCGVLLLSLVITLYC (SEQ ID NO:30)

Linker:
GGtTCCGGcAGCGGaTCTGGtAGcGGAAGCGGGTCCGGTAGCGGATCT (SEQ ID NO:31)
GSGSGSGSGSGSGSGS (SEQ ID NO:32)

FRB:
ATCCTCTGGCATGAGATGTGGCATGAAGGCCTGGAAGAGGCATCTCGTTTGTACTTTGGGGAAAGGAACG TGAAAGGCATGTTTGAGGTGCTGGAGCCCTTGCATGCTATGATGGAACGGGGCCCCCAGACTCTGAAGGA AACATCCTTTAATCAGGCCTATGGTCGAGATTTAATGGAGGCCCAAGAGTGGTGCAGGAAGTACATGAAA TCAGGGAATGTCAAGGACCTCCTCCAAGCCTGGGACCTCTATTATCATGTGTTCCGACGAATCTCAAAG (SEQ ID NO:33)

ILWHEMWHEGLEEASRLYFGERNVKGMFEVLEPLHAMMERGPQTLKETSFNQAYGRDLMEAQEWCRKYMK SGNVKDLLQAWDLYYHVFRRISK (SEQ ID NO:34)

Figure 7B
Linker:
GGAAGCGGGTCCGGTAGCGGATCTTCCCTA (SEQ ID NO:15)
GSGSGSGSSL (SEQ ID NO:16)

mCherry:
ATGGTGAGCAAGGGCGAGGAGGATAACATGGCCATCATCAAGGAGTTCATGCGCTTCAAGGTGCACATGG
AGGGCTCCGTGAACGGCCACGAGTTCGAGATCGAGGGCGAGGGCGAGGGCCGCCCCTACGAGGGCACCCA
GACCGCCAAGCTGAAGGTGACCAAGGGTGGCCCCCTGCCCTTCGCCTGGGACATCCTGTCCCCTCAGTTC
ATGTACGGCTCCAAGGCCTACGTGAAGCACCCCGCCGACATCCCCGACTACTTGAAGCTGTCCTTCCCCG
AGGGCTTCAAGTGGGAGCGCGTGATGAACTTCGAGGACGGCGGCGTGGTGACCGTGACCCAGGACTCCTC
CCTGCAGGACGGCGAGTTCATCTACAAGGTGAAGCTGCGCGGCACCAACTTCCCCTCCGACGGCCCCGTA
ATGCAGAAGAAGACCATGGGCTGGGAGGCCTCCTCCGAGCGGATGTACCCCGAGGACGGCGCCCTGAAGG
GCGAGATCAAGCAGAGGCTGAAGCTGAAGGACGGCGGCCACTACGACGCTGAGGTCAAGACCACCTACAA
GGCCAAGAAGCCCGTGCAGCTGCCCGGCGCCTACAACGTCAACATCAAGTTGGACATCACCTCCCACAAC
GAGGACTACACCATCGTGGAACAGTACGAACGCGCCGAGGGCCGCCACTCCACCGGCGGCATGGACGAGC
TGTACAAG (SEQ ID NO:21)

MVSKGEEDNMAIIKEFMRFKVHMEGSVNGHEFEIEGEGEGRPYEGTQTAKLKVTKGGPLPFAWDILSPQF
MYGSKAYVKHPADIPDYLKLSFPEGFKWERVMNFEDGGVVTVTQDSSLQDGEFIYKVLRGTNFPSDGPV
MQKKTMGWEASSERMYPEDGALKGEIKQRLKLKDGGHYDAEVKTTYKAKKPVQLPGAYNVNIKLDITSHN
EDYTIVEQYERAEGRHSTGGMDELYK (SEQ ID NO:22)

Figures 8A and 8B. Construct #197, encoding a polypeptide comprising "anti-CD19 scFv – CD8 alpha hinge and transmembrane domain – 4-1BB intracellular chain – FKBP"

Figure 8A

Signal peptide:
ATGGCCTTACCAGTGACCGCCTTGCTCCTGCCGCTGGCCTTGCTGCTCCACGCCGCCAGGCCG (SEQ ID NO:1)
MALPVTALLLPLALLLHAARP (SEQ ID NO:2)

Myc epitope tag:
GAGCAGAAGCTGATCAGCGAGGAGGACCTG (SEQ ID NO:3)
EQKLISEEDL (SEQ ID NO:4)

Anti-human CD19 scFv:
GACATCCAGATGACACAGACTACATCCTCCCTGTCTGCCTCTCTGGGAGACAGAGTCACCATCAGTTGCA
GGGCAAGTCAGGACATTAGTAAATATTTAAATTGGTATCAGCAGAAACCAGATGGAACTGTTAAACTCCT
GATCTACCATACATCAAGATTACACTCAGGAGTCCCATCAAGGTTCAGTGGCAGTGGGTCTGGAACAGAT
TATTCTCTCACCATTAGCAACCTGGAGCAAGAAGATATTGCCACTTACTTTTGCCAACAGGGTAATACGC
TTCCGTACACGTTCGGAGGGGGGACCAAGCTGGAGATCACAGGTGGCGGTGGCTCGGGCGGTGGTGGGTC
GGGTGGCGGCGGATCTGAGGTGAAACTGCAGGAGTCAGGACCTGGCCTGGTGGCGCCCTCACAGAGCCTG
TCCGTCACATGCACTGTCTCAGGGGTCTCATTACCCGACTATGGTGTAAGCTGGATTCGCCAGCCTCCAC
GAAAGGGTCTGGAGTGGCTGGGAGTAATATGGGGTAGTGAAACCACATACTATAATTCAGCTCTCAAATC
CAGACTGACCATCATCAAGGACAACTCCAAGAGCCAAGTTTTCTTAAAAATGAACAGTCTGCAAACTGAT
GACACAGCCATTTACTACTGTGCCAAACATTATTACTACGGTGGTAGCTATGCTATGGACTACTGGGGCC
AAGGAACCTCAGTCACCGTCTCCTCA (SEQ ID NO:5)

DIQMTQTTSSLSASLGDRVTISCRASQDISKYLNWYQQKPDGTVKLLIYHTSRLHSGVPSRFSGSGSGTD
YSLTISNLEQEDIATYFCQQGNTLPYTFGGGTKLEITGGGSGGGGSGGGGSEVKLQESGPGLVAPSQSL
SVTCTVSGVSLPDYGVSWIRQPPRKGLEWLGVIWGSETTYYNSALKSRLTIIKDNSKSQVFLKMNSLQTD
DTAIYYCAKHYYYGGSYAMDYWGQGTSVTVSS (SEQ ID NO:6)

Figure 8B
Human CD8 alpha extracellular spacer/hinge and transmembrane domain:
ACCACGACGCCAGCGCCGCGACCACCAACACCGGCGCCCACCATCGCGTCGCAGCCCCTGTCCCTGCGCC
CAGAGGCGTGCCGGCCAGCGGCGGGGGGCGCAGTGCACACGAGGGGGCTGGACTTCGCCTGTGATATCTA
CATCTGGGCGCCCTTGGCCGGGACTTGTGGGGTCCTTCTCCTGTCACTGGTTATCACCCTTTACTGC
(SEQ ID NO:7)

TTTPAPRPPTPAPTIASQPLSLRPEACRPAAGGAVHTRGLDFACDIYIWAPLAGTCGVLLLSLVITLYC
(SEQ ID NO:8)

Linker:
TCCCTA
SerLeu

Human 4-1BB intracellular chain:
AAACGGGGCAGAAAGAAACTCCTGTATATATTCAAACAACCATTTATGAGACCAGTACAAACTACTCAAG
AGGAAGATGGCTGTAGCTGCCGATTTCCAGAAGAAGAAGAAGGAGGATGTGAACTG (SEQ ID
NO:23)
KRGRKKLLYIFKQPFMRPVQTTQEEDGCSCRFPEEEEGGCEL (SEQ ID NO:24)

Linker:
TCGCGAGGAAGCGGGTCCGGTAGCGGATCT SEQ ID NO:19)
SRGSGSGSGS (SEQ ID NO:20)

FKBP:
ATGGGAGTcCAGGTGGAAACCATCTCCCCAGGAGACGGGCGCACCTTCCCCAAGCGCGGCCAGACCTGCG
TGGTGCACTACACCGGGATGCTTGAAGATGGAAAGAAATTTGATTCCTCCGGGACAGAAACAAGCCCTT
TAAGTTTATGCTAGGCAAGCAGGAGGTGATCCGAGGCTGGGAAGAAGGGGTTGCCCAGATGAGTGTGGGT
CAGAGAGCCAAACTGACTATATCTCCAGATTATGCCTATGGTGCCACTGGGCACCCAGGCATCATCCCAC
CACATGCCACTCTCGTCTTCGATGTGGAGCTTCTAAAACTGGAA (SEQ ID NO:11)

MGVQVETISPGDGRTFPKRGQTCVVHYTGMLEDGKKFDSSRDRNKPFKFMLGKQEVIRGWEEGVAQMSVG
QRAKLTISPDYAYGATGHPGIIPPHATLVFDVELLKLE (SEQ ID NO:12)

Figures 9A-C. Construct #206, encoding a polypeptide comprising "DAP10 extracellular domain - CD8 alpha transmembrane domain - 4-1BB intracellular chain - FRB - CD3 zeta intracellular chain - mCherry"

Figure 9A

Human DAP10 signal sequence and extracellular domain:
Atgatccatctgggtcacatcctcttcctgcttttgctcccagtggctgcagctcagacgactccaggag
agagatcatcactccctgccttttaccctggcacttcaggctcttgttccggatgtgggtccctctctct
gccg (SEQ ID NO:27)
MIHLGHILFLLLLPVAAAQTTPGERSSLPAFYPGTSGSCSGCGSLSLP (SEQ ID NO:28)

Human CD8alpha transmembrane domain:
ATCTACATCTGGGCGCCCTTGGCCGGGACTTGTGGGGTCCTTCTCCTGTCACTGGTTATCACCCTTTACT
GC (SEQ ID NO:29)
IYIWAPLAGTCGVLLLSLVITLYC (SEQ ID NO:30)

Linker:
Tctctg
SerLeu

Human 4-1BB intracellular chain:
AAACGGGGCAGAAAGAAACTCCTGTATATATTCAAACAACCATTTATGAGACCAGTACAAACTACTCAAG
AGGAAGATGGCTGTAGCTGCCGATTTCCAGAAGAAGAAGAAGGAGGATGTGAACTG (SEQ ID NO:23)
KRGRKKLLYIFKQPFMRPVQTTQEEDGCSCRFPEEEEGGCEL (SEQ ID NO:24)

Linker:
GGtTCCGGcAGCGGaTCTGGtAGcGGAAGCGGGTCCGGTAGCGGATCT (SEQ ID NO:31)
GSGSGSGSGSGSGSGS (SEQ ID NO:32)

Figure 9B
FRB:
ATCCTCTGGCATGAGATGTGGCATGAAGGCCTGGAAGAGGCATCTCGTTTGTACTTTGGGGAAAGGAACG
TGAAAGGCATGTTTGAGGTGCTGGAGCCCTTGCATGCTATGATGGAACGGGGCCCCCAGACTCTGAAGGA
AACATCCTTTAATCAGGCCTATGGTCGAGATTTAATGGAGGCCCAAGAGTGGTGCAGGAAGTACATGAAA
TCAGGGAATGTCAAGGACCTCCTCCAAGCCTGGGACCTCTATTATCATGTGTTCCGACGAATCTCAAAG
(SEQ ID NO:33)

ILWHEMWHEGLEEASRLYFGERNVKGMFEVLEPLHAMMERGPQTLKETSFNQAYGRDLMEAQEWCRKYMK
SGNVKDLLQAWDLYYHVFRRISK (SEQ ID NO:34)

Linker:
GGAAGCGGGTCCGGTAGCGGATCTTCCCTA (SEQ ID NO:15)
GSGSGSGSSL (SEQ ID NO:16)

Human CD3 zeta intracellular chain:
AGAGTGAAGTTCAGCAGGAGCGCAGACGCCCCCGCGTACCAGCAGGGCCAGAACCAGCTCTATAACGAGC
TCAATCTAGGACGAAGAGAGGAGTACGATGTTTTGGACAAGAGACGTGGCCGGGACCCTGAGATGGGGGG
AAAGCCGAGAAGGAAGAACCCTCAGGAAGGCCTGTACAATGAACTGCAGAAAGATAAGATGGCGGAGGCC
TACAGTGAGATTGGGATGAAAGGCGAGCGCCGGAGGGGCAAGGGGCACGATGGCCTTTACCAGGGTCTCA
GTACAGCCACCAAGGACACCTACGACGCCCTTCACATGCAGGCCCTGCCCCCTCGC (SEQ ID
NO:17)

RVKFSRSADAPAYQQGQNQLYNELNLGRREEYDVLDKRRGRDPEMGGKPRRKNPQEGLYNELQKDKMAEA
YSEIGMKGERRRGKGHDGLYQGLSTATKDTYDALHMQALPPR (SEQ ID NO:18)

Linker:
TCGCGAGGAAGCGGGTCCGGTAGCGGATCT SEQ ID NO:19)
SRGSGSGSGS (SEQ ID NO:20)

Figure 9C
mCherry:
ATGGTGAGCAAGGGCGAGGAGGATAACATGGCCATCATCAAGGAGTTCATGCGCTTCAAGGTGCACATGG
AGGGCTCCGTGAACGGCCACGAGTTCGAGATCGAGGGCGAGGGCGAGGGCCGCCCCTACGAGGGCACCCA
GACCGCCAAGCTGAAGGTGACCAAGGGTGGCCCCCTGCCCTTCGCCTGGGACATCCTGTCCCCTCAGTTC
ATGTACGGCTCCAAGGCCTACGTGAAGCACCCCGCCGACATCCCCGACTACTTGAAGCTGTCCTTCCCCG
AGGGCTTCAAGTGGGAGCGCGTGATGAACTTCGAGGACGGCGGCGTGGTGACCGTGACCCAGGACTCCTC
CCTGCAGGACGGCGAGTTCATCTACAAGGTGAAGCTGCGCGGCACCAACTTCCCCTCCGACGGCCCCGTA
ATGCAGAAGAAGACCATGGGCTGGGAGGCCTCCTCCGAGCGGATGTACCCCGAGGACGGCGCCCTGAAGG
GCGAGATCAAGCAGAGGCTGAAGCTGAAGGACGGCGGCCACTACGACGCTGAGGTCAAGACCACCTACAA
GGCCAAGAAGCCCGTGCAGCTGCCCGGCGCCTACAACGTCAACATCAAGTTGGACATCACCTCCCACAAC
GAGGACTACACCATCGTGGAACAGTACGAACGCGCCGAGGGCCGCCACTCCACCGGCGGCATGGACGAGC
TGTACAAG (SEQ ID NO:21)

MVSKGEEDNMAIIKEFMRFKVHMEGSVNGHEFEIEGEGEGRPYEGTQTAKLKVTKGGPLPFAWDILSPQF
MYGSKAYVKHPADIPDYLKLSFPEGFKWERVMNFEDGGVVTVTQDSSLQDGEFIYKVKLRGTNFPSDGPV
MQKKTMGWEASSERMYPEDGALKGEIKQRLKLKDGGHYDAEVKTTYKAKKPVQLPGAYNVNIKLDITSHN
EDYTIVEQYERAEGRHSTGGMDELYK (SEQ ID NO:22)

Figures 10A and 10B. Construct #207, encoding a polypeptide comprising "DAP10 extracellular domain – CD8 alpha transmembrane domain – 4-1BB intracellular chain – FRB – mCherry"

Figure 10A

Human DAP10 signal sequence and extracellular domain:
Atgatccatctgggtcacatcctcttcctgcttttgctcccagtggctgcagctcagacgactccaggag
agagatcatcactccctgccttttaccctggcacttcaggctcttgttccggatgtgggtccctctctct
gccg (SEQ ID NO:27)
MIHLGHILFLLLLPVAAAQTTPGERSSLPAFYPGTSGSCSGCGSLSLP (SEQ ID NO:28)

Human CD8alpha transmembrane domain:
ATCTACATCTGGGCGCCCTTGGCCGGGACTTGTGGGGTCCTTCTCCTGTCACTGGTTATCACCCTTTACT
GC (SEQ ID NO:29)
IYIWAPLAGTCGVLLLSLVITLYC (SEQ ID NO:30)

Linker:
Tctctg
SerLeu

Human 4-1BB intracellular chain:
AAACGGGGCAGAAAGAAACTCCTGTATATATTCAAACAACCATTTATGAGACCAGTACAAACTACTCAAG
AGGAAGATGGCTGTAGCTGCCGATTTCCAGAAGAAGAAGAAGGAGGATGTGAACTG (SEQ ID
NO:23)
KRGRKKLLYIFKQPFMRPVQTTQEEDGCSCRFPEEEEGGCEL (SEQ ID NO:24)

Linker:
GGtTCCGGcAGCGGaTCTGGtAGcGGAAGCGGGTCCGGTAGCGGATCT (SEQ ID NO:31)
GSGSGSGSGSGSGSGS (SEQ ID NO:32)

Figure 10B

FRB:
ATCCTCTGGCATGAGATGTGGCATGAAGGCCTGGAAGAGGCATCTCGTTTGTACTTTGGGGAAAGGAACG
TGAAAGGCATGTTTGAGGTGCTGGAGCCCTTGCATGCTATGATGGAACGGGGCCCCCAGACTCTGAAGGA
AACATCCTTTAATCAGGCCTATGGTCGAGATTTAATGGAGGCCCAAGAGTGGTGCAGGAAGTACATGAAA
TCAGGGAATGTCAAGGACCTCCTCCAAGCCTGGGACCTCTATTATCATGTGTTCCGACGAATCTCAAAG
(SEQ ID NO:33)

ILWHEMWHEGLEEASRLYFGERNVKGMFEVLEPLHAMMERGPQTLKETSFNQAYGRDLMEAQEWCRKYMK
SGNVKDLLQAWDLYYHVFRRISK (SEQ ID NO:34)

Linker:
GGAAGCGGGTCCGGTAGCGGATCTTCCCTA (SEQ ID NO:15)
GSGSGSGSSL (SEQ ID NO:16)

mCherry:
ATGGTGAGCAAGGGCGAGGAGGATAACATGGCCATCATCAAGGAGTTCATGCGCTTCAAGGTGCACATGG
AGGGCTCCGTGAACGGCCACGAGTTCGAGATCGAGGGCGAGGGCGAGGGCCGCCCCTACGAGGGCACCCA
GACCGCCAAGCTGAAGGTGACCAAGGGTGGCCCCCTGCCCTTCGCCTGGGACATCCTGTCCCCTCAGTTC
ATGTACGGCTCCAAGGCCTACGTGAAGCACCCCGCCGACATCCCCGACTACTTGAAGCTGTCCTTCCCCG
AGGGCTTCAAGTGGGAGCGCGTGATGAACTTCGAGGACGGCGGCGTGGTGACCGTGACCCAGGACTCCTC
CCTGCAGGACGGCGAGTTCATCTACAAGGTGAAGCTGCGCGGCACCAACTTCCCCTCCGACGGCCCCGTA
ATGCAGAAGAAGACCATGGGCTGGGAGGCCTCCTCCGAGCGGATGTACCCCGAGGACGGCGCCCTGAAGG
GCGAGATCAAGCAGAGGCTGAAGCTGAAGGACGGCGGCCACTACGACGCTGAGGTCAAGACCACCTACAA
GGCCAAGAAGCCCGTGCAGCTGCCCGGCGCCTACAACGTCAACATCAAGTTGGACATCACCTCCCACAAC
GAGGACTACACCATCGTGGAACAGTACGAACGCGCCGAGGGCCGCCACTCCACCGGCGGCATGGACGAGC
TGTACAAG (SEQ ID NO:21)

MVSKGEEDNMAIIKEFMRFKVHMEGSVNGHEFEIEGEGEGRPYEGTQTAKLKVTKGGPLP
FAWDILSPQFMYGSKAYVKHPADIPDYLKLSFPEGFKWERVMNFEDGGVVTVTQDSSLQD
GEFIYKVKLRGTNFPSDGPVMQKKTMGWEASSERMYPEDGALKGEIKQRLKLKDGGHYDA
EVKTTYKAKKPVQLPGAYNVNIKLDITSHNEDYTIVEQYERAEGRHSTGGMDELYK (SEQ ID
NO:22)

Figures 11A-C. Construct #199, encoding the fusion protein "FRB – Zap70 – mCherry"

Figure 11A
FRB:
ATGATCCTCTGGCATGAGATGTGGCATGAAGGCCTGGAAGAGGCATCTCGTTTGTACTTTGGGGAAAGGA
ACGTGAAAGGCATGTTTGAGGTGCTGGAGCCCTTGCATGCTATGATGGAACGGGGCCCCCAGACTCTGAA
GGAAACATCCTTTAATCAGGCCTATGGTCGAGATTTAATGGAGGCCCAAGAGTGGTGCAGGAAGTACATG
AAATCAGGGAATGTCAAGGACCTCCTCCAAGCCTGGGACCTCTATTATCATGTGTTCCGACGAATCTCAA
AG (SEQ ID NO:13)

MILWHEMWHEGLEEASRLYFGERNVKGMFEVLEPLHAMMERGPQTLKETSFNQAYGRDLMEAQEWCRKYM
KSGNVKDLLQAWDLYYHVFRRISK (SEQ ID NO:14)

Linker:
GGAAGCGGGTCCGGTAGCGGATCTTCCCTA (SEQ ID NO:15)
GSGSGSGSSL (SEQ ID NO:16)

Figure 11B
Human Zap70:
ATGCCAGACCCCGCGGCGCATCTGCCCTTCTTCTACGGCAGCATCTCGCGTGCCGAGGCCGAGGAGCACC
TGAAGCTGGCGGGCATGGCGGACGGGCTCTTCCTGCTGCGCCAGTGCCTGCGCTCGCTGGGCGGCTATGT
GCTGTCGCTCGTGCACGATGTGCGCTTCCACCACTTTCCCATCGAGCGCCAGCTCAACGGCACCTACGCC
ATTGCCGGCGGCAAAGCGCACTGTGGACCGGCAGAGCTCTGCGAGTTCTACTCGCGCGACCCCGACGGGC
TGCCCTGCAACCTGCGCAAGCCGTGCAACCGGCCGTCGGGCCTCGAGCCGCAGCCGGGGGTCTTCGACTG
CCTGCGAGACGCCATGGTGCGTGACTACGTGCGCCAGACGTGGAAGCTGGAGGGCGAGGCCCTGGAGCAG
GCCATCATCAGCCAGGCCCCGCAAGTGGAGAAGCTCATTGCTACGACGGCCCACGAGCGGATGCCCTGGT
ACCACAGCAGCCTGACGCGTGAGGAGGCCGAGCGCAAACTTTACTCTGGGGCGCAGACCGACGGCAAGTT
CCTGCTGAGGCCGCGGAAGGAGCAGGGCACATACGCCCTGTCCCTCATCTATGGGAAGACGGTGTACCAC
TACCTCATCAGCCAAGACAAGGCGGGCAAGTACTGCATTCCCGAGGGCACCAAGTTTGACACGCTCTGGC
AGCTGGTGGAGTATCTGAAGCTGAAGGCGGACGGGCTCATCTACTGCCTGAAGGAGGCCTGCCCCAACAG
CAGTGCCAGCAACGCCTCAGGGCTGCTGCTCCCACACTCCCAGCCCACCCATCCACGTTGACTCATCCT
CAGAGACGAATCGACACCCTCAACTCAGATGGATACACCCCTGAGCCAGCACGCATAACGTCCCCAGACA
AACCGCGGCCGATGCCCATGGACACGAGCGTGTATGAGAGCCCCTACAGCGACCCAGAGGAGCTCAAGGA
CAAGAAGCTCTTCCTGAAGCGCGATAACCTCCTCATAGCTGACATTGAACTTGGCTGCGGCAACTTTGGC
TCAGTGCGCCAGGGCGTGTACCGCATGCGCAAGAAGCAGATCGACGTGGCCATCAAGGTGCTGAAGCAGG
GCACGGAGAAGGCAGACACGGAAGAGATGATGCGCGAGGCGCAGATCATGCACCAGCTGGACAACCCCTA
CATCGTGCGGCTCATTGGCGTCTGCCAGGCCGAGGCCCTCATGCTGGTCATGGAGATGGCTGGGGGCGGG
CCGCTGCACAAGTTCCTGGTCGGCAAGAGGGAGGAGATCCCTGTGAGCAATGTGGCCGAGCTGCTGCACC
AGGTGTCCATGGGGATGAAGTACCTGGAGGAGAAGAACTTTGTGCACCGTGACCTGGCGGCCCGCAACGT
CCTGCTGGTTAACCGGCACTACGCCAAGATCAGCGACTTTGGCCTCTCCAAAGCACTGGGTGCCGACGAC
AGCTACTACACTGCCCGCTCAGCAGGGAAGTGGCCGCTCAAGTGGTACGCACCCGAATGCATCAACTTCC
GCAAGTTCTCCAGCCGCAGCGATGTCTGGAGCTATGGGGTCACCATGTGGGAGGCCTTGTCCTACGGCCA
GAAGCCCTACAAGAAGATGAAAGGGCCGGAGGTCATGGCCTTCATCGAGCAGGGCAAGCGGATGGAGTGC
CCACCAGAGTGTCCACCCGAACTGTACGCACTCATGAGTGACTGCTGGATCTACAAGTGGGAGGATCGCC
CCGACTTCCTGACCGTGGAGCAGCGCATGCGAGCCTGTTACTACAGCCTGGCCAGCAAGGTGGAAGGGCC
CCCAGGCAGCACACAGAAGGCTGAGGCTGCCTGTGCC (SEQ ID NO:35)

MPDPAAHLPFFYGSISRAEAEEHLKLAGMADGLFLLRQCLRSLGGYVLSLVHDVRFHHFPIERQLNGTYA
IAGGKAHCGPAELCEFYSRDPDGLPCNLRKPCNRPSGLEPQPGVFDCLRDAMVRDYVRQTWKLEGEALEQ
AIISQAPQVEKLIATTAHERMPWYHSSLTREEAERKLYSGAQTDGKFLLRPRKEQGTYALSLIYGKTVYH
YLISQDKAGKYCIPEGTKFDTLWQLVEYLKLKADGLIYCLKEACPNSSASNASGAAAPTLPAHPSTLTHP
QRRIDTLNSDGYTPEPARITSPDKPRPMPMDTSVYESPYSDPEELKDKKLFLKRDNLLIADIELGCGNFG
SVRQGVYRMRKKQIDVAIKVLKQGTEKADTEEMMREAQIMHQLDNPYIVRLIGVCQAEALMLVMEMAGGG
PLHKFLVGKREEIPVSNVAELLHQVSMGMKYLEEKNFVHRDLAARNVLLVNRHYAKISDFGLSKALGADD
SYYTARSAGKWPLKWYAPECINFRKFSSRSDVWSYGVTMWEALSYGQKPYKKMKGPEVMAFIEQGKRMEC
PPECPPELYALMSDCWIYKWEDRPDFLTVEQRMRACYYSLASKVEGPPGSTQKAEAACA (SEQ ID
NO:36)

Figure 11C
Linker:
TCGCGAGGAAGCGGGTCCGGTAGCGGATCT (SEQ ID NO:19)
SRGSGSGSGS (SEQ ID NO:20)

mCherry:
ATGGTGAGCAAGGGCGAGGAGGATAACATGGCCATCATCAAGGAGTTCATGCGCTTCAAGGTGCACATGG
AGGGCTCCGTGAACGGCCACGAGTTCGAGATCGAGGGCGAGGGCGAGGGCCGCCCCTACGAGGGCACCCA
GACCGCCAAGCTGAAGGTGACCAAGGGTGGCCCCCTGCCCTTCGCCTGGGACATCCTGTCCCCTCAGTTC
ATGTACGGCTCCAAGGCCTACGTGAAGCACCCCGCCGACATCCCCGACTACTTGAAGCTGTCCTTCCCCG
AGGGCTTCAAGTGGGAGCGCGTGATGAACTTCGAGGACGGCGGCGTGGTGACCGTGACCCAGGACTCCTC
CCTGCAGGACGGCGAGTTCATCTACAAGGTGAAGCTGCGCGGCACCAACTTCCCCTCCGACGGCCCCGTA
ATGCAGAAGAAGACCATGGGCTGGGAGGCCTCCTCCGAGCGGATGTACCCCGAGGACGGCGCCCTGAAGG
GCGAGATCAAGCAGAGGCTGAAGCTGAAGGACGGCGGCCACTACGACGCTGAGGTCAAGACCACCTACAA
GGCCAAGAAGCCCGTGCAGCTGCCCGGCGCCTACAACGTCAACATCAAGTTGGACATCACCTCCCACAAC
GAGGACTACACCATCGTGGAACAGTACGAACGCGCCGAGGGCCGCCACTCCACCGGCGGCATGGACGAGC
TGTACAAG (SEQ ID NO:21)

MVSKGEEDNMAIIKEFMRFKVHMEGSVNGHEFEIEGEGEGRPYEGTQTAKLKVTKGGPLPFAWDILSPQF
MYGSKAYVKHPADIPDYLKLSFPEGFKWERVMNFEDGGVVTVTQDSSLQDGEFIYKVKLRGTNFPSDGPV
MQKKTMGWEASSERMYPEDGALKGEIKQRLKLKDGGHYDAEVKTTYKAKKPVQLPGAYNVNIKLDITSHN
EDYTIVEQYERAEGRHSTGGMDELYK (SEQ ID NO:22)

Figure 18A

| | | | | |
|---|---|---|---|---|
| FKBP-FRB* / ITAM | FKBP-FRB* | FKBP-FRB* / ITAM | FKBP-FRB* / 4-1BB / ITAM | FKBP-FRB* |
| 122 + 123 | 122 + 126 | 122 + 168 | 122 + 169 | 122 + 170 |
| Induces modest NFAT-dependent transcription. | "No signaling" control for "122 + 123" | Stronger NFAT-dependent reporter gene induction than "122 + 123"; low IL-2 production. | Low IL-2 production. | "No signaling" control for "122 + 168/169/206" |

Figure 18B

| | | | |
|---|---|---|---|
| FKBP⊂⊃4-1BB<br>FRB*<br>ITAM | 4-1BB ⊂⊃FRB*<br>FKBP<br>ITAM | 4-1BB ┃ ┃ 4-1BB<br>FKBP⊂⊃FRB*<br>ITAM | 4-1BB ┃ ┃ 4-1BB<br>FKBP⊂⊃FRB* |
| 122 + 206 | 197 +168 | 197 + 206 | 197 + 207 |
| Strong reporter gene induction through NFAT; modest IL-2 production. | Strong reporter gene induction through NFAT; modest IL-2 production. | Strong cytokine production and cytotoxicity; robust On switch function. | "No ITAM" control for "197 + 168/206" |

357 + 206

270 + 206

300 + 206

365 + 367

399 + 400

366

398

Figures 22A and 22B. Construct #270, encoding a polypeptide comprising "anti-mesothelin SS1 scFv - CD8 alpha hinge and transmembrane domain - 4-1BB intracellular chain - FKBP"

Figure 22A
Signal peptide:
ATGGCCTTACCAGTGACCGCCTTGCTCCTGCCGCTGGCCTTGCTGCTCCACGCCGCCAGGCCG (SEQ ID NO:1)
MALPVTALLLPLALLLHAARP (SEQ ID NO:2)

Flag epitope tag:
GATTACAAGGATGACGATGACAAG (SEQ ID NO:132)
DYKDDDDK (SEQ ID NO:123)

Anti-human mesothelin SS1 scFv:
GGATCCCAGGTACAACTGCAGCAGTCTGGGCCTGAGCTGGAGAAGCCTGGCGCTTCAGTGAAGATATCCT
GCAAGGCTTCTGGTTACTCATTCACTGGCTACACCATGAACTGGGTGAAGCAGAGCCATGGAAAGAGCCT
TGAGTGGATTGGACTTATTACTCCTTACAATGGTGCTTCTAGCTACAACCAGAAGTTCAGGGGCAAGGCC
ACATTAACTGTAGACAAGTCATCCAGCACAGCCTACATGGACCTCCTCAGTCTGACATCTGAAGACTCTG
CAGTCTATTTCTGTGCAAGGGGGGGTTACGACGGGAGGGGTTTTGACTACTGGGGCCAAGGGACCACGGT
CACCGTCTCCTCAGGTGGAGGCGGTTCAGGCGGCGGTGGCTCTAGCGGTGGcGGATCGGACATCGAGCTC
ACTCAGTCTCCAGCAATCATGTCTGCATCTCCAGGGGAGAAGGTCACCATGACCTGCAGTGCCAGCTCAA
GTGTAAGTTACATGCACTGGTACCAGCAGAAGTCAGGCACCTCCCCCAAAAGATGGATTTATGACACATC
CAAACTGGCTTCTGGAGTCCCAGGTCGCTTCAGTGGCAGTGGGTCTGGAAACTCTTACTCTCTCACAATC
AGCAGCGTGGAGGCTGAAGATGATGCAACTTATTACTGCCAGCAGTGGAGTAAGCACCCTCTCACGTACG
GTGCTGGGACAAAGTTGGAAATCAAAGCTAGC (SEQ ID NO:133)

GSQVQLQQSGPELEKPGASVKISCKASGYSFTGYTMNWVKQSHGKSLEWIGLITPYNGAS
SYNQKFRGKATLTVDKSSSTAYMDLLSLTSEDSAVYFCARGGYDGRGFDYWGQGTTVTVS
SGGGGSGGGGSSGGGSDIELTQSPAIMSASPGEKVTMTCSASSSVSYMHWYQQKSGTSPK
RWIYDTSKLASGVPGRFSGSGSGNSYSLTISSVEADDATYYCQQWSKHPLTYGAGTKLE
IKAS (SEQ ID NO:134)

Figure 22B
Human CD8 alpha extracellular spacer/hinge and transmembrane domain:
ACCACGACGCCAGCGCCGCGACCACCAACACCGGCGCCCACCATCGCGTCGCAGCCCCTGTCCCTGCGCC
CAGAGGCGTGCCGGCCAGCGGCGGGGGGCGCAGTGCACACGAGGGGGCTGGACTTCGCCTGTGATATCTA
CATCTGGGCGCCCTTGGCCGGGACTTGTGGGGTCCTTCTCCTGTCACTGGTTATCACCCTTTACTGC
(SEQ ID NO:7)

TTTPAPRPPTPAPTIASQPLSLRPEACRPAAGGAVHTRGLDFACDIYIWAPLAGTCGVLL
LSLVITLYC (SEQ ID NO:8)

Linker:
TCCCTA
SL

Human 4-1BB intracellular chain:
AAACGGGGCAGAAAGAAACTCCTGTATATATTCAAACAACCATTTATGAGACCAGTACAAACTACTCAAG
AGGAAGATGGCTGTAGCTGCCGATTTCCAGAAGAAGAAGAAGGAGGATGTGAACTG (SEQ ID
NO:23)

KRGRKKLLYIFKQPFMRPVQTTQEEDGCSCRFPEEEEGGCEL (SEQ ID NO:24)

Linker:
TCGCGAGGAAGCGGGTCCGGTAGCGGATCT (SEQ ID NO:19)
SRGSGSGSGS (SEQ ID NO:20)

FKBP:
ATGGGAGTcCAGGTGGAAACCATCTCCCCAGGAGACGGGCGCACCTTCCCCAAGCGCGGCCAGACCTGCG
TGGTGCACTACACCGGGATGCTTGAAGATGGAAAGAAATTTGATTCCTCCCGGGACAGAAACAAGCCCTT
TAAGTTTATGCTAGGCAAGCAGGAGGTGATCCGAGGCTGGGAAGAAGGGGTTGCCCAGATGAGTGTGGGT
CAGAGAGCCAAACTGACTATATCTCCAGATTATGCCTATGGTGCCACTGGGCACCCAGGCATCATCCCAC
CACATGCCACTCTCGTCTTCGATGTGGAGCTTCTAAAACTGGAA (SEQ ID NO:11)

MGVQVETISPGDGRTFPKRGQTCVVHYTGMLEDGKKFDSSRDRNKPFKFMLGKQEVIRGW
EEGVAQMSVGQRAKLTISPDYAYGATGHPGIIPPHATLVFDVELLKLE (SEQ ID NO:12)

Figure 23A and 23B. Construct #300, encoding a polypeptide comprising "anti-mesothelin m912 scFv – CD8 alpha hinge and transmembrane domain – 4-1BB intracellular chain – FKBP"

Figure 23A
Signal peptide:
ATGGCCTTACCAGTGACCGCCTTGCTCCTGCCGCTGGCCTTGCTGCTCCACGCCGCCAGGCCG (SEQ ID NO:1)
MALPVTALLLPLALLLHAARP (SEQ ID NO:2)

Flag epitope tag:
GATTACAAGGATGACGATGACAAG (SEQ ID NO:132)
DYKDDDDK (SEQ ID NO:123)

Anti- mesothelin m912 scFv:
GGATCCCAGGTGCAGCTGCAGGAATCTGGCCCTGGCCTCGTGAAGCCCAGCGAGACACTGAGCCTGACCT
GTACCGTGTCTGGCGGCTCTGTGTCCAGCGGCAGCTACTACTGGTCCTGGATCAGACAGCCCCCTGGCAA
GGGCCTGGAATGGATCGGCTACATCTACTACAGCGGCTCCACCAACTACAACCCCAGCCTGAAGTCCAGA
GTGACCATCAGCGTGGACACCAGCAAGAACCAGTTCTCCCTGAAGCTGAGCAGCGTGACAGCCGCCGATA
CCGCCGTGTACTACTGTGCCAGAGAGGGCAAGAACGGCGCCTTCGACATCTGGGGCCAGGGCACAATGGT
CACCGTGTCATCTGGTGGAGGAGGATCTGGGGGAGGCGGAAGCGGAGGCGGCGGATCTGATATTCAGATG
ACCCAGAGCCCCAGCAGCCTGAGCGCCTCTGTGGGCGACAGAGTGACAATTACCTGCCGGGCCAGCCAGA
GCATCAGCAGCTACCTGAACTGGTATCAGCAGAAGCCCGGCAAGGCCCCCAAACTGCTGATCTACGCCGC
CAGCTCTCTGCAGTCTGGCGTGCCCAGCAGATTTTCCGGCTCTGGCAGCGGCACCGACTTCACCCTGACC
ATCTCTAGCCTGCAGCCCGAGGACTTCGCCACCTACTACTGCCAGCAGAGCTACAGCACCCCCCTGACCT
TTGGCGGAGGCACCAAGGTGGAAATCAAG (SEQ ID NO:135)

GSQVQLQESGPGLVKPSETLSLTCTVSGGSVSSGSYYWSWIRQPPGKGLEWIGYIYYSGS
TNYNPSLKSRVTISVDTSKNQFSLKLSSVTAADTAVYYCAREGKNGAFDIWGQGTMVTVS
SGGGGSGGGGSGGGGSDIQMTQSPSSLSASVGDRVTITCRASQSISSYLNWYQQKPGKAP
KLLIYAASSLQSGVPSRFSGSGSGTDFTLTISSLQPEDFATYYCQQSYSTPLTFGGGTKV
EIK (SEQ ID NO:136)

Figure 23B
Human CD8 alpha extracellular spacer/hinge and transmembrane domain:
ACCACGACGCCAGCGCCGCGACCACCAACACCGGCGCCCACCATCGCGTCGCAGCCCCTGTCCCTGCGCC
CAGAGGCGTGCCGGCCAGCGGCGGGGGGCGCAGTGCACACGAGGGGGCTGGACTTCGCCTGTGATATCTA
CATCTGGGCGCCCTTGGCCGGGACTTGTGGGGTCCTTCTCCTGTCACTGGTTATCACCCTTTACTGC
(SEQ ID NO:7)

TTTPAPRPPTPAPTIASQPLSLRPEACRPAAGGAVHTRGLDFACDIYIWAPLAGTCGVLL
LSLVITLYC (SEQ ID NO:8)

Linker:
TCCCTA
SL

Human 4-1BB intracellular chain:
AAACGGGGCAGAAAGAAACTCCTGTATATATTCAAACAACCATTTATGAGACCAGTACAAACTACTCAAG
AGGAAGATGGCTGTAGCTGCCGATTTCCAGAAGAAGAAGAAGGAGGATGTGAACTG (SEQ ID
NO:23)

KRGRKKLLYIFKQPFMRPVQTTQEEDGCSCRFPEEEEGGCEL (SEQ ID NO:24)

Linker:
TCGCGAGGAAGCGGGTCCGGTAGCGGATCT (SEQ ID NO:19)
SRGSGSGSGS (SEQ ID NO:20)

FKBP:
ATGGGAGTcCAGGTGGAAACCATCTCCCCAGGAGACGGGCGCACCTTCCCCAAGCGCGGCCAGACCTGCG
TGGTGCACTACACCGGGATGCTTGAAGATGGAAAGAAATTTGATTCCTCCCGGGACAGAAACAAGCCCTT
TAAGTTTATGCTAGGCAAGCAGGAGGTGATCCGAGGCTGGGAAGAAGGGGTTGCCCAGATGAGTGTGGGT
CAGAGAGCCAAACTGACTATATCTCCAGATTATGCCTATGGTGCCACTGGGCACCCAGGCATCATCCCAC
CACATGCCACTCTCGTCTTCGATGTGGAGCTTCTAAAACTGGAA (SEQ ID NO:11)

MGVQVETISPGDGRTFPKRGQTCVVHYTGMLEDGKKFDSSRDRNKPFKFMLGKQEVIRGW
EEGVAQMSVGQRAKLTISPDYAYGATGHPGIIPPHATLVFDVELLKLE (SEQ ID NO:12)

Figure 24A and 24B. Construct #336, encoding a polypeptide comprising "anti-CD19 scFv – CD8 alpha hinge and transmembrane domain – 4-1BB intracellular chain – GID1A"

Figure 24A
Signal peptide:
ATGGCCTTACCAGTGACCGCCTTGCTCCTGCCGCTGGCCTTGCTGCTCCACGCCGCCAGGCCG (SEQ ID NO:1)
MALPVTALLLPLALLLHAARP (SEQ ID NO:2)

Myc epitope tag:
GAGCAGAAGCTGATCAGCGAGGAGGACCTG (SEQ ID NO:3)
EQKLISEEDL (SEQ ID NO:4)

Anti-human CD19 scFv:
GACATCCAGATGACACAGACTACATCCTCCCTGTCTGCCTCTCTGGGAGACAGAGTCACCATCAGTTGCA
GGGCAAGTCAGGACATTAGTAAATATTTAAATTGGTATCAGCAGAAACCAGATGGAACTGTTAAACTCCT
GATCTACCATACATCAAGATTACACTCAGGAGTCCCATCAAGGTTCAGTGGCAGTGGGTCTGGAACAGAT
TATTCTCTCACCATTAGCAACCTGGAGCAAGAAGATATTGCCACTTACTTTTGCCAACAGGGTAATACGC
TTCCGTACACGTTCGGAGGGGGGACCAAGCTGGAGATCACAGGTGGCGGTGGCTCGGGCGGTGGTGGGTC
GGGTGGCGGCGGATCTGAGGTGAAACTGCAGGAGTCAGGACCTGGCCTGGTGGCGCCCTCACAGAGCCTG
TCCGTCACATGCACTGTCTCAGGGGTCTCATTACCCGACTATGGTGTAAGCTGGATTCGCCAGCCTCCAC
GAAAGGGTCTGGAGTGGCTGGGAGTAATATGGGGTAGTGAAACCACATACTATAATTCAGCTCTCAAATC
CAGACTGACCATCATCAAGGACAACTCCAAGAGCCAAGTTTTCTTAAAAATGAACAGTCTGCAAACTGAT
GACACAGCCATTTACTACTGTGCCAAACATTATTACTACGGTGGTAGCTATGCTATGGACTACTGGGGCC
AAGGAACCTCAGTCACCGTCTCCTCA (SEQ ID NO:5)

DIQMTQTTSSLSASLGDRVTISCRASQDISKYLNWYQQKPDGTVKLLIYHTSRLHSGVPS
RFSGSGSGTDYSLTISNLEQEDIATYFCQQGNTLPYTFGGGTKLEITGGGSGGGGSGGG
GSEVKLQESGPGLVAPSQSLSVTCTVSGVSLPDYGVSWIRQPPRKGLEWLGVIWGSETTY
YNSALKSRLTIIKDNSKSQVFLKMNSLQTDDTAIYYCAKHYYYGGSYAMDYWGQGTSVTV
SS (SEQ ID NO:6)

Human CD8 alpha extracellular spacer/hinge and transmembrane domain:
ACCACGACGCCAGCGCCGCGACCACCAACACCGGCGCCCACCATCGCGTCGCAGCCCCTGTCCCTGCGCC
CAGAGGCGTGCCGGCCAGCGGCGGGGGGCGCAGTGCACACGAGGGGGCTGGACTTCGCCTGTGATATCTA
CATCTGGGCGCCCTTGGCCGGGACTTGTGGGGTCCTTCTCCTGTCACTGGTTATCACCCTTTACTGC
(SEQ ID NO:7)

TTTPAPRPPTPAPTIASQPLSLRPEACRPAAGGAVHTRGLDFACDIYIWAPLAGTCGVLL
LSLVITLYC (SEQ ID NO:8)

Linker:
TCCCTA
SL

Figure 24B
Human 4-1BB intracellular chain:
AAACGGGGCAGAAAGAAACTCCTGTATATATTCAAACAACCATTTATGAGACCAGTACAAACTACTCAAG
AGGAAGATGGCTGTAGCTGCCGATTTCCAGAAGAAGAAGAAGGAGGATGTGAACTG (SEQ ID
NO:23)

KRGRKKLLYIFKQPFMRPVQTTQEEDGCSCRFPEEEEGGCEL (SEQ ID NO:24)

Linker:
TCGCGAGGAAGCGGGTCCGGTAGCGGATCT (SEQ ID NO:19)
SRGSGSGSGS (SEQ ID NO:20)

GID1A:
ATGGCTGCGAGCGATGAAGTTAATCTTATTGAGAGCAGAACAGTGGTTCCTCTCAATACATGGGTTTTAA
TATCCAACTTCAAAGTAGCCTACAATATCCTTCGTCGCCCTGATGGAACCTTTAACCGACACTTAGCTGA
GTATCTAGACCGTAAAGTCACTGCAAACGCCAATCCGGTTGATGGGGTTTTCTCGTTCGATGTCTTGATT
GATCGCAGGATCAATCTTCTAAGCAGAGTCTATAGACCAGCTTATGCAGATCAAGAGCAACCTCCTAGTA
TTTTAGATCTCGAGAAGCCTGTTGATGGCGACATTGTCCCTGTTATATTGTTCTTCCATGGAGGTAGCTT
TGCTCATTCTTCTGCAAACAGTGCCATCTACGATACTCTTTGTCGCAGGCTTGTTGGTTTGTGCAAGTGT
GTTGTTGTCTCTGTGAATTATCGGCGTGCACCAGAGAATCCATACCCTTGTGCTTATGATGATGGTTGGA
TTGCTCTTAATTGGGTTAACTCGAGATCTTGGCTTAAATCCAAGAAAGACTCAAAGGTCCATATTTTCTT
GGCTGGTGATAGCTCTGGAGGTAACATCGCGCATAATGTGGCTTTAAGAGCGGGTGAATCGGGAATCGAT
GTTTTGGGGAACATTCTGCTGAATCCTATGTTTGGTGGGAATGAGAGAACGGAGTCTGAGAAAAGTTTGG
ATGGGAAATACTTTGTGACGGTTAGAGACCGCGATTGGTACTGGAAAGCGTTTTTACCCGAGGGAGAAGA
TAGAGAGCATCCAGCGTGTAATCCGTTTAGCCCGAGAGGGAAAAGCTTAGAAGGAGTGAGTTTCCCCAAG
AGTCTTGTGGTTGTCGCGGGTTTGGATTTGATTAGAGATTGGCAGTTGGCATACGCGGAAGGGCTCAAGA
AAGCGGGTCAAGAGGTTAAGCTTATGCATTTAGAGAAAGCAACTGTTGGGTTTTACCTCTTGCCTAATAA
CAATCATTTCCATAATGTTATGGATGAGATTTCGGCGTTTGTAAACGCGGAATGTATGCGTGAC (SEQ
ID NO:137)

MAASDEVNLIESRTVVPLNTWVLISNFKVAYNILRRPDGTFNRHLAEYLDRKVTANANPV
DGVFSFDVLIDRRINLLSRVYRPAYADQEQPPSILDLEKPVDGDIVPVILFFHGGSFAHS
SANSAIYDTLCRRLVGLCKCVVVSVNYRRAPENPYPCAYDDGWIALNWVNSRSWLKSKKD
SKVHIFLAGDSSGGNIAHNVALRAGESGIDVLGNILLNPMFGGNERTESEKSLDGKYFVT
VRDRDWYWKAFLPEGEDREHPACNPFSPRGKSLEGVSFPKSLVVVAGLDLIRDWQLAYAE
GLKKAGQEVKLMHLEKATVGFYLLPNNNHFHNVMDEISAFVNAECMRD (SEQ ID NO:138)

Figure 25A and 25B. Construct #337, encoding a polypeptide comprising "DAP10 extracellular domain - CD8 alpha transmembrane domain - 4-1BB intracellular chain - GAI - CD3 zeta intracellular chain - mCherry"

Figure 25A
Human DAP10 signal sequence and extracellular domain:
Atgatccatctgggtcacatcctcttcctgcttttgctcccagtggctgcagctcagacgactccaggag
agagatcatcactccctgccttttaccctggcacttcaggctcttgttccggatgtgggtccctctctct
gccg (SEQ ID NO:27)

MIHLGHILFLLLLPVAAAQTTPGERSSLPAFYPGTSGSCSGCGSLSLP (SEQ ID NO:28)

Human CD8alpha transmembrane domain:
ATCTACATCTGGGCGCCCTTGGCCGGGACTTGTGGGGTCCTTCTCCTGTCACTGGTTATCACCCTTTACT
GC (SEQ ID NO:29)

IYIWAPLAGTCGVLLLSLVITLYC (SEQ ID NO:30)

Linker:
Tctctg
SL

Human 4-1BB intracellular chain:
AAACGGGGCAGAAAGAAACTCCTGTATATATTCAAACAACCATTTATGAGACCAGTACAAACTACTCAAG
AGGAAGATGGCTGTAGCTGCCGATTTCCAGAAGAAGAAGAAGGAGGATGTGAACTG (SEQ ID
NO:23)

KRGRKKLLYIFKQPFMRPVQTTQEEDGCSCRFPEEEEGGCEL (SEQ ID NO:24)

Linker:
GGtTCCGGcAGCGGaTCTGGtAGcGGAAGCGGGTCCGGTAGCGGATCT (SEQ ID NO:31)
GSGSGSGSGSGSGSGS (SEQ ID NO:32)

GAI N terminus:
ATGAAGAGAGATCATCATCATCATCATCATCAAGATAAGAAGACTATGATGATGAATGAAGAAGACGACG
GTAACGGCATGGATGAGCTTCTAGCTGTTCTTGGTTACAAGGTTAGGTCATCCGAAATGGCTGATGTTGC
TCAGAAACTCGAGCAGCTTGAAGTTATGATGTCTAATGTTCAAGAAGACGATCTTTCTCAACTCGCTACT
GAGACTGTTCACTATAATCCGGCGGAGCTTTACACGTGGCTTGATTCTATGCTCACCGACCTTAAT
(SEQ ID NO:139)

MKRDHHHHHHQDKKTMMMNEEDDGNGMDELLAVLGYKVRSSEMADVAQKLEQLEVMMSNV
QEDDLSQLATETVHYNPAELYTWLDSMLTDLN (SEQ ID NO:140)

Figure 25B
Linker:
GGAAGCGGGTCCGGTAGCGGATCTTCCCTA (SEQ ID NO:15)
GSGSGSGSSL (SEQ ID NO:16)

Human CD3 zeta intracellular chain:
AGAGTGAAGTTCAGCAGGAGCGCAGACGCCCCCGCGTACCAGCAGGGCCAGAACCAGCTCTATAACGAGC
TCAATCTAGGACGAAGAGAGGAGTACGATGTTTTGGACAAGAGACGTGGCCGGGACCCTGAGATGGGGGG
AAAGCCGAGAAGGAAGAACCCTCAGGAAGGCCTGTACAATGAACTGCAGAAAGATAAGATGGCGGAGGCC
TACAGTGAGATTGGGATGAAAGGCGAGCGCCGGAGGGGCAAGGGGCACGATGGCCTTTACCAGGGTCTCA
GTACAGCCACCAAGGACACCTACGACGCCCTTCACATGCAGGCCCTGCCCCCTCGC (SEQ ID
NO:17)

RVKFSRSADAPAYQQGQNQLYNELNLGRREEYDVLDKRRGRDPEMGGKPRRKNPQEGLYN
ELQKDKMAEAYSEIGMKGERRRGKGHDGLYQGLSTATKDTYDALHMQALPPR (SEQ ID NO:18)

Linker:
TCGCGAGGAAGCGGGTCCGGTAGCGGATCT (SEQ ID NO:19)
SRGSGSGSGS (SEQ ID NO:20)

mCherry:
ATGGTGAGCAAGGGCGAGGAGGATAACATGGCCATCATCAAGGAGTTCATGCGCTTCAAGGTGCACATGG
AGGGCTCCGTGAACGGCCACGAGTTCGAGATCGAGGGCGAGGGCGAGGGCCGCCCCTACGAGGGCACCCA
GACCGCCAAGCTGAAGGTGACCAAGGGTGGCCCCCTGCCCTTCGCCTGGGACATCCTGTCCCCTCAGTTC
ATGTACGGCTCCAAGGCCTACGTGAAGCACCCCGCCGACATCCCCGACTACTTGAAGCTGTCCTTCCCCG
AGGGCTTCAAGTGGGAGCGCGTGATGAACTTCGAGGACGGCGGCGTGGTGACCGTGACCCAGGACTCCTC
CCTGCAGGACGGCGAGTTCATCTACAAGGTGAAGCTGCGCGGCACCAACTTCCCCTCCGACGGCCCCGTA
ATGCAGAAGAAGACCATGGGCTGGGAGGCCTCCTCCGAGCGGATGTACCCCGAGGACGGCGCCCTGAAGG
GCGAGATCAAGCAGAGGCTGAAGCTGAAGGACGGCGGCCACTACGACGCTGAGGTCAAGACCACCTACAA
GGCCAAGAAGCCCGTGCAGCTGCCCGGCGCCTACAACGTCAACATCAAGTTGGACATCACCTCCCACAAC
GAGGACTACACCATCGTGGAACAGTACGAACGCGCCGAGGGCCGCCACTCCACCGGCGGCATGGACGAGC
TGTACAAG (SEQ ID NO:21)

MVSKGEEDNMAIIKEFMRFKVHMEGSVNGHEFEIEGEGEGRPYEGTQTAKLKVTKGGPLP
FAWDILSPQFMYGSKAYVKHPADIPDYLKLSFPEGFKWERVMNFEDGGVVTVTQDSSLQD
GEFIYKVKLRGTNFPSDGPVMQKKTMGWEASSERMYPEDGALKGEIKQRLKLKDGGHYDA
EVKTTYKAKKPVQLPGAYNVNIKLDITSHNEDYTIVEQYERAEGRHSTGGMDELYK (SEQ ID
NO:22)

Figure 26A and 26B. Construct #357, encoding a polypeptide comprising "anti-mesothelin HN1 scFv – CD8 alpha hinge and transmembrane domain – 4-1BB intracellular chain – FKBP"

Figure 26A
Signal peptide:
ATGGCCTTACCAGTGACCGCCTTGCTCCTGCCGCTGGCCTTGCTGCTCCACGCCGCCAGGCCG (SEQ ID NO:1)
MALPVTALLLPLALLLHAARP (SEQ ID NO:2)

Flag epitope tag:
GATTACAAGGATGACGATGACAAG (SEQ ID NO:132)
DYKDDDDK (SEQ ID NO:123)

Anti-human mesothelin HN1 scFv:
GGATCCCAGGTGCAGCTGGTGCAGTCTGGCGCCGAAGTGAAAAGACCAGGCGCCAGCGTGCAGGTCTCCT
GTAGAGCCAGCGGCTACAGCATCAACACCTACTACATGCAGTGGGTGCGCCAGGCCCCAGGCGCTGGACT
GGAATGGATGGGCGTGATCAACCCCAGCGGCGTGACAAGCTACGCCCAGAAATTCCAGGGCAGAGTGACC
CTGACCAACGACACCAGCACCAACACAGTGTACATGCAGCTGAACAGCCTGACCAGCGCCGACACCGCCG
TGTACTACTGTGCCAGATGGGCCCTGTGGGGCGACTTCGGCATGGATGTGTGGGGCAAGGGCACCCTCGT
GACCGTGTCTAGCGGAGGCGGAGGATCTGGCGGAGGGGGATCTGGAGGCGGCGGAAGCGACATCCAGATG
ACCCAGAGCCCTAGCACCCTGAGCGCCAGCATCGGCGATAGAGTGACCATCACCTGTCGGGCCAGCGAGG
GCATCTATCACTGGCTGGCCTGGTATCAGCAGAAGCCCGGCAAGGCCCCCAAGCTGCTGATCTACAAGGC
CAGCTCTCTGGCCTCTGGCGCCCCTAGCAGATTTTCTGGCAGCGGCTCCGGCACCGACTTCACCCTGACA
ATCAGCAGCCTGCAGCCCGACGACTTCGCCACCTACTATTGCCAGCAGTACAGCAACTACCCCCTGACCT
TCGGCGGAGGCACCAAGCTGGAAATCAAG (SEQ ID NO:141)

GSQVQLVQSGAEVKRPGASVQVSCRASGYSINTYYMQWVRQAPGAGLEWMGVINPSGVTS
YAQKFQGRVTLTNDTSTNTVYMQLNSLTSADTAVYYCARWALWGDFGMDVWGKGTLVTVS
SGGGGSGGGGSGGGGSDIQMTQSPSTLSASIGDRVTITCRASEGIYHWLAWYQQKPGKAP
KLLIYKASSLASGAPSRFSGSGSGTDFTLTISSLQPDDFATYYCQQYSNYPLTFGGGTKL
EIK (SEQ ID NO:142)

Figure 26B
Human CD8 alpha extracellular spacer/hinge and transmembrane domain:
ACCACGACGCCAGCGCCGCGACCACCAACACCGGCGCCCACCATCGCGTCGCAGCCCCTGTCCCTGCGCC
CAGAGGCGTGCCGGCCAGCGGCGGGGGCGCAGTGCACACGAGGGGGCTGGACTTCGCCTGTGATATCTA
CATCTGGGCGCCCTTGGCCGGGACTTGTGGGGTCCTTCTCCTGTCACTGGTTATCACCCTTTACTGC
(SEQ ID NO:7)

TTTPAPRPPTPAPTIASQPLSLRPEACRPAAGGAVHTRGLDFACDIYIWAPLAGTCGVLL
LSLVITLYC (SEQ ID NO:8)

Linker:
TCCCTA
SL

Human 4-1BB intracellular chain:
AAACGGGGCAGAAAGAAACTCCTGTATATATTCAAACAACCATTTATGAGACCAGTACAAACTACTCAAG
AGGAAGATGGCTGTAGCTGCCGATTTCCAGAAGAAGAAGAAGGAGGATGTGAACTG (SEQ ID
NO:23)

KRGRKKLLYIFKQPFMRPVQTTQEEDGCSCRFPEEEEGGCEL (SEQ ID NO:24)

Linker:
TCGCGAGGAAGCGGGTCCGGTAGCGGATCT (SEQ ID NO:19)
SRGSGSGSGS (SEQ ID NO:20)

FKBP:
ATGGGAGTcCAGGTGGAAACCATCTCCCCAGGAGACGGGCGCACCTTCCCCAAGCGCGGCCAGACCTGCG
TGGTGCACTACACCGGGATGCTTGAAGATGGAAAGAAATTTGATTCCTCCCGGGACAGAAACAAGCCCTT
TAAGTTTATGCTAGGCAAGCAGGAGGTGATCCGAGGCTGGGAAGAAGGGGTTGCCCAGATGAGTGTGGGT
CAGAGAGCCAAACTGACTATATCTCCAGATTATGCCTATGGTGCCACTGGGCACCCAGGCATCATCCCAC
CACATGCCACTCTCGTCTTCGATGTGGAGCTTCTAAAACTGGAA (SEQ ID NO:11)

MGVQVETISPGDGRTFPKRGQTCVVHYTGMLEDGKKFDSSRDRNKPFKFMLGKQEVIRGW
EEGVAQMSVGQRAKLTISPDYAYGATGHPGIIPPHATLVFDVELLKLE (SEQ ID NO:12)

Figure 27A and 27B. Construct #365, encoding a polypeptide comprising "anti-CD19 scFv – CD8 alpha hinge – CD28 transmembrane domain and intracellular chain – FKBP"

Figure 27A
Signal peptide:
ATGGCCTTACCAGTGACCGCCTTGCTCCTGCCGCTGGCCTTGCTGCTCCACGCCGCCAGGCCG (SEQ ID NO:1)
MALPVTALLLPLALLLHAARP (SEQ ID NO:2)

Myc epitope tag:
GAGCAGAAGCTGATCAGCGAGGAGGACCTG (SEQ ID NO:3)
EQKLISEEDL (SEQ ID NO:4)

Anti-human CD19 scFv:
GACATCCAGATGACACAGACTACATCCTCCCTGTCTGCCTCTCTGGGAGACAGAGTCACCATCAGTTGCA
GGGCAAGTCAGGACATTAGTAAATATTTAAATTGGTATCAGCAGAAACCAGATGGAACTGTTAAACTCCT
GATCTACCATACATCAAGATTACACTCAGGAGTCCCATCAAGGTTCAGTGGCAGTGGGTCTGGAACAGAT
TATTCTCTCACCATTAGCAACCTGGAGCAAGAAGATATTGCCACTTACTTTTGCCAACAGGGTAATACGC
TTCCGTACACGTTCGGAGGGGGGACCAAGCTGGAGATCACAGGTGGCGGTGGCTCGGGCGGTGGTGGGTC
GGGTGGCGGCGGATCTGAGGTGAAACTGCAGGAGTCAGGACCTGGCCTGGTGGCGCCCTCACAGAGCCTG
TCCGTCACATGCACTGTCTCAGGGGTCTCATTACCCGACTATGGTGTAAGCTGGATTCGCCAGCCTCCAC
GAAAGGGTCTGGAGTGGCTGGGAGTAATATGGGGTAGTGAAACCACATACTATAATTCAGCTCTCAAATC
CAGACTGACCATCATCAAGGACAACTCCAAGAGCCAAGTTTTCTTAAAAATGAACAGTCTGCAAACTGAT
GACACAGCCATTTACTACTGTGCCAAACATTATTACTACGGTGGTAGCTATGCTATGGACTACTGGGGCC
AAGGAACCTCAGTCACCGTCTCCTCA (SEQ ID NO:5)

DIQMTQTTSSLSASLGDRVTISCRASQDISKYLNWYQQKPDGTVKLLIYHTSRLHSGVPS
RFSGSGSGTDYSLTISNLEQEDIATYFCQQGNTLPYTFGGGTKLEITGGGSGGGSGGG
GSEVKLQESGPGLVAPSQSLSVTCTVSGVSLPDYGVSWIRQPPRKGLEWLGVIWGSETTY
YNSALKSRLTIIKDNSKSQVFLKMNSLQTDDTAIYYCAKHYYYGGSYAMDYWGQGTSVTV
SS (SEQ ID NO:6)

Figure 27B
Human CD8 alpha extracellular spacer/hinge:
ACCACGACGCCAGCGCCGCGACCACCAACACCGGCGCCCACCATCGCGTCGCAGCCCCTGTCCCTGCGCC
CAGAGGCGTGCCGGCCAGCGGCGGGGGGCGCAGTGCACACGAGGGGGCTGGACTTCGCCTGTGAT (SEQ
ID NO:143)

TTTPAPRPPTPAPTIASQPLSLRPEACRPAAGGAVHTRGLDFACD (SEQ ID NO:56)

Human CD28 transmembrane domain and intracellular signaling chain:
TTTTGGGTGCTGGTGGTGGTTGGTGGAGTCCTGGCTTGCTATAGCTTGCTAGTAACAGTGGCCTTTATTA
TTTTCTGGGTGAGGAGTAAGAGGAGCAGGCTCCTGCACAGTGACTACATGAACATGACTCCCCGCCGCCC
CGGGCCCACCCGCAAGCATTACCAGCCCTATGCCCCACCACGCGACTTCGCAGCCTATCGCTCC (SEQ
ID NO:144)

FWVLVVVGGVLACYSLLVTVAFIIFWVRSKRSRLLHSDYMNMTPRRPGPTRKHYQPYAPP
RDFAAYRS (SEQ ID NO:121)

Linker:
TCGCGAGGAAGCGGGTCCGGTAGCGGATCT (SEQ ID NO:19)
SRGSGSGSGS (SEQ ID NO:20)

FKBP:
ATGGGAGTcCAGGTGGAAACCATCTCCCCAGGAGACGGGCGCACCTTCCCCAAGCGCGGCCAGACCTGCG
TGGTGCACTACACCGGGATGCTTGAAGATGGAAAGAAATTTGATTCCTCCCGGGACAGAAACAAGCCCTT
TAAGTTTATGCTAGGCAAGCAGGAGGTGATCCGAGGCTGGGAAGAAGGGGTTGCCCAGATGAGTGTGGGT
CAGAGAGCCAAACTGACTATATCTCCAGATTATGCCTATGGTGCCACTGGGCACCCAGGCATCATCCCAC
CACATGCCACTCTCGTCTTCGATGTGGAGCTTCTAAAACTGGAA (SEQ ID NO:11)

MGVQVETISPGDGRTFPKRGQTCVVHYTGMLEDGKKFDSSRDRNKPFKFMLGKQEVIRGW
EEGVAQMSVGQRAKLTISPDYAYGATGHPGIIPPHATLVFDVELLKLE (SEQ ID NO:12)

Figure 28A and 28B. Construct #366, encoding a polypeptide comprising a conventional CAR "anti-CD19 scFv – CD8 alpha hinge – CD28 transmembrane domain and intracellular chain – CD3 zeta intracellular chain"

Figure 28A
Signal peptide:
ATGGCCTTACCAGTGACCGCCTTGCTCCTGCCGCTGGCCTTGCTGCTCCACGCCGCCAGGCCG (SEQ ID NO:1)
MALPVTALLLPLALLLHAARP (SEQ ID NO:2)

Myc epitope tag:
GAGCAGAAGCTGATCAGCGAGGAGGACCTG (SEQ ID NO:3)
EQKLISEEDL (SEQ ID NO:4)

Anti-human CD19 scFv:
GACATCCAGATGACACAGACTACATCCTCCCTGTCTGCCTCTCTGGGAGACAGAGTCACCATCAGTTGCA
GGGCAAGTCAGGACATTAGTAAATATTTAAATTGGTATCAGCAGAAACCAGATGGAACTGTTAAACTCCT
GATCTACCATACATCAAGATTACACTCAGGAGTCCCATCAAGGTTCAGTGGCAGTGGGTCTGGAACAGAT
TATTCTCTCACCATTAGCAACCTGGAGCAAGAAGATATTGCCACTTACTTTTGCCAACAGGGTAATACGC
TTCCGTACACGTTCGGAGGGGGGACCAAGCTGGAGATCACAGGTGGCGGTGGCTCGGGCGGTGGTGGGTC
GGGTGGCGGCGGATCTGAGGTGAAACTGCAGGAGTCAGGACCTGGCCTGGTGGCGCCCTCACAGAGCCTG
TCCGTCACATGCACTGTCTCAGGGGTCTCATTACCCGACTATGGTGTAAGCTGGATTCGCCAGCCTCCAC
GAAAGGGTCTGGAGTGGCTGGGAGTAATATGGGGTAGTGAAACCACATACTATAATTCAGCTCTCAAATC
CAGACTGACCATCATCAAGGACAACTCCAAGAGCCAAGTTTTCTTAAAAATGAACAGTCTGCAAACTGAT
GACACAGCCATTTACTACTGTGCCAAACATTATTACTACGGTGGTAGCTATGCTATGGACTACTGGGGCC
AAGGAACCTCAGTCACCGTCTCCTCA (SEQ ID NO:5)

DIQMTQTTSSLSASLGDRVTISCRASQDISKYLNWYQQKPDGTVKLLIYHTSRLHSGVPS
RFSGSGSGTDYSLTISNLEQEDIATYFCQQGNTLPYTFGGGTKLEITGGGSGGGGSGGG
GSEVKLQESGPGLVAPSQSLSVTCTVSGVSLPDYGVSWIRQPPRKGLEWLGVIWGSETTY
YNSALKSRLTIIKDNSKSQVFLKMNSLQTDDTAIYYCAKHYYYGGSYAMDYWGQGTSVTV
SS (SEQ ID NO:6)

Figure 28B
Human CD8 alpha extracellular spacer/hinge:
ACCACGACGCCAGCGCCGCGACCACCAACACCGGCGCCCACCATCGCGTCGCAGCCCCTGTCCCTGCGCC
CAGAGGCGTGCCGGCCAGCGGCGGGGGGCGCAGTGCACACGAGGGGGCTGGACTTCGCCTGTGAT (SEQ
ID NO:143)

TTTPAPRPPTPAPTIASQPLSLRPEACRPAAGGAVHTRGLDFACD (SEQ ID NO:56)

Human CD28 transmembrane domain and intracellular chain:
TTTTGGGTGCTGGTGGTGGTTGGTGGAGTCCTGGCTTGCTATAGCTTGCTAGTAACAGTGGCCTTTATTA
TTTTCTGGGTGAGGAGTAAGAGGAGCAGGCTCCTGCACAGTGACTACATGAACATGACTCCCCGCCGCCC
CGGGCCCACCCGCAAGCATTACCAGCCCTATGCCCCACCACGCGACTTCGCAGCCTATCGCTCC (SEQ
ID NO:144)

FWVLVVVGGVLACYSLLVTVAFIIFWVRSKRSRLLHSDYMNMTPRRPGPTRKHYQPYAPP
RDFAAYRS (SEQ ID NO:121)

Linker:
TCGCGAGGAAGCGGGTCCGGTAGCGGATCT (SEQ ID NO:19)
SRGSGSGSGS (SEQ ID NO:20)

Human CD3 zeta intracellular chain:
AGAGTGAAGTTCAGCAGGAGCGCAGACGCCCCCGCGTACAAGCAGGGCCAGAACCAGCTCTATAACGAGC
TCAATCTAGGACGAAGAGAGGAGTACGATGTTTTGGACAAGAGACGTGGCCGGGACCCTGAGATGGGGGG
AAAGCCGAGAAGGAAGAACCCTCAGGAAGGCCTGTACAATGAACTGCAGAAAGATAAGATGGCGGAGGCC
TACAGTGAGATTGGGATGAAAGGCGAGCGCCGGAGGGGCAAGGGGCACGATGGCCTTTACCAGGGTCTCA
GTACAGCCACCAAGGACACCTACGACGCCCTTCACATGCAGGCCCTGCCtCCTCGC (SEQ ID
NO:25)

RVKFSRSADAPAYKQGQNQLYNELNLGRREEYDVLDKRRGRDPEMGGKPRRKNPQEGLYN
ELQKDKMAEAYSEIGMKGERRRGKGHDGLYQGLSTATKDTYDALHMQALPPR (SEQ ID NO:26)

Figure 29A and 29B. Construct #367, encoding a polypeptide comprising "DAP10 extracellular domain – CD28 transmembrane domain and intracellular chain – FRB – CD3 zeta intracellular chain – mCherry"

Figure 29A
Human DAP10 signal sequence and extracellular domain:
Atgatccatctgggtcacatcctcttcctgcttttgctcccagtggctgcagctcagacgactccaggag
agagatcatcactccctgccttttaccctggcacttcaggctcttgttccggatgtgggtccctctctct
gccg (SEQ ID NO:27)

MIHLGHILFLLLLPVAAAQTTPGERSSLPAFYPGTSGSCSGCGSLSLP (SEQ ID NO:28)

Human CD28 transmembrane domain and intracellular signaling chain:
TTTTGGGTGCTGGTGGTGGTTGGTGGAGTCCTGGCTTGCTATAGCTTGCTAGTAACAGTGGCCTTTATTA
TTTTCTGGGTGAGGAGTAAGAGGAGCAGGCTCCTGCACAGTGACTACATGAACATGACTCCCCGCCGCCC
CGGGCCCACCCGCAAGCATTACCAGCCCTATGCCCCACCACGCGACTTCGCAGCCTATCGCTCC (SEQ
ID NO:144)

FWVLVVVGGVLACYSLLVTVAFIIFWVRSKRSRLLHSDYMNMTPRRPGPTRKHYQPYAPP
RDFAAYRS (SEQ ID NO:121)

Linker:
GGtTCCGGcAGCGGaTCTGGtAGcGGAAGCGGGTCCGGTAGCGGATCT (SEQ ID NO:31)
GSGSGSGSGSGSGSGS (SEQ ID NO:32)

FRB:
ATCCTCTGGCATGAGATGTGGCATGAAGGCCTGGAAGAGGCATCTCGTTTGTACTTTGGGGAAAGGAACG
TGAAAGGCATGTTTGAGGTGCTGGAGCCCTTGCATGCTATGATGGAACGGGGCCCCCAGACTCTGAAGGA
AACATCCTTTAATCAGGCCTATGGTCGAGATTTAATGGAGGCCCAAGAGTGGTGCAGGAAGTACATGAAA
TCAGGGAATGTCAAGGACCTCCTCCAAGCCTGGGACCTCTATTATCATGTGTTCCGACGAATCTCAAAG
(SEQ ID NO:33)

ILWHEMWHEGLEEASRLYFGERNVKGMFEVLEPLHAMMERGPQTLKETSFNQAYGRDLME
AQEWCRKYMKSGNVKDLLQAWDLYYHVFRRISK (SEQ ID NO:34)

Linker:
GGAAGCGGGTCCGGTAGCGGATCTTCCCTA (SEQ ID NO:15)
GSGSGSGSSL (SEQ ID NO:16)

Figure 29B
Human CD3 zeta intracellular chain:
AGAGTGAAGTTCAGCAGGAGCGCAGACGCCCCCGCGTACCAGCAGGGCCAGAACCAGCTCTATAACGAGC
TCAATCTAGGACGAAGAGAGGAGTACGATGTTTTGGACAAGAGACGTGGCCGGGACCCTGAGATGGGGGG
AAAGCCGAGAAGGAAGAACCCTCAGGAAGGCCTGTACAATGAACTGCAGAAAGATAAGATGGCGGAGGCC
TACAGTGAGATTGGGATGAAAGGCGAGCGCCGGAGGGGCAAGGGGCACGATGGCCTTTACCAGGGTCTCA
GTACAGCCACCAAGGACACCTACGACGCCCTTCACATGCAGGCCCTGCCCCCTCGC (SEQ ID
NO:17)

RVKFSRSADAPAYQQGQNQLYNELNLGRREEYDVLDKRRGRDPEMGGKPRRKNPQEGLYN
ELQKDKMAEAYSEIGMKGERRRGKGHDGLYQGLSTATKDTYDALHMQALPPR (SEQ ID NO:18)

Linker:
TCGCGAGGAAGCGGGTCCGGTAGCGGATCT (SEQ ID NO:19)
SRGSGSGSGS (SEQ ID NO:20)

mCherry:
ATGGTGAGCAAGGGCGAGGAGGATAACATGGCCATCATCAAGGAGTTCATGCGCTTCAAGGTGCACATGG
AGGGCTCCGTGAACGGCCACGAGTTCGAGATCGAGGGCGAGGGCGAGGGCCGCCCCTACGAGGGCACCCA
GACCGCCAAGCTGAAGGTGACCAAGGGTGGCCCCCTGCCCTTCGCCTGGGACATCCTGTCCCCTCAGTTC
ATGTACGGCTCCAAGGCCTACGTGAAGCACCCCGCCGACATCCCCGACTACTTGAAGCTGTCCTTCCCCG
AGGGCTTCAAGTGGGAGCGCGTGATGAACTTCGAGGACGGCGGCGTGGTGACCGTGACCCAGGACTCCTC
CCTGCAGGACGGCGAGTTCATCTACAAGGTGAAGCTGCGCGGCACCAACTTCCCCTCCGACGGCCCCGTA
ATGCAGAAGAAGACCATGGGCTGGGAGGCCTCCTCCGAGCGGATGTACCCCGAGGACGGCGCCCTGAAGG
GCGAGATCAAGCAGAGGCTGAAGCTGAAGGACGGCGGCCACTACGACGCTGAGGTCAAGACCACCTACAA
GGCCAAGAAGCCCGTGCAGCTGCCCGGCGCCTACAACGTCAACATCAAGTTGGACATCACCTCCCACAAC
GAGGACTACACCATCGTGGAACAGTACGAACGCGCCGAGGGCCGCCACTCCACCGGCGGCATGGACGAGC
TGTACAAG (SEQ ID NO:21)

MVSKGEEDNMAIIKEFMRFKVHMEGSVNGHEFEIEGEGEGRPYEGTQTAKLKVTKGGPLP
FAWDILSPQFMYGSKAYVKHPADIPDYLKLSFPEGFKWERVMNFEDGGVVTVTQDSSLQD
GEFIYKVKLRGTNFPSDGPVMQKKTMGWEASSERMYPEDGALKGEIKQRLKLKDGGHYDA
EVKTTYKAKKPVQLPGAYNVNIKLDITSHNEDYTIVEQYERAEGRHSTGGMDELYK (SEQ ID
NO:22)

Figure 30A and 30B. Construct #398, encoding a polypeptide comprising a conventional CAR "anti-CD19 scFv – CD8 alpha hinge and transmembrane domain – OX40 & CD3 zeta intracellular chains"

Figure 30A
Signal peptide:
ATGGCCTTACCAGTGACCGCCTTGCTCCTGCCGCTGGCCTTGCTGCTCCACGCCGCCAGGCCG (SEQ ID NO:1)
MALPVTALLLPLALLLHAARP (SEQ ID NO:2)

Myc epitope tag:
GAGCAGAAGCTGATCAGCGAGGAGGACCTG (SEQ ID NO:3)
EQKLISEEDL (SEQ ID NO:4)

Anti-human CD19 scFv:
GACATCCAGATGACACAGACTACATCCTCCCTGTCTGCCTCTCTGGGAGACAGAGTCACCATCAGTTGCA
GGGCAAGTCAGGACATTAGTAAATATTTAAATTGGTATCAGCAGAAACCAGATGGAACTGTTAAACTCCT
GATCTACCATACATCAAGATTACACTCAGGAGTCCCATCAAGGTTCAGTGGCAGTGGGTCTGGAACAGAT
TATTCTCTCACCATTAGCAACCTGGAGCAAGAAGATATTGCCACTTACTTTTGCCAACAGGGTAATACGC
TTCCGTACACGTTCGGAGGGGGGACCAAGCTGGAGATCACAGGTGGCGGTGGCTCGGGCGGTGGTGGGTC
GGGTGGCGGCGGATCTGAGGTGAAACTGCAGGAGTCAGGACCTGGCCTGGTGGCGCCCTCACAGAGCCTG
TCCGTCACATGCACTGTCTCAGGGGTCTCATTACCCGACTATGGTGTAAGCTGGATTCGCCAGCCTCCAC
GAAAGGGTCTGGAGTGGCTGGGAGTAATATGGGGTAGTGAAACCACATACTATAATTCAGCTCTCAAATC
CAGACTGACCATCATCAAGGACAACTCCAAGAGCCAAGTTTTCTTAAAAATGAACAGTCTGCAAACTGAT
GACACAGCCATTTACTACTGTGCCAAACATTATTACTACGGTGGTAGCTATGCTATGGACTACTGGGGCC
AAGGAACCTCAGTCACCGTCTCCTCA (SEQ ID NO:5)

DIQMTQTTSSLSASLGDRVTISCRASQDISKYLNWYQQKPDGTVKLLIYHTSRLHSGVPS
RFSGSGSGTDYSLTISNLEQEDIATYFCQQGNTLPYTFGGGTKLEITGGGSGGGGSGGG
GSEVKLQESGPGLVAPSQSLSVTCTVSGVSLPDYGVSWIRQPPRKGLEWLGVIWGSETTY
YNSALKSRLTIIKDNSKSQVFLKMNSLQTDDTAIYYCAKHYYYGGSYAMDYWGQGTSVTV
SS (SEQ ID NO:6)

Human CD8 alpha extracellular spacer/hinge and transmembrane domain:
ACCACGACGCCAGCGCCGCGACCACCAACACCGGCGCCCACCATCGCGTCGCAGCCCCTGTCCCTGCGCC
CAGAGGCGTGCCGGCCAGCGGCGGGGGCGCAGTGCACACGAGGGGGCTGGACTTCGCCTGTGATATCTA
CATCTGGGCGCCCTTGGCCGGGACTTGTGGGGTCCTTCTCCTGTCACTGGTTATCACCCTTTACTGC
(SEQ ID NO:7)

TTTPAPRPPTPAPTIASQPLSLRPEACRPAAGGAVHTRGLDFACDIYIWAPLAGTCGVLL
LSLVITLYC (SEQ ID NO:8)

Linker:
TCCCTA
SL

Figure 30B
Human OX40 intracellular chain:
CGGAGGGACCAGAGGCTGCCCCCCGATGCCCACAAGCCCCCTGGGGGAGGCAGTTTCCGGACCCCCATCC
AAGAGGAGCAGGCCGACGCCCACTCCACCCTGGCCAAGATC (SEQ ID NO:145)

RRDQRLPPDAHKPPGGGSFRTPIQEEQADAHSTLAKI (SEQ ID NO:65)

Linker:
TCGCGAGGAAGCGGGTCCGGTAGCGGATCT (SEQ ID NO:19)
SRGSGSGSGS (SEQ ID NO:20)

Human CD3 zeta intracellular chain:
AGAGTGAAGTTCAGCAGGAGCGCAGACGCCCCCGCGTACAAGCAGGGCCAGAACCAGCTCTATAACGAGC
TCAATCTAGGACGAAGAGAGGAGTACGATGTTTTGGACAAGAGACGTGGCCGGGACCCTGAGATGGGGGG
AAAGCCGAGAAGGAAGAACCCTCAGGAAGGCCTGTACAATGAACTGCAGAAAGATAAGATGGCGGAGGCC
TACAGTGAGATTGGGATGAAAGGCGAGCGCCGGAGGGGCAAGGGGCACGATGGCCTTTACCAGGGTCTCA
GTACAGCCACCAAGGACACCTACGACGCCCTTCACATGCAGGCCCTGCCtCCTCGC (SEQ ID NO:25)

RVKFSRSADAPAYKQGQNQLYNELNLGRREEYDVLDKRRGRDPEMGGKPRRKNPQEGLYN
ELQKDKMAEAYSEIGMKGERRRGKGHDGLYQGLSTATKDTYDALHMQALPPR (SEQ ID NO:26)

Figure 31A and 31B. Construct #399, encoding a polypeptide comprising "anti-CD19 scFv - CD8 alpha hinge and transmembrane domain - OX40 intracellular chain - FKBP"

Figure 31A
Signal peptide:
ATGGCCTTACCAGTGACCGCCTTGCTCCTGCCGCTGGCCTTGCTGCTCCACGCCGCCAGGCCG (SEQ ID NO:1)
MALPVTALLLPLALLLHAARP (SEQ ID NO:2)

Myc epitope tag:
GAGCAGAAGCTGATCAGCGAGGAGGACCTG (SEQ ID NO:3)
EQKLISEEDL (SEQ ID NO:4)

Anti-human CD19 scFv:
GACATCCAGATGACACAGACTACATCCTCCCTGTCTGCCTCTCTGGGAGACAGAGTCACCATCAGTTGCA
GGGCAAGTCAGGACATTAGTAAATATTTAAATTGGTATCAGCAGAAACCAGATGGAACTGTTAAACTCCT
GATCTACCATACATCAAGATTACACTCAGGAGTCCCATCAAGGTTCAGTGGCAGTGGGTCTGGAACAGAT
TATTCTCTCACCATTAGCAACCTGGAGCAAGAAGATATTGCCACTTACTTTTGCCAACAGGGTAATACGC
TTCCGTACACGTTCGGAGGGGGGACCAAGCTGGAGATCACAGGTGGCGGTGGCTCGGGCGGTGGTGGGTC
GGGTGGCGGCGGATCTGAGGTGAAACTGCAGGAGTCAGGACCTGGCCTGGTGGCGCCCTCACAGAGCCTG
TCCGTCACATGCACTGTCTCAGGGGTCTCATTACCCGACTATGGTGTAAGCTGGATTCGCCAGCCTCCAC
GAAAGGGTCTGGAGTGGCTGGGAGTAATATGGGGTAGTGAAACCACATACTATAATTCAGCTCTCAAATC
CAGACTGACCATCATCAAGGACAACTCCAAGAGCCAAGTTTTCTTAAAAATGAACAGTCTGCAAACTGAT
GACACAGCCATTTACTACTGTGCCAAACATTATTACTACGGTGGTAGCTATGCTATGGACTACTGGGGCC
AAGGAACCTCAGTCACCGTCTCCTCA (SEQ ID NO:5)

DIQMTQTTSSLSASLGDRVTISCRASQDISKYLNWYQQKPDGTVKLLIYHTSRLHSGVPS
RFSGSGSGTDYSLTISNLEQEDIATYFCQQGNTLPYTFGGGTKLEITGGGSGGGGSGGG
GSEVKLQESGPGLVAPSQSLSVTCTVSGVSLPDYGVSWIRQPPRKGLEWLGVIWGSETTY
YNSALKSRLTIIKDNSKSQVFLKMNSLQTDDTAIYYCAKHYYYGGSYAMDYWGQGTSVTV
SS (SEQ ID NO:6)

Human CD8 alpha extracellular spacer/hinge and transmembrane domain:
ACCACGACGCCAGCGCCGCGACCACCAACACCGGCGCCCACCATCGCGTCGCAGCCCCTGTCCCTGCGCC
CAGAGGCGTGCCGGCCAGCGGCGGGGGCGCAGTGCACACGAGGGGGCTGGACTTCGCCTGTGATATCTA
CATCTGGGCGCCCTTGGCCGGGACTTGTGGGGTCCTTCTCCTGTCACTGGTTATCACCCTTTACTGC
(SEQ ID NO:7)

TTTPAPRPPTPAPTIASQPLSLRPEACRPAAGGAVHTRGLDFACDIYIWAPLAGTCGVLL
LSLVITLYC (SEQ ID NO:8)

Figure 31B
Linker:
TCCCTA
SL

Human OX40 intracellular chain:
CGGAGGGACCAGAGGCTGCCCCCCGATGCCCACAAGCCCCCTGGGGGAGGCAGTTTCCGGACCCCCATCC
AAGAGGAGCAGGCCGACGCCCACTCCACCCTGGCCAAGATC (SEQ ID NO:145)

RRDQRLPPDAHKPPGGGSFRTPIQEEQADAHSTLAKI (SEQ ID NO:65)

Linker:
TCGCGAGGAAGCGGGTCCGGTAGCGGATCT (SEQ ID NO:19)
SRGSGSGSGS (SEQ ID NO:20)

FKBP:
ATGGGAGTcCAGGTGGAAACCATCTCCCCAGGAGACGGGCGCACCTTCCCCAAGCGCGGCCAGACCTGCG
TGGTGCACTACACCGGGATGCTTGAAGATGGAAAGAAATTTGATTCCTCCCGGGACAGAAACAAGCCCTT
TAAGTTTATGCTAGGCAAGCAGGAGGTGATCCGAGGCTGGGAAGAAGGGGTTGCCCAGATGAGTGTGGGT
CAGAGAGCCAAACTGACTATATCTCCAGATTATGCCTATGGTGCCACTGGGCACCCAGGCATCATCCCAC
CACATGCCACTCTCGTCTTCGATGTGGAGCTTCTAAAACTGGAA (SEQ ID NO:11)

MGVQVETISPGDGRTFPKRGQTCVVHYTGMLEDGKKFDSSRDRNKPFKFMLGKQEVIRGW
EEGVAQMSVGQRAKLTISPDYAYGATGHPGIIPPHATLVFDVELLKLE (SEQ ID NO:12)

Figure 32A and 32B. Construct #400, encoding a polypeptide comprising "DAP10 extracellular domain - CD8 alpha transmembrane domain - OX40 intracellular chain - FRB - CD3 zeta intracellular chain - mCherry"

Figure 32A
Human DAP10 signal sequence and extracellular domain:
Atgatccatctgggtcacatcctcttcctgcttttgctcccagtggctgcagctcagacgactccaggag
agagatcatcactccctgccttttaccctggcacttcaggctcttgttccggatgtgggtccctctctct
gccg (SEQ ID NO:27)

MIHLGHILFLLLLPVAAAQTTPGERSSLPAFYPGTSGSCSGCGSLSLP (SEQ ID NO:28)

Human CD8alpha transmembrane domain:
ATCTACATCTGGGCGCCCTTGGCCGGGACTTGTGGGGTCCTTCTCCTGTCACTGGTTATCACCCTTTACT
GC (SEQ ID NO:29)

IYIWAPLAGTCGVLLLSLVITLYC (SEQ ID NO:30)

Linker:
Tctctg
SL

Human OX40 intracellular chain:
CGGAGGGACCAGAGGCTGCCCCCCGATGCCCACAAGCCCCCTGGGGGAGGCAGTTTCCGGACCCCCATCC
AAGAGGAGCAGGCCGACGCCCACTCCACCCTGGCCAAGATC (SEQ ID NO:145)

RRDQRLPPDAHKPPGGGSFRTPIQEEQADAHSTLAKI (SEQ ID NO:65)

Linker:
GGtTCCGGcAGCGGaTCTGGtAGcGGAAGCGGGTCCGGTAGCGGATCT (SEQ ID NO:31)
GSGSGSGSGSGSGSGS (SEQ ID NO:32)

FRB:
ATCCTCTGGCATGAGATGTGGCATGAAGGCCTGGAAGAGGCATCTCGTTTGTACTTTGGGGAAAGGAACG
TGAAAGGCATGTTTGAGGTGCTGGAGCCCTTGCATGCTATGATGGAACGGGGCCCCCAGACTCTGAAGGA
AACATCCTTTAATCAGGCCTATGGTCGAGATTTAATGGAGGCCCAAGAGTGGTGCAGGAAGTACATGAAA
TCAGGGAATGTCAAGGACCTCCTCCAAGCCTGGGACCTCTATTATCATGTGTTCCGACGAATCTCAAAG
(SEQ ID NO:33)

ILWHEMWHEGLEEASRLYFGERNVKGMFEVLEPLHAMMERGPQTLKETSFNQAYGRDLME
AQEWCRKYMKSGNVKDLLQAWDLYYHVFRRISK (SEQ ID NO:34)

Figure 32B
Linker:
GGAAGCGGGTCCGGTAGCGGATCTTCCCTA (SEQ ID NO:15)
GSGSGSGSSL (SEQ ID NO:16)

Human CD3 zeta intracellular chain:
AGAGTGAAGTTCAGCAGGAGCGCAGACGCCCCCGCGTACCAGCAGGGCCAGAACCAGCTCTATAACGAGC
TCAATCTAGGACGAAGAGAGGAGTACGATGTTTTGGACAAGAGACGTGGCCGGGACCCTGAGATGGGGGG
AAAGCCGAGAAGGAAGAACCCTCAGGAAGGCCTGTACAATGAACTGCAGAAAGATAAGATGGCGGAGGCC
TACAGTGAGATTGGGATGAAAGGCGAGCGCCGGAGGGGCAAGGGGCACGATGGCCTTTACCAGGGTCTCA
GTACAGCCACCAAGGACACCTACGACGCCCTTCACATGCAGGCCCTGCCCCCTCGC (SEQ ID
NO:17)

RVKFSRSADAPAYQQGQNQLYNELNLGRREEYDVLDKRRGRDPEMGGKPRRKNPQEGLYN
ELQKDKMAEAYSEIGMKGERRRGKGHDGLYQGLSTATKDTYDALHMQALPPR (SEQ ID NO:18)

Linker:
TCGCGAGGAAGCGGGTCCGGTAGCGGATCT (SEQ ID NO:19)
SRGSGSGSGS (SEQ ID NO:20)

mCherry:
ATGGTGAGCAAGGGCGAGGAGGATAACATGGCCATCATCAAGGAGTTCATGCGCTTCAAGGTGCACATGG
AGGGCTCCGTGAACGGCCACGAGTTCGAGATCGAGGGCGAGGGCGAGGGCCGCCCCTACGAGGGCACCCA
GACCGCCAAGCTGAAGGTGACCAAGGGTGGCCCCCTGCCCTTCGCCTGGGACATCCTGTCCCCTCAGTTC
ATGTACGGCTCCAAGGCCTACGTGAAGCACCCCGCCGACATCCCCGACTACTTGAAGCTGTCCTTCCCCG
AGGGCTTCAAGTGGGAGCGCGTGATGAACTTCGAGGACGGCGGCGTGGTGACCGTGACCCAGGACTCCTC
CCTGCAGGACGGCGAGTTCATCTACAAGGTGAAGCTGCGCGGCACCAACTTCCCCTCCGACGGCCCCGTA
ATGCAGAAGAAGACCATGGGCTGGGAGGCCTCCTCCGAGCGGATGTACCCCGAGGACGGCGCCCTGAAGG
GCGAGATCAAGCAGAGGCTGAAGCTGAAGGACGGCGGCCACTACGACGCTGAGGTCAAGACCACCTACAA
GGCCAAGAAGCCCGTGCAGCTGCCCGGCGCCTACAACGTCAACATCAAGTTGGACATCACCTCCCACAAC
GAGGACTACACCATCGTGGAACAGTACGAACGCGCCGAGGGCCGCCACTCCACCGGCGGCATGGACGAGC
TGTACAAG (SEQ ID NO:21)

MVSKGEEDNMAIIKEFMRFKVHMEGSVNGHEFEIEGEGEGRPYEGTQTAKLKVTKGGPLP
FAWDILSPQFMYGSKAYVKHPADIPDYLKLSFPEGFKWERVMNFEDGGVVTVTQDSSLQD
GEFIYKVKLRGTNFPSDGPVMQKKTMGWEASSERMYPEDGALKGEIKQRLKLKDGGHYDA
EVKTTYKAKKPVQLPGAYNVNIKLDITSHNEDYTIVEQYERAEGRHSTGGMDELYK (SEQ ID
NO:22)

Figure 33A and 33B. Construct #358, encoding a polypeptide comprising a conventional CAR "anti-mesothelin HN1 scFv – CD8 alpha hinge and transmembrane domain – 4-1BB & CD3 zeta intracellular chains"

Figure 33A
Signal peptide:
ATGGCCTTACCAGTGACCGCCTTGCTCCTGCCGCTGGCCTTGCTGCTCCACGCCGCCAGGCCG (SEQ ID NO:1)
MALPVTALLLPLALLLHAARP (SEQ ID NO:2)

Flag epitope tag:
GATTACAAGGATGACGATGACAAG (SEQ ID NO:132)
DYKDDDDK (SEQ ID NO:123)

Anti-human mesothelin HN1 scFv:
GGATCCCAGGTGCAGCTGGTGCAGTCTGGCGCCGAAGTGAAAAGACCAGGCGCCAGCGTGCAGGTCTCCT
GTAGAGCCAGCGGCTACAGCATCAACACCTACTACATGCAGTGGGTGCGCCAGGCCCCAGGCGCTGGACT
GGAATGGATGGGCGTGATCAACCCCAGCGGCGTGACAAGCTACGCCCAGAAATTCCAGGGCAGAGTGACC
CTGACCAACGACACCAGCACCAACACAGTGTACATGCAGCTGAACAGCCTGACCAGCGCCGACACCGCCG
TGTACTACTGTGCCAGATGGGCCCTGTGGGGCGACTTCGGCATGGATGTGTGGGGCAAGGGCACCCTCGT
GACCGTGTCTAGCGGAGGCGGAGGATCTGGCGGAGGGGGATCTGGAGGCGGCGGAAGCGACATCCAGATG
ACCCAGAGCCCTAGCACCCTGAGCGCCAGCATCGGCGATAGAGTGACCATCACCTGTCGGGCCAGCGAGG
GCATCTATCACTGGCTGGCCTGGTATCAGCAGAAGCCCGGCAAGGCCCCCAAGCTGCTGATCTACAAGGC
CAGCTCTCTGGCCTCTGGCGCCCCTAGCAGATTTTCTGGCAGCGGCTCCGGCACCGACTTCACCCTGACA
ATCAGCAGCCTGCAGCCCGACGACTTCGCCACCTACTATTGCCAGCAGTACAGCAACTACCCCCTGACCT
TCGGCGGAGGCACCAAGCTGGAAATCAAG (SEQ ID NO:141)

GSQVQLVQSGAEVKRPGASVQVSCRASGYSINTYYMQWVRQAPGAGLEWMGVINPSGVTS
YAQKFQGRVTLTNDTSTNTVYMQLNSLTSADTAVYYCARWALWGDFGMDVWGKGTLVTVS
SGGGGSGGGGSGGGGSDIQMTQSPSTLSASIGDRVTITCRASEGIYHWLAWYQQKPGKAP
KLLIYKASSLASGAPSRFSGSGSGTDFTLTISSLQPDDFATYYCQQYSNYPLTFGGGTKL
EIK (SEQ ID NO:142)

Human CD8 alpha extracellular spacer/hinge and transmembrane domain:
ACCACGACGCCAGCGCCGCGACCACCAACACCGGCGCCCACCATCGCGTCGCAGCCCCTGTCCCTGCGCC
CAGAGGCGTGCCGGCCAGCGGCGGGGGGCGCAGTGCACACGAGGGGGCTGGACTTCGCCTGTGATATCTA
CATCTGGGCGCCCTTGGCCGGGACTTGTGGGGTCCTTCTCCTGTCACTGGTTATCACCCTTTACTGC
(SEQ ID NO:7)

TTTPAPRPPTPAPTIASQPLSLRPEACRPAAGGAVHTRGLDFACDIYIWAPLAGTCGVLL
LSLVITLYC (SEQ ID NO:8)

Figure 33B
Linker:
TCCCTA
SL

Human 4-1BB intracellular chain:
AAACGGGGCAGAAAGAAACTCCTGTATATATTCAAACAACCATTTATGAGACCAGTACAAACTACTCAAG
AGGAAGATGGCTGTAGCTGCCGATTTCCAGAAGAAGAAGAAGGAGGATGTGAACTG (SEQ ID
NO:23)

KRGRKKLLYIFKQPFMRPVQTTQEEDGCSCRFPEEEEGGCEL (SEQ ID NO:24)

Human CD3 zeta intracellular chain:
AGAGTGAAGTTCAGCAGGAGCGCAGACGCCCCCGCGTACAAGCAGGGCCAGAACCAGCTCTATAACGAGC
TCAATCTAGGACGAAGAGAGGAGTACGATGTTTTGGACAAGAGACGTGGCCGGGACCCTGAGATGGGGGG
AAAGCCGAGAAGGAAGAACCCTCAGGAAGGCCTGTACAATGAACTGCAGAAAGATAAGATGGCGGAGGCC
TACAGTGAGATTGGGATGAAAGGCGAGCGCCGGAGGGGCAAGGGGCACGATGGCCTTTACCAGGGTCTCA
GTACAGCCACCAAGGACACCTACGACGCCCTTCACATGCAGGCCCTGCCtCCTCGC (SEQ ID
NO:25)

RVKFSRSADAPAYKQGQNQLYNELNLGRREEYDVLDKRRGRDPEMGGKPRRKNPQEGLYN
ELQKDKMAEAYSEIGMKGERRRGKGHDGLYQGLSTATKDTYDALHMQALPPR (SEQ ID NO:26)

SEQUENCE LISTING

```
Sequence total quantity: 145
SEQ ID NO: 1             moltype = DNA  length = 63
FEATURE                  Location/Qualifiers
misc_feature             1..63
                         note = synthetic polynucleotide
source                   1..63
                         mol_type = other DNA
                         organism = synthetic construct
SEQUENCE: 1
atggccttac cagtgaccgc cttgctcctg ccgctggcct tgctgctcca cgccgccagg   60
ccg                                                                 63

SEQ ID NO: 2             moltype = AA   length = 21
FEATURE                  Location/Qualifiers
REGION                   1..21
                         note = synthetic polypeptide
source                   1..21
                         mol_type = protein
                         organism = synthetic construct
SEQUENCE: 2
MALPVTALLL PLALLLHAAR P                                             21
```

```
SEQ ID NO: 3               moltype = DNA  length = 30
FEATURE                    Location/Qualifiers
misc_feature               1..30
                           note = synthetic polynucleotide
source                     1..30
                           mol_type = other DNA
                           organism = synthetic construct
SEQUENCE: 3
gagcagaagc tgatcagcga ggaggacctg                                           30

SEQ ID NO: 4               moltype = AA  length = 10
FEATURE                    Location/Qualifiers
REGION                     1..10
                           note = synthetic polypeptide
source                     1..10
                           mol_type = protein
                           organism = synthetic construct
SEQUENCE: 4
EQKLISEEDL                                                                 10

SEQ ID NO: 5               moltype = DNA  length = 726
FEATURE                    Location/Qualifiers
misc_feature               1..726
                           note = synthetic polynucleotide
source                     1..726
                           mol_type = other DNA
                           organism = synthetic construct
SEQUENCE: 5
gacatccaga tgacacagac tacatcctcc ctgtctgcct ctctgggaga cagagtcacc          60
atcagttgca gggcaagtca ggacattagt aaatatttaa attggtatca gcagaaacca        120
gatggaactg ttaaactcct gatctaccat acatcaagat tacactcagg agtccccatca       180
aggttcagtg gcagtgggtc tggaacagat tattctctca ccattagcaa cctggagcaa        240
gaagatattg ccacttactt ttgccaacag ggtaatacgc ttccgtacac gttcggaggg        300
gggaccaagc tggagatcac aggtggcggt ggctcgggcg gtggtgggtc gggtggcggc        360
ggatctgagg tgaaactgca ggagtcagga cctggcctgg tggcgccctc acagagcctg        420
tccgtcacat gcactgtctc aggggtctca ttacccgact atggtgtaag ctggattcgc        480
cagcctccac gaaagggtct ggagtggctg ggagtaatat ggggtagtga aaccacatac        540
tataattcag ctctcaaatc cagactgacc atcatcaagg acaactccaa gagccaagtt        600
ttcttaaaaa tgaacagtct gcaaactgat gacacagcca tttactactg tgccaaacat        660
tattactacg gtggtagcta tgctatggac tactgggccc aaggaacctc agtcaccgtc        720
tcctca                                                                   726

SEQ ID NO: 6               moltype = AA  length = 242
FEATURE                    Location/Qualifiers
REGION                     1..242
                           note = synthetic polypeptide
source                     1..242
                           mol_type = protein
                           organism = synthetic construct
SEQUENCE: 6
DIQMTQTTSS LSASLGDRVT ISCRASQDIS KYLNWYQQKP DGTVKLLIYH TSRLHSGVPS          60
RFSGSGSGTD YSLTISNLEQ EDIATYFCQQ GNTLPYTFGG GTKLEITGGG GSGGGGSGGG         120
GSEVKLQESG PGLVAPSQSL SVTCTVSGVS LPDYGVSWIR QPPRKGLEWL GVIWGSETTY        180
YNSALKSRLT IIKDNSKSQV FLKMNSLQTD DTAIYYCAKH YYYGGSYAMD YWGQGTSVTV        240
SS                                                                        242

SEQ ID NO: 7               moltype = DNA  length = 207
FEATURE                    Location/Qualifiers
misc_feature               1..207
                           note = synthetic polynucleotide
source                     1..207
                           mol_type = other DNA
                           organism = synthetic construct
SEQUENCE: 7
accacgacgc cagcgccgcg accaccaaca ccggcgccca ccatcgcgtc gcagcccctg          60
tccctgcgcc cagaggcgtg ccggccagcg gcggggggcg cagtgcacac gagggggctg        120
gacttcgcct gtgatatcta catctgggcg cccttggccg ggacttgtgg ggtccttctc        180
ctgtcactgg ttatcaccct ttactgc                                            207

SEQ ID NO: 8               moltype = AA  length = 69
FEATURE                    Location/Qualifiers
REGION                     1..69
                           note = synthetic polypeptide
source                     1..69
                           mol_type = protein
                           organism = synthetic construct
SEQUENCE: 8
TTTPAPRPPT PAPTIASQPL SLRPEACRPA AGGAVHTRGL DFACDIYIWA PLAGTCGVLL          60
LSLVITLYC                                                                  69
```

```
SEQ ID NO: 9              moltype = DNA  length = 30
FEATURE                   Location/Qualifiers
misc_feature              1..30
                          note = synthetic polynucleotide
source                    1..30
                          mol_type = other DNA
                          organism = synthetic construct
SEQUENCE: 9
tccctaggaa gcgggtccgg tagcggatct                                        30

SEQ ID NO: 10             moltype = AA  length = 10
FEATURE                   Location/Qualifiers
REGION                    1..10
                          note = synthetic polypeptide
source                    1..10
                          mol_type = protein
                          organism = synthetic construct
SEQUENCE: 10
SLGSGSGSGS                                                              10

SEQ ID NO: 11             moltype = DNA  length = 324
FEATURE                   Location/Qualifiers
misc_feature              1..324
                          note = synthetic polynucleotide
source                    1..324
                          mol_type = other DNA
                          organism = synthetic construct
SEQUENCE: 11
atgggagtcc aggtggaaac catctcccca ggagacgggc gcaccttccc caagcgcggc        60
cagacctgcg tggtgcacta caccgggatg cttgaagatg gaaagaaatt tgattcctcc       120
cgggacagaa acaagccctt taagtttatg ctaggcaagc aggaggtgat ccgaggctgg       180
gaagaagggg ttgcccagat gagtgtgggt cagagagcca aactgactat atctccagat       240
tatgcctatg gtgccactgg gcacccaggc atcatcccac acatgccac tctcgtcttc        300
gatgtggagc ttctaaaact ggaa                                              324

SEQ ID NO: 12             moltype = AA  length = 108
FEATURE                   Location/Qualifiers
REGION                    1..108
                          note = synthetic polypeptide
source                    1..108
                          mol_type = protein
                          organism = synthetic construct
SEQUENCE: 12
MGVQVETISP GDGRTFPKRG QTCVVHYTGM LEDGKKFDSS RDRNKPFKFM LGKQEVIRGW        60
EEGVAQMSVG QRAKLTISPD YAYGATGHPG IIPPHATLVF DVELLKLE                    108

SEQ ID NO: 13             moltype = DNA  length = 282
FEATURE                   Location/Qualifiers
misc_feature              1..282
                          note = synthetic polynucleotide
source                    1..282
                          mol_type = other DNA
                          organism = synthetic construct
SEQUENCE: 13
atgatcctct ggcatgagat gtggcatgaa ggcctggaag aggcatctcg tttgtacttt        60
ggggaaagga acgtgaaagg catgtttgag gtgctggagc ccttgcatgc tatgatggaa       120
cggggccccc agactctgaa ggaaacatcc tttaatcagg cctatggtcg agatttaatg       180
gaggcccaag agtggtgcag gaagtacatg aaatcaggga atgtcaagga cctcctccaa       240
gcctgggacc tctattatca tgtgttccga cgaatctcaa ag                          282

SEQ ID NO: 14             moltype = AA  length = 94
FEATURE                   Location/Qualifiers
REGION                    1..94
                          note = synthetic polypeptide
source                    1..94
                          mol_type = protein
                          organism = synthetic construct
SEQUENCE: 14
MILWHEMWHE GLEEASRLYF GERNVKGMFE VLEPLHAMME RGPQTLKETS FNQAYGRDLM        60
EAQEWCRKYM KSGNVKDLLQ AWDLYYHVFR RISK                                    94

SEQ ID NO: 15             moltype = DNA  length = 30
FEATURE                   Location/Qualifiers
misc_feature              1..30
                          note = synthetic polynucleotide
source                    1..30
                          mol_type = other DNA
                          organism = synthetic construct
```

```
SEQUENCE: 15
ggaagcgggt ccggtagcgg atcttcccta                                       30

SEQ ID NO: 16           moltype = AA  length = 10
FEATURE                 Location/Qualifiers
REGION                  1..10
                        note = synthetic polypeptide
source                  1..10
                        mol_type = protein
                        organism = synthetic construct
SEQUENCE: 16
GSGSGSGSSL                                                             10

SEQ ID NO: 17           moltype = DNA  length = 336
FEATURE                 Location/Qualifiers
misc_feature            1..336
                        note = synthetic polynucleotide
source                  1..336
                        mol_type = other DNA
                        organism = synthetic construct
SEQUENCE: 17
agagtgaagt tcagcaggag cgcagacgcc cccgcgtacc agcagggcca gaaccagctc       60
tataacgagc tcaatctagg acgaagagag gagtacgatg ttttggacaa gagacgtggc      120
cgggaccctg agatgggggg aaagccgaga aggaagaacc ctcaggaagg cctgtacaat      180
gaactgcaga aagataagat ggcggaggcc tacagtgaga ttgggatgaa aggcgagcgc      240
cggaggggca aggggcacga tggcctttac cagggtctca gtacagccac caaggacacc      300
tacgacgccc ttcacatgca ggccctgccc cctcgc                                336

SEQ ID NO: 18           moltype = AA  length = 112
FEATURE                 Location/Qualifiers
REGION                  1..112
                        note = synthetic polypeptide
source                  1..112
                        mol_type = protein
                        organism = synthetic construct
SEQUENCE: 18
RVKFSRSADA PAYQQGQNQL YNELNLGRRE EYDVLDKRRG RDPEMGGKPR RKNPQEGLYN       60
ELQKDKMAEA YSEIGMKGER RRGKGHDGLY QGLSTATKDT YDALHMQALP PR              112

SEQ ID NO: 19           moltype = DNA  length = 30
FEATURE                 Location/Qualifiers
misc_feature            1..30
                        note = synthetic polynucleotide
source                  1..30
                        mol_type = other DNA
                        organism = synthetic construct
SEQUENCE: 19
tcgcgaggaa gcgggtccgg tagcggatct                                       30

SEQ ID NO: 20           moltype = AA  length = 10
FEATURE                 Location/Qualifiers
REGION                  1..10
                        note = synthetic polypeptide
source                  1..10
                        mol_type = protein
                        organism = synthetic construct
SEQUENCE: 20
SRGSGSGSGS                                                             10

SEQ ID NO: 21           moltype = DNA  length = 708
FEATURE                 Location/Qualifiers
misc_feature            1..708
                        note = synthetic polynucleotide
source                  1..708
                        mol_type = other DNA
                        organism = synthetic construct
SEQUENCE: 21
atggtgagca agggcgagga ggataacatg gccatcatca aggagttcat gcgcttcaag       60
gtgcacatgg agggctccgt gaacggccac gagttcgaga tcgagggcga gggcgagggc      120
cgcccctacg agggcaccca gaccgccaag ctgaaggtga ccaagggtgg ccccctgccc      180
ttcgcctggg acatcctgtc ccctcagttc atgtacggct ccaaggccta cgtgaagcac      240
cccgccgaca tccccgacta cttgaagctg tccttccccg agggcttcaa gtgggagcgc      300
gtgatgaact tcgaggacgg cggcgtggtg accgtgaccc aggactcctc cctgcaggac      360
ggcgagttca tctacaaggt gaagctgcgc ggcaccaact tcccctccga cggccccgta      420
atgcagaaga gaccatgggg ctgggaggcc tcctccgagc ggatgtaccc cgaggacggc      480
gccctgaagg gcgagatcaa gcagaggctg aagctgaagg acggcggcca ctacgacgct      540
gaggtcaaga ccacctacaa ggccaagaag cccgtgcagc tgcccggcgc ctacaacgtc      600
aacatcaagt tggacatcac ctcccacaac gaggactaca ccatcgtgga acagtacgaa      660
cgcgccgagg gccgccactc caccggcggc atggacgagc tgtacaag                   708
```

```
SEQ ID NO: 22           moltype = AA  length = 236
FEATURE                 Location/Qualifiers
REGION                  1..236
                        note = synthetic polypeptide
source                  1..236
                        mol_type = protein
                        organism = synthetic construct
SEQUENCE: 22
MVSKGEEDNM AIIKEFMRFK VHMEGSVNGH EFEIEGEGEG RPYEGTQTAK LKVTKGGPLP    60
FAWDILSPQF MYGSKAYVKH PADIPDYLKL SFPEGFKWER VMNFEDGGVV TVTQDSSLQD   120
GEFIYKVKLR GTNFPSDGPV MQKKTMGWEA SSERMYPEDG ALKGEIKQRL KLKDGGHYDA   180
EVKTTYKAKK PVQLPGAYNV NIKLDITSHN EDYTIVEQYE RAEGRHSTGG MDELYK       236

SEQ ID NO: 23           moltype = DNA  length = 126
FEATURE                 Location/Qualifiers
misc_feature            1..126
                        note = synthetic polynucleotide
source                  1..126
                        mol_type = other DNA
                        organism = synthetic construct
SEQUENCE: 23
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                              126

SEQ ID NO: 24           moltype = AA  length = 42
FEATURE                 Location/Qualifiers
REGION                  1..42
                        note = synthetic polypeptide
source                  1..42
                        mol_type = protein
                        organism = synthetic construct
SEQUENCE: 24
KRGRKKLLYI FKQPFMRPVQ TTQEEDGCSC RFPEEEEGGC EL                       42

SEQ ID NO: 25           moltype = DNA  length = 336
FEATURE                 Location/Qualifiers
misc_feature            1..336
                        note = synthetic polynucleotide
source                  1..336
                        mol_type = other DNA
                        organism = synthetic construct
SEQUENCE: 25
agagtgaagt tcagcaggag cgcagacgcc cccgcgtaca agcagggcca gaaccagctc    60
tataacgagc tcaatctagg acgaagagag gagtacgatg tttttggacaa gagacgtggc  120
cgggaccctg agatgggggg aaagccgaga aggaagaacc ctcaggaagg cctgtacaat   180
gaactgcaga agataagat ggcggaggcc tacagtgaga ttgggatgaa aggcgagcgc    240
cggaggggca aggggcacga tggcctttac cagggtctca gtacagccac caaggacacc   300
tacgacgccc ttcacatgca ggccctgcct cctcgc                             336

SEQ ID NO: 26           moltype = AA  length = 112
FEATURE                 Location/Qualifiers
REGION                  1..112
                        note = synthetic polypeptide
source                  1..112
                        mol_type = protein
                        organism = synthetic construct
SEQUENCE: 26
RVKFSRSADA PAYKQGQNQL YNELNLGRRE EYDVLDKRRG RDPEMGGKPR RKNPQEGLYN    60
ELQKDKMAEA YSEIGMKGER RRGKGHDGLY QGLSTATKDT YDALHMQALP PR           112

SEQ ID NO: 27           moltype = DNA  length = 144
FEATURE                 Location/Qualifiers
misc_feature            1..144
                        note = synthetic polynucleotide
source                  1..144
                        mol_type = other DNA
                        organism = synthetic construct
SEQUENCE: 27
atgatccatc tgggtcacat cctcttcctg cttttgctcc cagtggctgc agctcagacg    60
actccaggag agagatcatc actccctgcc ttttaccctg gcacttcagg ctcttgttcc   120
ggatgtgggt ccctctctct gccg                                          144

SEQ ID NO: 28           moltype = AA  length = 48
FEATURE                 Location/Qualifiers
REGION                  1..48
                        note = synthetic polypeptide
```

```
source                  1..48
                        mol_type = protein
                        organism = synthetic construct
SEQUENCE: 28
MIHLGHILFL LLLPVAAAQT TPGERSSLPA FYPGTSGSCS GCGSLSLP                    48

SEQ ID NO: 29           moltype = DNA   length = 72
FEATURE                 Location/Qualifiers
misc_feature            1..72
                        note = synthetic polynucleotide
source                  1..72
                        mol_type = other DNA
                        organism = synthetic construct
SEQUENCE: 29
atctacatct gggcgccctt ggccgggact tgtggggtcc ttctcctgtc actggttatc       60
acccttact gc                                                           72

SEQ ID NO: 30           moltype = AA   length = 24
FEATURE                 Location/Qualifiers
REGION                  1..24
                        note = synthetic polypeptide
source                  1..24
                        mol_type = protein
                        organism = synthetic construct
SEQUENCE: 30
IYIWAPLAGT CGVLLLSLVI TLYC                                             24

SEQ ID NO: 31           moltype = DNA   length = 48
FEATURE                 Location/Qualifiers
misc_feature            1..48
                        note = synthetic polynucleotide
source                  1..48
                        mol_type = other DNA
                        organism = synthetic construct
SEQUENCE: 31
ggttccggca gcggatctgg tagcggaagc gggtccggta gcggatct                   48

SEQ ID NO: 32           moltype = AA   length = 16
FEATURE                 Location/Qualifiers
REGION                  1..16
                        note = synthetic polypeptide
source                  1..16
                        mol_type = protein
                        organism = synthetic construct
SEQUENCE: 32
GSGSGSGSGS GSGSGS                                                      16

SEQ ID NO: 33           moltype = DNA   length = 279
FEATURE                 Location/Qualifiers
misc_feature            1..279
                        note = synthetic polynucleotide
source                  1..279
                        mol_type = other DNA
                        organism = synthetic construct
SEQUENCE: 33
atcctctggc atgagatgtg gcatgaaggc ctggaagagg catctcgttt gtactttggg      60
gaaaggaacg tgaaaggcat gtttgaggtg ctggagccct tgcatgctat gatggaacgg     120
ggcccccaga ctctgaagga acatcccttt aatcaggcca tggtcgaga tttaatggag      180
gcccaagagt ggtgcaggaa gtacatgaaa tcagggaatg tcaaggacct cctccaagcc    240
tgggacctct attatcatgt gttccgacga atctcaaag                            279

SEQ ID NO: 34           moltype = AA   length = 93
FEATURE                 Location/Qualifiers
REGION                  1..93
                        note = synthetic polypeptide
source                  1..93
                        mol_type = protein
                        organism = synthetic construct
SEQUENCE: 34
ILWHEMWHEG LEEASRLYFG ERNVKGMFEV LEPLHAMMER GPQTLKETSF NQAYGRDLME      60
AQEWCRKYMK SGNVKDLLQA WDLYYHVFRR ISK                                   93

SEQ ID NO: 35           moltype = DNA   length = 1857
FEATURE                 Location/Qualifiers
misc_feature            1..1857
                        note = synthetic polynucleotide
source                  1..1857
                        mol_type = other DNA
                        organism = synthetic construct
```

-continued

```
SEQUENCE: 35
atgccagacc ccgcggcgca tctgcccttc ttctacggca gcatctcgcg tgccgaggcc    60
gaggagcacc tgaagctggc gggcatggcg gacgggctct cctgctgcg ccagtgcctg    120
cgctcgctgg gcggctatgt gctgtcgctc gtgcacgatg tgcgcttcca ccactttccc    180
atcgagcgac agctcaacgg cacctacgcc attgccgacg gcaaagcgca ctgtggaccg    240
gcagagctct gcgagttcta ctcgcgcgac cccgacgggc tgccctgcaa cctgcgcaag    300
ccgtgcaacc ggccgtcggg cctcgagccg cagccggggg tcttcgactg cctgcgagac    360
gccatggtgc gtgactacgt gcgccagacg tggaagctgg agggcgaggc cctggagcag    420
gccatcatca gccaggcccc gcaagtggag aagctcattg ctacgacggc cacgagcgg    480
atgccctggt accacagcag cctgacgcgt gaggaggccg agcgcaaact ttactctggc    540
gcgcagaccg acggcaagtt cctgctgagg ccgcggaagg agcagggcac atacgccctg    600
tccctcatct atgggaagac ggtgtaccac tacctcatca gccaagacaa ggcgggcaag    660
tactgcattc ccgagggcac caagtttgac acgtctctgg cagctggtgga gtatctgaag    720
ctgaaggcgg acgggctcat ctactgcctg aaggaggcct gccccaacag cagtgccagc    780
aacgcctcag gggctgctgc tcccacactc ccagcccacc catccacgtt gactcatcct    840
cagagacgaa tcgacaccct caactcagat ggatacaccc tgagccagc acgcataacg    900
tccccagaca aaccgcggcc gatgcccatg gacacgagcg tgtatgagag ccctacagc    960
gacccagagg agctcaagga caagaagctc ttcctgaagg gcgataacct cctcatagct   1020
gacattgaac ttggctgcgg caactttggc tcagtgcgcc agggcgtgta ccgcatgcgc   1080
aagaagcaga tcgacgtggc catcaaggtg ctgaagcagg gcacggagaa ggcagacacg   1140
gaagagatga tgcgcgaggc gcagatcatg caccagctgg acaacccta catcgtgcgg   1200
ctcattggcg tctgccaggc cgaggccctc atgctggtga tggagatggc tggggcgagg   1260
ccgctgcaca agttcctggt cggcaagagg gaggagatcc ctgtgagcaa tgtggccgag   1320
ctgctgcacc aggtgtccat ggggatgaag tacctggagg agaagaactt tgtgcaccgt   1380
gacctggcg cccgcaacgt cctgctggtt aaccggcact acgccaagat cagcgacttt   1440
ggcctctcca aagcactggg tgccgacgac agctactaca ctgcccgctc agcaggaag   1500
tggccgctca gtggtacgc acccgaatgc atcaacttcc gcaagttctc cagccgcagc   1560
gatgtctgga gctatggggt caccatgtgg gaggccttgt cctacggcca gaagccctac   1620
aagaagatga aagggccgga ggtcatggcc ttcatcgagc agggcaagcg gatggagtgc   1680
ccaccagagt gtccaccgga actgtacgca ctcatgagcg actgtggat ctacaagtgg   1740
gaggatcgcc ccgacttcct gaccgtggga cagcgcatgc gagcctgtta ctacagcctg   1800
gccagcaagg tggaagggcc cccaggcagc acacagaagg ctgaggctgc ctgtgcc      1857

SEQ ID NO: 36          moltype = AA   length = 619
FEATURE                Location/Qualifiers
REGION                 1..619
                       note = synthetic polypeptide
source                 1..619
                       mol_type = protein
                       organism = synthetic construct
SEQUENCE: 36
MPDPAAHLPF FYGSISRAEA EEHLKLAGMA DGLFLLRQCL RSLGGYVLSL VHDVRFHHFP    60
IERQLNGTYA IAGGKAHCGP AELCEFYSRD PDGLPCNLRK PCNRPSGLEP QPGVFDCLRD   120
AMVRDYVRQT WKLEGEALEQ AIISQAPQVE KLIATTAHER MPWYHSSLTR EEAERKLYSG   180
AQTDGKFLLR PRKEQGTYAL SLIYGKTVYH YLISQDKAGK YCIPEGTKFD TLWQLVEYLK   240
LKADGLIYCL KEACPNSSAS NASGAAAPTL PAHPSTLTHP QRRIDTLNSD GYTPEPARIT   300
SPDKPRPMPM DTSVYESPYS DPEELKDKKL FLKRDNLLIA DIELGCGNFG SVRQGVYRMR   360
KKQIDVAIKV LKQGTEKADT EEMMREAQIM HQLDNPYIVR LIGVCQAEAL MLVMEMAGGG   420
PLHKFLVGKR EEIPVSNVAE LLHQVSMGMK YLEEKNFVHR DLAARNVLLV NRHYAKISDF   480
GLSKALGADD SYYTARSAGK WPLKWYAPEC INFRKFSSRS DVWSYGVTMW EALSYGQKPY   540
KKMKGPEVMA FIEQGKRMEC PPECPPELYA LMSDCWIYKW EDRPDFLTVE QRMRACYYSL   600
ASKVEGPPGS TQKAEAACA                                                619

SEQ ID NO: 37          moltype = AA   length = 5
FEATURE                Location/Qualifiers
REGION                 1..5
                       note = synthetic polypeptide
REPEAT                 1..5
                       note = the amino acids in this region can be repeated n
                        times, where n is an integer of at least one
source                 1..5
                       mol_type = protein
                       organism = synthetic construct
SEQUENCE: 37
GSGGS                                                                 5

SEQ ID NO: 38          moltype = AA   length = 4
FEATURE                Location/Qualifiers
REGION                 1..4
                       note = synthetic polypeptide
REPEAT                 1..4
                       note = the amino acids in this region can be repeated n
                        times, where n is an integer of at least one
source                 1..4
                       mol_type = protein
                       organism = synthetic construct
SEQUENCE: 38
GGGS                                                                  4
```

```
SEQ ID NO: 39            moltype = AA   length = 4
FEATURE                  Location/Qualifiers
REGION                   1..4
                         note = synthetic polypeptide
source                   1..4
                         mol_type = protein
                         organism = synthetic construct
SEQUENCE: 39
GGSG                                                                     4

SEQ ID NO: 40            moltype = AA   length = 5
FEATURE                  Location/Qualifiers
REGION                   1..5
                         note = synthetic polypeptide
source                   1..5
                         mol_type = protein
                         organism = synthetic construct
SEQUENCE: 40
GGSGG                                                                    5

SEQ ID NO: 41            moltype = AA   length = 5
FEATURE                  Location/Qualifiers
REGION                   1..5
                         note = synthetic polypeptide
source                   1..5
                         mol_type = protein
                         organism = synthetic construct
SEQUENCE: 41
GSGSG                                                                    5

SEQ ID NO: 42            moltype = AA   length = 5
FEATURE                  Location/Qualifiers
REGION                   1..5
                         note = synthetic polypeptide
source                   1..5
                         mol_type = protein
                         organism = synthetic construct
SEQUENCE: 42
GSGGG                                                                    5

SEQ ID NO: 43            moltype = AA   length = 5
FEATURE                  Location/Qualifiers
REGION                   1..5
                         note = synthetic polypeptide
source                   1..5
                         mol_type = protein
                         organism = synthetic construct
SEQUENCE: 43
GGGSG                                                                    5

SEQ ID NO: 44            moltype = AA   length = 5
FEATURE                  Location/Qualifiers
REGION                   1..5
                         note = synthetic polypeptide
source                   1..5
                         mol_type = protein
                         organism = synthetic construct
SEQUENCE: 44
GSSSG                                                                    5

SEQ ID NO: 45            moltype = AA   length = 5
FEATURE                  Location/Qualifiers
REGION                   1..5
                         note = synthetic polypeptide
source                   1..5
                         mol_type = protein
                         organism = synthetic construct
SEQUENCE: 45
DKTHT                                                                    5

SEQ ID NO: 46            moltype = AA   length = 4
FEATURE                  Location/Qualifiers
REGION                   1..4
                         note = synthetic polypeptide
source                   1..4
                         mol_type = protein
                         organism = synthetic construct
SEQUENCE: 46
CPPC                                                                     4
```

| | | |
|---|---|---|
| SEQ ID NO: 47<br>FEATURE<br>REGION<br><br>source | moltype = AA   length = 15<br>Location/Qualifiers<br>1..15<br>note = synthetic polypeptide<br>1..15<br>mol_type = protein<br>organism = synthetic construct | |
| SEQUENCE: 47<br>CPEPKSCDTP PPCPR | | 15 |
| SEQ ID NO: 48<br>FEATURE<br>REGION<br><br>source | moltype = AA   length = 12<br>Location/Qualifiers<br>1..12<br>note = synthetic polypeptide<br>1..12<br>mol_type = protein<br>organism = synthetic construct | |
| SEQUENCE: 48<br>ELKTPLGDTT HT | | 12 |
| SEQ ID NO: 49<br>FEATURE<br>REGION<br><br>source | moltype = AA   length = 10<br>Location/Qualifiers<br>1..10<br>note = synthetic polypeptide<br>1..10<br>mol_type = protein<br>organism = synthetic construct | |
| SEQUENCE: 49<br>KSCDKTHTCP | | 10 |
| SEQ ID NO: 50<br>FEATURE<br>REGION<br><br>source | moltype = AA   length = 7<br>Location/Qualifiers<br>1..7<br>note = synthetic polypeptide<br>1..7<br>mol_type = protein<br>organism = synthetic construct | |
| SEQUENCE: 50<br>KCCVDCP | | 7 |
| SEQ ID NO: 51<br>FEATURE<br>REGION<br><br>source | moltype = AA   length = 7<br>Location/Qualifiers<br>1..7<br>note = synthetic polypeptide<br>1..7<br>mol_type = protein<br>organism = synthetic construct | |
| SEQUENCE: 51<br>KYGPPCP | | 7 |
| SEQ ID NO: 52<br>FEATURE<br>REGION<br><br>source | moltype = AA   length = 15<br>Location/Qualifiers<br>1..15<br>note = synthetic polypeptide<br>1..15<br>mol_type = protein<br>organism = synthetic construct | |
| SEQUENCE: 52<br>EPKSCDKTHT CPPCP | | 15 |
| SEQ ID NO: 53<br>FEATURE<br>REGION<br><br>source | moltype = AA   length = 12<br>Location/Qualifiers<br>1..12<br>note = synthetic polypeptide<br>1..12<br>mol_type = protein<br>organism = synthetic construct | |
| SEQUENCE: 53<br>ERKCCVECPP CP | | 12 |
| SEQ ID NO: 54<br>FEATURE<br>REGION<br><br>source | moltype = AA   length = 17<br>Location/Qualifiers<br>1..17<br>note = synthetic polypeptide<br>1..17<br>mol_type = protein<br>organism = synthetic construct | |

```
SEQUENCE: 54
ELKTPLGDTT HTCPRCP                                                17

SEQ ID NO: 55           moltype = AA  length = 12
FEATURE                 Location/Qualifiers
REGION                  1..12
                        note = synthetic polypeptide
source                  1..12
                        mol_type = protein
                        organism = synthetic construct
SEQUENCE: 55
SPNMVPHAHH AQ                                                     12

SEQ ID NO: 56           moltype = AA  length = 45
FEATURE                 Location/Qualifiers
REGION                  1..45
                        note = synthetic polypeptide
source                  1..45
                        mol_type = protein
                        organism = synthetic construct
SEQUENCE: 56
TTTPAPRPPT PAPTIASQPL SLRPEACRPA AGGAVHTRGL DFACD                 45

SEQ ID NO: 57           moltype = AA  length = 23
FEATURE                 Location/Qualifiers
REGION                  1..23
                        note = synthetic polypeptide
source                  1..23
                        mol_type = protein
                        organism = synthetic construct
SEQUENCE: 57
LGLLVAGVLV LLVSLGVAIH LCC                                         23

SEQ ID NO: 58           moltype = AA  length = 25
FEATURE                 Location/Qualifiers
REGION                  1..25
                        note = synthetic polypeptide
source                  1..25
                        mol_type = protein
                        organism = synthetic construct
SEQUENCE: 58
ALIVLGGVAG LLLFIGLGIF FCVRC                                       25

SEQ ID NO: 59           moltype = AA  length = 23
FEATURE                 Location/Qualifiers
REGION                  1..23
                        note = synthetic polypeptide
source                  1..23
                        mol_type = protein
                        organism = synthetic construct
SEQUENCE: 59
LCYLLDGILF IYGVILTALF LRV                                         23

SEQ ID NO: 60           moltype = AA  length = 26
FEATURE                 Location/Qualifiers
REGION                  1..26
                        note = synthetic polypeptide
source                  1..26
                        mol_type = protein
                        organism = synthetic construct
SEQUENCE: 60
WVLVVVGGVL ACYSLLVTVA FIIFWV                                      26

SEQ ID NO: 61           moltype = AA  length = 26
FEATURE                 Location/Qualifiers
REGION                  1..26
                        note = synthetic polypeptide
source                  1..26
                        mol_type = protein
                        organism = synthetic construct
SEQUENCE: 61
VAAILGLGLV LGLLGPLAIL LALYLL                                      26

SEQ ID NO: 62           moltype = AA  length = 24
FEATURE                 Location/Qualifiers
REGION                  1..24
                        note = synthetic polypeptide
```

```
                              source            1..24
                                                mol_type = protein
                                                organism = synthetic construct
SEQUENCE: 62
ALPAALAVIS FLLGLGLGVA CVLA                                              24

SEQ ID NO: 63             moltype = AA    length = 44
FEATURE                   Location/Qualifiers
REGION                    1..44
                          note = synthetic polypeptide
source                    1..44
                          mol_type = protein
                          organism = synthetic construct
SEQUENCE: 63
FWVRSKRSRL LHSDYMNMTP RRPGPTRKHY QPYAPPRDFA AYRS                         44

SEQ ID NO: 64             moltype = AA    length = 35
FEATURE                   Location/Qualifiers
REGION                    1..35
                          note = synthetic polypeptide
source                    1..35
                          mol_type = protein
                          organism = synthetic construct
SEQUENCE: 64
TKKKYSSSVH DPNGEYMFMR AVNTAKKSRL TDVTL                                   35

SEQ ID NO: 65             moltype = AA    length = 37
FEATURE                   Location/Qualifiers
REGION                    1..37
                          note = synthetic polypeptide
source                    1..37
                          mol_type = protein
                          organism = synthetic construct
SEQUENCE: 65
RRDQRLPPDA HKPPGGGSFR TPIQEEQADA HSTLAKI                                 37

SEQ ID NO: 66             moltype = AA    length = 114
FEATURE                   Location/Qualifiers
REGION                    1..114
                          note = synthetic polypeptide
source                    1..114
                          mol_type = protein
                          organism = synthetic construct
SEQUENCE: 66
CCLRRHQGKQ NELSDTAGRE INLVDAHLKS EQTEASTRQN SQVLLSETGI YDNDPDLCFR        60
MQEGSEVYSN PCLEENKPGI VYASLNHSVI GPNSRLARNV KEAPTEYASI CVRS             114

SEQ ID NO: 67             moltype = AA    length = 49
FEATURE                   Location/Qualifiers
REGION                    1..49
                          note = synthetic polypeptide
source                    1..49
                          mol_type = protein
                          organism = synthetic construct
SEQUENCE: 67
HQRRKYRSNK GESPVEPAEP CRYSCPREEE GSTIPIQEDY RKPEPACSP                    49

SEQ ID NO: 68             moltype = AA    length = 187
FEATURE                   Location/Qualifiers
REGION                    1..187
                          note = synthetic polypeptide
source                    1..187
                          mol_type = protein
                          organism = synthetic construct
SEQUENCE: 68
RRACRKRIRQ KLHLCYPVQT SQPKLELVDS RPRRSSTQLR SGASVTEPVA EERGLMSQPL        60
METCHSVGAA YLESLPLQDA SPAGGPSSPR DLPEPRVSTE HTNNKIEKIY IMKADTVIVG       120
TVKAELPEGR GLAGPAEPEL EEELEADHTP HYPEQETEPP LGSCSDVMLS VEEEGKEDPL       180
PTAASGK                                                                187

SEQ ID NO: 69             moltype = AA    length = 54
FEATURE                   Location/Qualifiers
REGION                    1..54
                          note = synthetic polypeptide
source                    1..54
                          mol_type = protein
                          organism = synthetic construct
SEQUENCE: 69
HIWQLRSQCM WPRETQLLLE VPPSTEDARS CQFPEEERGE RSAEEKGRLG DLWV              54
```

```
SEQ ID NO: 70            moltype = AA   length = 60
FEATURE                  Location/Qualifiers
REGION                   1..60
                         note = synthetic polypeptide
source                   1..60
                         mol_type = protein
                         organism = synthetic construct
SEQUENCE: 70
CVKRRKPRGD VVKVIVSVQR KRQEAEGEAT VIEALQAPPD VTTVAVEETI PSFTGRSPNH    60

SEQ ID NO: 71            moltype = AA   length = 292
FEATURE                  Location/Qualifiers
REGION                   1..292
                         note = synthetic polypeptide
source                   1..292
                         mol_type = protein
                         organism = synthetic construct
SEQUENCE: 71
LEESVALRII TEGASILRQE KNLLDIDAPV TVCGDIHGQF FDLMKLFEVG GSPANTRYLF    60
LGDYVDRGYF SIECVLYLWA LKILYPKTLF LLRGNHECRH LTEYFTFKQE CKIKYSERVY   120
DACMDAFDCL PLAALMNQQF LCVHGGLSPE INTLDDIRKL DRFKEPPAYG PMCDILWSDP   180
LEDFGNEKTQ EHFTHNTVRG CSYFYSYPAV CEFLQHNNLL SILRAHEAQD AGYRMYRKSQ   240
TTGFPSLITI FSAPNYLDVY NNKAAVLKYE NNVMNIRQFN CSPHPYWLPN FM           292

SEQ ID NO: 72            moltype = AA   length = 165
FEATURE                  Location/Qualifiers
REGION                   1..165
                         note = synthetic polypeptide
source                   1..165
                         mol_type = protein
                         organism = synthetic construct
SEQUENCE: 72
MVNPTVFFDI AVDGEPLGRV SFELFADKVP KTAENFRALS TGEKGFGYKG SCFHRIIPGF    60
MCQGGDFTRH NGTGGKSIYG EKFEDENFIL KHTGPGILSM ANAGPNTNGS QFFICTAKTE   120
WLDGKHVVFG KVKEGMNIVE AMERFGSRNG KTSKKITIAD CGQLE                   165

SEQ ID NO: 73            moltype = AA   length = 804
FEATURE                  Location/Qualifiers
REGION                   1..804
                         note = synthetic polypeptide
source                   1..804
                         mol_type = protein
                         organism = synthetic construct
SEQUENCE: 73
MSNSYDSSSI KVLKGLDAVR KRPGMYIGDT DDGTGLHHMV FEVVDNAIDE ALAGHCKEII    60
VTIHADNSVS VQDDGRGIPT GIHPEEGVSA AEVIMTVLHA GGKFDDNSYK VSGGLHGVGV   120
SVVNALSQKL ELVIQREGKI HRQIYEHGVP QAPLAVTGET EKTGTMVRFW PSLETFTNVT   180
EFEYEILAKR LRELSFLNSG VSIRLRDKRD GKEDHFHYEG GIKAFVEYLN KNKTPIHPNI   240
FYFSTEKDGI GVEVALQWND GFQENIYCFT NNIPQRDGGT HLAGFRAAMT RTLNAYMDKE   300
GYSKKAKVSA TGDDAREGLI AVVSVKVPDP KFSSQTKDKL VSSEVKSAVE QQMNELLAEY   360
LLENPTDAKI VVGKIIDAAR AREAARRARE MTRRKGALDL AGLPGKLADC QERDPALSEL   420
YLVEGDSAGG SAKQGRNRKN QAILPLKGKI LNVEKARFDK MLSSQEVATL ITALGCGIGR   480
DEYNPDKLRY HSIIIMTDAD VDGSHIRTLL LTFFYRQMPE IVERGHVYIA QPPLYKVKKG   540
KQEQYIKDDE AMDQYQISIA LDGATLHTNA SAPALAGEAL EKLVSEYNAT QKMINRMERR   600
YPKAMLKELI YQPTLTEADL SDEQTVTRWV NALVSELNDK EQHGSQWKFD VHTNAEQNLF   660
EPIVRVRTHG VDTDYPLDHE FITGGEYRRI CTLGEKLRGL LEEDAFIERG ERRQPVASFE   720
QALDWLVKES RRGLSIQRYK GLGEMNPEQL WETTMDPESR RMLRVTVKDA IAADQLFTTL   780
MGDAVEPRRA FIEENALKAA NIDI                                         804

SEQ ID NO: 74            moltype = AA   length = 187
FEATURE                  Location/Qualifiers
REGION                   1..187
                         note = synthetic polypeptide
source                   1..187
                         mol_type = protein
                         organism = synthetic construct
SEQUENCE: 74
MVGSLNCIVA VSQNMGIGKN GDLPWPPLRN EFRYFQRMTT TSSVEGKQNL VIMGKKTWFS    60
IPEKNRPLKG RINLVLSREL KEPPQGAHFL SRSLDDALKL TEQPELANKV DMWIVGGSS    120
VYKEAMNHPG HLKLFVTRIM QDFESDTFFP EIDLEKYKLL PEYPGVLSDV QEEKGIKYKF   180
EVYEKND                                                             187

SEQ ID NO: 75            moltype = AA   length = 111
FEATURE                  Location/Qualifiers
REGION                   1..111
                         note = synthetic polypeptide
```

```
source                  1..111
                        mol_type = protein
                        organism = synthetic construct
SEQUENCE: 75
MASRGVQVET ISPGDGRTFP KRGQTCVVHY TGMLEDGKKV DSSRDRNKPF KFMLGKQEVI    60
RGWEEGVAQM SVGQRAKLTI SPDYAYGATG HPGIIPPHAT LVFDVELLKL E           111

SEQ ID NO: 76           moltype = AA  length = 183
FEATURE                 Location/Qualifiers
REGION                  1..183
                        note = synthetic polypeptide
source                  1..183
                        mol_type = protein
                        organism = synthetic construct
SEQUENCE: 76
MNGDETKKVE SEYIKKHHRH ELVESQCSST LVKHIKAPLH LVWSIVRRFD EPQKYKPFIS    60
RCVVQGKKLE VGSVREVDLK SGLPATKSTE VLEILDDNEH ILGIRIVGGD HRLKNYSSTI   120
SLHSETIDGK TGTLAIESFV VDVPEGNTKE ETCFFVEALI QCNLNSLADV TERLQAESME   180
KKI                                                                 183

SEQ ID NO: 77           moltype = AA  length = 161
FEATURE                 Location/Qualifiers
REGION                  1..161
                        note = synthetic polypeptide
source                  1..161
                        mol_type = protein
                        organism = synthetic construct
SEQUENCE: 77
METSQKYHTC GSTLVQTIDA PLSLVWSILR RFDNPQAYKQ FVKTCNLSSG DGGEGSVREV    60
TVVSGLPAEF SRERLDELDD ESHVMMISII GGDHRLVNYR SKTMAFVAAD TEEKTVVVES   120
YVVDVPEGNS EEETTSFADT IVGFNLKSLA KLSERVAHLK L                       161

SEQ ID NO: 78           moltype = AA  length = 159
FEATURE                 Location/Qualifiers
REGION                  1..159
                        note = synthetic polypeptide
source                  1..159
                        mol_type = protein
                        organism = synthetic construct
SEQUENCE: 78
MKTSQEQHVC GSTVVQTINA PLPLVWSILR RFDNPKTFKH FVKTCKLRSG DGGEGSVREV    60
TVVSDLPASF SLERLDELDD ESHVMVISII GGDHRLVNYQ SKTTVFVAAE EEKTVVVESY   120
VVDVPEGNTE EETTLFADTI VGCNLRSLAK LSEKMMELT                          159

SEQ ID NO: 79           moltype = AA  length = 164
FEATURE                 Location/Qualifiers
REGION                  1..164
                        note = synthetic polypeptide
source                  1..164
                        mol_type = protein
                        organism = synthetic construct
SEQUENCE: 79
MESSKQKRCR SSVVETIEAP LPLVWSILRS FDKPQAYQRF VKSCTMRSGG GGGKGGEGKG    60
SVRDVTLVSG FPADFSTERL EELDDESHVM VVSIIGGNHR LVNYKSKTKV VASPEDMAKK   120
TVVVESYVVD VPEGTSEEDT IFFVDNIIRY NLTSLAKLTK KMMK                    164

SEQ ID NO: 80           moltype = AA  length = 221
FEATURE                 Location/Qualifiers
REGION                  1..221
                        note = synthetic polypeptide
source                  1..221
                        mol_type = protein
                        organism = synthetic construct
SEQUENCE: 80
MANSESSSSP VNEEENSQRI STLHHQTMPS DLTQDEFTQL SQSIAEFHTY QLGNGRCSSL    60
LAQRIHAPPE TVWSVVRRFD RPQIYKHFIK SCNVSEDFEM RVGCTRDVNV ISGLPANTSR   120
ERLDLLDDDR RVTGFSITGG EHRLRNYKSV TTVHRFEKEE EEERIWTVVL ESYVVDVPEG   180
NSEEDTRLFA DTVIRLNLQK LASITEAMNR NNNNNNSSQV R                       221

SEQ ID NO: 81           moltype = AA  length = 190
FEATURE                 Location/Qualifiers
REGION                  1..190
                        note = synthetic polypeptide
source                  1..190
                        mol_type = protein
                        organism = synthetic construct
SEQUENCE: 81
MSSSPAVKGL TDEEQKTLEP VIKTYHQFEP DPTTCTSLIT QRIHAPASVV WPLIRRFDNP    60
ERYKHFVKRC RLISGDGDVG SVREVTVISG LPASTSTERL EFVDDDHRVL SFRVGGEHR   120
```

```
LKNYKSVTSV NEFLNQDSGK VYTVVLESYT VDIPEGNTEE DTKMFVDTVV KLNLQKLGVA    180
ATSAPMHDDE                                                          190

SEQ ID NO: 82           moltype = AA  length = 209
FEATURE                 Location/Qualifiers
REGION                  1..209
                        note = synthetic polypeptide
source                  1..209
                        mol_type = protein
                        organism = synthetic construct
SEQUENCE: 82
MNLAPIHDPS SSSTTTTSSS TPYGLTKDEF STLDSIIRTH HTFPRSPNTC TSLIAHRVDA    60
PAHAIWRFVR DFANPNKYKH FIKSCTIRVN GNGIKEIKVG TIREVSVVSG LPASTSVEIL    120
EVLDEEKRIL SFRVLGGEHR LNNYRSVTSV NEFVVLEKDK KKRVYSVVLE SYIVDIPQGN    180
TEEDTRMFVD TVVKSNLQNL AVISTASPT                                      209

SEQ ID NO: 83           moltype = AA  length = 207
FEATURE                 Location/Qualifiers
REGION                  1..207
                        note = synthetic polypeptide
source                  1..207
                        mol_type = protein
                        organism = synthetic construct
SEQUENCE: 83
MLAVHRPSSA VSDGDSVQIP MMIASFQKRF PSLSRDSTAA RFHTHEVGPN QCCSAVIQEI    60
SAPISTVWSV VRRFDNPQAY KHFLKSCSVI GGDGDNVGSL RQVHVVSGLP AASSTERLDI    120
LDDERHVISF SVVGGDHRLS NYRSVTTLHP SPISGTVVVE SYVVDVPPGN TKEETCDFVD    180
VIVRCNLQSL AKIAENTAAE SKKKMSL                                        207

SEQ ID NO: 84           moltype = AA  length = 203
FEATURE                 Location/Qualifiers
REGION                  1..203
                        note = synthetic polypeptide
source                  1..203
                        mol_type = protein
                        organism = synthetic construct
SEQUENCE: 84
MRSPVQLQHG SDATNGFHTL QPHDQTDGPI KRVCLTRGMH VPEHVAMHHT HDVGPDQCCS    60
SVVQMIHAPP ESVWALVRRF DNPKVYKNFI RQCRIVQGDG LHVGDLREVM VVSGLPAVSS    120
TERLEILDEE RHVISFSVVG GDHRLKNYRS VTTLHASDDE GTVVVESYIV DVPPGNTEEE    180
TLSFVDTIVR CNLQSLARST NRQ                                            203

SEQ ID NO: 85           moltype = AA  length = 215
FEATURE                 Location/Qualifiers
REGION                  1..215
                        note = synthetic polypeptide
source                  1..215
                        mol_type = protein
                        organism = synthetic construct
SEQUENCE: 85
MPTSIQFQRS STAAEAANAT VRNYPHHQK QVQKVSLTRG MADVPEHVEL SHTHVVGPSQ     60
CFSVVVQDVE APVSTVWSIL SRFEHPQAYK HFVKSCHVVI GDGREVGSVR EVRVVSGLPA    120
AFSLERLEIM DDDRHVISFS VVGGDHRLMN YKSVTTVHES EEDSDGKKRT RVVESYVVDV    180
PAGNDKEETC SFADTIVRCN LQSLAKLAEN TSKFS                               215

SEQ ID NO: 86           moltype = AA  length = 211
FEATURE                 Location/Qualifiers
REGION                  1..211
                        note = synthetic polypeptide
source                  1..211
                        mol_type = protein
                        organism = synthetic construct
SEQUENCE: 86
MEMIGGDDTD TEMYGALVTA QSLRLRHLHH CRENQCTSVL VKYIQAPVHL VWSLVRRFDQ    60
PQKYKPFISR CTVNGDPEIG CLREVNVKSG LPATTSTERL EQLDDEEHIL GINIIGGDHR    120
LKNYSSILTV HPEMIDGRSG TMVMESFVVD VPQGNTKDDT CYFVESLIKC NLKSLACVSE    180
RLAAQDITNS IATFCNASNG YREKNHTETN L                                   211

SEQ ID NO: 87           moltype = AA  length = 188
FEATURE                 Location/Qualifiers
REGION                  1..188
                        note = synthetic polypeptide
source                  1..188
                        mol_type = protein
                        organism = synthetic construct
```

```
SEQUENCE: 87
MEANGIENLT NPNQEREFIR RHHKHELVDN QCSSTLVKHI NAPVHIVWSL VRRFDQPQKY      60
KPFISRCVVK GNMEIGTVRE VDVKSGLPAT RSTERLELLD DNEHILSIRI VGGDHRLKNY     120
SSIISLHPET IEGRIGTLVI ESFVVDVPEG NTKDETCYFV EALIKCNLKS LADISERLAV    180
QDTTESRV                                                             188

SEQ ID NO: 88           moltype = AA   length = 187
FEATURE                 Location/Qualifiers
REGION                  1..187
                        note = synthetic polypeptide
source                  1..187
                        mol_type = protein
                        organism = synthetic construct
SEQUENCE: 88
MMDGVEGGTA MYGGLETVQY VRTHHQHLCR ENQCTSALVK HIKAPLHLVW SLVRRFDQPQ     60
KYKPFVSRCT VIGDPEIGSL REVNVKSGLP ATTSTERLEL LDDEEHILGI KIIGGDHRLK    120
NYSSILTVHP EIIEGRAGTM VIESFVVDVP QGNTKDETCY FVEALIRCNL KSLADVSERL    180
ASQDITQ                                                              187

SEQ ID NO: 89           moltype = AA   length = 191
FEATURE                 Location/Qualifiers
REGION                  1..191
                        note = synthetic polypeptide
source                  1..191
                        mol_type = protein
                        organism = synthetic construct
SEQUENCE: 89
MPSELTPEER SELKNSIAEF HTYQLDPGSC SSLHAQRIHA PPELVWSIVR RFDKPQTYKH     60
FIKSCSVEQN FEMRVGCTRD VIVISGLPAN TSTERLDILD DERRVTGFSI IGGEHRLTNY    120
KSVTTVHRFE KENRIWTVVL ESYVVDMPEG NSEDDTRMFA DTVVKLNLQK LATVAEAMAR    180
NSGDGSGSQV T                                                         191

SEQ ID NO: 90           moltype = AA   length = 434
FEATURE                 Location/Qualifiers
REGION                  1..434
                        note = synthetic polypeptide
source                  1..434
                        mol_type = protein
                        organism = synthetic construct
SEQUENCE: 90
MEEVSPAIAG PFRPFSETQM DFTGIRLGKG YCNNQYSNQD SENGDLMVSL PETSSCSVSG     60
SHGSESRKVL ISRINSPNLN MKESAAADIV VVDISAGDEI NGSDITSEKK MISRTESRSL    120
FEFKSVPLYG FTSICGRRPE MEDAVSTIPR FLQSSSGSML DGRFDPQSAA HFFGVYDGHG    180
GSQVANYCRE RMHLALAEEI AKEKPMLCDG DTWLEKWKKA LFNSFLRVDS EIESVAPETV    240
GSTSVVAVVF PSHIFVANCG DSRAVLCRGK TALPLSVDHK PDREDEAARI EAAGGKVIQW    300
NGARVFGVLA MSRSIGDRYL KPSIIPDPEV TAVKRVKEDD CLILASDGVW DVMTDEEACE    360
MARKRILLWH KKNAVAGDAS LLADERRKEG KDPAAMSAAE YLSKLAIQRG SKDNISVVVV    420
DLKPRRKLKS KPLN                                                      434

SEQ ID NO: 91           moltype = AA   length = 423
FEATURE                 Location/Qualifiers
REGION                  1..423
                        note = synthetic polypeptide
source                  1..423
                        mol_type = protein
                        organism = synthetic construct
SEQUENCE: 91
MDEVSPAVAV PFRPFTDPHA GLRGYCNGES RVTLPESSCS GDGAMKDSSF EINTRQDSLT     60
SSSSAMAGVD ISAGDEINGS DEFDPRSMNQ SEKKVLSRTE SRSLFEFKCV PLYGVTSICG    120
RRPEMEDSVS TIPRFLQVSS SSLLDGRVTN GFNPHLSAHF FGVYDGHGGS QVANYCRERM    180
HLALTEEIVK EKPEFCDGDT WQEKWKKALF NSFMRVDSEI ETVAHAPETV GSTSVVAVVF    240
PTHIFVANCG DSRAVLCRGK TPLALSVDHK PDRDDEAARI EAAGGKVIRW NGARVFGVLA    300
MSRSIGDRYL KPSVIPDPEV TSVRRVKEDD CLILASDGLW DVMTNEEVCD LARKRILLWH    360
KKNAMAGEAL LPAEKRGEGK DPAAMSAAEY LSKMALQKGS KDNISVVVVD LKGIRKFKSK    420
SLN                                                                  423

SEQ ID NO: 92           moltype = AA   length = 612
FEATURE                 Location/Qualifiers
REGION                  1..612
                        note = synthetic polypeptide
source                  1..612
                        mol_type = protein
                        organism = synthetic construct
SEQUENCE: 92
MKMDKKTIVW FRRDLRIEDN PALAAAAHEG SVFPVFIWCP EEEGQFYPGR ASRWWMKQSL     60
AHLSQSLKAL GSDLTIKTH NTISAILDCI RVTGATKVVF NHLYDPVSLV RDHTVKEKLV    120
ERGISVQSYN GDLLYEPWEI YCEKGKPFTS FNSYWKKCLD MSIESVMLPP PWRLMPITAA    180
AEAIWACSIE ELGLENEAEK PSNALLTRAW SPGWSNADKL LNEFIEKQLI DYAKNSKKVV    240
GNSTSLLSPY LHFGEISVRH VFQCARMKQI IWARDKNSEG EESADLFLRG IGLREYSRYI    300
```

```
CFNFPFTHEQ SLLSHLRFFP WDADVDKFKA WRQGRTGYPL VDAGMRELWA TGWMHNRIRV    360
IVSSFAVKFL LLPWKWGMKY FWDTLLDADL ECDILGWQYI SGSIPDGHEL DRLDNPALQG    420
AKYDPEGEYI RQWLPELARL PTEWIHHPWD APLTVLKASG VELGTNYAKP IVDIDTAREL    480
LAKAISRTRE AQIMIGAAPD EIVADSFEAL GANTIKEPGL CPSVSSNDQQ VPSAVRYNGS    540
KRVKPEEEEE RDMKKSRGFD ERELFSTAES SSSSSVFFVS QSCSLASEGK NLEGIQDSSD    600
QITTSLGKNG CK                                                        612

SEQ ID NO: 93           moltype = AA  length = 335
FEATURE                 Location/Qualifiers
REGION                  1..335
                        note = synthetic polypeptide
source                  1..335
                        mol_type = protein
                        organism = synthetic construct
SEQUENCE: 93
MNGAIGGDLL LNFPDMSVLE RQRAHLKYLN PTFDSPLAGF FADSSMITGG EMDSYLSTAG     60
LNLPMMYGET TVEGDSRLSI SPETTLGTGN FKKRKFDTET KDCNEKKKKM TMNRDDLVEE    120
GEEEKSKITE QNNGSTKSIK KMKHKAKKEE NNFSNDSSKV TKELEKTDYI HVRARRGQAT    180
DSHSIAERVR REKISERMKF LQDLVPGCDK ITGKAGMLDE IINYVQSLQR QIEFLSMKLA    240
IVNPRPDFDM DDIFAKEVAS TPMTVVPSPE MVLSGYSHEM VHSGYSSEMV NSGYLHVNPM    300
QQVNTSSDPL SCFNNGEAPS MWDSHVQNLY GNLGV                              335

SEQ ID NO: 94           moltype = AA  length = 533
FEATURE                 Location/Qualifiers
REGION                  1..533
                        note = synthetic polypeptide
source                  1..533
                        mol_type = protein
                        organism = synthetic construct
SEQUENCE: 94
MKRDHHHHHH QDKKTMMMNE EDDGNGMDEL LAVLGYKVRS SEMADVAQKL EQLEVMMSNV     60
QEDDLSQLAT ETVHYNPAEL YTWLDSMLTD LNPPSSNAEY DLKAIPGDAI LNQFAIDSAS    120
SSNQGGGGDT YTTNKRLKCS NGVVETTTAT AESTRHVVLV DSQENGVRLV HALLACAEAV    180
QKENLTVAEA LVKQIGFLAV SQIGAMRKVA TYFAEALARR IYRLSPSQSP IDHSLSDTLQ    240
MHFYETCPYL KFAHFTANQA ILEAFQGKKR VHVIDFSMSQ GLQWPALMQA LALRPGGPPV    300
FRLTGIGPPA PDNFDYLHEV GCKLAHLAEA IHVEFEYRGF VANTLADLDA SMLELRPSEI    360
ESVAVNSVFE LHKLLGRPGA IDKVLGVVNQ IKPEIFTVVE QESNHNSPIF LDRFTESLHY    420
YSTLFDSLEG VPSGQDKVMS EVYLGKQICN VVACDGPDRV ERHETLSQWR NRFGSAGFAA    480
AHIGSNAFKQ ASMLLALFNG GEGYRVEESD GCLMLGWHTR PLIATSAWKL STN            533

SEQ ID NO: 95           moltype = AA  length = 345
FEATURE                 Location/Qualifiers
REGION                  1..345
                        note = synthetic polypeptide
source                  1..345
                        mol_type = protein
                        organism = synthetic construct
SEQUENCE: 95
MAASDEVNLI ESRTVVPLNT WVLISNFKVA YNILRRPDGT FNRHLAEYLD RKVTANANPV     60
DGVFSFDVLI DRRINLLSRV YRPAYADQEQ PPSILDLEKP VDGDIVPVIL FFHGGSFAHS    120
SANSAIYDTL CRRLVGLCKC VVVSVNYRRA PENPYPCAYD DGWIALNWVN SRSWLKSKKD    180
SKVHIFLAGD SSGGNIAHNV ALRAGESGID VLGNILLNPM FGGNERTESE KSLDGKYFVT    240
VRDRDWYWKA FLPEGEDREH PACNPFSPRG KSLEGVSFPK SLVVVAGLDL IRDWQLAYAE    300
GLKKAGQEVK LMHLEKATVG FYLLPNNNHF HNVMDEISAF VNAEC                    345

SEQ ID NO: 96           moltype = AA  length = 358
FEATURE                 Location/Qualifiers
REGION                  1..358
                        note = synthetic polypeptide
source                  1..358
                        mol_type = protein
                        organism = synthetic construct
SEQUENCE: 96
MAGGNEVNLN ECKRIVPLNT WVLISNFKLA YKVLRRPDGS FNRDLAEFLD RKVPANSFPL     60
DGVFSFDHVD STTNLLTRIY QPASLLHQTR HGTLELTKPL STTEIVPVLI FFHGGSFTHS    120
SANSAIYDTF CRRLVTICGV VVVSVDYRRS PEHRYPCAYD DGWNALNWVK SRVWLQSGKD    180
SNVYVYLAGD SSGGNIAHNV AVRATNEGVK VLGNILHPM FGGQERTQSE KTLDGKYFVT     240
IQDRDWYWRA YLPEGEDRDH PACNPFGPRG QSLKGVNFPK SLVVVAGLDL VQDWQLAYVD    300
GLKKTGLEVN LLYLKQATIG FYFLPNNDHF HCLMEELNKF VHSIEDSQSK SSPVLLTP      358

SEQ ID NO: 97           moltype = AA  length = 344
FEATURE                 Location/Qualifiers
REGION                  1..344
                        note = synthetic polypeptide
source                  1..344
                        mol_type = protein
                        organism = synthetic construct
```

-continued

```
SEQUENCE: 97
MAGSEEVNLI ESKTVVPLNT WVLISNFKLA YNLLRRPDGT FNRHLAEFLD RKVPANANPV   60
NGVFSFDVII DRQTNLLSRV YRPADAGTSP SITDLQNPVD GEIVPVIVFF HGGSFAHSSA  120
NSAIYDTLCR RLVGLCGAVV VSVNYRRAPE NRYPCAYDDG WAVLKWVNSS SWLRSKKDSK  180
VRIFLAGDSS GGNIVHNVAV RAVESRIDVL GNILLNPMFG GTERTESEKR LDGKYFVTVR  240
DRDWYWRAFL PEGEDREHPA CSPFGPRSKS LEGLSFPKSL VVVAGLDLIQ DWQLKYAEGL  300
KKAGQEVKLL YLEQATIGFY LLPNNNHFHT VMDEIAAFVN AECQ                  344

SEQ ID NO: 98              moltype = AA  length = 113
FEATURE                    Location/Qualifiers
REGION                     1..113
                           note = synthetic polypeptide
source                     1..113
                           mol_type = protein
                           organism = synthetic construct
SEQUENCE: 98
MGGLEPCSRL LLLPLLLAVS GLRPVQAQAQ SDCSCSTVSP GVLAGIVMGD LVLTVLIALA   60
VYFLGRLVPR GRGAAEAATR KQRITETESP YQELQGQRSD VYSDLNTQRP YYK         113

SEQ ID NO: 99              moltype = AA  length = 112
FEATURE                    Location/Qualifiers
REGION                     1..112
                           note = synthetic polypeptide
source                     1..112
                           mol_type = protein
                           organism = synthetic construct
SEQUENCE: 99
MGGLEPCSRL LLLPLLLAVS GLRPVQAQAQ SDCSCSTVSP GVLAGIVMGD LVLTVLIALA   60
VYFLGRLVPR GRGAAEATRK QRITETESPY QELQGQRSDV YSDLNTQRPY YK          112

SEQ ID NO: 100             moltype = AA  length = 102
FEATURE                    Location/Qualifiers
REGION                     1..102
                           note = synthetic polypeptide
source                     1..102
                           mol_type = protein
                           organism = synthetic construct
SEQUENCE: 100
MGGLEPCSRL LLLPLLLAVS DCSCSTVSPG VLAGIVMGDL VLTVLIALAV YFLGRLVPRG   60
RGAAEAATRK QRITETESPY QELQGQRSDV YSDLNTQRPY YK                     102

SEQ ID NO: 101             moltype = AA  length = 101
FEATURE                    Location/Qualifiers
REGION                     1..101
                           note = synthetic polypeptide
source                     1..101
                           mol_type = protein
                           organism = synthetic construct
SEQUENCE: 101
MGGLEPCSRL LLLPLLLAVS DCSCSTVSPG VLAGIVMGDL VLTVLIALAV YFLGRLVPRG   60
RGAAEATRKQ RITETESPYQ ELQGQRSDVY SDLNTQRPYY K                      101

SEQ ID NO: 102             moltype = AA  length = 21
FEATURE                    Location/Qualifiers
REGION                     1..21
                           note = synthetic polypeptide
source                     1..21
                           mol_type = protein
                           organism = synthetic construct
SEQUENCE: 102
ESPYQELQGQ RSDVYSDLNT Q                                             21

SEQ ID NO: 103             moltype = AA  length = 86
FEATURE                    Location/Qualifiers
REGION                     1..86
                           note = synthetic polypeptide
source                     1..86
                           mol_type = protein
                           organism = synthetic construct
SEQUENCE: 103
MIPAVVLLLL LLVEQAAALG EPQLCYILDA ILFLYGIVLT LLYCRLKIQV RKAAITSYEK   60
SDGVYTGLST RNQETYETLK HEKPPQ                                        86

SEQ ID NO: 104             moltype = AA  length = 21
FEATURE                    Location/Qualifiers
REGION                     1..21
                           note = synthetic polypeptide
```

| | | |
|---|---|---|
| source | 1..21<br>mol_type = protein<br>organism = synthetic construct | |
| SEQUENCE: 104 | | |
| DGVYTGLSTR NQETYETLKH E | | 21 |

| | | |
|---|---|---|
| SEQ ID NO: 105<br>FEATURE<br>REGION | moltype = AA   length = 171<br>Location/Qualifiers<br>1..171<br>note = synthetic polypeptide | |
| source | 1..171<br>mol_type = protein<br>organism = synthetic construct | |
| SEQUENCE: 105 | | |
| MEHSTFLSGL VLATLLSQVS PFKIPIEELE DRVFVNCNTS ITWVEGTVGT LLSDITRLDL | | 60 |
| GKRILDPRGI YRCNGTDIYK DKESTVQVHY RMCQSCVELD PATVAGIIVT DVIATLLLAL | | 120 |
| GVFCFAGHET GRLSGAADTQ ALLRNDQVYQ PLRDRDDAQY SHLGGNWARN K | | 171 |

| | | |
|---|---|---|
| SEQ ID NO: 106<br>FEATURE<br>REGION | moltype = AA   length = 127<br>Location/Qualifiers<br>1..127<br>note = synthetic polypeptide | |
| source | 1..127<br>mol_type = protein<br>organism = synthetic construct | |
| SEQUENCE: 106 | | |
| MEHSTFLSGL VLATLLSQVS PFKIPIEELE DRVFVNCNTS ITWVEGTVGT LLSDITRLDL | | 60 |
| GKRILDPRGI YRCNGTDIYK DKESTVQVHY RTADTQALLR NDQVYQPLRD RDDAQYSHLG | | 120 |
| GNWARNK | | 127 |

| | | |
|---|---|---|
| SEQ ID NO: 107<br>FEATURE<br>REGION | moltype = AA   length = 21<br>Location/Qualifiers<br>1..21<br>note = synthetic polypeptide | |
| source | 1..21<br>mol_type = protein<br>organism = synthetic construct | |
| SEQUENCE: 107 | | |
| DQVYQPLRDR DDAQYSHLGG N | | 21 |

| | | |
|---|---|---|
| SEQ ID NO: 108<br>FEATURE<br>REGION | moltype = AA   length = 207<br>Location/Qualifiers<br>1..207<br>note = synthetic polypeptide | |
| source | 1..207<br>mol_type = protein<br>organism = synthetic construct | |
| SEQUENCE: 108 | | |
| MQSGTHWRVL GLCLLSVGVW GQDGNEEMGG ITQTPYKVSI SGTTVILTCP QYPGSEILWQ | | 60 |
| HNDKNIGGDE DDKNIGSDED HLSLKEFSEL EQSGYYVCYP RGSKPEDANF YLYLRARVCE | | 120 |
| NCMEMDVMSV ATIVIVDICI TGGLLLLVYY WSKNRKAKAK PVTRGAGAGG RQRGQNKERP | | 180 |
| PPVPNPDYEP IRKGQRDLYS GLNQRRI | | 207 |

| | | |
|---|---|---|
| SEQ ID NO: 109<br>FEATURE<br>REGION | moltype = AA   length = 21<br>Location/Qualifiers<br>1..21<br>note = synthetic polypeptide | |
| source | 1..21<br>mol_type = protein<br>organism = synthetic construct | |
| SEQUENCE: 109 | | |
| NPDYEPIRKG QRDLYSGLNQ R | | 21 |

| | | |
|---|---|---|
| SEQ ID NO: 110<br>FEATURE<br>REGION | moltype = AA   length = 182<br>Location/Qualifiers<br>1..182<br>note = synthetic polypeptide | |
| source | 1..182<br>mol_type = protein<br>organism = synthetic construct | |
| SEQUENCE: 110 | | |
| MEQGKGLAVL ILAIILLQGT LAQSIKGNHL VKVYDYQEDG SVLLTCDAEA KNITWFKDGK | | 60 |
| MIGFLTEDKK KWNLGSNAKD PRGMYQCKGS QNKSKPLQVY RMCQNCIEL NAATISGFLF | | 120 |
| AEIVSIFVLA VGVYFIAGQD GVRQSRASDK QTLLPNDQLY QPLKDREDDQ YSHLQGNQLR | | 180 |
| RN | | 182 |

```
SEQ ID NO: 111          moltype = AA  length = 21
FEATURE                 Location/Qualifiers
REGION                  1..21
                        note = synthetic polypeptide
source                  1..21
                        mol_type = protein
                        organism = synthetic construct
SEQUENCE: 111
DQLYQPLKDR EDDQYSHLQG N                                              21

SEQ ID NO: 112          moltype = AA  length = 163
FEATURE                 Location/Qualifiers
REGION                  1..163
                        note = synthetic polypeptide
source                  1..163
                        mol_type = protein
                        organism = synthetic construct
SEQUENCE: 112
MKWKALFTAA ILQAQLPITE AQSFGLLDPK LCYLLDGILF IYGVILTALF LRVKFSRSAD    60
APAYQQGQNQ LYNELNLGRR EEYDVLDKRR GRDPEMGGKP RRKNPQEGLY NELQKDKMAE   120
AYSEIGMKGE RRRGKGHDGL YQGLSTATKD TYDALHMQAL PPR                     163

SEQ ID NO: 113          moltype = AA  length = 164
FEATURE                 Location/Qualifiers
REGION                  1..164
                        note = synthetic polypeptide
source                  1..164
                        mol_type = protein
                        organism = synthetic construct
SEQUENCE: 113
MKWKALFTAA ILQAQLPITE AQSFGLLDPK LCYLLDGILF IYGVILTALF LRVKFSRSAD    60
APAYQQGQNQ LYNELNLGRR EEYDVLDKRR GRDPEMGGKP QRRKNPQEGL YNELQKDKMA   120
EAYSEIGMKG ERRRGKGHDG LYQGLSTATK DTYDALHMQA LPPR                    164

SEQ ID NO: 114          moltype = AA  length = 21
FEATURE                 Location/Qualifiers
REGION                  1..21
                        note = synthetic polypeptide
source                  1..21
                        mol_type = protein
                        organism = synthetic construct
SEQUENCE: 114
NQLYNELNLG RREEYDVLDK R                                              21

SEQ ID NO: 115          moltype = AA  length = 22
FEATURE                 Location/Qualifiers
REGION                  1..22
                        note = synthetic polypeptide
source                  1..22
                        mol_type = protein
                        organism = synthetic construct
SEQUENCE: 115
EGLYNELQKD KMAEAYSEIG MK                                             22

SEQ ID NO: 116          moltype = AA  length = 21
FEATURE                 Location/Qualifiers
REGION                  1..21
                        note = synthetic polypeptide
source                  1..21
                        mol_type = protein
                        organism = synthetic construct
SEQUENCE: 116
DGLYQGLSTA TKDTYDALHM Q                                              21

SEQ ID NO: 117          moltype = AA  length = 226
FEATURE                 Location/Qualifiers
REGION                  1..226
                        note = synthetic polypeptide
source                  1..226
                        mol_type = protein
                        organism = synthetic construct
SEQUENCE: 117
MPGGPGVLQA LPATIFLLFL LSAVYLGPGC QALWMHKVPA SLMVSLGEDA HFQCPHNSSN    60
NANVTWWRVL HGNYTWPPEF LGPGEDPNGT LIIQNVNKSH GGIYVCRVQE GNESYQQSCG   120
TYLRVRQPPP RPFLDMGEGT KNRIITAEGI ILLFCAVVPG TLLLFRKRWQ NEKLGLDAGD   180
EYEDENLYEG LNLDDCSMYE DISRGLQGTY QDVGSLNIGD VQLEKP                  226
```

```
SEQ ID NO: 118         moltype = AA   length = 188
FEATURE                Location/Qualifiers
REGION                 1..188
                       note = synthetic polypeptide
source                 1..188
                       mol_type = protein
                       organism = synthetic construct
SEQUENCE: 118
MPGGPGVLQA LPATIFLLFL LSAVYLGPGC QALWMHKVPA SLMVSLGEDA HFQCPHNSSN    60
NANVTWWRVL HGNYTWPPEF LGPGEDPNEP PPRPFLDMGE GTKNRIITAE GIILLFCAVV   120
PGTLLLFRKR WQNEKLGLDA GDEYEDENLY EGLNLDDCSM YEDISRGLQG TYQDVGSLNI   180
GDVQLEKP                                                           188

SEQ ID NO: 119         moltype = AA   length = 21
FEATURE                Location/Qualifiers
REGION                 1..21
                       note = synthetic polypeptide
source                 1..21
                       mol_type = protein
                       organism = synthetic construct
SEQUENCE: 119
ENLYEGLNLD DCSMYEDISR G                                             21

SEQ ID NO: 120         moltype = AA   length = 20
FEATURE                Location/Qualifiers
REGION                 1..20
                       note = synthetic polypeptide
source                 1..20
                       mol_type = protein
                       organism = synthetic construct
SEQUENCE: 120
RPRRSPAQDG KVYINMPGRG                                               20

SEQ ID NO: 121         moltype = AA   length = 68
FEATURE                Location/Qualifiers
REGION                 1..68
                       note = synthetic polypeptide
source                 1..68
                       mol_type = protein
                       organism = synthetic construct
SEQUENCE: 121
FWVLVVVGGV LACYSLLVTV AFIIFWVRSK RSRLLHSDYM NMTPRRPGPT RKHYQPYAPP    60
RDFAAYRS                                                            68

SEQ ID NO: 122         moltype = AA   length = 9
FEATURE                Location/Qualifiers
REGION                 1..9
                       note = synthetic polypeptide
source                 1..9
                       mol_type = protein
                       organism = synthetic construct
SEQUENCE: 122
YPYDVPDYA                                                            9

SEQ ID NO: 123         moltype = AA   length = 8
FEATURE                Location/Qualifiers
REGION                 1..8
                       note = synthetic polypeptide
source                 1..8
                       mol_type = protein
                       organism = synthetic construct
SEQUENCE: 123
DYKDDDDK                                                             8

SEQ ID NO: 124         moltype = AA   length = 5
FEATURE                Location/Qualifiers
REGION                 1..5
                       note = synthetic polypeptide
source                 1..5
                       mol_type = protein
                       organism = synthetic construct
SEQUENCE: 124
HHHHH                                                                5

SEQ ID NO: 125         moltype = AA   length = 6
FEATURE                Location/Qualifiers
REGION                 1..6
                       note = synthetic polypeptide
```

```
source                  1..6
                        mol_type = protein
                        organism = synthetic construct
SEQUENCE: 125
HHHHHH                                                                    6

SEQ ID NO: 126          moltype = AA   length = 8
FEATURE                 Location/Qualifiers
REGION                  1..8
                        note = synthetic polypeptide
source                  1..8
                        mol_type = protein
                        organism = synthetic construct
SEQUENCE: 126
WSHPQFEK                                                                  8

SEQ ID NO: 127          moltype = AA   length = 5
FEATURE                 Location/Qualifiers
REGION                  1..5
                        note = synthetic polypeptide
source                  1..5
                        mol_type = protein
                        organism = synthetic construct
SEQUENCE: 127
RYIRS                                                                     5

SEQ ID NO: 128          moltype = AA   length = 4
FEATURE                 Location/Qualifiers
REGION                  1..4
                        note = synthetic polypeptide
source                  1..4
                        mol_type = protein
                        organism = synthetic construct
SEQUENCE: 128
FHHT                                                                      4

SEQ ID NO: 129          moltype = AA   length = 17
FEATURE                 Location/Qualifiers
REGION                  1..17
                        note = synthetic polypeptide
source                  1..17
                        mol_type = protein
                        organism = synthetic construct
SEQUENCE: 129
WEAAAREACC RECCARA                                                       17

SEQ ID NO: 130          moltype =      length =
SEQUENCE: 130
000

SEQ ID NO: 131          moltype =      length =
SEQUENCE: 131
000

SEQ ID NO: 132          moltype = DNA   length = 24
FEATURE                 Location/Qualifiers
misc_feature            1..24
                        note = synthetic polynucleotide
source                  1..24
                        mol_type = other DNA
                        organism = synthetic construct
SEQUENCE: 132
gattacaagg atgacgatga caag                                               24

SEQ ID NO: 133          moltype = AA   length = 732
FEATURE                 Location/Qualifiers
REGION                  1..732
                        note = synthetic polypeptide
source                  1..732
                        mol_type = protein
                        organism = synthetic construct
SEQUENCE: 133
GGATCCCAGG TACAACTGCA GCAGTCTGGG CCTGAGCTGG AGAAGCCTGG CGCTTCAGTG    60
AAGATATCCT GCAAGGCTTC TGGTTACTCA TTCACTGGCT ACACCATGAA CTGGGTGAAG   120
CAGAGCCATG GAAAGAGCCT TGAGTGGATT GGACTTATTA CTCCTTACAA TGGTGCTTCT   180
AGCTACAACC AGAAGTTCAG GGGCAAGGCC ACATTAACTG TAGACAAGTC ATCCAGCACA   240
GCCTACATGG AACTCCTCAG TCTGACATCT GAAGACTCTG CAGTCTATTT CTGTGCAAGG   300
GGGGGTTACG ACGGGAGGGG TTTTGACTAC TGGGGCCAAG GACCACGGT CACCGTCTCC    360
TCAGGTGGAG GCGGTTCAGG CGGCGGTGGC TCTAGCGGTG GCGGATCGGA CATCGAGCTC   420
```

```
ACTCAGTCTC CAGCAATCAT GTCTGCATCT CCAGGGGAGA AGGTCACCAT GACCTGCAGT    480
GCCAGCTCAA GTGTAAGTTA CATGCACTGG TACCAGCAGA AGTCAGGCAC CTCCCCCAAA    540
AGATGGATTT ATGACACATC CAAACTGGCT TCTGGAGTCC CAGGTCGCTT CAGTGGCAGT    600
GGGTCTGGAA ACTCTTACTC TCTCACAATC AGCAGCGTGG AGGCTGAAGA TGATGCAACT    660
TATTACTGCC AGCAGTGGAG TAAGCACCCT CTCACGTACG GTGCTGGGAC AAAGTTGGAA    720
ATCAAAGCTA GC                                                       732

SEQ ID NO: 134          moltype = AA  length = 244
FEATURE                 Location/Qualifiers
REGION                  1..244
                        note = synthetic polypeptide
source                  1..244
                        mol_type = protein
                        organism = synthetic construct
SEQUENCE: 134
GSQVQLQQSG PELEKPGASV KISCKASGYS FTGYTMNWVK QSHGKSLEWI GLITPYNGAS     60
SYNQKFRGKA TLTVDKSSST AYMDLLSLTS EDSAVYFCAR GGYDGRGFDY WGQGTTVTVS    120
SGGGGSGGGG SSGGGSDIEL TQSPAIMSAS PGEKVTMTCS ASSSVSYMHW YQQKSGTSPK    180
RWIYDTSKLA SGVPGRFSGS GSGNSYSLTI SSVEAEDDAT YYCQQWSKHP LTYGAGTKLE    240
IKAS                                                                244

SEQ ID NO: 135          moltype = DNA  length = 729
FEATURE                 Location/Qualifiers
misc_feature            1..729
                        note = synthetic polynucleotide
source                  1..729
                        mol_type = other DNA
                        organism = synthetic construct
SEQUENCE: 135
ggatcccagg tgcagctgca ggaatctggc cctggcctcg tgaagccagc gagacactg      60
agcctgacct gtaccgtgtc tggcggctct gtgtccagcg gcagctacta ctggtcctgg    120
atcagacagc cccctggcaa gggcctggaa tggatcggct acatctacta cagcggctcc    180
accaactaca accccagcct gaagtccaga gtgaccatca gcgtggacac cagcaagaac    240
cagttctccc tgaagctgag cagcgtgaca gccgccgata ccgccgtgta ctactgtgcc    300
agagagggca agaacggcgc cttcgacatc tggggccagg gcacaatggt caccgtgtca    360
tctggtggag gaggatctgg gggaggcgga agcggaggcg gcggatctga tattcagatg    420
acccagagcc ccagcagcct gagcgcctct gtgggcgaca gagtgacaat tacctgccgg    480
gccagccaga gcatcagcag ctacctgaac tggtatcagc agaagcccgg caaggccccc    540
aaactgctga tctacgccgc cagctctctg cagtctggcg tgcccagcag attttccggc    600
tctggcagcg gcaccgactt caccctgacc atctctagcc tgcagcccga ggacttcgcc    660
acctactact gccagcagag ctacagcacc cccctgacct ttggcggagg caccaaggtg    720
gaaatcaag                                                           729

SEQ ID NO: 136          moltype = AA  length = 243
FEATURE                 Location/Qualifiers
REGION                  1..243
                        note = synthetic polypeptide
source                  1..243
                        mol_type = protein
                        organism = synthetic construct
SEQUENCE: 136
GSQVQLQESG PGLVKPSETL SLTCTVSGGS VSSGSYYWSW IRQPPGKGLE WIGYIYYSGS     60
TNYNPSLKSR VTISVDTSKN QFSLKLSSVT AADTAVYYCA REGKNGAFDI WGQGTMVTVS    120
SGGGGSGGGG SGGGGSDIQM TQSPSSLSAS VGDRVTITCR ASQSISSYLN WYQQKPGKAP    180
KLLIYAASSL QSGVPSRFSG SGSGTDFTLT ISSLQPEDFA TYYCQQSYST PLTFGGGTKV    240
EIK                                                                 243

SEQ ID NO: 137          moltype = DNA  length = 1044
FEATURE                 Location/Qualifiers
misc_feature            1..1044
                        note = synthetic polynucleotide
source                  1..1044
                        mol_type = other DNA
                        organism = synthetic construct
SEQUENCE: 137
atggctgcga gcgatgaagt taatcttatt gagagcagaa cagtggttcc tctcaataca     60
tgggttttaa tatccaactt caaagtagcc tacaatatcc ttcgtcgccc tgatggaacc    120
tttaaccgac acttagctga gtatctagac cgtaaagtca ctgcaaacgc caatccggtt    180
gatggggttt tctcgttcga tgtcttgatt gatcgcaagt tcaatcttcc aagcagagtc    240
tatagaccag cttatgcaga tcaagagcaa cctcctagta ttttagatct cgagaagcct    300
gttgatggcg acattgtccc tgttatattg ttccttccatg gaggtagctt tgctcattct    360
tctgcaaaca gtgccatcta cgatactctt gtcgcaggc ttgttggttt gtgcaagtgt    420
gttgttgtct ctgtgaatta tcggcgtgca ccagagaatc catacccttg tgcttatgat    480
gatggttga ttgctcttaa ttgggttaac tcgagatctg ggcttaaatc caagaaagac    540
tcaaaggtcc atattttctt ggctggtgat agctctggag taacatcgc gcataatgtg    600
gctttaagag cgggtgaatc gggaatcgat gttttgggga acattctgct gaatcctatg    660
tttggtggga atgagagaac ggagtctgag aaaagtttgg atgggaaata ctttgtgacg    720
gttagagacc gcgattggta ctgaaaagcg ttttacccg agggagaaga tagagagcat    780
ccagcgtgta atccgtttag ccccgagggg aaaagctag aaggagtgag ttttcccaag    840
```

```
agtcttgtgg ttgtcgcggg tttggatttg attagagatt ggcagttggc atacgcggaa    900
gggctcaaga aagcgggtca agaggttaag cttatgcatt tagagaaagc aactgttggg    960
ttttacctct tgcctaataa caatcatttc cataatgtta tggatgagat ttcggcgttt   1020
gtaaacgcgg aatgtatgcg tgac                                          1044

SEQ ID NO: 138            moltype = AA  length = 348
FEATURE                   Location/Qualifiers
REGION                    1..348
                          note = synthetic polypeptide
source                    1..348
                          mol_type = protein
                          organism = synthetic construct
SEQUENCE: 138
MAASDEVNLI ESRTVVPLNT WVLISNFKVA YNILRRPDGT FNRHLAEYLD RKVTANANPV     60
DGVFSFDVLI DRRINLLSRV YRPAYADQEQ PPSILDLEKP VDGDIVPVIL FFHGGSFAHS    120
SANSAIYDTL CRRLVGLCKC VVVSVNYRRA PENPYPCAYD DGWIALNWVN SRSWLKSKKD    180
SKVHIFLAGD SSGGNIAHNV ALRAGESGID VLGNILLNPM FGGNERTESE KSLDGKYFVT    240
VRDRDWYWKA FLPEGEDREH PACNPFSPRG KSLEGVSFPK SLVVVAGLDL IRDWQLAYAE    300
GLKKAGQEVK LMHLEKATVG FYLLPNNNHF HNVMDEISAF VNAECMRD                 348

SEQ ID NO: 139            moltype = DNA  length = 276
FEATURE                   Location/Qualifiers
misc_feature              1..276
                          note = synthetic polynucleotide
source                    1..276
                          mol_type = other DNA
                          organism = synthetic construct
SEQUENCE: 139
atgaagagag atcatcatca tcatcatcat caagataaga agactatgat gatgaatgaa     60
gaagacgacg gtaacggcat ggatgagctt ctagctgttc ttggttacaa ggttaggtca    120
tccgaaatgg ctgatgttgc tcagaaactc gagcagcttg aagttatgat gtctaatgtt    180
caagaagacg atctttctca actcgctact gagactgttc actataatcc ggcggagctt    240
tacacgtggc ttgattctat gctcaccgac cttaat                              276

SEQ ID NO: 140            moltype = AA  length = 92
FEATURE                   Location/Qualifiers
REGION                    1..92
                          note = synthetic polypeptide
source                    1..92
                          mol_type = protein
                          organism = synthetic construct
SEQUENCE: 140
MKRDHHHHHH QDKKTMMMNE EDDGNGMDEL LAVLGYKVRS SEMADVAQKL EQLEVMMSNV     60
QEDDLSQLAT ETVHYNPAEL YTWLDSMLTD LN                                   92

SEQ ID NO: 141            moltype = DNA  length = 729
FEATURE                   Location/Qualifiers
misc_feature              1..729
                          note = synthetic polynucleotide
source                    1..729
                          mol_type = other DNA
                          organism = synthetic construct
SEQUENCE: 141
ggatcccagg tgcagctggt gcagtctggc gccgaagtga aaagaccagg cgccagcgtg     60
caggtctcct gtagagccag cggctacagc atcaacacct actacatgca gtgggtgcgc    120
caggcccacg gcgctggact ggaatggatg ggcgtgatca cccccagcgg cgtgacaagc    180
tacgcccaga aattccaggg cagagtgacc ctgaccaacg acaccagcac caacacagtg    240
tacatgcagc tgaacagcct gaccagcgcc gacaccgccg tgtactactg tgccagatgg    300
gccctgtggg gcgacttcgg catggatgtg tggggcaagg gcaccctcgt gaccgtgtct    360
agcggaggcg gaggatctgg cggaggggga tctggaggcg gcggaagcga catccagatg    420
acccagagcc ctagcaccct gagcgccagc atcggcgata gagtgaccat cacctgtcgg    480
gccagcgacg gcatctatca ctggctggcc tggtatcagc agaagcccgg caaggccccc    540
aagctgctga tctacaaggc cagctctctg gcctctggcg ccctagcag attttctgtt    600
agcggctccg gcaccgactt caccctgaca atcagcagcc tgcagccga cgacttcgcc    660
acctactatt gccagcagta cagcaactac cccctgacct tcggcggagg caccaagctg    720
gaaatcaag                                                            729

SEQ ID NO: 142            moltype = AA  length = 243
FEATURE                   Location/Qualifiers
REGION                    1..243
                          note = synthetic polypeptide
source                    1..243
                          mol_type = protein
                          organism = synthetic construct
SEQUENCE: 142
GSQVQLVQSG AEVKRPGASV QVSCRASGYS INTYYMQWVR QAPGAGLEWM GVINPSGVTS     60
YAQKFQGRVT LTNDTSTNTV YMQLNSLTSA DTAVYYCARW ALWGDFGMDV WGKGTLVTVS    120
SGGGGSGGGG SGGGGSDIQM TQSPSTLSAS IGDRVTITCR ASEGIYHWLA WYQQKPGKAP    180
```

```
KLLIYKASSL ASGAPSRFSG SGSGTDFTLT ISSLQPDDFA TYYCQQYSNY PLTFGGGTKL    240
EIK                                                                 243

SEQ ID NO: 143          moltype = DNA  length = 135
FEATURE                 Location/Qualifiers
misc_feature            1..135
                        note = synthetic polynucleotide
source                  1..135
                        mol_type = other DNA
                        organism = synthetic construct
SEQUENCE: 143
accacgacgc cagcgccgcg accaccaaca ccggcgccca ccatcgcgtc gcagccctg     60
tccctgcgcc cagaggcgtg ccggccagcg gcggggggcg cagtgcacac gaggggctg    120
gacttcgcct gtgat                                                    135

SEQ ID NO: 144          moltype = DNA  length = 204
FEATURE                 Location/Qualifiers
misc_feature            1..204
                        note = synthetic polynucleotide
source                  1..204
                        mol_type = other DNA
                        organism = synthetic construct
SEQUENCE: 144
ttttgggtgc tggtggtggt tggtggagtc ctggcttgct atagcttgct agtaacagtg    60
gcctttatta ttttctgggt gaggagtaag aggagcaggc tcctgcacag tgactacatg   120
aacatgactc cccgccgccc cgggcccacc cgcaagcatt accagccta tgccccacca    180
cgcgacttcg cagcctatcg ctcc                                          204

SEQ ID NO: 145          moltype = DNA  length = 111
FEATURE                 Location/Qualifiers
misc_feature            1..111
                        note = synthetic polynucleotide
source                  1..111
                        mol_type = other DNA
                        organism = synthetic construct
SEQUENCE: 145
cggagggacc agaggctgcc ccccgatgcc cacaagcccc ctgggggagg cagtttccgg    60
accccatcc aagaggagca ggccgacgcc cactccaccc tggccaagat c             111
```

CHIMERIC ANTIGEN RECEPTOR AND METHODS OF USE THEREOF

CROSS-REFERENCE

This application is a continuation of U.S. patent application Ser. No. 16/824,434, filed on Mar. 19, 2020, which is a continuation of U.S. patent application Ser. No. 15/669,707, filed on Aug. 4, 2017, now issued as U.S. Pat. No. 10,632,152, which is a continuation of U.S. patent application Ser. No. 14/766,105, filed on Aug. 5, 2015, which is a national stage filing under 35 U.S.C. § 371 of PCT/US2014/016527, filed on Feb. 14, 2014, which claims the benefit of U.S. Provisional Patent Application No. 61/765,585, filed Feb. 15, 2013, each of which applications is incorporated herein by reference in its entirety.

STATEMENT REGARDING FEDERALLY SPONSORED RESEARCH

This invention was made with government support under Grant Nos. EY016546 and GM101782 awarded by the National Institutes of Health. The government has certain rights in the invention.

INCORPORATION BY REFERENCE OF SEQUENCE LISTING PROVIDED AS AN XML FILE

A Sequence Listing is provided herewith as a Sequence Listing XML, "UCSF-464CON7-SequenceListing" created on Sep. 14, 2022 and having a size of 199 KB. The contents of the text file are incorporated by reference herein in their entirety.

INTRODUCTION

In cell-based adoptive immunotherapy, immune cells isolated from a patient can be modified to express synthetic proteins that enable the cells to perform new therapeutic functions after they are subsequently transferred back into the patient. An example of such a synthetic protein is a chimeric antigen receptor (CAR). An example of a currently used CAR is a fusion of an extracellular recognition domain (e.g., an antigen-binding domain), a transmembrane domain, and one or more intracellular signaling domains. Upon antigen engagement, the intracellular signaling portion of the CAR can initiate an activation-related response in an immune cell, such as release of cytolytic molecules to induce tumor cell death, etc. However, such CARs are not capable of being pharmacologically controlled. There is a need in the art for a conditionally activatable CAR that can be controlled pharmacologically.

SUMMARY

The present disclosure provides a heterodimeric, conditionally active chimeric antigen receptor (CAR), and a nucleic acid comprising a nucleotide sequence encoding the CAR. The present disclosure provides cells genetically modified to produce the CAR. A CAR of the present disclosure can be used in various methods, which are also provided.

BRIEF DESCRIPTION OF THE DRAWINGS

FIGS. 1A and 1B provide nucleotide and amino acid sequences of the domains of construct #122.

FIGS. 2A and 2B provide nucleotide and amino acid sequences of the domains of construct #123.

FIGS. 3A and 3B provide nucleotide and amino acid sequences of the domains of construct #125.

FIG. 4 provides nucleotide and amino acid sequences of the domains of construct #126.

FIGS. 5A and 5B provide nucleotide and amino acid sequences of the domains of construct #168.

FIGS. 6A-C provide nucleotide and amino acid sequences of the domains of construct #169.

FIGS. 7A and 7B provide nucleotide and amino acid sequences of the domains of construct #170.

FIGS. 8A and 8B provide nucleotide and amino acid sequences of the domains of construct #197.

FIGS. 9A-C provide nucleotide and amino acid sequences of the domains of construct #206.

FIGS. 10A and 10B provide nucleotide and amino acid sequences of the domains of construct #207.

FIGS. 11A-C provide nucleotide and amino acid sequences of the domains of construct #199.

FIGS. 18A and 18B depict various exemplary On-switch CAR.

FIGS. 22A and 22B provide nucleotide and amino acid sequences of the domains of construct #270.

FIGS. 23A and 23B provide nucleotide and amino acid sequences of the domains of construct #300.

FIGS. 24A and 24B provide nucleotide and amino acid sequences of the domains of construct #336.

FIGS. 25A and 25B provide nucleotide and amino acid sequences of the domains of construct #337.

FIGS. 26A and 26B provide nucleotide and amino acid sequences of the domains of construct #357.

FIGS. 27A and 27B provide nucleotide and amino acid sequences of the domains of construct #365.

FIGS. 28A and 28B provide nucleotide and amino acid sequences of the domains of construct #366.

FIGS. 29A and 29B provide nucleotide and amino acid sequences of the domains of construct #367.

FIGS. 30A and 30B provide nucleotide and amino acid sequences of the domains of construct #398.

FIGS. 31A and 31B provide nucleotide and amino acid sequences of the domains of construct #399.

FIGS. 32A and 32B provide nucleotide and amino acid sequences of the domains of construct #400.

FIGS. 33A and 33B provide nucleotide and amino acid sequences of the domains of construct #358.

DEFINITIONS

Figure 12:
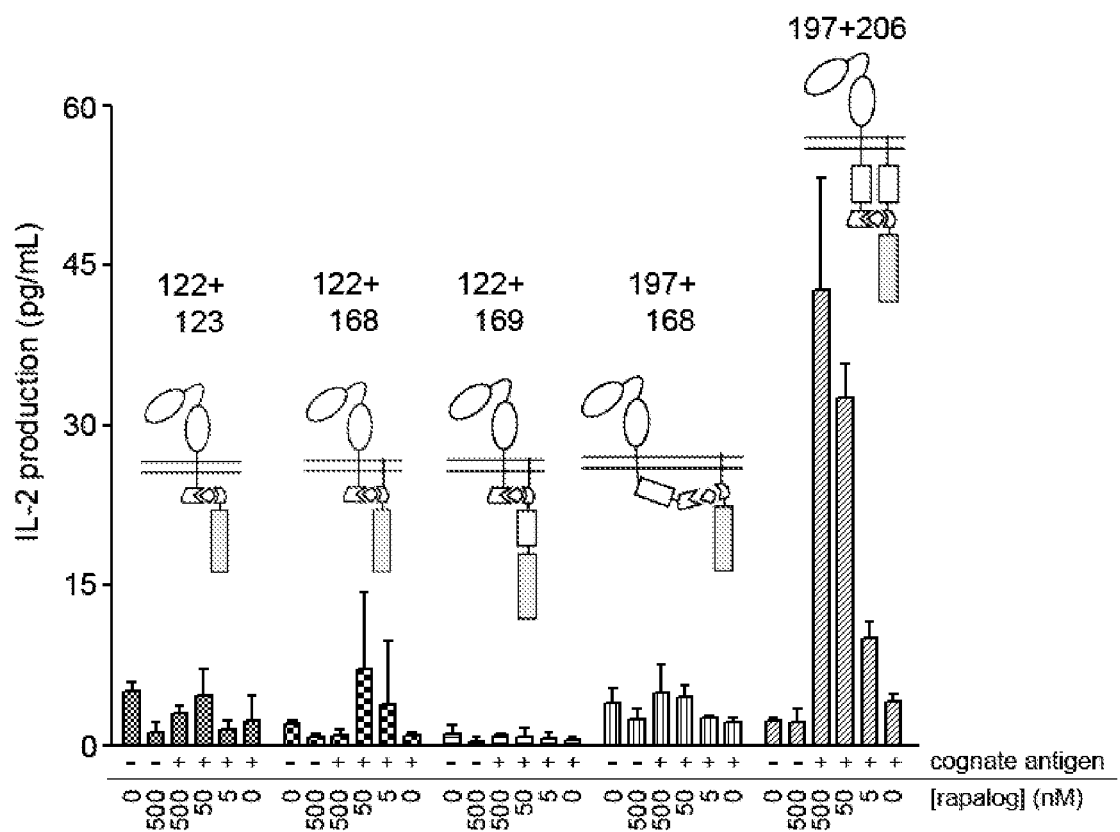
FIG. 12 depicts IL-2 production triggered by five On-switch CAR variants.

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein.

"Antibody fragments" comprise a portion of an intact antibody, for example, the antigen binding or variable region of the intact antibody. Examples of antibody fragments include Fab, Fab', F(ab')$_2$, and Fv fragments; diabodies; linear antibodies (Zapata et al., Protein Eng. 8(10): 1057-1062 (1995)); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen combining sites and is still capable of cross-linking antigen.

"Single-chain Fv" or "sFv" antibody fragments comprise the $V_H$ and $V_L$ domains of antibody, wherein these domains are present in a single polypeptide chain. In some embodiments, the Fv polypeptide further comprises a polypeptide linker between the $V_H$ and $V_L$ domains, which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994).

As used herein, the term "affinity" refers to the equilibrium constant for the reversible binding of two agents and is expressed as a dissociation constant (Kd). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater, or more, than the affinity of an antibody for unrelated amino acid sequences. Affinity of an antibody to a target protein can be, for example, from about 100 nanomolar (nM) to about 0.1 nM, from about 100 nM to about 1 picomolar (pM), or from about 100 nM to about 1 femtomolar (fM) or more. As used herein, the term "avidity" refers to the resistance of a complex of two or more agents to dissociation after dilution. The terms "immunoreactive" and "preferentially binds" are used interchangeably herein with respect to antibodies and/or antigen-binding fragments.

The term "binding" refers to a direct association between two molecules, due to, for example, covalent, electrostatic, hydrophobic, and ionic and/or hydrogen-bond interactions, including interactions such as salt bridges and water bridges. Non-specific binding would refer to binding with an affinity of less than about $10^{-7}$ M, e.g., binding with an affinity of $10^{-6}$ M, $10^{-5}$ M, $10^{-4}$ M, etc.

As used herein, the term "hinge region" refers to a flexible polypeptide connector region (also referred to herein as "hinge" or "spacer") providing structural flexibility and spacing to flanking polypeptide regions and can consist of natural or synthetic polypeptides. A "hinge region" derived from an immunoglobulin (e.g., IgG1) is generally defined as stretching from Glu$_{216}$ to Pro$_{230}$ of human IgG1 (Burton (1985) *Molec. Immunol.*, 22:161-206). Hinge regions of other IgG isotypes may be aligned with the IgG1 sequence by placing the first and last cysteine residues forming inter-heavy chain disulfide (S—S) bonds in the same positions. The hinge region may be of natural occurrence or non-natural occurrence, including but not limited to an altered hinge region as described in U.S. Pat. No. 5,677,425. The hinge region can include complete hinge region derived from an antibody of a different class or subclass from that of the CH1 domain. The term "hinge region" can also include regions derived from CD8 and other receptors that provide a similar function in providing flexibility and spacing to flanking regions.

An "isolated" polypeptide is one that has been identified and separated and/or recovered from a component of its natural environment. Contaminant components of its natural environment are materials that would interfere with diagnostic or therapeutic uses for the polypeptide, and may include enzymes, hormones, and other proteinaceous or nonproteinaceous solutes. In some embodiments, the polypeptide will be purified (1) to greater than 90%, greater than 95%, or greater than 98%, by weight of antibody as determined by the Lowry method, for example, more than 99% by weight, (2) to a degree sufficient to obtain at least 15 residues of N-terminal or internal amino acid sequence by use of a spinning cup sequenator, or (3) to homogeneity by sodium dodecyl sulfate-polyacrylamide gel electrophoresis (SDS-PAGE) under reducing or nonreducing conditions using Coomassie blue or silver stain. Isolated polypeptide includes the polypeptide in situ within recombinant cells since at least one component of the polypeptide's natural environment will not be present. In some instances, isolated polypeptide will be prepared by at least one purification step.

As used herein, the term "immune cells" generally includes white blood cells (leukocytes) which are derived from hematopoietic stem cells (HSC) produced in the bone marrow. "Immune cells" includes, e.g., lymphocytes (T cells, B cells, natural killer (NK) cells) and myeloid-derived cells (neutrophil, eosinophil, basophil, monocyte, macrophage, dendritic cells).

"T cell" includes all types of immune cells expressing CD3 including T-helper cells (CD4$^+$ cells), cytotoxic T-cells (CD8$^+$ cells), T-regulatory cells (Treg) and gamma-delta T cells.

A "cytotoxic cell" includes CD8$^+$ T cells, natural-killer (NK) cells, and neutrophils, which cells are capable of mediating cytotoxicity responses.

As used herein, the term "stem cell" generally includes pluripotent or multipotent stem cells. "Stem cells" includes, e.g., embryonic stem cells (ES); mesenchymal stem cells (MSC); induced-pluripotent stem cells (iPS); and committed progenitor cells (hematopoeitic stem cells (HSC); bone marrow derived cells, etc.).

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, e.g., in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to a mammal, including, but not limited to, murines (e.g., rats, mice), lagomorphs (e.g., rabbits), non-human primates, humans, canines, felines, ungulates (e.g., equines, bovines, ovines, porcines, caprines), etc.

A "therapeutically effective amount" or "efficacious amount" refers to the amount of an agent, or combined amounts of two agents, that, when administered to a mammal or other subject for treating a disease, is sufficient to effect such treatment for the disease. The "therapeutically effective amount" will vary depending on the agent(s), the disease and its severity and the age, weight, etc., of the subject to be treated.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a chimeric antigen receptor" includes a plurality of such chimeric antigen receptor and reference to "the dimerizer-binding pair" includes reference to one or more dimerizer-binding pairs and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides a heterodimeric, conditionally active chimeric antigen receptor (CAR), and a nucleic acid comprising a nucleotide sequence encoding the CAR. The present disclosure provides cells genetically modified to produce the CAR. A CAR of the present disclosure can be used in various methods, which are also provided.

Heterodimeric, Conditionally Active Chimeric Antigen Receptor.

The present disclosure provides a heterodimeric, conditionally active chimeric antigen receptor, which, for simplicity, is referred to herein as "CAR."

In some embodiments, a CAR of the present disclosure comprises: a) a first polypeptide comprising: i) a member of a specific binding pair (e.g., an antigen-binding domain); ii) a first modulatory domain; iii) a first member of a dimerization pair; and iv) a transmembrane domain interposed between the member of a specific binding pair (e.g., an antigen-binding domain) and the first modulatory domain; and b) a second polypeptide comprising: i) a transmembrane domain; ii) a second modulatory domain; iii) a second member of the dimerization pair; and iv) an intracellular signaling domain. The modulatory domain can be a co-stimulatory domain.

In some embodiments, a CAR of the present disclosure comprises: a) a first polypeptide comprising: i) a member of a specific binding pair (e.g., an antigen-binding domain); ii) a first co-stimulatory domain; iii) a first member of a dimerization pair (e.g., a dimerizer-binding pair); and iv) a transmembrane domain interposed between the member of a specific binding pair (e.g., an antigen-binding domain) and the first co-stimulatory domain; and b) a second polypeptide comprising: i) a transmembrane domain; ii) a second co-stimulatory domain; iii) a second member of the dimerization pair (e.g., the dimerizer-binding pair); and iv) an intracellular signaling domain.

In some embodiments, a CAR of the present disclosure comprises: a) a first polypeptide comprising: i) a member of a specific binding pair (e.g., an antigen-binding domain); ii) a modulatory domain; iii) a first member of a dimerization pair (e.g., a dimerizer-binding pair); iv) a transmembrane domain interposed between the member of a specific binding pair (e.g., an antigen-binding domain) and the modulatory domain; and b) a second polypeptide comprising: i) a second member of the dimerization pair (e.g., the dimerizer-binding pair); and ii) an intracellular signaling domain. The modulatory domain can be a co-stimulatory domain.

In some embodiments, a CAR of the present disclosure comprises: a) a first polypeptide comprising: i) a member of a specific binding pair (e.g., an antigen-binding domain); ii) a co-stimulatory domain; iii) a first member of a dimerization pair (e.g., a dimerizer-binding pair); iv) a transmembrane domain interposed between the member of a specific binding pair (e.g., an antigen-binding domain) and the co-stimulatory domain; and b) a second polypeptide comprising: i) a second member of the dimerization pair (e.g., the dimerizer-binding pair); and ii) an intracellular signaling domain.

Figure 17:
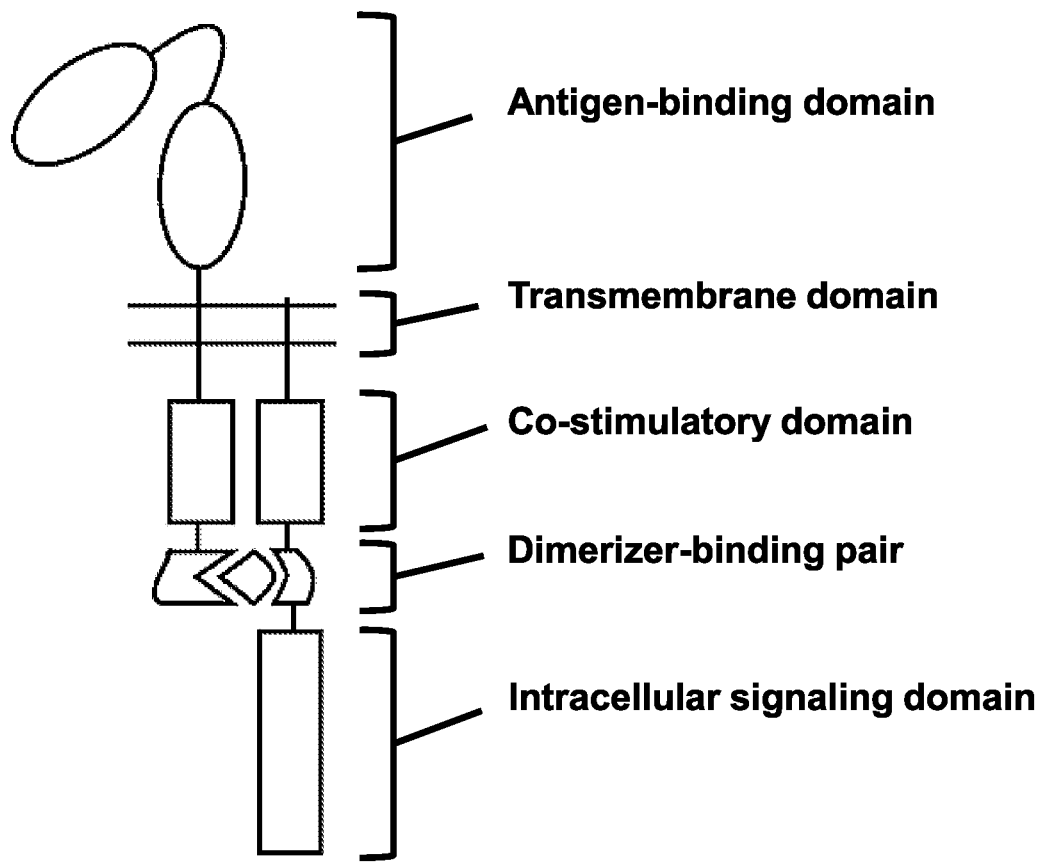
FIG. 17 is a schematic representation of an exemplary On-switch CAR.

An example of a subject CAR is represented schematically in FIG. 17. A CAR of the present disclosure can be present in the plasma membrane of a eukaryotic cell, e.g., a mammalian cell, where suitable mammalian cells include, but are not limited to, a cytotoxic cell, a T lymphocyte, a stem cell, a progeny of a stem cell, a progenitor cell, a progeny of a progenitor cell, and an NK cell. When present in the plasma membrane of a eukaryotic cell, a CAR of the present disclosure is active in the presence of: 1) a dimerizing agent binds to the first and second members of the dimerizer-binding pair in the CAR, or otherwise induces dimerization of the first and second members of the dimer; and 2) a factor that binds the member of a specific binding pair (e.g., an antigen-binding domain), e.g., an antigen that binds the antigen-binding domain of the CAR. The factor that binds the member of the specific binding pair is a second member of the specific binding pair. The second member of the specific binding pair can be a soluble (e.g., not bound to a cell) factor; a factor present on the surface of a cell such as a target cell; a factor presented on a solid surface; a factor present in a lipid bilayer; and the like. Where the member of a specific binding pair is an antibody, and the second member of the specific binding pair is an antigen, the antigen can be a soluble (e.g., not bound to a cell) antigen; an antigen present on the surface of a cell such as a target cell; an antigen presented on a solid surface; an antigen present in a lipid bilayer; and the like.

In some instances, a CAR of the present disclosure, when present in the plasma membrane of a eukaryotic cell, and when activated by a second member of a specific binding pair that binds the member of the specific-binding pair of the CAR (e.g., an antigen that binds the antigen-binding domain of the CAR) and a dimerizing agent, increases expression of at least one nucleic acid in the cell. For example, in some cases, a CAR of the present disclosure, when present in the plasma membrane of a eukaryotic cell, and when activated by an antigen that binds the antigen-binding domain of the CAR and a dimerizing agent, increases expression of at least one nucleic acid in the cell by at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared with the level of transcription of the nucleic acid in the absence of the antigen and/or the dimerizing agent.

As an example, the second polypeptide of a CAR of the present disclosure can include an immunoreceptor tyrosine-based activation motif (ITAM)-containing intracellular signaling polypeptide; in such cases, a CAR of the present disclosure, when present in the plasma membrane of a eukaryotic cell, and when activated by an antigen that binds the antigen-binding domain of the CAR and a dimerizing agent, increases nuclear factor of activated T cells (NFAT)-dependent transcription. NFAT-dependent transcription includes transcription induced by any member of the NFAT family, including, e.g., NFATc1, NFATc2, NFATc3, NFATc4, NFAT5; AP-1; Sp1; NFκB; and the like.

A CAR of the present disclosure, when present in the plasma membrane of a eukaryotic cell, and when activated by an antigen that binds the antigen-binding domain of the CAR and a dimerizing agent, can, in some instances, result in increased production of one or more cytokines by the cell. For example, a CAR of the present disclosure, when present in the plasma membrane of a eukaryotic cell, and when activated by an antigen that binds the antigen-binding domain of the CAR and a dimerizing agent, can increase production of a cytokine by the cell by at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared with the amount of cytokine produced by the cell in the absence of the antigen and/or the dimerizing agent. Cytokines whose production can be increased include, but are not limited to, an interferon, e.g., IL-2, interferon gamma (IFN-γ), tumor necrosis factor-alpha (TNF-α), IL-15, IL-12, IL-4, IL-5, IL-10; a chemokine; a growth factor; and the like.

In some cases, a CAR of the present disclosure, when present in the plasma membrane of a eukaryotic cell, and when activated by an antigen that binds the antigen-binding domain of the CAR and a dimerizing agent, can result in both an increase in transcription of a nucleic acid in the cell and an increase in production of a cytokine by the cell.

In some instances, a CAR of the present disclosure, when present in the plasma membrane of a eukaryotic cell, and when activated by a dimerizing agent, results in cytotoxic activity by the cell toward a target cell that expresses on its cell surface an antigen to which the antigen-binding domain of the first polypeptide of the CAR binds. For example, where the eukaryotic cell is a cytotoxic cell (e.g., an NK cell or a cytotoxic T lymphocyte), a CAR of the present disclosure, when present in the plasma membrane of the cell, and when activated by a dimerizing agent, increases cytotoxic activity of the cell toward a target cell that expresses on its cell surface an antigen to which the antigen-binding domain of the first polypeptide of the CAR binds. For example, where the eukaryotic cell is an NK cell or a T lymphocyte, a CAR of the present disclosure, when present in the plasma membrane of the cell, and when activated by a dimerizing agent, increases cytotoxic activity of the cell by at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared to the cytotoxic activity of the cell in the absence of the dimerizing agent.

In some cases, a CAR of the present disclosure, when present in the plasma membrane of a eukaryotic cell, and when activated by an antigen that binds the antigen-binding domain of the CAR and a dimerizing agent, can result in other CAR activation related events such as proliferation and expansion (either due to increased cellular division or anti-apoptotic responses).

In some cases, a CAR of the present disclosure, when present in the plasma membrane of a eukaryotic cell, and when activated by an antigen that binds the antigen-binding domain of the CAR and a dimerizing agent, can result in other CAR activation related events such as intracellular signaling modulation, cellular differentiation, or cell death.

A CAR of the present disclosure can be present in a eukaryotic cell membrane, where the first and second polypeptides of the CAR are not covalently linked to one another. A CAR of the present disclosure can be present in a eukaryotic cell membrane as a single heterodimer that is not covalently linked to any other polypeptide in the membrane.

Alternatively, a first CAR of the present disclosure can be present in a eukaryotic cell membrane as a heterodimer that is covalently or non-covalently linked to a second CAR of the present disclosure. In some cases, the first and the second CAR are covalently linked via a disulfide bond formed between cysteines present in a hinge region present in both the first polypeptide of the first CAR and the first polypeptide of the second CAR.

In some cases, a CAR of the present disclosure can be present in a eukaryotic cell membrane, where the first polypeptides of the CAR comprise an antibody fragment and the second polypeptides of the CAR comprise a signal transducing domain derived from a cytokine receptor, such that, upon dimerization, the CAR may represent a heterodimeric-signalobody CAR, e.g., a signalobody composed of at least two independent polypeptides. A "signalobody", as it is known in the art, is a single chimeric macromolecule composed of an antibody fragment and a signal transduction domain derived from a cytokine receptor. In certain instances, a heterodimeric-signalobody CAR of the present disclosure, when present in the cell membrane of a eukaryotic cell, dimerized by a dimerizer, and activated by an antigen, e.g., an oligomerized antigen, may induce the oligomerization of the heterodimeric-signalobody CAR. Such ligand-induced oligomerization of a heterodimeric-signalobody CAR may activate, e.g., increase, or perpetuate, e.g., maintain, signal transduction, e.g., ligand-induced oligomerization of a heterodimeric-signalobody CAR may transmit a signal eliciting a cellular response. In some instances, a plurality of heterodimeric-signalobody CARs may be utilized combinatorially to elicit a desired cellular response.

Member of a Specific Binding Pair

A CAR of the present disclosure includes a member of a specific binding pair. Specific binding pairs include, but are not limited to, antigen-antibody binding pairs; ligand-receptor binding pairs; and the like. Thus, a member of a specific binding pair suitable for use in a CAR of the present disclosure includes an antigen; an antibody; a ligand; and a ligand-binding receptor.

Antigen-Binding Domain

An antigen-binding domain suitable for use in a CAR of the present disclosure can be any antigen-binding polypeptide, a wide variety of which are known in the art. In some instances, the antigen-binding domain is a single chain Fv (scFv). Other antibody based recognition domains (cAb VHH (camelid antibody variable domains) and humanized versions, IgNAR VH (shark antibody variable domains) and humanized versions, sdAb VH (single domain antibody variable domains) and "camelized" antibody variable domains are suitable for use. In some instances, T-cell receptor (TCR) based recognition domains such as single chain TCR (scTv, single chain two-domain TCR containing VαVβ) are also suitable for use.

An antigen-binding domain suitable for use in a CAR of the present disclosure can have a variety of antigen-binding specificities. In some cases, the antigen-binding domain is specific for an epitope present in an antigen that is expressed by (synthesized by) a cancer cell, i.e., a cancer cell associated antigen. The cancer cell associated antigen can be an antigen associated with, e.g., a breast cancer cell, a B cell lymphoma, a Hodgkin lymphoma cell, an ovarian cancer cell, a prostate cancer cell, a mesothelioma cell, a lung cancer cell (e.g., a small cell lung cancer cell), a non-Hodgkin B-cell lymphoma (B-NHL) cell, an ovarian cancer cell, a prostate cancer cell, a mesothelioma cell, a lung cancer cell (e.g., a small cell lung cancer cell), a melanoma cell, a chronic lymphocytic leukemia cell, an acute lymphocytic leukemia cell, a neuroblastoma cell, a glioma, a glioblastoma, a medulloblastoma, a colorectal cancer cell, etc. A cancer cell associated antigen may also be expressed by a non-cancerous cell.

Non-limiting examples of antigens to which an antigen-binding domain of a subject CAR can bind include, e.g., CD19, CD20, CD38, CD30, Her2/neu, ERBB2, CA125, MUC-1, prostate-specific membrane antigen (PSMA), CD44 surface adhesion molecule, mesothelin, carcinoembryonic antigen (CEA), epidermal growth factor receptor (EGFR), EGFRvIII, vascular endothelial growth factor receptor-2 (VEGFR2), high molecular weight-melanoma associated antigen (HMW-MAA), MAGE-A1, IL-13R-a2, GD2, and the like.

Ligand

In some cases, a member of a specific binding pair suitable for use in a subject CAR is a ligand for a receptor. Ligands include, but are not limited to, cytokines (e.g., IL-13, etc.); growth factors (e.g., heregulin; vascular endothelial growth factor (VEGF); and the like); an integrin-binding peptide (e.g., a peptide comprising the sequence Arg-Gly-Asp); and the like.

Where the member of a specific binding pair in a subject CAR is a ligand, the CAR can be activated in the presence of both a dimerizer agent and a second member of the specific binding pair, where the second member of the specific binding pair is a receptor for the ligand. For example, where the ligand is VEGF, the second member of the specific binding pair can be a VEGF receptor, including a soluble VEGF receptor. As another example, where the ligand is heregulin, the second member of the specific binding pair can be Her2.

Receptors

As noted above, in some cases, the member of a specific binding pair that is included in a subject CAR is a receptor, e.g., a receptor for a ligand, a co-receptor, etc. The receptor can be a ligand-binding fragment of a receptor. Suitable receptors include, but are not limited to, a growth factor receptor (e.g., a VEGF receptor); a killer cell lectin-like receptor subfamily K, member 1 (NKG2D) polypeptide (receptor for MICA, MICB, and ULB6); a cytokine receptor (e.g., an IL-13 receptor; an IL-2 receptor; etc.); Her2; CD27; a natural cytotoxicity receptor (NCR) (e.g., NKP30 (NCR3/CD337) polypeptide (receptor for HLA-B—associated transcript 3 (BAT3) and B7-H6); etc.); etc.

Hinge Region

In some cases, the first polypeptide of a subject CAR comprises a hinge region (also referred to herein as a "spacer"), where the hinge region is interposed between the antigen-binding domain and the transmembrane domain. In some cases, the hinge region is an immunoglobulin heavy chain hinge region. In some cases, the hinge region is a hinge region polypeptide derived from a receptor (e.g., a CD8-derived hinge region).

The hinge region can have a length of from about 4 amino acids to about 50 amino acids, e.g., from about 4 aa to about 10 aa, from about 10 aa to about 15 aa, from about 15 aa to about 20 aa, from about 20 aa to about 25 aa, from about 25 aa to about 30 aa, from about 30 aa to about 40 aa, or from about 40 aa to about 50 aa.

Suitable spacers can be readily selected and can be of any of a number of suitable lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and can be 1, 2, 3, 4, 5, 6, or 7 amino acids.

Exemplary spacers include glycine polymers $(G)_n$, glycine-serine polymers (including, for example, $(GS)_n$, $(GSGGS)_n$ (SEQ ID NO:37) and $(GGGS)_n$ (SEQ ID NO:38), where n is an integer of at least one), glycine-alanine polymers, alanine-serine polymers, and other flexible linkers known in the art. Glycine and glycine-serine polymers can be used; both Gly and Ser are relatively unstructured, and therefore can serve as a neutral tether between components. Glycine polymers can be used; glycine accesses significantly more phi-psi space than even alanine, and is much less restricted than residues with longer side chains (see Scheraga, *Rev. Computational Chem.* 11173-142 (1992)). Exemplary spacers can comprise amino acid sequences including, but not limited to, GGSG (SEQ ID NO:39), GGSGG (SEQ ID NO:40), GSGSG (SEQ ID NO:41), GSGGG (SEQ ID NO:42), GGGSG (SEQ ID NO:43), GSSSG (SEQ ID NO:44), and the like.

In some cases, the hinge region in the first polypeptide of a subject CAR includes at least one cysteine. For example, in some cases, the hinge region can include the sequence Cys-Pro-Pro-Cys. If present, a cysteine in the hinge region of a first CAR can be available to form a disulfide bond with a hinge region in a second CAR.

Immunoglobulin hinge region amino acid sequences are known in the art; see, e.g., Tan et al. (1990) *Proc. Natl. Acad. Sci. USA* 87:162; and Huck et al. (1986) *Nucl. Acids Res.* 14:1779. As non-limiting examples, an immunoglobulin hinge region can include one of the following amino acid sequences: DKTHT (SEQ ID NO:45); CPPC (SEQ ID NO:46); CPEPKSCDTPPPCPR (SEQ ID NO:47) (see, e.g., Glaser et al. (2005) *J. Biol. Chem.* 280:41494); ELKTPLGDTTHT (SEQ ID NO:48); KSCDKTHTCP (SEQ ID NO:49); KCCVDCP (SEQ ID NO:50); KYGPPCP (SEQ ID NO:51); EPKSCDKTHTCPPCP (SEQ ID NO:52) (human IgG1 hinge); ERKCCVECPPCP (SEQ ID NO:53) (human IgG2 hinge); ELKTPLGDTTHTCPRCP (SEQ ID NO:54) (human IgG3 hinge); SPNMVPHAHHAQ (SEQ ID NO:55) (human IgG4 hinge); and the like.

The hinge region can comprise an amino acid sequence of a human IgG1, IgG2, IgG3, or IgG4, hinge region. The hinge region can include one or more amino acid substitutions and/or insertions and/or deletions compared to a wild-type (naturally-occurring) hinge region. For example, $His_{229}$ of human IgG1 hinge can be substituted with Tyr, so that the hinge region comprises the sequence EPKSCDKTYTCPPCP (SEQ ID NO:52); see, e.g., Yan et al. (2012) *J. Biol. Chem.* 287:5891.

The hinge region can comprise an amino acid sequence derived from human CD8; e.g., the hinge region can comprise the amino acid sequence:

(SEQ ID NO: 56)
TTTPAPRPPTPAPTIASQPLSLRPEACRPAAGGAVHTRGLDFACD, or a variant thereof.

Transmembrane Domain

The first and the second polypeptides of a CAR of the present disclosure include transmembrane domains for insertion into a eukaryotic cell membrane. The transmembrane domain of the first polypeptide is interposed between the antigen-binding domain and the co-stimulatory domain. Where the first polypeptide includes a hinge region, the transmembrane domain is interposed between the hinge region and the co-stimulatory domain, such that the first polypeptide comprises, in order from the amino terminus (N-terminus) to the carboxyl terminus (C-terminus): an antigen-binding domain; a hinge region; a transmembrane domain; a first co-stimulatory domain; and a first member of a dimerizer-binding pair.

The transmembrane domain of the second polypeptide is at or near the N-terminus of the polypeptide, such that the second polypeptide comprises, in order from N-terminus to C-terminus: a transmembrane domain; a second co-stimulatory domain; a second member of the dimerizer-binding pair; and an intracellular signaling domain.

Any transmembrane (TM) domain that provides for insertion of a polypeptide into the cell membrane of a eukaryotic (e.g., mammalian) cell is suitable for use. As one non-limiting example, the TM sequence IYIWAPLAGTCGVLLLSLVITLYC (SEQ ID NO:30) can be used. Additional non-limiting examples of suitable TM sequences include: a) CD8 beta derived: LGLLVAGVLVLLVSLGVAIHLCC (SEQ ID NO:57); b) CD4 derived: ALIVLGGVAGLLLFIGLGIFFCVRC (SEQ ID NO:58); c) CD3 zeta derived: LCYLLDGILFIYGVILTALFLRV (SEQ ID NO:59); d) CD28 derived: WVLVVVGGVLACYSLLVTVAFIIFWV (SEQ ID NO:60); e) CD134 (OX40) derived: VAAILGLGLVLGLLGPLAILLALYLL (SEQ ID NO:61); and f) CD7 derived: ALPAALAVISFLLGLGLGVACVLA (SEQ ID NO:62).

Linkers

In some cases, a first polypeptide of a subject CAR includes a linker between any two adjacent domains. For example, a linker can be disposed between the transmembrane domain and the first co-stimulatory domain of the first polypeptide. As another example, a linker can be disposed between the first co-stimulatory domain and the first member of a dimerizer-binding pair of the first polypeptide. As another example, a linker can be disposed between the transmembrane domain and the second co-stimulatory domain of the second polypeptide. As another example, a linker can be disposed between the second co-stimulatory domain and the second member of the dimerizer-binding pair of the second polypeptide. As another example, a linker can be disposed between the second member of the dimerizer-binding pair and the intracellular signaling domain of the second polypeptide.

The linker peptide may have any of a variety of amino acid sequences. Proteins can be joined by a spacer peptide, generally of a flexible nature, although other chemical linkages are not excluded. A linker can be a peptide of between about 6 and about 40 amino acids in length, or between about 6 and about 25 amino acids in length. These linkers can be produced by using synthetic, linker-encoding oligonucleotides to couple the proteins. Peptide linkers with a degree of flexibility can be used. The linking peptides may have virtually any amino acid sequence, bearing in mind that suitable linkers will have a sequence that results in a generally flexible peptide. The use of small amino acids, such as glycine and alanine, are of use in creating a flexible peptide. The creation of such sequences is routine to those of skill in the art.

Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Exemplary flexible linkers include glycine polymers $(G)_n$, glycine-serine polymers (including, for example, $(GS)_n$, $GSGGS_n$ (SEQ ID NO:37) and $GGGS_n$ (SEQ ID NO:38), where n is an integer of at least one), glycine-alanine polymers, alanine-serine polymers, and other flexible linkers known in the art. Glycine and glycine-serine polymers are of interest since both of these amino acids are relatively unstructured, and therefore may serve as a neutral tether between components. Glycine polymers are of particular interest since glycine accesses significantly more phi-psi space than even alanine, and is much less restricted than residues with longer side chains (see Scheraga, *Rev. Computational Chem.* 11173-142 (1992)). Exemplary flexible linkers include, but are not limited GGSG (SEQ ID NO:39), GGSGG (SEQ ID NO:40), GSGSG (SEQ ID NO:41), GSGGG (SEQ ID NO:42), GGGSG (SEQ ID NO:43), GSSSG (SEQ ID NO:44), and the like. The ordinarily skilled artisan will recognize that design of a peptide conjugated to any elements described above can include linkers that are all or partially flexible, such that the linker can include a flexible linker as well as one or more portions that confer less flexible structure.

Modulatory Domains

Modulatory domains suitable for use in a CAR of the present disclosure include co-stimulatory domains.

In some cases, the modulatory domain on the first polypeptide of a subject CAR has substantially the same amino acid sequence as the modulatory domain on the second polypeptide of the CAR. For example, in some cases, the modulatory domain on the first polypeptide of a CAR comprises an amino acid sequence that is at least about 90%, at least about 95%, at least about 98%, at least about 99%, or 100%, identical to the amino acid sequence of the modulatory domain on the second polypeptide of the CAR. The modulatory domain of the first polypeptide of a subject CAR can have substantially the same length as the modulatory domain of the second polypeptide of a subject CAR; e.g., the first and second modulatory domains can differ in length from one another by fewer than 10 amino acids, or fewer than 5 amino acids. In some cases, the first and second modulatory domains have the same length.

A modulatory domain suitable for inclusion in the first and the second polypeptide of a subject CAR can have a length of from about 30 amino acids to about 70 amino acids (aa), e.g., a modulatory domain can have a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa. In other cases, modulatory domain can have a length of from about 70 aa to about 100 aa, from about 100 aa to about 200 aa, or greater than 200 aa.

Co-stimulatory domains suitable for use in a CAR of the present disclosure are generally polypeptides derived from receptors. In some embodiments, co-stimulatory domains homodimerize. A subject co-stimulatory domain can be an intracellular portion of a transmembrane protein (i.e., the co-stimulatory domain can be derived from a transmembrane protein). Non-limiting examples of suitable co-stimulatory polypeptides include, but are not limited to, 4-1BB (CD137), CD28, ICOS, OX-40, BTLA, CD27, CD30, GITR, and HVEM.

In some cases, the co-stimulatory domain on the first polypeptide of a subject CAR has substantially the same amino acid sequence as the co-stimulatory domain on the second polypeptide of the CAR. For example, in some cases, the co-stimulatory domain on the first polypeptide of a CAR comprises an amino acid sequence that is at least about 90%, at least about 95%, at least about 98%, at least about 99%, or 100%, identical to the amino acid sequence of the co-stimulatory domain on the second polypeptide of the CAR. The co-stimulatory domain of the first polypeptide of a subject CAR can have substantially the same length as the co-stimulatory domain of the second polypeptide of a subject CAR; e.g., the first and second co-stimulatory domains can differ in length from one another by fewer than 10 amino acids, or fewer than 5 amino acids. In some cases, the first and second co-stimulatory domains have the same length.

A co-stimulatory domain suitable for inclusion in the first and the second polypeptide of a subject CAR can have a length of from about 30 amino acids to about 70 amino acids (aa), e.g., a co-stimulatory domain can have a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa. In other cases, the co-stimulatory domain can have a length of from about 70 aa to about 100 aa, from about 100 aa to about 200 aa, or greater than 200 aa.

In some cases, the co-stimulatory domain is derived from an intracellular portion of the transmembrane protein 4-1BB (also known as TNFRSF9; CD137; 4-1BB; CDw137; ILA; etc.). For example, a suitable co-stimulatory domain can comprise an amino acid sequence having at least about 75%, at least about 80%, at least about 85%, at least about 90%, at least about 95%, at least about 98%, or 100% amino acid sequence identity to the following amino acid sequence: KRGRKKLLY-IFKQPFMRPVQTTQEEDGCSCRFPEEEEGGCEL (SEQ ID NO:24). In some of these embodiments, the co-stimulatory domain of both the first and the second polypeptide has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

In some cases, the co-stimulatory domain is derived from an intracellular portion of the transmembrane protein CD28 (also known as Tp44). For example, a suitable co-stimulatory domain can comprise an amino acid sequence having at least about 75%, at least about 80%, at least about 85%, at least about 90%, at least about 95%, at least about 98%, or 100% amino acid sequence identity to the following amino acid sequence:

```
                                              (SEQ ID NO: 63)
FWVRSKRSRLLHSDYMNMTPRRPGPTRKHYQPYAPPRDFAAYRS.
```

In some of these embodiments, the co-stimulatory domain of both the first and the second polypeptide has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

In some cases, the co-stimulatory domain is derived from an intracellular portion of the transmembrane protein ICOS (also known as AILIM, CD278, and CVID1). For example, a suitable co-stimulatory domain can comprise an amino acid sequence having at least about 75%, at least about 80%, at least about 85%, at least about 90%, at least about 95%, at least about 98%, or 100% amino acid sequence identity to the following amino acid sequence:
TKKKYSSSVHDPNGEYMFMRAVNTAKKSRLTDVTL (SEQ ID NO:64). In some of these embodiments, the co-stimulatory domain of both the first and the second polypeptide has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

In some cases, the co-stimulatory domain is derived from an intracellular portion of the transmembrane protein OX-40 (also known as TNFRSF4, RP5-902P8.3, ACT35, CD134, OX40, TXGP1L). For example, a suitable co-stimulatory domain can comprise an amino acid sequence having at least about 75%, at least about 80%, at least about 85%, at least about 90%, at least about 95%, at least about 98%, or 100% amino acid sequence identity to the following amino acid sequence:
RRDQRLPPDAHKPPGGGSFRTPIQEEQADAHSTLAKI (SEQ ID NO:65). In some of these embodiments, the co-stimulatory domain of both the first and the second polypeptide has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

In some cases, the co-stimulatory domain is derived from an intracellular portion of the transmembrane protein BTLA (also known as BTLA1 and CD272). For example, a suitable co-stimulatory domain can comprise an amino acid sequence having at least about 75%, at least about 80%, at least about 85%, at least about 90%, at least about 95%, at least about 98%, or 100% amino acid sequence identity to the following amino acid sequence:

```
                                          (SEQ ID NO: 66)
CCLRRHQGKQNELSDTAGREINLVDAHLKSEQTEASTRQNSQVLLSETG

IYDNDPDLCFRMQEGSEVYSNPCLEENKPGIVYASLNHSVIGPNSRLAR

NVKEAPTEYASICVRS.
```

In some cases, the co-stimulatory domain is derived from an intracellular portion of the transmembrane protein CD27 (also known as S152, T14, TNFRSF7, and Tp55). For example, a suitable co-stimulatory domain can comprise an amino acid sequence having at least about 75%, at least about 80%, at least about 85%, at least about 90%, at least about 95%, at least about 98%, or 100% amino acid sequence identity to the following amino acid sequence:
HQRRKYRSNKGESPVEPAEPCRYSCPREEEGSTIP-IQEDYRKPEPACSP (SEQ ID NO:67). In some of these embodiments, the co-stimulatory domain of both the first and the second polypeptide has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

In some cases, the co-stimulatory domain is derived from an intracellular portion of the transmembrane protein CD30 (also known as TNFRSF8, D1S166E, and Ki-1). For example, a suitable co-stimulatory domain can comprise an amino acid sequence having at least about 75%, at least about 80%, at least about 85%, at least about 90%, at least about 95%, at least about 98%, or 100% amino acid sequence identity to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, from about 150 aa to about 160 aa, or from about 160 aa to about 185 aa of the following amino acid sequence:

```
                                          (SEQ ID NO: 68)
RRACRKRIRQKLHLCYPVQTSQPKLELVDSRPRRSSTQLRSGASVTEPV

AEERGLMSQPLMETCHSVGAAYLESLPLQDASPAGGPSSPRDLPEPRVS

TEHTNNKIEKIYIMKADTVIVGTVKAELPEGRGLAGPAEPELEEELEAD

HTPHYPEQETEPPLGSCSDVMLSVEEEGKEDPLPTAASGK.
```

In some cases, the co-stimulatory domain is derived from an intracellular portion of the transmembrane protein GITR (also known as TNFRSF18, RP5-902P8.2, AITR, CD357, and GITR-D). For example, a suitable co-stimulatory domain can comprise an amino acid sequence having at least about 75%, at least about 80%, at least about 85%, at least about 90%, at least about 95%, at least about 98%, or 100% amino acid sequence identity to the following amino acid sequence:
HIWQLRSQCMWPRETQLLLEVPPSTE-DARSCQFPEEERGERSAEEKGRLGDLWV (SEQ ID NO:69). In some of these embodiments, the co-stimulatory domain of both the first and the second polypeptide has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

In some cases, the co-stimulatory domain derived from an intracellular portion of the transmembrane protein HVEM (also known as TNFRSF14, RP3-395M20.6, ATAR, CD270, HVEA, HVEM, LIGHTR, and TR2). For example, a suitable co-stimulatory domain can comprise an amino acid sequence having at least about 75%, at least about 80%, at least about 85%, at least about 90%, at least about 95%, at least about 98%, or 100% amino acid sequence identity to the following amino acid sequence:
CVKRRKPRGDVVKVIVSVQRKRQEAEGEAT-VIEALQAPPDVTTVAVEETIPSFTGRS PNH (SEQ ID NO:70). In some of these embodiments, the co-stimulatory domain of both the first and the second polypeptide has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

Dimer Pairs

Dimer pairs suitable for use in a subject CAR include dimerizer-binding pairs. Dimerizer-binding pairs suitable for use in a CAR of the present disclosure are in some embodiments polypeptides that bind to a different site of the same molecule (referred to herein as a "dimerizer"). In the presence of a dimerizer, both members of the dimerizer-binding pair bind to a different site of the dimerizer and are thus brought into proximity with one another. In some embodiments, binding to the dimerizer is reversible. In some embodiments, binding to the dimerizer is irreversible. In some embodiments, binding to the dimerizer is non-covalent. In some embodiments, binding to the dimerizer is covalent.

Other dimer pairs suitable for use include dimerizer-binding pairs that dimerize upon binding of a first member of a dimer pair to a dimerizing agent, where the dimerizing agent induces a conformational change in the first member of the dimer pair, and where the conformational change allows the first member of the dimer pair to bind (covalently or non-covalently) to a second member of the dimer pair.

Other dimer pairs suitable for use include dimer pairs in which exposure to light (e.g., blue light) induces dimerization of the dimer pair.

Regardless of the mechanism, the dimer pair will dimerize upon exposure to an agent that induces dimerization, where the agent is in some cases a small molecule, or, in other cases, light. Thus, for simplicity, the discussion below referring to "dimerizer-binding pairs" includes dimer pairs that dimerize regardless of the mechanism.

Non-limiting examples of suitable dimers (e.g., dimerizer-binding pairs) include, but are not limited to:
  a) FK506 binding protein (FKBP) and FKBP;
  b) FKBP and calcineurin catalytic subunit A (CnA);
  c) FKBP and cyclophilin;
  d) FKBP and FKBP-rapamycin associated protein (FRB);
  e) gyrase B (GyrB) and GyrB;
  f) dihydrofolate reductase (DHFR) and DHFR;
  g) DmrB and DmrB;
  h) PYL and ABI;
  i) Cry2 and CIB1; and
  j) GAI and GID1.

A first or a second member of a dimer (e.g., a dimerizer-binding pair) of a subject CAR can have a length of from about 50 amino acids to about 300 amino acids or more; e.g., a first or a second member of a dimer (e.g., a dimerizer-binding pair) of a subject CAR can have a length of from about 50 aa to about 100 aa, from about 100 aa to about 150 aa, from about 150 aa to about 200 aa, from about 200 aa to about 250 aa, from about 250 aa to about 300 aa, or more than 300 aa.

In some cases, a member of a dimer (e.g., a dimerizer-binding pair) of a subject CAR is derived from FKBP. For example, a suitable dimerizer-binding pair member can comprise an amino acid sequence having at least about 75%, at least about 80%, at least about 85%, at least about 90%, at least about 95%, at least about 98%, or 100% amino acid sequence identity to the following amino acid sequence:

(SEQ ID NO: 12)
MGVQVETISPGDGRTFPKRGQTCVVHYTGMLEDGKKFDSSRDRNKPFKF

MLGKQEVIRGWEEGVAQMSVGQRAKLTISPDYAYGATGHPGIIPPHATL

VFDVELLKLE.

In some cases, a member of a dimerizer-binding pair of a subject CAR is derived from calcineurin catalytic subunit A (also known as PPP3CA; CALN; CALNA; CALNA1; CCN1; CNA1; PPP2B; CAM-PRP catalytic subunit; calcineurin A alpha; calmodulin-dependent calcineurin A subunit alpha isoform; protein phosphatase 2B, catalytic subunit, alpha isoform; etc.). For example, a suitable dimerizer-binding pair member can comprise an amino acid sequence having at least about 75%, at least about 80%, at least about 85%, at least about 90%, at least about 95%, at least about 98%, or 100% amino acid sequence identity to the following amino acid sequence (PP2Ac domain):

(SEQ ID NO: 71)
LEESVALRIITEGASILRQEKNLLDIDAPVTVCGDIHGQFFDLMKLFEV

GGSPANTRYLFLGDYVDRGYFSIECVLYLWALKILYPKTLFLLRGNHEC

RHLTEYFTFKQECKIKYSERVYDACMDAFDCLPLAALMNQQFLCVHGGL

SPEINTLDDIRKLDRFKEPPAYGPMCDILWSDPLEDFGNEKTQEHFTHN

TVRGCSYFYSYPAVCEFLQHNNLLSILRAHEAQDAGYRMYRKSQTTGFP

SLITIFSAPNYLDVYNNKAAVLKYENNVMNIRQFNCSPHPYWLPNFM.

In some cases, a member of a dimer (e.g., a dimerizer-binding pair) is derived from cyclophilin (also known cyclophilin A, PPIA, CYPA, CYPH, PPIase A, etc.). For example, a suitable dimerizer-binding pair member can comprise an amino acid sequence having at least about 75%, at least about 80%, at least about 85%, at least about 90%, at least about 95%, at least about 98%, or 100% amino acid sequence identity to the following amino acid sequence:

(SEQ ID NO: 72)
MVNPTVFFDIAVDGEPLGRVSFELFADKVPKTAENFRALSTGEKGFGYK

GSCFHRIIPGFMCQGGDFTRHNGTGGKSIYGEKFEDENFILKHTGPGIL

SMANAGPNTNGSQFFICTAKTEWLDGKHVVFGKVKEGMNIVEAMERFGS

RNGKTSKKITIADCGQLE.

In some cases, a member of a dimer (e.g., a dimerizer-binding pair) is derived from MTOR (also known as FKBP-rapamycin associated protein; FK506 binding protein 12-rapamycin associated protein 1; FK506 binding protein 12-rapamycin associated protein 2; FK506-binding protein 12-rapamycin complex-associated protein 1; FRAP; FRAP1; FRAP2; RAFT1; and RAPT1). For example, a suitable dimerizer-binding pair member can comprise an amino acid sequence having at least about 75%, at least about 80%, at least about 85%, at least about 90%, at least about 95%, at least about 98%, or 100% amino acid sequence identity to the following amino acid sequence (also known as "Frb": Fkbp-Rapamycin Binding Domain):

(SEQ ID NO: 14)
MILWHEMWHEGLEEASRLYFGERNVKGMFEVLEPLHAMMERGPQTLKET

SFNQAYGRDLMEAQEWCRKYMKSGNVKDLLQAWDLYYHVFRRISK.

In some cases, a member of a dimer (e.g., a dimerizer-binding pair) is derived from GyrB (also known as DNA gyrase subunit B). For example, a suitable dimerizer-binding pair member can comprise an amino acid sequence having at least about 75%, at least about 80%, at least about 85%, at least about 90%, at least about 95%, at least about 98%, or 100% amino acid sequence identity to a contiguous stretch of from about 100 amino acids to about 200 amino acids (aa), from about 200 aa to about 300 aa, from about 300 aa to about 400 aa, from about 400 aa to about 500 aa, from about 500 aa to about 600 aa, from about 600 aa to about 700 aa, or from about 700 aa to about 800 aa, of the following GyrB amino acid sequence from *Escherichia coli* (or to the DNA gyrase subunit B sequence from any organism):
MSNSYDSSSIKVLKGLDAVRKRPG-
MYIGDTDDGTGLHHMVFEVVDNAIDEALAGH
CKEIIVTIHADNSVSVQDDGRGIPTGIHPEEGVSAAE-
VIMTVLHAGGKFDDNSYKVS GGLHGVGVSVVNALSQKLELVIQREGKIHRQI-
YEHGVPQAPLAVTGETEKTGTMV RFWPS-
LETFTNVTEFEYEILAKRLRELSFLNSGV-
SIRLRDKRDGKEDHFHYEGGIKAF
VEYLNKNKTPIHPNIFYFSTEKDG-
IGVEVALQWNDGFQENIYCFTNNIPQRDGGTHL
AGFRAAMTRTLNAYMDKEGYSKKAKVSATGD-
DAREGLIAVVSVKVPDPKFSSQT KDKLVSSEV-
KSAVEQQMNELLAEYLLENPTDAKIVVGKIIDAARA-
REAARRAREM
TRRKGALDLAGLPGKLADCQERDPALSELYLVEGD-
SAGGSAKQGRNRKNQAILPL KGKILN-
VEKARFDKMLSSQEVATLITALGCGIGRDEYNPDKL-
RYHSIIIMTDADVDG
SHIRTLLLTFFYRQMPEIVERGHVYIAQP-
PLYKVKKGKQEQYIKDDEAMDQYQISIA LDGATLHT-
NASAPALAGEALEKLVSEYNATQKMINRMER-
RYPKAMLKELIYQPTL
TEADLSDEQTVTRWVNALVSELND-
KEQHGSQWKFDVHTNAEQNLFEPIVRVRTHG
VDTDYPLDHEFITGGEYRRICTLGEKLR-
GLLEEDAFIERGERRQPVASFEQALDWLV KESRR-
GLS IQRYKGLGEMNPEQLWET-
TMDPESRRMLRVTVKDAIAADQLFTTLMG
DAVEPRRAFIEENALKAANIDI (SEQ ID NO:73). In some cases, a member of a dimerizer-binding pair comprises an amino acid sequence having at least about 75%, at least about 80%, at least about 85%, at least about 90%, at least about 95%, at least about 98%, or 100% amino acid sequence identity to amino acids 1-220 of the above-listed GyrB amino acid sequence from *Escherichia coli*.

In some cases, a member of a dimer (e.g., a dimerizer-binding pair) is derived from DHFR (also known as dihydrofolate reductase, DHFRP1, and DYR). For example, a suitable dimerizer-binding pair member can comprise an amino acid sequence having at least about 75%, at least about 80%, at least about 85%, at least about 90%, at least about 95%, at least about 98%, or 100% amino acid sequence identity to the following amino acid sequence:

(SEQ ID NO: 74)
MVGSLNCIVAVSQNMGIGKNGDLPWPPLRNEFRYFQRMTTTSSVEGKQN

LVIMGKKTWFSIPEKNRPLKGRINLVLSRELKEPPQGAHFLSRSLDDAL

KLTEQPELANKVDMVWIVGGSSVYKEAMNHPGHLKLFVTRIMQDFESDT

FFPEIDLEKYKLLPEYPGVLSDVQEEKGIKYKFEVYEKND.

In some cases, a member of a dimer (e.g., a dimerizer-binding pair) is derived from the DmrB binding domain (i.e., DmrB homodimerization domain). For example, a suitable dimerizer-binding pair member can comprise an amino acid sequence having at least about 75%, at least about 80%, at least about 85%, at least about 90%, at least about 95%, at least about 98%, or 100% amino acid sequence identity to the following amino acid sequence:

(SEQ ID NO: 75)
MASRGVQVETISPGDGRTFPKRGQTCVVHYTGMLEDGKKVDSSRDRNKP

FKFMLGKQEVIRGWEEGVAQMSVGQRAKLTISPDYAYGATGHPGIIPPH

ATLVFDVELLKLE.

In some cases, a member of a dimer (e.g., a dimerizer-binding pair) is derived from a PYL protein (also known as abscisic acid receptor and as RCAR). For example a member of a subject dimerizer-binding pair can be derived from proteins such as those of *Arabidopsis thaliana*: PYR1, RCAR1(PYL9), PYL1, PYL2, PYL3, PYL4, PYL5, PYL6, PYL7, PYL8 (RCAR3), PYL10, PYL11, PYL12, PYL13. For example, a suitable dimerizer-binding pair member can comprise an amino acid sequence having at least about 75%, at least about 80%, at least about 85%, at least about 90%, at least about 95%, at least about 98%, or 100% amino acid sequence identity to any of the following amino acid sequences:

```
PYL10:
                                        (SEQ ID NO: 76)
MNGDETKKVESEYIKKHHRHELVESQCSSTLVKHIKAPLHLVWSIVRRFDEPQKYK

PFISRCVVQGKKLEVGSVREVDLKSGLPATKSTEVLEILDDNEHILGIRIVGGDHRLK

NYSSTISLHSETIDGKTGTLAIESFVVDVPEGNTKEETCFFVEALIQCNLNSLADVTE

RLQAESMEKKI.

PYL11:
                                        (SEQ ID NO: 77)
METSQKYHTCGSTLVQTIDAPLSLVWSILRRFDNPQAYKQFVKTCNLSSGDGGEGS

VREVTWSGLPAEFSRERLDELDDESHVMMISIIGGDHRLVNYRSKTMAFVAADTE

EKTVVVESYVVDVPEGNSEEETTSFADTIVGFNLKSLAKLSERVAHLKL

PYL12:
                                        (SEQ ID NO: 78)
MKTSQEQHVCGSTVVQTINAPLPLVWSILRRFDNPKTFKHFVKTCKLRSGDGGEGS

VREVTVVSDLPASFSLERLDELDDESHVMVISIIGGDHRLVNYQSKTTVFVAAEEEK

TVVVESYVVDVPEGNTEEETTLFADTIVGCNLRSLAKLSEKMMELT.

PYL13:
                                        (SEQ ID NO: 79)
MESSKQKRCRSSVVETIEAPLPLVWSILRSFDKPQAYQRFVKSCTMRSGGGGKGG

EGKGSVRDVTLVSGFPADFSTERLEELDDESHVMVVSIIGGNHRLVNYKSKTKVVA

SPEDMAKKTVVVESYVVDVPEGTSEEDTIFFVDNIIRYNLTSLAKLTKKMMK.
```

-continued

PYL1:
(SEQ ID NO: 80)
MANSESSSSPVNEEENSQRISTLHHQTMPSDLTQDEFTQLSQSIAEFHTYQLGNGRC
SSLLAQRIHAPPETVWSVVRRFDRPQIYKHFIKSCNVSEDFEMRVGCTRDVNVISGL
PANTSRERLDLLDDDRRVTGFSITGGEHRLRNYKSVTTVHRFEKEEEEERIWTVVLE
SYVVDVPEGNSEEDTRLFADTVIRLNLQKLASITEAMNRNNNNNNSSQVR.

PYL2:
(SEQ ID NO: 81)
MSSSPAVKGLTDEEQKTLEPVIKTYHQFEPDPTTCTSLITQRIHAPASVVWPLIRRFD
NPERYKHFVKRCRLISGDGDVGSVREVTVISGLPASTSTERLEFVDDDHRVLSFRVV
GGEHRLKNYKSVTSVNEFLNQDSGKVYTVVLESYTVDIPEGNTEEDTKMFVDTVV
KLNLQKLGVAATSAPMHDDE.

PYL3:
(SEQ ID NO: 82)
MNLAPIHDPSSSSTTTTSSSTPYGLTKDEFSTLDSIIRTHHTFPRSPNTCTSLIAHRVDA
PAHAIWRFVRDFANPNKYKHFIKSCTIRVNGNGIKEIKVGTIREVSVVSGLPASTSVE
ILEVLDEEKRILSFRVLGGEHRLNNYRSVTSVNEFVVLEKDKKKRVYSVVLESYIVD
IPQGNTEEDTRMFVDTVVKSNLQNLAVISTASPT.

PYL4:
(SEQ ID NO: 83)
MLAVHRPSSAVSDGDSVQIPMMIASFQKRFPSLSRDSTAARFHTHEVGPNQCCSAVI
QEISAPISTVWSVVRRFDNPQAYKHFLKSCSVIGGDGDNVGSLRQVHVVSGLPAAS
STERLDILDDERHVISFSVVGGDHRLSNYRSVTTLHPSPISGTVVVESYVVDVPPGNT
KEETCDFVDVIVRCNLQSLAKIAENTAAESKKKMSL.

PYL5:
(SEQ ID NO: 84)
MRSPVQLQHGSDATNGFHTLQPHDQTDGPIKRVCLTRGMHVPEHVAMHHTHDVG
PDQCCSSVVQMIHAPPESVWALVRRFDNPKVYKNFIRQCRIVQGDGLHVGDLREV
MVVSGLPAVSSTERLEILDEERHVISFSVVGGDHRLKNYRSVTTLHASDDEGTVVV
ESYIVDVPPGNTEEETLSFVDTIVRCNLQSLARSTNRQ.

PYL6:
(SEQ ID NO: 85)
MPTSIQFQRSSTAAEAANATVRNYPHHHQKQVQKVSLTRGMADVPEHVELSHTHV
VGPSQCFSVVVQDVEAPVSTVWSILSRFEHPQAYKHFVKSCHVVIGDGREVGSVRE
VRVVSGLPAAFSLERLEIMDDDRHVISFSVVGGDHRLMNYKSVTTVHESEEDSDGK
KRTRVVESYVVDVPAGNDKEETCSFADTIVRCNLQSLAKLAENTSKFS.

PYL7:
(SEQ ID NO: 86)
MEMIGGDDTDTEMYGALVTAQSLRLRHLHHCRENQCTSVLVKYIQAPVHLVWSL
VRRFDQPQKYKPFISRCTVNGDPEIGCLREVNVKSGLPATTSTERLEQLDDEEHILGI
NIIGGDHRLKNYSSILTVHPEMIDGRSGTMVMESFVVDVPQGNTKDDTCYFVESLIK
CNLKSLACVSERLAAQDITNSIATFCNASNGYREKNHTETNL.

PYL8:
(SEQ ID NO: 87)
MEANGIENLTNPNQEREFIRRHHKHELVDNQCSSTLVKHINAPVHIVWSLVRRFDQ
PQKYKPFISRCVVKGNMEIGTVREVDVKSGLPATRSTERLELLDDNEHILSIRIVGGD
HRLKNYSSIISLHPETIEGRIGTLVIESFVVDVPEGNTKDETCYFVEALIKCNLKSLAD
ISERLAVQDTTESRV.

PYL9:
(SEQ ID NO: 88)
MMDGVEGGTAMYGGLETVQYVRTHHQHLCRENQCTSALVKHIKAPLHLVWSLV

RRFDQPQKYKPFVSRCTVIGDPEIGSLREVNVKSGLPATTSTERLELLDDEEHILGIKI

IGGDHRLKNYSSILTVHPEIIEGRAGTMVIESFVVDVPQGNTKDETCYFVEALIRCNL

KSLADVSERLASQDITQ.

PYR1:
(SEQ ID NO: 89)
MPSELTPEERSELKNSIAEFHTYQLDPGSCSSLHAQRIHAPPELVWSIVRRFDKPQTY

KHFIKSCSVEQNFEMRVGCTRDVIVISGLPANTSTERLDILDDERRVTGFSIIGGEHR

LTNYKSVTTVHRFEKENRIWTVVLESYVVDMPEGNSEDDTRMFADTVVKLNLQKL

ATVAEAMARNSGDGSGSQVT.

In some cases, a member of a dimer (e.g., a dimerizer-binding pair) is derived from an ABI protein (also known as Abscisic Acid-Insensitive). For example a member of a subject dimerizer-binding pair can be derived from proteins such as those of *Arabidopsis thaliana*: ABI1 (Also known as ABSCISIC ACID-INSENSITIVE 1, Protein phosphatase 2C 56, AtPP2C56, P2C56, and PP2C ABI1) and/or ABI2 (also known as P2C77, Protein phosphatase 2C 77, AtPP2C77, ABSCISIC ACID-INSENSITIVE 2, Protein phosphatase 2C ABI2, and PP2C ABI2). For example, a suitable dimerizer-binding pair member can comprise an amino acid sequence having at least about 75%, at least about 80%, at least about 85%, at least about 90%, at least about 95%, at least about 98%, or 100% amino acid sequence identity to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, from about 150 aa to about 160 aa, from about 160 aa to about 170 aa, from about 170 aa to about 180 aa, from about 180 aa to about 190 aa, or from about 190 aa to about 200 aa of any of the following amino acid sequences:

ABI1:
(SEQ ID NO: 90)
MEEVSPAIAGPFRPFSETQMDFTGIRLGKGYCNNQYSNQDSENGDLMVS

LPETSSCSVSGSHGSESRKVLISRINSPNLNMKESAAADIVVVDISAGD

EINGSDITSEKKMISRTESRSLFEFKSVPLYGFTSICGRRPEMEDAVST

IPRFLQSSSGSMLDGRFDPQSAAHFFGVYDGHGGSQVANYCRERMHLAL

AEEIAKEKPMLCDGDTWLEKWKKALFNSFLRVDSEIESVAPETVGSTSV

VAVVFPSHIFVANCGDSRAVLCRGKTALPLSVDHKPDREDEAARIEAAG

GKVIQWNGARVFGVLAMSRSIGDRYLKPSIIPDPEVTAVKRVKEDDCLI

LASDGVWDVMTDEEACEMARKRILLWHKKNAVAGDASLLADERRKEGKD

PAAMSAAEYLSKLAIQRGSKDNISVVVVDLKPRRKLKSKPLN.

ABI2:
(SEQ ID NO: 91)
MDEVSPAVAVPFRPFTDPHAGLRGYCNGESRVTLPESSCSGDGAMKDSS

FEINTRQDSLTSSSSAMAGVDISAGDEINGSDEFDPRSMNQSEKKVLSR

TESRSLFEFKCVPLYGVTSICGRRPEMEDSVSTIPRFLQVSSSSLLDGR

-continued
VTNGFNPHLSAHFFGVYDGHGGSQVANYCRERMHLALTEEIVKEKPEFC

DGDTWQEKWKKALFNSFMRVDSEIETVAHAPETVGSTSVVAVVFPTHIF

VANCGDSRAVLCRGKTPLALSVDHKPDRDDEAARIEAAGGKVIRWNGAR

VFGVLAMSRSIGDRYLKPSVIPDPEVTSVRRVKEDDCLILASDGLWDVM

TNEEVCDLARKRILLWHKKNAMAGEALLPAEKRGEGKDPAAMSAAEYLS

KMALQKGSKDNISVVVVDLKGIRKFKSKSLN.

In some cases, a member of a dimer (e.g., a dimerizer-binding pair) is derived from a Cry2 protein (also known as cryptochrome 2). For example a member of a subject dimer (e.g., a dimerizer-binding pair) can be derived from Cry2 proteins from any organism (e.g., a plant) such as, but not limited to, those of *Arabidopsis thaliana*. For example, a suitable dimerizer-binding pair member can comprise an amino acid sequence having at least about 75%, at least about 80%, at least about 85%, at least about 90%, at least about 95%, at least about 98%, or 100% amino acid sequence identity to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, from about 150 aa to about 160 aa, from about 160 aa to about 170 aa, from about 170 aa to about 180 aa, from about 180 aa to about 190 aa, or from about 190 aa to about 200 aa of any of the following amino acid sequences:

Cry2 (*Arabidopsis thaliana*)
(SEQ ID NO: 92)
MKMDKKTIVWFRRDLRIEDNPALAAAAHEGSVFPVFIWCPEEEGQFYPG

RASRWWMKQSLAHLSQSLKALGSDLTLIKTHNTISAILDCIRVTGATKV

VFNHLYDPVSLVRDHTVKEKLVERGISVQSYNGDLLYEPWEIYCEKGKP

FTSFNSYWKKCLDMSIESVMLPPPWRLMPITAAAEAIWACSIEELGLEN

EAEKPSNALLTRAWSPGWSNADKLLNEFIEKQLIDYAKNSKKVVGNSTS

LLSPYLHFGEISVRHVFQCARMKQIIWARDKNSEGEESADLFLRGIGLR

EYSRYICFNFPFTHEQSLLSHLRFFPWDADVDKFKAWRQGRTGYPLVDA

GMRELWATGWMHNRIRVIVSSFAVKFLLLPWKWGMKYFWDTLLDADLEC

DILGWQYISGSIPDGHELDRLDNPALQGAKYDPEGEYIRQWLPELARLP

TEWIHHPWDAPLTVLKASGVELGTNYAKPIVDIDTARELLAKAISRTRE

AQIMIGAAPDEIVADSFEALGANTIKEPGLCPSVSSNDQQVPSAVRYNG

SKRVKPEEEEERDMKKSRGFDERELFSTAESSSSSSVFFVSQSCSLASE

GKNLEGIQDSSDQITTSLGKNGCK.

In some cases, a member of a dimer (e.g., a dimerizer-binding pair) is derived from the CIB 1 *Arabidopsis thaliana* protein (also known as transcription factor bHLH63). For example, a suitable dimer (e.g., a dimerizer-binding pair) member can comprise an amino acid sequence having at least about 75%, at least about 80%, at least about 85%, at least about 90%, at least about 95%, at least about 98%, or 100% amino acid sequence identity to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, from about 150 aa to about 160 aa, from about 160 aa to about 170 aa, from about 170 aa to about 180 aa, from about 180 aa to about 190 aa, or from about 190 aa to about 200 aa of the following amino acid sequence:

(SEQ ID NO: 93)
MNGAIGGDLLLNFPDMSVLERQRAHLKYLNPTFDSPLAGFFADSSMITG

GEMDSYLSTAGLNLPMMYGETTVEGDSRLSISPETTLGTGNFKKRKFDT

ETKDCNEKKKKMTMNRDDLVEEGEEEKSKITEQNNGSTKSIKKMKHKAK

KEENNFSNDSSKVTKELEKTDYIHVRARRGQATDSHSIAERVRREKISE

RMKFLQDLVPGCDKITGKAGMLDEIINYVQSLQRQIEFLSMKLAIVNPR

PDFDMDDIFAKEVASTPMTVVPSPEMVLSGYSHEMVHSGYSSEMVNSGY

LHVNPMQQVNTSSDPLSCFNNGEAPSMWDSHVQNLYGNLGV.

In some cases, a member of a dimer (e.g., a dimerizer-binding pair) is derived from the GAI *Arabidopsis thaliana* protein (also known as Gibberellic Acid Insensitive, and DELLA protein GAI). For example, a suitable dimerizer-binding pair member can comprise an amino acid sequence having at least about 75%, at least about 80%, at least about 85%, at least about 90%, at least about 95%, at least about 98%, or 100% amino acid sequence identity to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, from about 150 aa to about 160 aa, from about 160 aa to about 170 aa, from about 170 aa to about 180 aa, from about 180 aa to about 190 aa, or from about 190 aa to about 200 aa of the following amino acid sequence:

(SEQ ID NO: 94)
MKRDHHHHHHQDKKTMMMNEEDDGNGMDELLAVLGYKVRSSEMADVAQK

LEQLEVMMSNVQEDDLSQLATETVHYNPAELYTWLDSMLTDLNPPSSNA

EYDLKAIPGDAILNQFAIDSASSSNQGGGGDTYTTNKRLKCSNGVVETT

TATAESTRHVVLVDSQENGVRLVHALLACAEAVQKENLTVAEALVKQIG

FLAVSQIGAMRKVATYFAEALARRIYRLSPSQSPIDHSLSDTLQMHFYE

TCPYLKFAHFTANQAILEAFQGKKRVHVIDFSMSQGLQWPALMQALALR

PGGPPVFRLTGIGPPAPDNFDYLHEVGCKLAHLAEAIHVEFEYRGFVAN

TLADLDASMLELRPSEIESVAVNSVFELHKLLGRPGAIDKVLGVVNQIK

PEIFTVVEQESNHNSPIFLDRFTESLHYYSTLFDSLEGVPSGQDKVMSE

VYLGKQICNVVACDGPDRVERHETLSQWRNRFGSAGFAAAHIGSNAFKQ

ASMLLALFNGGEGYRVEESDGCLMLGWHTRPLIATSAWKLSTN.

In some cases, a member of a dimer (e.g., a dimerizer-binding pair) is derived from a GID1 *Arabidopsis thaliana* protein (also known as Gibberellin receptor GID1). For example, a suitable dimer member can comprise an amino acid sequence having at least about 75%, at least about 80%, at least about 85%, at least about 90%, at least about 95%, at least about 98%, or 100% amino acid sequence identity to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, from about 150 aa to about 160 aa, from about 160 aa to about 170 aa, from about 170 aa to about 180 aa, from about 180 aa to about 190 aa, or from about 190 aa to about 200 aa of any of the following amino acid sequences:

GID1A:
(SEQ ID NO: 95)
MAASDEVNLIESRTVVPLNTWVLISNFKVAYNILRRPDGTFNRHLAEYLD

RKVTANANPVDGVFSFDVLIDRRINLLSRVYRPAYADQEQPPSILDLEKP

VDGDIVPVILFFHGGSFAHSSANSAIYDTLCRRLVGLCKCVVVSVNYRRA

PENPYPCAYDDGWIALNWVNSRSWLKSKKDSKVHIFLAGDSSGGNIAHNV

ALRAGESGIDVLGNILLNPMFGGNERTESEKSLDGKYFVTVRDRDWYWKA

FLPEGEDREHPACNPFSPRGKSLEGVSFPKSLVVVAGLDLIRDWQLAYAE

GLKKAGQEVKLMHLEKATVGFYLLPNNNHFHNVMDEISAFVNAEC.

GID1B:
(SEQ ID NO: 96)
MAGGNEVNLNECKRIVPLNTWVLISNFKLAYKVLRRPDGSFNRDLAEFLD

RKVPANSFPLDGVFSFDHVDSTTNLLTRIYQPASLLHQTRHGTLELTKPL

STTEIVPVLIFFHGGSFTHSSANSAIYDTFCRRLVTICGVVVVSVDYRRS

PEHRYPCAYDDGWNALNWVKSRVWLQSGKDSNVYVYLAGDSSGGNIAHNV

AVRATNEGVKVLGNILLHPMFGGQERTQSEKTLDGKYFVTIQDRDWYWRA

YLPEGEDRDHPACNPFGPRGQSLKGVNFPKSLVVVAGLDLVQDWQLAYVD

GLKKTGLEVNLLYLKQATIGFYFLPNNDHFHCLMEELNKFVHSIEDSQSK

SSPVLLTP

GID1C:
(SEQ ID NO: 97)
MAGSEEVNLIESKTVVPLNTWVLISNFKLAYNLLRRPDGTFNRHLAEFLD

RKVPANANPVNGVFSFDVIIDRQTNLLSRVYRPADAGTSPSITDLQNPVD

GEIVPVIVFFHGGSFAHSSANSAIYDTLCRRLVGLCGAVVVSVNYRRAPE

NRYPCAYDDGWAVLKWVNSSSWLRSKKDSKVRIFLAGDSSGGNIVHNVAV

RAVESRIDVLGNILLNPMFGGTERTESEKRLDGKYFVTVRDRDWYWRAFL

PEGEDREHPACSPFGPRSKSLEGLSFPKSLVVVAGLDLIQDWQLKYAEGL

KKAGQEVKLLYLEQATIGFYLLPNNNHFHTVMDEIAAFVNAECQ.

Dimerizers

Dimerizers ("dimerizing agents) that can provide for dimerization of a first member of a dimerizer-binding pair and a second member of a dimerizer-binding pair include, e.g. (where the dimerizer is in parentheses following the dimerizer-binding pair:

a) FKBP and FKBP (rapamycin);
b) FKBP and CnA (rapamycin);
c) FKBP and cyclophilin (rapamycin);
d) FKBP and FRG (rapamycin);
e) GyrB and GyrB (coumermycin);
f) DHFR and DHFR (methotrexate);
g) DmrB and DmrB (AP20187);
h) PYL and ABI (abscisic acid);
i) Cry2 and CIB1 (blue light); and
j) GAI and GID1 (gibberellin).

As noted above, rapamycin can serve as a dimerizer. Alternatively, a rapamycin derivative or analog can be used. See, e.g., WO96/41865; WO 99/36553; WO 01/14387; and Ye et al (1999) *Science* 283:88-91. For example, analogs, homologs, derivatives and other compounds related structurally to rapamycin ("rapalogs") include, among others, variants of rapamycin having one or more of the following modifications relative to rapamycin: demethylation, elimination or replacement of the methoxy at C7, C42 and/or C29; elimination, derivatization or replacement of the hydroxy at C13, C43 and/or C28; reduction, elimination or derivatization of the ketone at C14, C24 and/or C30; replacement of the 6-membered pipecolate ring with a 5-membered prolyl ring; and alternative substitution on the cyclohexyl ring or replacement of the cyclohexyl ring with a substituted cyclopentyl ring. Additional information is presented in, e.g., U.S. Pat. Nos. 5,525,610; 5,310,903 5,362,718; and 5,527,907. Selective epimerization of the C-28 hydroxyl group has been described; see, e.g., WO 01/14387. Additional synthetic dimerizing agents suitable for use as an alternative to rapamycin include those described in U.S. Patent Publication No. 2012/0130076.

Rapamycin has the structure:

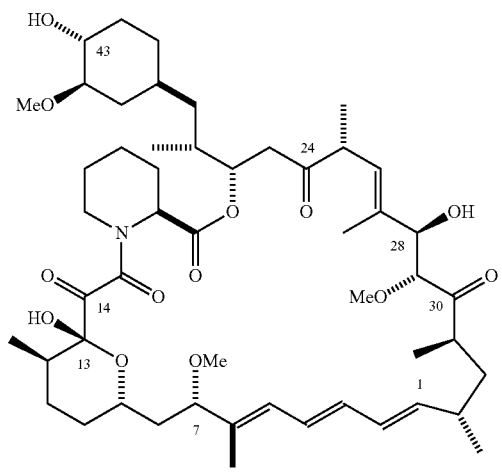

Rapamycin

Suitable rapalogs include, e.g.,

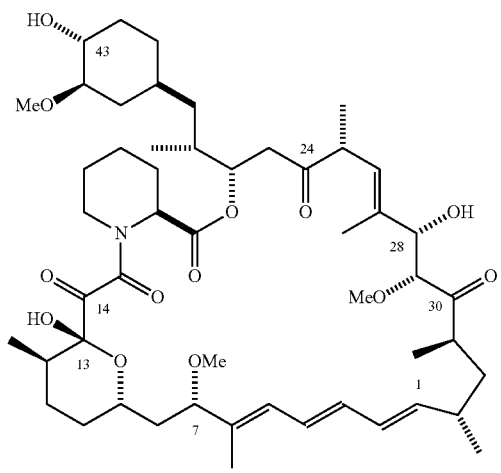

28-epirapamycin

Also suitable as a rapalog is a compound of the formula:

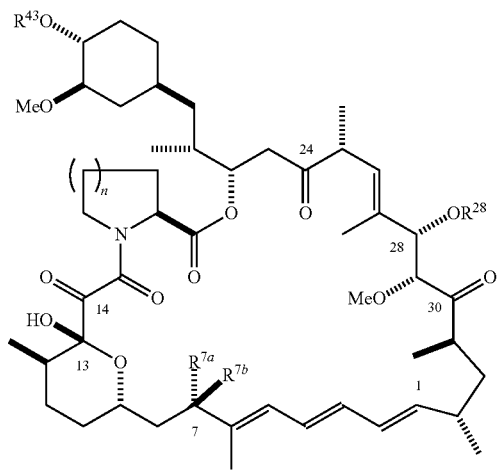

where n is 1 or 2; $R^{28}$ and $R^{43}$ are independently H, or a substituted or unsubstituted aliphatic or acyl moiety; one of $R^{7a}$ and $R^{7b}$ is H and the other is halo, $R^A$, $OR^A$, $SR^A$, —OC(O)$R^A$, —OC(O)NR$^A$R$^B$, —NR$^A$R$^B$, —NR$^B$C(OR) $R^A$, NR$^B$C(O)$R^A$, —NR$^B$SO$_2$R$^A$, or NR$^B$SO$_2$NR$^A$R$^{B'}$; or R$^{7a}$ and R$^{7b}$, taken together, are H in the tetraene moiety:

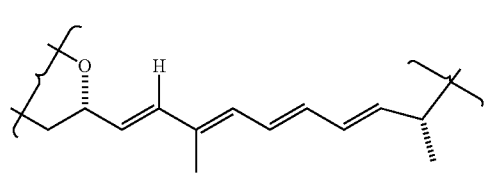

where $R^A$ is H or a substituted or unsubstituted aliphatic, heteroaliphatic, aryl, or heteroaryl moiety and where $R^B$ and $R^{B'}$ are independently H, OH, or a substituted or unsubstituted aliphatic, heteroaliphatic, aryl, or heteroaryl moiety.

As noted above, coumermycin can serve as a dimerizing agent. Alternatively, a coumermycin analog can be used. See, e.g., Farrar et al. (1996) *Nature* 383:178-181; and U.S. Pat. No. 6,916,846.

As noted above, in some cases, the dimerizing agent is methotrexate, e.g., a non-cytotoxic, homo-bifunctional methotrexate dimer. See, e.g., U.S. Pat. No. 8,236,925.

Intracellular Signaling Domain

Intracellular signaling domains suitable for use in a CAR of the present disclosure include any desired signaling domain that provides a distinct and detectable signal (e.g., increased production of one or more cytokines by the cell; change in transcription of a target gene; change in activity of a protein; change in cell behavior, e.g., cell death; cellular proliferation; cellular differentiation; cell survival; modulation of cellular signaling responses; etc.) in response to activation of the CAR (i.e., activated by antigen and dimerizing agent). In some embodiments, the intracellular signaling domain includes at least one (e.g., one, two, three, four, five, six, etc.) ITAM motifs as described below. In some embodiments, the intracellular signaling domain includes DAP10/CD28 type signaling chains. In some embodiments, the intracellular signaling domain is not covalently attached to the membrane bound CAR, but is instead diffused in the cytoplasm.

ITAM

Intracellular signaling domains suitable for use in a CAR of the present disclosure include immunoreceptor tyrosine-based activation motif (ITAM)-containing intracellular signaling polypeptides. An ITAM motif is $YX_1X_2L/I$, where $X_1$ and $X_2$ are independently any amino acid (SEQ ID NO:130). In some cases, the intracellular signaling domain of a subject CAR comprises 1, 2, 3, 4, or 5 ITAM motifs. In some cases, an ITAM motif is repeated twice in an intracellular signaling domain, where the first and second instances of the ITAM motif are separated from one another by 6 to 8 amino acids, e.g., $(YX_1X_2L/I)(X_3)_n(YX_1X_2L/I)$, where n is an integer from 6 to 8, and each of the 6-8 $X_3$ can be any amino acid (SEQ ID NO:131). In some cases, the intracellular signaling domain of a subject CAR comprises 3 ITAM motifs.

A suitable intracellular signaling domain can be an ITAM motif-containing portion that is derived from a polypeptide that contains an ITAM motif. For example, a suitable intracellular signaling domain can be an ITAM motif-containing domain from any ITAM motif-containing protein. Thus, a suitable intracellular signaling domain need not contain the entire sequence of the entire protein from which it is derived. Examples of suitable ITAM motif-containing polypeptides include, but are not limited to: DAP12; FCER1G (Fc epsilon receptor I gamma chain); CD3D (CD3 delta); CD3E (CD3 epsilon); CD3G (CD3 gamma); CD3Z (CD3 zeta); and CD79A (antigen receptor complex-associated protein alpha chain).

In some cases, the intracellular signaling domain is derived from DAP12 (also known as TYROBP; TYRO protein tyrosine kinase binding protein; KARAP; PLOSL; DNAX-activation protein 12; KAR-associated protein; TYRO protein tyrosine kinase-binding protein; killer activating receptor associated protein; killer-activating receptor-associated protein; etc.). For example, a suitable intracellular signaling domain polypeptide can comprise an amino acid sequence having at least about 75%, at least about 80%, at least about 85%, at least about 90%, at least about 95%, at least about 98%, or 100%, amino acid sequence identity to any of the following amino acid sequences (4 isoforms):

```
                                           (SEQ ID NO: 98)
MGGLEPCSRLLLLPLLLAVSGLRPVQAQAQSDCSCSTVSPGVLAGIVMGD

LVLTVLIALAVYFLGRLVPRGRGAAEAATRKQRITETESPYQELQGQRSD

VYSDLNTQRPYYK;

(SEQ ID NO: 99)
MGGLEPCSRLLLLPLLLAVSGLRPVQAQAQSDCSCSTVSPGVLAGIVMGD

LVLTVLIALAVYFLGRLVPRGRGAAEATRKQRITETESPYQELQGQRSDV

YSDLNTQRPYYK;

(SEQ ID NO: 100)
MGGLEPCSRLLLLPLLLAVSDCSCSTVSPGVLAGIVMGDLVLTVLIALAV

YFLGRLVPRGRGAAEAATRKQRITETESPYQELQGQRSDVYSDLNTQRPY

YK;
or (SEQ ID NO: 101)
MGGLEPCSRLLLLPLLLAVSDCSCSTVSPGVLAGIVMGDLVLTVLIALAV

YFLGRLVPRGRGAAEATRKQRITETESPYQELQGQRSDVYSDLNTQRPYY

K, where the IT AM motifs are in bold and are underlined.
```

Likewise, a suitable intracellular signaling domain polypeptide can comprise an ITAM motif-containing portion of the full length DAP12 amino acid sequence. Thus, a suitable intracellular signaling domain polypeptide can comprise an amino acid sequence having at least about 75%, at least about 80%, at least about 85%, at least about 90%, at least about 95%, at least about 98%, or 100%, amino acid sequence identity to the following amino acid sequence:

```
                                          (SEQ ID NO: 102)
ESPYQELQGQRSDVYSDLNTQ, where the ITAM motifs are in bold and are underlined.
```

In some cases, the intracellular signaling domain is derived from FCER1G (also known as FCRG; Fc epsilon receptor I gamma chain; Fc receptor gamma-chain; fc-epsilon RI-gamma; fcRgamma; fceRl gamma; high affinity immunoglobulin epsilon receptor subunit gamma; immunoglobulin E receptor, high affinity, gamma chain; etc.). For example, a suitable intracellular signaling domain polypeptide can comprise an amino acid sequence having at least about 75%, at least about 80%, at least about 85%, at least about 90%, at least about 95%, at least about 98%, or 100% amino acid sequence identity to the following amino acid sequence:

```
                                          (SEQ ID NO: 103)
MIPAVVLLLLLLVEQAAALGEPQLCYILDAILFLYGIVLTLLYCRLKIQ

VRKAAITSYEKSDGVYTGLSTRNQETYETLKHEKPPQ, where the

ITAM motifs are in bold and are underlined.
```

Likewise, a suitable intracellular signaling domain polypeptide can comprise an ITAM motif-containing portion of the full length FCER1G amino acid sequence. Thus, a suitable intracellular signaling domain polypeptide can comprise an amino acid sequence having at least about 75%, at least about 80%, at least about 85%, at least about 90%, at least about 95%, at least about 98%, or 100%, amino acid sequence identity to the following amino acid sequence:

(SEQ ID NO: 104)
DGVYTGLSTRNQETYETLKHE, where the ITAM motifs are in bold and are underlined.

In some cases, the intracellular signaling domain is derived from T-cell surface glycoprotein CD3 delta chain (also known as CD3D; CD3-DELTA; T3D; CD3 antigen, delta subunit; CD3 delta; CD3d antigen, delta polypeptide (TiT3 complex); OKT3, delta chain; T-cell receptor T3 delta chain; T-cell surface glycoprotein CD3 delta chain; etc.). For example, a suitable intracellular signaling domain polypeptide can comprise an amino acid sequence having at least about 75%, at least about 80%, at least about 85%, at least about 90%, at least about 95%, at least about 98%, or 100%, amino acid sequence identity to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 170 aa, of either of the following amino acid sequences (2 isoforms):

(SEQ ID NO: 105)
MEHSTFLSGLVLATLLSQVSPFKIPIEELEDRVFVNCNTSITWVEGTVGT

LLSDITRLDLGKRILDPRGIYRCNGTDIYKDKESTVQVHYRMCQSCVELD

PATVAGIIVTDVIATLLLALGVFCFAGHETGRLSGAADTQALLRNDQVYQ

PLRDRDDAQYSHLGGNWARNK
or (SEQ ID NO: 106)
MEHSTFLSGLVLATLLSQVSPFKIPIEELEDRVFVNCNTSITWVEGTVGT

LLSDITRLDLGKRILDPRGIYRCNGTDIYKDKESTVQVHYRTADTQALLR

NDQVYQPLRDRDDAQYSHLGGNWARNK, where the ITAM motifs are in bold and are underlined.

Likewise, a suitable intracellular signaling domain polypeptide can comprise an ITAM motif-containing portion of the full length CD3 delta amino acid sequence. Thus, a suitable intracellular signaling domain polypeptide can comprise an amino acid sequence having at least about 75%, at least about 80%, at least about 85%, at least about 90%, at least about 95%, at least about 98%, or 100%, amino acid sequence identity to the following amino acid sequence:

(SEQ ID NO: 107)
DQVYQPLRDRDDAQYSHLGGN, where the ITAM motifs are in bold and are underlined.

In some cases, the intracellular signaling domain is derived from T-cell surface glycoprotein CD3 epsilon chain (also known as CD3e, T-cell surface antigen T3/Leu-4 epsilon chain, T-cell surface glycoprotein CD3 epsilon chain, AI504783, CD3, CD3epsilon, T3e, etc.). For example, a suitable intracellular signaling domain polypeptide can comprise an amino acid sequence having at least about 75%, at least about 80%, at least about 85%, at least about 90%, at least about 95%, at least about 98%, or 100%, amino acid sequence identity to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 205 aa, of the following amino acid sequence:

(SEQ ID NO: 108)
MQSGTHWRVLGLCLLSVGVWGQDGNEEMGGITQTPYKVSISGTTVILTCP

QYPGSEILWQHNDKNIGGDEDDKNIGSDEDHLSLKEFSELEQSGYYVCYP

RGSKPEDANFYLYLRARVCENCMEMDVMSVATIVIVDICITGGLLLLVYY

WSKNRKAKAKPVTRGAGAGGRQRGQNKERPPPVPNPDYEPIRKGQRDLYS

GLNQRRI, where the ITAM motifs are in bold and are underlined.

Likewise, a suitable intracellular signaling domain polypeptide can comprise an ITAM motif-containing portion of the full length CD3 epsilon amino acid sequence. Thus, a suitable intracellular signaling domain polypeptide can comprise an amino acid sequence having at least about 75%, at least about 80%, at least about 85%, at least about 90%, at least about 95%, at least about 98%, or 100%, amino acid sequence identity to the following amino acid sequence:

(SEQ ID NO: 109)
NPDYEPIRKGQRDLYSGLNQR, where the ITAM motifs are in bold and are underlined.

In some cases, the intracellular signaling domain is derived from T-cell surface glycoprotein CD3 gamma chain (also known as CD3G, T-cell receptor T3 gamma chain, CD3-GAMMA, T3G, gamma polypeptide (TiT3 complex), etc.). For example, a suitable intracellular signaling domain polypeptide can comprise an amino acid sequence having at least about 75%, at least about 80%, at least about 85%, at least about 90%, at least about 95%, at least about 98%, or 100%, amino acid sequence identity to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 180 aa, of the following amino acid sequence:

(SEQ ID NO: 110)
MEQGKGLAVLILAIILLQGTLAQSIKGNHLVKVYDYQEDGSVLLTCDAEA

KNITWFKDGKMIGFLTEDKKKWNLGSNAKDPRGMYQCKGSQNKSKPLQVY

YRMCQNCIELNAATISGFLFAEIVSIFVLAVGVYFIAGQDGVRQSRASDK

QTLLPNDQLYQPLKDREDDQYSHLQGNQLRRN, where the ITAM motifs are in bold and are underlined.

Likewise, a suitable intracellular signaling domain polypeptide can comprise an ITAM motif-containing portion of the full length CD3 gamma amino acid sequence. Thus, a suitable intracellular signaling domain polypeptide can comprise an amino acid sequence having at least about 75%, at least about 80%, at least about 85%, at least about 90%, at least about 95%, at least about 98%, or 100%, amino acid sequence identity to the following amino acid sequence:

```
                                                (SEQ ID NO: 111)
DQLYQPLKDREDDQYSHLQGN, where the ITAM motifs are
```
in bold and are underlined.

In some cases, the intracellular signaling domain is derived from T-cell surface glycoprotein CD3 zeta chain (also known as CD3Z, T-cell receptor T3 zeta chain, CD247, CD3-ZETA, CD3H, CD3Q, T3Z, TCRZ, etc.). For example, a suitable intracellular signaling domain polypeptide can comprise an amino acid sequence having at least about 75%, at least about 80%, at least about 85%, at least about 90%, at least about 95%, at least about 98%, or 100%, amino acid sequence identity to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 160 aa, of either of the following amino acid sequences (2 isoforms):

```
                                                (SEQ ID NO: 112)
MKWKALFTAAILQAQLPITEAQSFGLLDPKLCYLLDGILFIYGVILTALF

LRVKFSRSADAPAYQQGQNQLYNELNLGRREEYDVLDKRRGRDPEMGGKP

RRKNPQEGLYNELQKDKMAEAYSEIGMKGERRRGKGHDGLYQGLSTATKD

TYDALHMQALPPR
or
                                                (SEQ ID NO: 113)
MKWKALFTAAILQAQLPITEAQSFGLLDPKLCYLLDGILFIYGVILTALF

LRVKFSRSADAPAYQQGQNQLYNELNLGRREEYDVLDKRRGRDPEMGGKP

QRRKNPQEGLYNELQKDKMAEAYSEIGMKGERRRGKGHDGLYQGLSTATK

DTYDALHMQALPPR, where the ITAM motifs are in bold
```
and are underlined.

Likewise, a suitable intracellular signaling domain polypeptide can comprise an ITAM motif-containing portion of the full length CD3 zeta amino acid sequence. Thus, a suitable intracellular signaling domain polypeptide can comprise an amino acid sequence having at least about 75%, at least about 80%, at least about 85%, at least about 90%, at least about 95%, at least about 98%, or 100%, amino acid sequence identity to any of the following amino acid sequences:

```
                                                (SEQ ID NO: 18)
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR;
                                                (SEQ ID NO: 114)
NQLYNELNLGRREEYDVLDKR;

(SEQ ID NO: 115)
EGLYNELQKDKMAEAYSEIGMK;
or
                                                (SEQ ID NO: 116)
DGLYQGLSTATKDTYDALHMQ, where the ITAM motifs are
```
in bold and are underlined.

In some cases, the intracellular signaling domain is derived from CD79A (also known as B-cell antigen receptor complex-associated protein alpha chain; CD79a antigen (immunoglobulin-associated alpha); MB-1 membrane glycoprotein; ig-alpha; membrane-bound immunoglobulin-associated protein; surface IgM-associated protein; etc.). For example, a suitable intracellular signaling domain polypeptide can comprise an amino acid sequence having at least about 75%, at least about 80%, at least about 85%, at least about 90%, at least about 95%, at least about 98%, or 100%, amino acid sequence identity to a contiguous stretch of from about 100 amino acids to about 110 amino acids (aa), from about 110 aa to about 115 aa, from about 115 aa to about 120 aa, from about 120 aa to about 130 aa, from about 130 aa to about 150 aa, from about 150 aa to about 200 aa, or from about 200 aa to about 220 aa, of either of the following amino acid sequences (2 isoforms):

```
                                                (SEQ ID NO: 117)
MPGGPGVLQALPATIFLLFLLSAVYLGPGCQALWMHKVPASLMVSLGEDA

HFQCPHNSSNNANVTWWRVLHGNYTWPPEFLGPGEDPNGTLIIQNVNKSH

GGIYVCRVQEGNESYQQSCGTYLRVRQPPPRPFLDMGEGTKNRIITAEGI

ILLFCAVVPGTLLLFRKRWQNEKLGLDAGDEYEDENLYEGLNLDDCSMYE

DISRGLQGTYQDVGSLNIGDVQLEKP;
or
                                                (SEQ ID NO: 118)
MPGGPGVLQALPATIFLLFLLSAVYLGPGCQALWMHKVPASLMVSLGEDA

HFQCPHNSSNNANVTWWRVLHGNYTWPPEFLGPGEDPNEPPPRPFLDMGE

GTKNRIITAEGIILLFCAVVPGTLLLFRKRWQNEKLGLDAGDEYEDENLY

EGLNLDDCSMYEDISRGLQGTYQDVGSLNIGDVQLEKP, where the
```
ITAM motifs are in bold and are underlined.

Likewise, a suitable intracellular signaling domain polypeptide can comprise an ITAM motif-containing portion of the full length CD79A amino acid sequence. Thus, a suitable intracellular signaling domain polypeptide can comprise an amino acid sequence having at least about 75%, at least about 80%, at least about 85%, at least about 90%, at least about 95%, at least about 98%, or 100%, amino acid sequence identity to the following amino acid sequence:

```
                                                (SEQ ID NO: 119)
ENLYEGLNLDDCSMYEDISRG, where the ITAM motifs are
```
in bold and are underlined.

DAP10/CD28

Intracellular signaling domains suitable for use in a CAR of the present disclosure include a DAP10/CD28 type signaling chain.

An example of a DAP10 signaling chain is the amino acid sequence is:

```
                                                (SEQ ID NO: 120)
                    RPRRSPAQDGKVYINMPGRG.
```

In some embodiments, a suitable intracellular signaling domain comprises an amino acid sequence having at least about 85%, at least about 90%, at least about 95%, at least about 98%, or at least about 99%, amino acid sequence identity to the entire length of the amino acid sequence

RPRRSPAQDGKVYINMPGRG. (SEQ ID NO: 120)

An example of a CD28 signaling chain is the amino acid sequence is

FWVLVVVGGVLACYSLLVTVAFIIFWVRSKRSRLLHSDYMNMTPRRPGPT (SEQ ID NO: 121)

RKHYQPYAPPRDFAAYRS.

In some embodiments, a suitable intracellular signaling domain comprises an amino acid sequence having at least about 85%, at least about 90%, at least about 95%, at least about 98%, or at least about 99%, amino acid sequence identity to the entire length of the amino acid sequence

FWVLVVVGGVLACYSLLVTVAFIIFWVRSKRSRLLHSDYMNMTPRRPGPT (SEQ ID NO: 121)

RKHYQPYAPPRDFAAYRS.

ZAP70

Intracellular signaling domains suitable for use in a CAR of the present disclosure include a ZAP70 polypeptide, e.g., a polypeptide comprising an amino acid sequence having at least about 85%, at least about 90%, at least about 95%, at least about 98%, at least about 99%, or 100%, amino acid sequence identity to a contiguous stretch of from about 300 amino acids to about 400 amino acids, from about 400 amino acids to about 500 amino acids, or from about 500 amino acids to 619 amino acids, of the following amino acid sequence:

(SEQ ID NO: 36)
MPDPAAHLPFFYGSISRAEAEEHLKLAGMADGLFLLRQCLRSLGGYVLSL

VHDVRFHHFPIERQLNGTYAIAGGKAHCGPAELCEFYSRDPDGLPCNLRK

PCNRPSGLEPQPGVFDCLRDAMVRDYVRQTWKLEGEALEQAIISQAPQVE

KLIATTAHERMPWYHSSLTREEAERKLYSGAQTDGKFLLRPRKEQGTYAL

SLIYGKTVYHYLISQDKAGKYCIPEGTKFDTLWQLVEYLKLKADGLIYCL

KEACPNSSASNASGAAAPTLPAHPSTLTHPQRRIDTLNSDGYTPEPARIT

SPDKPRPMPMDTSVYESPYSDPEELKDKKLFLKRDNLLIADIELGCGNFG

SVRQGVYRMRKKQIDVAIKVLKQGTEKADTEEMMREAQIMHQLDNPYIVR

LIGVCQAEALMLVMEMAGGGPLHKFLVGKREEIPVSNVAELLHQVSMGMK

YLEEKNFVHRDLAARNVLLVNRHYAKISDFGLSKALGADDSYYTARSAGK

WPLKWYAPECINFRKFSSRSDVWSYGVTMWEALSYGQKPYKKMKGPEVMA

FIEQGKRMECPPECPPELYALMSDCWIYKWEDRPDFLTVEQRMRACYYSL

ASKVEGPPGSTQKAEAACA.

Additional Sequences

The first and/or the second polypeptide of a subject CAR can further include one or more additional polypeptide domains, where such domains include, but are not limited to, a signal sequence; an epitope tag; an affinity domain; and a polypeptide that produces a detectable signal.

Signal Sequences

Signal sequences that are suitable for use in a subject CAR, e.g., in the first polypeptide of a subject CAR, include any eukaryotic signal sequence, including a naturally-occurring signal sequence, a synthetic (e.g., man-made) signal sequence, etc.

Epitope Tag

Suitable epitope tags include, but are not limited to, hemagglutinin (HA; e.g., YPYDVPDYA (SEQ ID NO:122); FLAG (e.g., DYKDDDDK (SEQ ID NO:123); c-myc (e.g., EQKLISEEDL; SEQ ID NO:4), and the like.

Affinity Domain

Affinity domains include peptide sequences that can interact with a binding partner, e.g., such as one immobilized on a solid support, useful for identification or purification. DNA sequences encoding multiple consecutive single amino acids, such as histidine, when fused to the expressed protein, may be used for one-step purification of the recombinant protein by high affinity binding to a resin column, such as nickel sepharose. Exemplary affinity domains include His5 (HHHHH) (SEQ ID NO:124), HisX6 (HHHHHH) (SEQ ID NO:125), C-myc (EQKLISEEDL) (SEQ ID NO:4), Flag (DYKDDDDK) (SEQ ID NO:123), StrepTag (WSHPQFEK) (SEQ ID NO:126), hemagluttinin, e.g., HA Tag (YPYDVPDYA) (SEQ ID NO:122), GST, thioredoxin, cellulose binding domain, RYIRS (SEQ ID NO:127), Phe-His-His-Thr (SEQ ID NO:128), chitin binding domain, S-peptide, T7 peptide, SH2 domain, C-end RNA tag, WEAAAREACCRECCARA (SEQ ID NO:129), metal binding domains, e.g., zinc binding domains or calcium binding domains such as those from calcium-binding proteins, e.g., calmodulin, troponin C, calcineurin B, myosin light chain, recoverin, S-modulin, visinin, VILIP, neurocalcin, hippocalcin, frequenin, caltractin, calpain large-subunit, S100 proteins, parvalbumin, calbindin D9K, calbindin D28K, and calretinin, inteins, biotin, streptavidin, MyoD, Id, leucine zipper sequences, and maltose binding protein.

Detectable Signal-Producing Polypeptides

Suitable detectable signal-producing proteins include, e.g., fluorescent proteins;

enzymes that catalyze a reaction that generates a detectable signal as a product; and the like.

Suitable fluorescent proteins include, but are not limited to, green fluorescent protein (GFP) or variants thereof, blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Topaz (TYFP), Venus, Citrine, mCitrine, GFPuv, destabilised EGFP (dEGFP), destabilised ECFP (dECFP), destabilised EYFP (dEYFP), mCFPm, Cerulean, T-Sapphire, CyPet, YPet, mKO, HcRed, t-HcRed, DsRed, DsRed2, DsRed-monomer, J-Red, dimer2, t-dimer2(12), mRFP1, pocilloporin, Renilla GFP, Monster GFP, paGFP, Kaede protein and kindling protein, Phycobiliproteins and Phycobiliprotein conjugates including B-Phycoerythrin, R-Phycoerythrin and Allophycocyanin. Other examples of fluorescent proteins include mHoneydew, mBanana, mOrange, dTomato, tdTomato, mTangerine, mStrawberry, mCherry, mGrape1, mRaspberry, mGrape2, mPlum (Shaner et al. (2005) *Nat. Methods* 2:905-909), and the like. Any of a variety of fluorescent and colored proteins from Anthozoan species, as described in, e.g., Matz et al. (1999) *Nature Biotechnol.* 17:969-973, is suitable for use.

Suitable enzymes include, but are not limited to, horse radish peroxidase (HRP), alkaline phosphatase (AP), beta-galactosidase (GAL), glucose-6-phosphate dehydrogenase, beta-N-acetylglucosaminidase, β-glucuronidase, invertase, Xanthine Oxidase, firefly luciferase, glucose oxidase (GO), and the like.

Recombination of Sequences

In certain instances, sequences of the polypeptides of a CAR, e.g., CAR domains, may be rearranged or deleted in a cell through the use of site-specific recombination technology. In certain embodiments, the cellular activation-related response to a particular CAR can be changed by site-specific recombination, e.g., a first intracellular signaling domain of a CAR eliciting a first activation-related response may be exchanged for a second intracellular signaling domain eliciting a second activation-related response. In certain instances, the response to a particular dimerizer of a CAR can be changed by site-specific recombination, e.g., a first dimerizer-binding pair causing the dimerization of a CAR in the presence of a first dimerizer may be exchanged for a second dimerizer-binding pair causing the dimerization of the CAR in the presence of a second dimerizer. As will be clear to one skilled in the art, site-specific recombination can be used in a cell to exchange any domain or sequence of a CAR with any other domain or sequence as disclosed herein. As will also be clear to one skilled in the art, site-specific recombination can be used in a cell to delete any domain or sequence of a CAR. Such exchange and excision of sequences and domains is known in the art, see, e.g., domain switching in signalobodies as described in Tone et al. (2013) *Biotechnology and Bioengineering*, 3219-3226, the disclosure of which is disclosed herein by reference. Mechanisms and requirements for performing site-specific recombination in vivo are also well known in the art, see, e.g., Grindley et al. (2006) *Annual Review of Biochemistry*, 567-605 and Tropp (2012) Molecular Biology (Jones & Bartlett Publishers, Sudbury, MA), the disclosures of which are incorporated herein by reference.

Nucleic Acids

The present disclosure provides a nucleic acid that comprises a nucleotide sequence encoding the first and/or the second polypeptide of a heterodimeric, conditionally active CAR of the present disclosure. A nucleic acid comprising a nucleotide sequence encoding the first and/or the second polypeptide of a heterodimeric, conditionally active CAR of the present disclosure will in some embodiments be DNA, including, e.g., a recombinant expression vector. A nucleic acid comprising a nucleotide sequence encoding the first and/or the second polypeptide of a heterodimeric, conditionally active CAR of the present disclosure will in some embodiments be RNA, e.g., in vitro synthesized RNA.

In some cases, a nucleic acid of the present disclosure comprises a nucleotide sequence encoding only the first polypeptide (and not the second polypeptide) of a heterodimeric, conditionally active CAR of the present disclosure. In some cases, a nucleic acid of the present disclosure comprises a nucleotide sequence encoding only the second polypeptide (and not the first polypeptide) of a heterodimeric, conditionally active CAR of the present disclosure. In some cases, a nucleic acid of the present disclosure comprises a nucleotide sequence encoding both the first polypeptide and the second polypeptide of a heterodimeric, conditionally active CAR of the present disclosure.

In some cases, a subject nucleic acid provides for production of a CAR of the present disclosure, e.g., in a mammalian cell. In other cases, a subject nucleic acid provides for amplification of the CAR-encoding nucleic acid.

A nucleotide sequence encoding the first and/or the second polypeptide of a CAR of the present disclosure can be operably linked to a transcriptional control element, e.g., a promoter, and enhancer, etc.

Suitable promoter and enhancer elements are known in the art. For expression in a bacterial cell, suitable promoters include, but are not limited to, lacI, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters.

Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

In some instances, the locus or construct or transgene containing the suitable promoter is irreversibly switched through the induction of an inducible system. Suitable systems for induction of an irreversible switch are well known in the art, e.g., induction of an irreversible switch may make use of a Cre-lox-mediated recombination (see, e.g., Fuhrmann-Benzakein, et al., *PNAS* (2000) 28:e99, the disclosure of which is incorporated herein by reference). Any suitable combination of recombinase, endonuclease, ligase, recombination sites, etc. known to the art may be used in generating an irreversibly switchable promoter. Methods, mechanisms, and requirements for performing site-specific recombination, described elsewhere herein, find use in generating irreversibly switched promoters and are well known in the art, see, e.g., Grindley et al. (2006) *Annual Review of Biochemistry*, 567-605 and Tropp (2012) Molecular Biology (Jones & Bartlett Publishers, Sudbury, MA), the disclosures of which are incorporated herein by reference.

In some cases, the promoter is a CD8 cell-specific promoter, a CD4 cell-specific promoter, a neutrophil-specific promoter, or an NK-specific promoter. For example, a CD4 gene promoter can be used; see, e.g., Salmon et al. (1993) *Proc. Natl. Acad. Sci. USA* 90:7739; and Marodon et al. (2003) *Blood* 101:3416. As another example, a CD8 gene promoter can be used. NK cell-specific expression can be achieved by use of an Ncr1 (p46) promoter; see, e.g., Eckelhart et al. (2011) *Blood* 117:1565.

In some embodiments, e.g., for expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHO5 promoter, a CUP1 promoter, a GAL7 promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in *Pichia*). Selection of the appropriate vector and promoter is well within the level of ordinary skill in the art.

Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, *J. Bacteriol.*, 1991: 173(1): 86-93; Alpuche-Aranda et al., PNAS, 1992; 89(21): 10079-83), a nirB promoter (Harborne et al. (1992) *Mol. Micro.* 6:2805-2813), and the like (see, e.g., Dunstan et al. (1999) *Infect. Immun.* 67:5133-5141; McKelvie et al. (2004) *Vaccine* 22:3243-3255; and Chatfield et al. (1992) *Biotechnol.* 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spy promoter, and the like; a promoter derived from the pathogenicity island SPI-2 (see, e.g., WO96/17951); an actA promoter (see, e.g., Shetron-Rama et al. (2002) *Infect. Immun.* 70:1087-1096); an rpsM promoter (see, e.g., Valdivia and Falkow (1996). *Mol. Microbiol.* 22:367); a tet promoter (see, e.g., Hillen, W. and Wissmann, A. (1989) In Saenger, W. and Heinemann, U. (eds), *Topics in Molecular and Structural Biology, Protein-Nucleic Acid Interaction.* Macmillan, London, UK, Vol. 10, pp. 143-162); an SP6 promoter (see, e.g., Melton et al. (1984) *Nucl. Acids Res.* 12:7035); and the like. Suitable strong promoters for use in prokaryotes such as *Escherichia coli* include, but are not limited to Trc, Tac, T5, T7, and $P_{Lambda}$. Non-limiting examples of operators for use in bacterial host cells include a lactose promoter operator (LacI repressor protein changes conformation when contacted with lactose, thereby preventing the LacI repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator (see, for example, deBoer et al. (1983) Proc. Natl. Acad. Sci. U.S.A. 80:21-25).

A nucleotide sequence encoding a subject CAR can be present in an expression vector and/or a cloning vector. Where a subject CAR comprises two separate polypeptides, nucleotide sequences encoding the two polypeptides can be cloned in the same or separate vectors. An expression vector can include a selectable marker, an origin of replication, and other features that provide for replication and/or maintenance of the vector. Suitable expression vectors include, e.g., plasmids, viral vectors, and the like.

Large numbers of suitable vectors and promoters are known to those of skill in the art; many are commercially available for generating a subject recombinant constructs. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host may be present. Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

As noted above, in some embodiments, a nucleic acid comprising a nucleotide sequence encoding the first and/or the second polypeptide of a heterodimeric, conditionally active CAR of the present disclosure will in some embodiments be RNA, e.g., in vitro synthesized RNA. Methods for in vitro synthesis of RNA are known in the art; any known method can be used to synthesize RNA comprising a nucleotide sequence encoding the first and/or the second polypeptide of a heterodimeric, conditionally active CAR of the present disclosure. Methods for introducing RNA into a host cell are known in the art. See, e.g., Zhao et al. (2010) Cancer Res. 15:9053. Introducing RNA comprising a nucleotide sequence encoding the first and/or the second polypeptide of a heterodimeric, conditionally active CAR of the present disclosure into a host cell can be carried out in vitro or ex vivo or in vivo. For example, a host cell (e.g., an NK cell, a cytotoxic T lymphocyte, etc.) can be electroporated in vitro or ex vivo with RNA comprising a nucleotide sequence encoding the first and/or the second polypeptide of a heterodimeric, conditionally active CAR of the present disclosure.

Cells

The present disclosure provides a mammalian cell that is genetically modified to produce a heterodimeric, conditionally active CAR of the present disclosure.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, Hut-78, Jurkat, HL-60, NK cell lines (e.g., NKL, NK92, and YTS), and the like.

In some instances, the cell is not an immortalized cell line, but is instead a cell (e.g., a primary cell) obtained from an individual. For example, in some cases, the cell is an immune cell obtained from an individual. As an example, the cell is a T lymphocyte obtained from an individual. As another example, the cell is a cytotoxic cell obtained from an individual. As another example, the cell is a stem cell or progenitor cell obtained from an individual.

Methods of Activating an Immune Cell

The present disclosure provides methods of activating an immune cell in vitro, in vivo, or ex vivo. The methods generally involve contacting an immune cell (in vitro, in vivo, or ex vivo) with a dimerizing agent and an antigen, where the immune cell is genetically modified to produce a heterodimeric, conditionally active CAR of the present disclosure. In the presence of the dimerizing agent and the antigen, the heterodimeric, conditionally active CAR dimerizes and activates the immune cell, thereby producing an activated immune cell. Immune cells include, e.g., a cytotoxic T lymphocyte, an NK cell, a $CD4^+$ T cell, a T regulatory (Treg) cell, etc.

Contacting the genetically modified immune cell (e.g., a T lymphocyte, an NK cell) with a dimerizing agent and a second member of a specific binding pair (e.g., an antigen, a ligand, a receptor) can increase production of a cytokine by the immune cell by at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared with the amount of cytokine produced by the immune cell in the absence of the second member of a specific binding pair and/or the dimerizing agent. Cytokines whose production can be increased include, but are not limited to, IL-2 and IFN-γ.

Contacting the genetically modified immune cell (e.g., a T lymphocyte, an NK cell) with a dimerizing agent and an antigen can increase production of a cytokine by the immune cell by at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared with the amount of cytokine produced by the immune cell in the absence of the antigen and/or the dimerizing agent. Cytokines whose production can be increased include, but are not limited to, IL-2 and IFN-γ.

Contacting a genetically modified cytotoxic cell (e.g., cytotoxic T lymphocyte) with a dimerizing agent and a second member of a specific binding pair (e.g., an antigen, a ligand, a receptor) can increase cytotoxic activity of the cytotoxic cell by at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared to the cytotoxic activity of the cytotoxic cell in the absence of the dimerizing agent.

Contacting a genetically modified cytotoxic cell (e.g., cytotoxic T lymphocyte) with a dimerizing agent and an antigen can increase cytotoxic activity of the cytotoxic cell by at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared to the cytotoxic activity of the cytotoxic cell in the absence of the dimerizing agent.

In other embodiments, e.g., depending on the host immune cell, contacting a genetically modified host cell with a dimerizing agent and an antigen can increase or decrease cell proliferation, cell survival, cell death, and the like.

Methods of Generating a Conditionally Activatable Cell

The present disclosure provides a method of generating a conditionally activatable cell. The method generally involves genetically modifying a mammalian cell with an expression vector, or an RNA (e.g., in vitro transcribed RNA), comprising nucleotide sequences encoding a heterodimeric, conditionally active CAR of the present disclosure. The genetically modified cell is conditionally activatable in the presence of: a) an antigen to which the first polypeptide of the CAR binds; and b) a dimerizer (a dimerizing agent). The genetic modification can be carried out in vivo, in vitro, or ex vivo. The cell can be an immune cell (e.g., a T lymphocyte or NK cell), a stem cell, a progenitor cell, etc.

In some cases, the genetic modification is carried out ex vivo. For example, a T lymphocyte, a stem cell, or an NK cell is obtained from an individual; and the cell obtained from the individual is genetically modified to express a CAR of the present disclosure. The genetically modified cell is conditionally activatable in the presence of: a) an antigen to which the first polypeptide of the CAR binds; and b) a dimerizer. In some cases, the genetically modified cell is activated ex vivo. In other cases, the genetically modified cell is introduced into an individual (e.g., the individual from whom the cell was obtained); and the genetically modified cell is activated in vivo, e.g., by administering to the individual a dimerizer. For example, where the antigen is present on the surface of a cell in the individual, there is no need to administer the antigen. The genetically modified cell comes into contact with the antigen present on the surface of a cell in the individual; and, upon administration to the individual of a dimerizer, the genetically modified cell is activated. For example, where the genetically modified cell is a T lymphocyte, the genetically modified cell can exhibit cytotoxicity toward a cell that presents an antigen on its surface to which the CAR binds.

Treatment Methods

The present disclosure provides various treatment methods using a subject CAR.

Cytotoxicity Methods

A CAR of the present disclosure, when present in a T lymphocyte or an NK cell, can mediate cytotoxicity toward a target cell. A CAR of the present disclosure binds to an antigen present on a target cell, thereby mediating killing of a target cell by a T lymphocyte or an NK cell genetically modified to produce the CAR. The antigen-binding domain of the CAR binds to an antigen present on the surface of a target cell.

Target cells include, but are not limited to, cancer cells. Thus, the present disclosure provides methods of killing, or inhibiting the growth of, a target cancer cell, the method involving contacting a cytotoxic immune effector cell (e.g., a cytotoxic T cell, or an NK cell) that is genetically modified to produce a subject CAR, such that the T lymphocyte or NK cell recognizes an antigen present on the surface of a target cancer cell, and mediates killing of the target cell.

The present disclosure provides a method of treating cancer in an individual having a cancer, the method comprising: i) genetically modifying T lymphocytes obtained from the individual with an expression vector comprising nucleotide sequences encoding the heterodimeric, conditionally active CAR of the present disclosure, where the antigen-binding domain of the heterodimeric, conditionally active CAR is specific for an epitope on a cancer cell in the individual, and where the genetic modification is carried out ex vivo; ii) introducing the genetically modified T lymphocytes into the individual; and iii) administering to the individual an effective amount of a dimerizing agent, wherein the dimerizing agent induces dimerization of the heterodimeric, conditionally active CAR, wherein said dimerization provides for activation of the genetically modified T lymphocytes and killing of the cancer cell, thereby treating the cancer.

Carcinomas that can be amenable to therapy by a method disclosed herein include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelial carcinoma, and nasopharyngeal carcinoma.

Sarcomas that can be amenable to therapy by a method disclosed herein include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

Other solid tumors that can be amenable to therapy by a method disclosed herein include, but are not limited to, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Leukemias that can be amenable to therapy by a method disclosed herein include, but are not limited to, a) chronic myeloproliferative syndromes (neoplastic disorders of multipotential hematopoietic stem cells); b) acute myelogenous leukemias (neoplastic transformation of a multipotential hematopoietic stem cell or a hematopoietic cell of restricted lineage potential; c) chronic lymphocytic leukemias (CLL; clonal proliferation of immunologically immature and functionally incompetent small lymphocytes), including B-cell CLL, T-cell CLL prolymphocytic leukemia, and hairy cell leukemia; and d) acute lymphoblastic leukemias (characterized by accumulation of lymphoblasts). Lymphomas that can be treated using a subject method include, but are not limited to, B-cell lymphomas (e.g., Burkitt's lymphoma); Hodgkin's lymphoma; non-Hodgkin's lymphoma, and the like.

Other cancers that can be amenable to treatment according to the methods disclosed herein include atypical meningioma (brain), islet cell carcinoma (pancreas), medullary carcinoma (thyroid), mesenchymoma (intestine), hepatocellular carcinoma (liver), hepatoblastoma (liver), clear cell carcinoma (kidney), and neurofibroma mediastinum.

Immunomodulatory Methods

A subject method can also be used to treat inflammatory conditions and autoimmune disease. A subject CAR is expressed in a T-helper cell or a Tregs for use in an immunomodulatory method. Immunomodulatory methods include, e.g., enhancing an immune response in a mammalian subject toward a pathogen; enhancing an immune response in a subject who is immunocompromised; reducing an inflammatory response; reducing an immune response in a mammalian subject to an autoantigen, e.g., to treat an autoimmune disease; and reducing an immune response in a mammalian subject to a transplanted organ or tissue, to reduce organ or tissue rejection.

Where the method involves reducing an immune response to an autoantigen, the antigen used to activate the CAR is an autoantigen. Where the method involves reducing an immune response to a transplanted organ or tissue, the antigen used to activate the CAR is an antigen specific to the transplanted organ.

Formulations, Dosages, and Routes of Administration

As discussed above, a treatment method of the present disclosure involves administration to an individual in need thereof of an effective amount of a dimerizer agent, and may also involve administration of an antigen.

An "effective amount" of a dimerizer agent is in some cases an amount that, when administered in one or more doses to an individual in need thereof, increases the level of cytotoxic activity of a T lymphocyte expressing a subject CAR by at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared to the cytotoxic activity of the T lymphocyte in the absence of the dimerizing agent.

An "effective amount" of a dimerizer agent is in some cases an amount that, when administered in one or more doses to an individual in need thereof, increases the level of cytotoxic activity of an NK cell expressing a subject CAR by at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared to the cytotoxic activity of the NK cell in the absence of the dimerizing agent.

An "effective amount" of a dimerizer agent is in some cases an amount that, when administered in one or more doses to an individual in need thereof, reduces the number of cancer cells in the individual and/or reduces tumor mass in the individual, by at least about 10%, at least about 15%, at least about 20%, at least about 25%, at least about 30%, at least about 40%, at least about 50%, at least about 75%, or more than 75%, compared to the number of cancer cells and/or tumor mass in the absence of the dimerizing agent.

In some embodiments, an effective amount of a dimerizer is an amount that, when administered alone (e.g., in monotherapy) or in combination (e.g., in combination therapy) with one or more additional therapeutic agents, in one or more doses, is effective to reduce one or more of tumor growth rate, cancer cell number, and tumor mass, by at least about 5%, at least about 10%, at least about 15%, at least about 20%, at least about 25%, at least about 30%, at least about 40%, at least about 50%, at least about 60%, at least about 70%, at least about 80%, at least about 90%, or more, compared to the tumor growth rate, cancer cell number, or tumor mass in the absence of treatment with the dimerizer.

Formulations

In the subject methods, a dimerizer can be administered to the host using any convenient means capable of resulting in the desired therapeutic effect or diagnostic effect. Thus, the dimerizer can be incorporated into a variety of formulations for therapeutic administration. More particularly, a dimerizer can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, a dimerizer can be administered in the form of their pharmaceutically acceptable salts, or they may also be used alone or in appropriate association, as well as in combination, with other pharmaceutically active compounds. The following methods and excipients are merely exemplary and are in no way limiting.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pennsylvania, 17th edition, 1985. The composition or formulation to be administered will, in any event, contain a quantity of a dimerizer adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

For oral preparations, a dimerizer can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

A dimerizer can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Pharmaceutical compositions comprising a dimerizer are prepared by mixing the dimerizer having the desired degree of purity with optional physiologically acceptable carriers, excipients, stabilizers, surfactants, buffers and/or tonicity agents. Acceptable carriers, excipients and/or stabilizers are nontoxic to recipients at the dosages and concentrations employed, and include buffers such as phosphate, citrate, and other organic acids; antioxidants including ascorbic acid, glutathione, cysteine, methionine and citric acid; preservatives (such as ethanol, benzyl alcohol, phenol, m-cresol, p-chlor-m-cresol, methyl or propyl parabens, benzalkonium chloride, or combinations thereof); amino acids such as arginine, glycine, ornithine, lysine, histidine, glutamic acid, aspartic acid, isoleucine, leucine, alanine, phenylalanine, tyrosine, tryptophan, methionine, serine, proline and combinations thereof; monosaccharides, disaccharides and other carbohydrates; low molecular weight (less than about 10 residues) polypeptides; proteins, such as gelatin or serum albumin; chelating agents such as EDTA; sugars such as trehalose, sucrose, lactose, glucose, mannose, maltose, galactose, fructose, sorbose, raffinose, glucosamine, N-methylglucosamine, galactosamine, and neuraminic acid; and/or non-ionic surfactants such as Tween, Brij Pluronics, Triton-X, or polyethylene glycol (PEG).

The pharmaceutical composition may be in a liquid form, a lyophilized form or a liquid form reconstituted from a lyophilized form, wherein the lyophilized preparation is to be reconstituted with a sterile solution prior to administration. The standard procedure for reconstituting a lyophilized composition is to add back a volume of pure water (typically equivalent to the volume removed during lyophilization); however solutions comprising antibacterial agents may be used for the production of pharmaceutical compositions for parenteral administration; see also Chen (1992) Drug Dev Ind Pharm 18, 1311-54.

The term "unit dosage form," as used herein, refers to physically discrete units suitable as unitary dosages for human and animal subjects, each unit containing a predetermined quantity a dimerizer calculated in an amount sufficient to produce the desired effect in association with a pharmaceutically acceptable diluent, carrier or vehicle. The specifications for a given dimerizer may depend on the particular dimerizer employed and the effect to be achieved, and the pharmacodynamics associated with each dimerizer in the host.

In some embodiments, a dimerizer is formulated in a controlled release formulation. Sustained-release preparations may be prepared using methods well known in the art. Suitable examples of sustained-release preparations include semipermeable matrices of solid hydrophobic polymers containing the dimerizer in which the matrices are in the form of shaped articles, e.g. films or microcapsules. Examples of sustained-release matrices include polyesters, copolymers of L-glutamic acid and ethyl-L-glutamate, non-degradable ethylene-vinyl acetate, hydrogels, polylactides, degradable lactic acid-glycolic acid copolymers and poly-D-(−)-3-hydroxybutyric acid. Possible loss of biological activity may be prevented by using appropriate additives, by controlling moisture content and by developing specific polymer matrix compositions.

Dosages

A suitable dosage can be determined by an attending physician or other qualified medical personnel, based on various clinical factors. As is well known in the medical arts, dosages for any one patient depend upon many factors, including the patient's size, body surface area, age, the particular dimerizer to be administered, sex of the patient, time, and route of administration, general health, and other drugs being administered concurrently. A dimerizer may be administered in amounts between 1 ng/kg body weight and 20 mg/kg body weight per dose, e.g. between 0.1 mg/kg body weight to 10 mg/kg body weight, e.g. between 0.5 mg/kg body weight to 5 mg/kg body weight; however, doses below or above this exemplary range are envisioned, especially considering the aforementioned factors. If the regimen is a continuous infusion, it can also be in the range of 1 μg to 10 mg per kilogram of body weight per minute.

Those of skill will readily appreciate that dose levels can vary as a function of the specific dimerizer, the severity of the symptoms and the susceptibility of the subject to side effects. Preferred dosages for a given compound are readily determinable by those of skill in the art by a variety of means.

Routes of Administration

A dimerizer is administered to an individual using any available method and route suitable for drug delivery, including in vivo and ex vivo methods, as well as systemic and localized routes of administration.

Conventional and pharmaceutically acceptable routes of administration include intratumoral, peritumoral, intramuscular, intratracheal, intracranial, subcutaneous, intradermal, topical application, intravenous, intraarterial, rectal, nasal, oral, and other enteral and parenteral routes of administration. Routes of administration may be combined, if desired, or adjusted depending upon the dimerizer and/or the desired effect. A dimerizer can be administered in a single dose or in multiple doses. In some embodiments, a dimerizer is administered orally. In some embodiments, a dimerizer is administered via an inhalational route. In some embodiments, a dimerizer is administered intranasally. In some embodiments, a dimerizer is administered locally. In some embodiments, a dimerizer is administered intratumorally. In some embodiments, a dimerizer is administered peritumorally. In some embodiments, a dimerizer is administered intracranially. In some embodiments, a dimerizer is administered intravenously.

The agent can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, transdermal, subcutaneous, intramuscular, intraorbital, intracapsular, intraspinal, intrasternal, intratumoral, peritumoral, and intravenous routes, i.e., any route of administration other than through the alimentary canal. Parenteral administration can be carried to effect systemic or local delivery of a dimerizer. Where systemic delivery is desired, administration typically involves invasive or systemically absorbed topical or mucosal administration of pharmaceutical preparations.

A dimerizer can also be delivered to the subject by enteral administration. Enteral routes of administration include, but are not necessarily limited to, oral and rectal (e.g., using a suppository) delivery.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as cancer. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

In some embodiments, a dimerizer is administered by injection and/or delivery, e.g., to a site in a brain artery or directly into brain tissue. A dimerizer can also be administered directly to a target site e.g., by direct injection, by implantation of a drug delivery device such as an osmotic pump or slow release particle, by biolistic delivery to the target site, etc.

Combination Therapy

In some embodiments, a dimerizer is administered as an adjuvant therapy to a standard cancer therapy. Standard cancer therapies include surgery (e.g., surgical removal of cancerous tissue), radiation therapy, bone marrow transplantation, chemotherapeutic treatment, antibody treatment, biological response modifier treatment, and certain combinations of the foregoing.

Radiation therapy includes, but is not limited to, x-rays or gamma rays that are delivered from either an externally applied source such as a beam, or by implantation of small radioactive sources.

Suitable antibodies for use in cancer treatment include, but are not limited to, naked antibodies, e.g., trastuzumab (Herceptin), bevacizumab (Avastin™), cetuximab (Erbitux™), panitumumab (Vectibix™), Ipilimumab (Yervoy™), rituximab (Rituxan), alemtuzumab (Lemtrada™), Ofatumumab (Arzerra™), Oregovomab (OvaRex™) Lambrolizumab (MK-3475), pertuzumab (Perjeta™), ranibizumab (Lucentis™) etc., and conjugated antibodies, e.g., gemtuzumab ozogamicin (Mylortarg™), Brentuximab vedotin (Adcetris™), $^{90}$Y-labelled ibritumomab tiuxetan (Zevalin™), $^{131}$I-labelled tositumoma (Bexxar™), etc. Suitable antibodies for use in cancer treatment include, but are not limited to, antibodies raised against tumor-associated antigens. Such antigens include, but are not limited to, CD20, CD30, CD33, CD52, EpCAM, CEA, gpA33, Mucins, TAG-72, CAIX, PSMA, Folate-binding protein, Gangliosides (e.g., GD2, GD3, GM2, etc.), Le$^y$, VEGF, VEGFR, Integrin alpha-V-beta-3, Integrin alpha-5-beta-1, EGFR, ERBB2, ERBB3, MET, IGF1R, EPHA3, TRAILR1, TRAILR2, RANKL, FAP, Tenascin, etc.

Biological response modifiers suitable for use in connection with the methods of the present disclosure include, but are not limited to, (1) inhibitors of tyrosine kinase (RTK) activity; (2) inhibitors of serine/threonine kinase activity; (3) tumor-associated antigen antagonists, such as antibodies that bind specifically to a tumor antigen; (4) apoptosis receptor agonists; (5) interleukin-2; (6) interferon-α; (7) interferon-γ; (8) colony-stimulating factors; (9) inhibitors of angiogenesis; and (10) antagonists of tumor necrosis factor.

Chemotherapeutic agents are non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones.

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (Cytoxan™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxol®), Taxol® derivatives, docetaxel (Taxotere®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex®. Estrogens stimulate proliferation and differentiation, therefore compounds that bind to the estrogen receptor are used to block this activity. Corticosteroids may inhibit T cell proliferation.

Other chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); Iressa® (ZD 1839, 4-(3-chloro-4-fluorophenylamino)-7-methoxy-6-(3-(4-morpholinyl)propoxy)quinazoline); etc.

"Taxanes" include paclitaxel, as well as any active taxane derivative or pro-drug. "Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus yannanensis*).

Paclitaxel should be understood to refer to not only the common chemically available form of paclitaxel, but analogs and derivatives (e.g., Taxotere™ docetaxel, as noted above) and paclitaxel conjugates (e.g., paclitaxel-PEG, paclitaxel-dextran, or paclitaxel-xylose).

Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

Subjects Suitable for Treatment

A variety of subjects are suitable for treatment with a subject method of treating cancer. Suitable subjects include any individual, e.g., a human or non-human animal who has cancer, who has been diagnosed with cancer, who is at risk for developing cancer, who has had cancer and is at risk for recurrence of the cancer, who has been treated with an agent other than a dimerizer for the cancer and failed to respond to such treatment, or who has been treated with an agent other than a dimerizer for the cancer but relapsed after initial response to such treatment.

Subjects suitable for treatment with a subject immunomodulatory method include individuals who have an autoimmune disorder; individuals who are organ or tissue transplant recipients; and the like; individuals who are immunocompromised; and individuals who are infected with a pathogen.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s);

Example 1: Generation of CAR

Materials and Methods

The anti-human CD19 scFv was selected as the antigen recognition domain in CARs throughout the design optimization process. FIGS. 18A and 18B summarize the molecular structure of each CAR consisting of two numerically identified polypeptides. All membrane-anchored polypeptides are di-sulfide bonded homo-dimers. The membrane-anchored polypeptides are depicted as monomers for graphical simplicity.

Generation of CAR Constructs

Sequence encoding the anti-human CD19 scFv was cloned from a construct. The human 4-1BB co-stimulation and CD3 zeta ITAM signaling chains were cloned from cDNAs supplied by Open Biosystems. FKBP- and FRB-encoding sequences were cloned from plasmids supplied by Addgene.

Standard molecular cloning techniques (polymerase chain reaction (PCR), restriction digestion, ligation, etc.) were applied to generate lentiviral expression plasmids.

Effector and Target Cell Culturing Conditions

Human primary CD8+ T cells were isolated from anonymous donor's blood after apheresis (Trima residuals from Blood Centers of the Pacific, San Francisco, CA) by negative selection using RosetteSep Human CD8+ T Cell Enrichment Cocktail (STEMCELL Technologies #15063) as approved by University Institutional Review Board. Cells were cultured in human T cell medium, consisting of X-VIVO15 (Lonza #04-418Q), 5% human AB serum (Valley Biomedical Inc., #HP1022), 10 mM N-acetyl L-Cysteine (Sigma-Aldrich #A9165) and 100 IU/mL recombinant human IL-2 (NCI/BRB Preclinical Repository). A Jurkat cell line expressing the Green Fluorescent Protein (GFP) upon NFAT activation was maintained in RPMI-1640 medium supplemented with 10% fetal bovine serum (FBS), penicillin and streptomycin. K562 target cells from U. Penn were cultured in IMDM supplemented with 10% FBS.

Effector and Target Cell Engineering with Lentivirus

Pantropic VSV-G pseudotyped lentivirus was produced from Lenti-X 293T cells (Clontech Laboratories #632180) co-transfected with a pHR'SIN:CSW transgene expression vector, viral packaging plasmids pCMVdR8.91 and pMD2.G using Lipofectamine LTX (Life Technologies #15338). Infection medium supernatant was collected 48 hours after transfection and used directly for transduction.

Twenty four hours prior to viral transduction, primary human T cells were activated using the human T-Activator CD3/CD28 Dynabeads (Life Technologies #111-31D) at a 1:3 cell:bead ratio. Jurkat and K562 cells were split 1-2 days in advance to ensure that cultures would be in log phase at the time of transduction. Transduced Jurkat and K562 cells were cultured for at least 7 days before experiments were conducted. Primary T cells were maintained at ~10^6/mL in human T cell medium for about two weeks until cells returned to a resting state. Expression levels of CARs encoded in the lentiviral constructs were quantified by detecting either fluorophore-conjugated antibodies or fluorescent reporter proteins using a flow cytometer.

Quantitation of IL-2 Production and NFAT Activity

Jurkat CD4+ T cells expressing CARs were mixed with cognate or non-cognate K562 target cells from U. Penn at a 1:2 effector:target ratio. The rapalog A/C Heterodimerizer (Clontech Laboratories #635055) were serially diluted in medium and added to reaction mixtures. After 20-24 hours of incubation, medium supernatants were collected and analyzed with BD OptEIA Human IL-2 ELISA Set (BD Biosciences #555190). Flow cytometry was performed to quantify NFAT-dependent GFP reporter expression in Jurkat cells as a separate indicator for CAR activity.

Flow Cytometry-Bbased Re-Directed Cytotoxicity Assay

The cognate and non-cognate K562 target cells were engineered to express distinct fluorescent proteins so that both cell types in a mixture could be simultaneously quantified by flow cytometry. The target cell types were mixed at a 1:1 ratio and co-incubated with human primary CD8+ effector T cells at a 5:2 effector:target ratio. 100 IU/mL human IL-2 and varying amounts of the rapalog (Clontech Laboratories #635055) were added to reaction mixtures. After 24 hours of incubation, samples were centrifuged at 400 g for 5 minutes. Pelleted cells were resuspended in wash buffer (PBS+0.5% BSA+0.1% sodium azide) and fixed with an equal volume of BD Cytofix (BD cat #554655) prior to flow cytometry. Ratios of the surviving cognate target cells to non-cognate target cells were calculated for each sample to enumerate re-directed cytotoxic activities of the effector cells.

Results

IL-2 production elicited by the various CAR constructs was assessed. The data are presented in FIG. 12.

FIG. 12. IL-2 production triggered by five On-switch CAR variants. Effector=human CD4+ Jurkat T cells engineered with CARs. Target=K562 cell lines with or without the cognate CD19 antigen. Amounts of secreted IL-2 by effector cells were quantified by enzyme-linked immunosorbent assay (ELISA).

Figure 13:
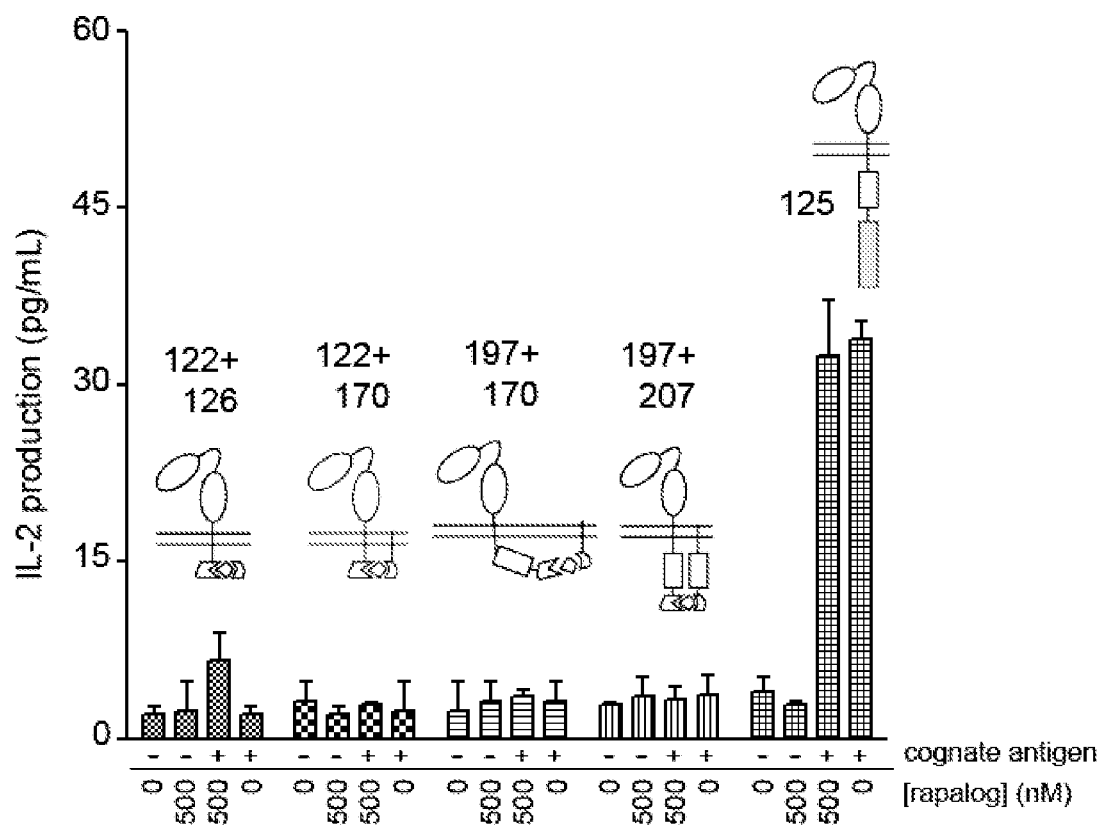
FIG. 13 depicts IL-2 production by control Jurkat lines.

FIG. 13. IL-2 production by control Jurkat lines in the same experiment as that described in FIG. 12. Construct "125" encodes a conventional control currently used in clinical trials.

Figure 14:
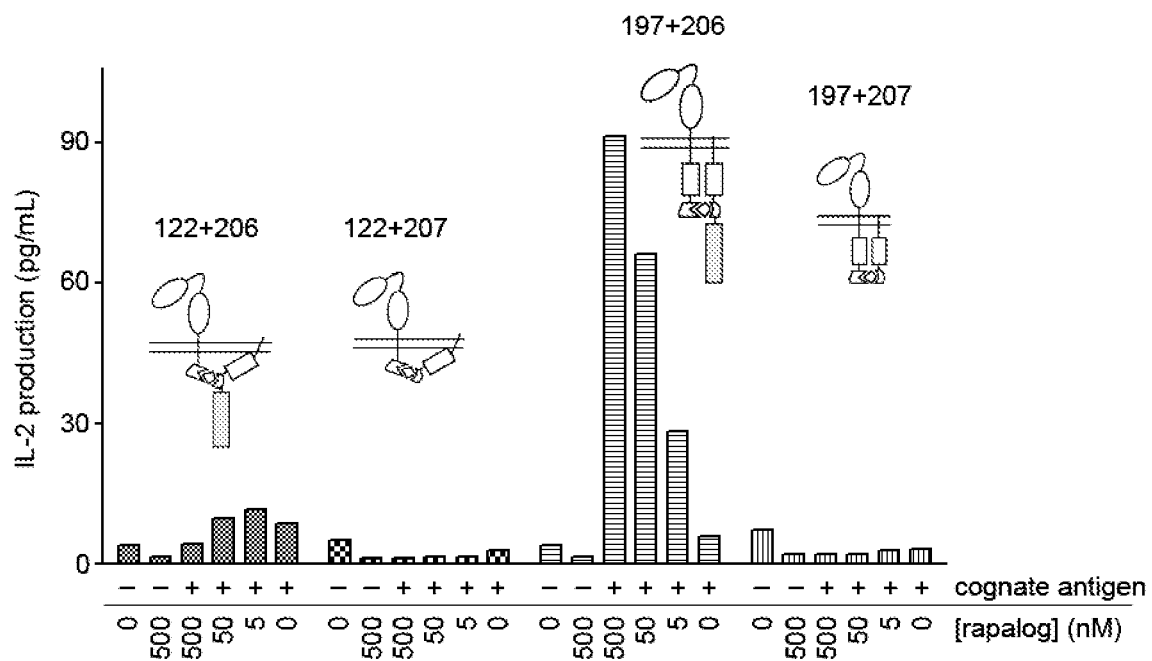
FIG. 14 depicts a comparison between CAR constructs "122+206" and "197+206".

FIG. 14. Comparison between "122+206" and "197+206" in a separate experiment under conditions identical to those described in FIG. 12.

Figure 15:
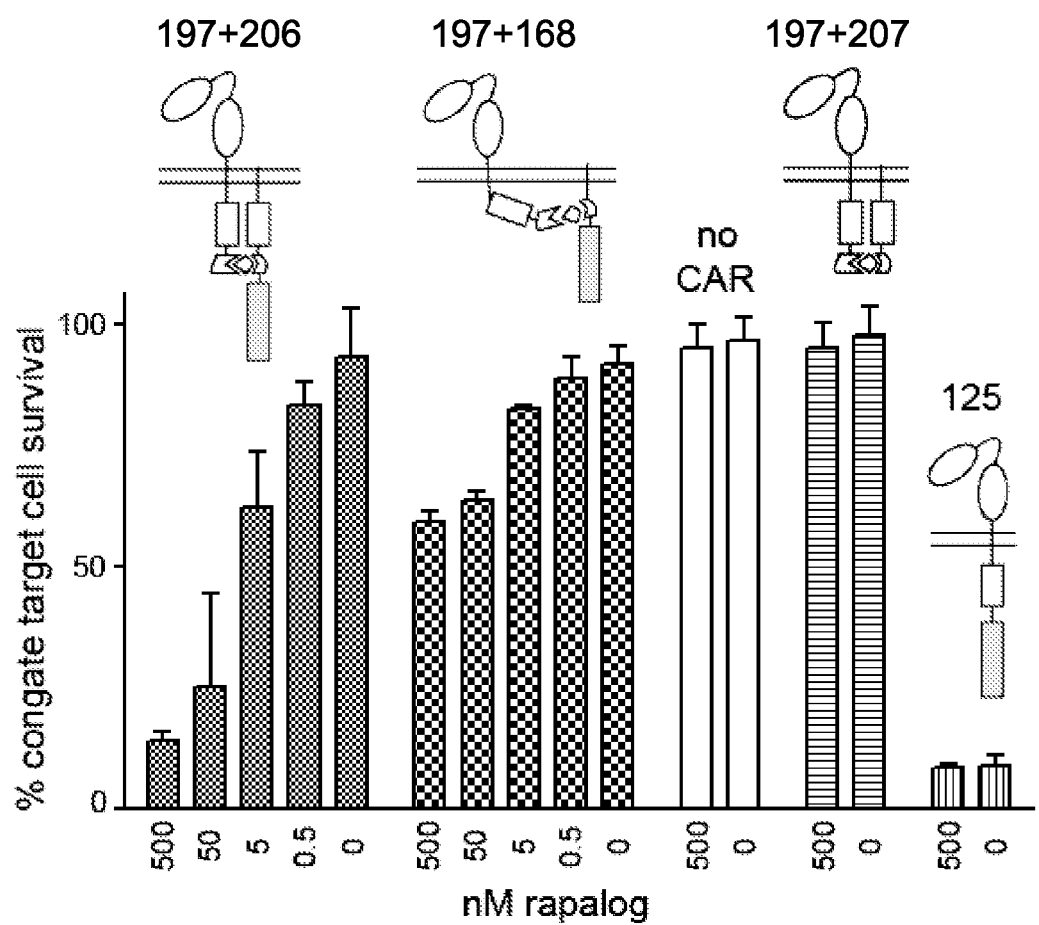
FIG. 15 depicts cytotoxicity data with the On-switch CAR "197+206."

FIG. 15 demonstrates pharmacologically titratable cytotoxicity conferred by the On-switch CAR "197+206" In the presence of the small molecule rapalog, the CAR effectively mediates re-directed cytotoxicity towards cognate target cells. At high dosages of rapalog, this On-switch CAR can signal as strongly as the "125" conventional CAR. Effector=human primary CD8+ T cells engineered with CARs or a control vector. Target=fluorescent derivatives of K562 cell lines expressing either the cognate human CD19 antigen or the non-cognate human mesothelin antigen.

Figure 16:
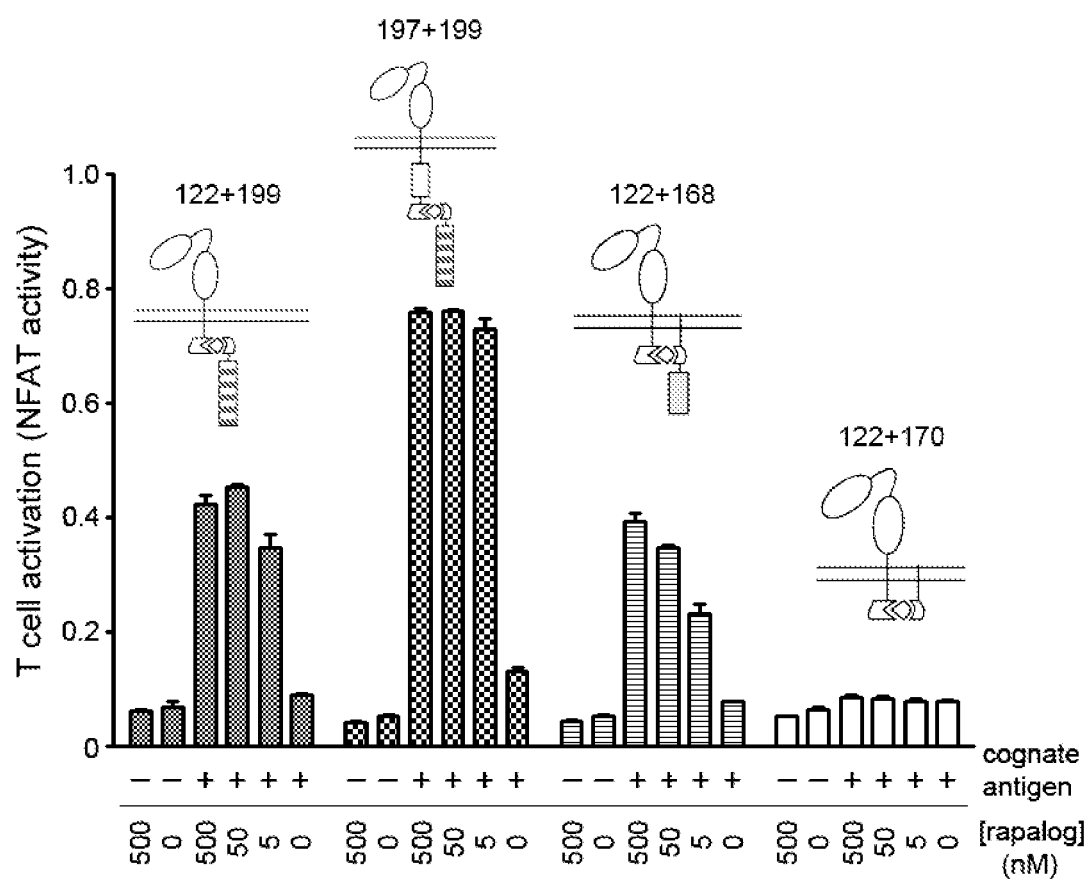
FIG. 16 depicts T cell activation data using CAR constructs "122+199"; "197+199"; and "122+168."

FIG. 16 depicts data for CARs constructed with the cytoplasmic tyrosine kinase Zap70 from the T cell receptor pathway as the intracellular signaling domain.

FIG. 16 shows data from Jurkat cells engineered with several variants of On-switch CARs. The engineered Jurkat cells were co-incubated with K562 target cells with or without the cognate antigen (CD19) and the indicated concentrations of rapalog. As a CAR component, the Zap70 kinase (first and second structures from left featuring "199") was as effective as the ITAM (third structure from left featuring "168") in activating NFAT function. Addition of the 4-1BB signaling domain increased surface expression of the antigen recognition portion of the receptor and led to stronger signaling by "197+199". A non-signaling CAR (far-right) was included as a negative control.

Example 2: CARs Targeting Mesothelin

Materials and Methods

Figure 19A:
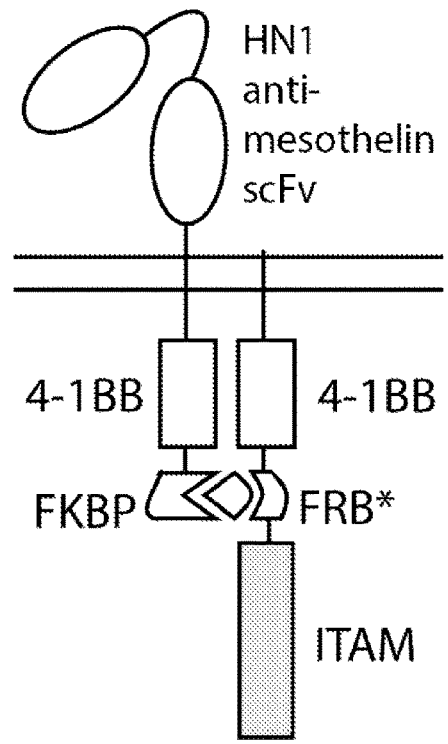
FIGS. 19A-G depict IL-2 production triggered by 3 different On-switch CAR variants recognizing human mesothelin.
Figure 19B:
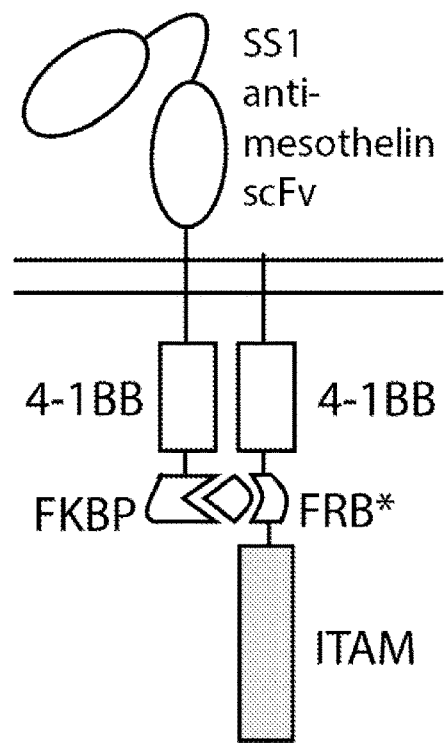
Figure 19C:
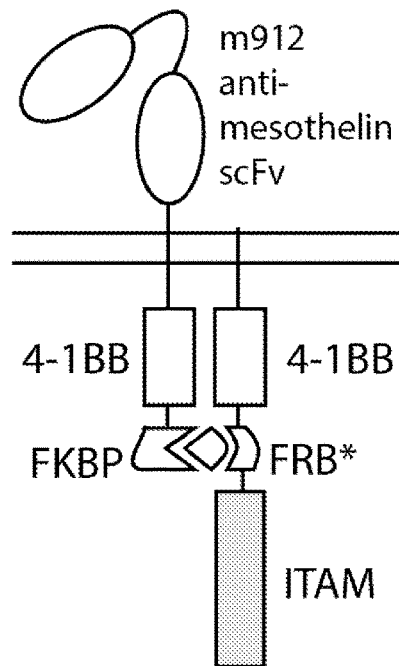

A number of chimeric antigen receptor constructs were made and tested. The constructs shown here encode three different anti-human mesothelin scFv as the antigen recognition domains. FIGS. 19A, 19B, and 19C summarize the molecular structure of each anti-human mesothelin CAR, with each CAR comprising two polypeptides. The intercellular portion of each anti-human mesothelin CAR comprises two 4-1BB co-stimulatory domains, an FKBP and FRB dimerizer-binding pair, and an ITAM intracellular signaling domain. The three different antigen recognition domains shown here are anti-mesothelin HN1 scFv, SS1 scFv, and m912 scFv. All membrane-anchored polypeptides are di-sulfide bonded homo-dimers.

Generation of CAR Constructs

Sequences encoding the anti-mesothelin were cloned from constructs or synthesized via gene assembly by PCR. The human 4-1BB co-stimulation and CD3 zeta ITAM signaling chains were cloned from cDNAs supplied by Open Biosystems. HN1 scFv-, SS1 scFv-, and m912 scFv-encoding sequences were synthesized by PCR and, in some cases, codon optimized. FKBP- and FRB-encoding sequences were cloned from Addgene plasmids.

Standard molecular cloning techniques (polymerase chain reaction (PCR), restriction digestion, ligation, etc.) were applied to generate lentiviral expression plasmids.

Effector and Target Cell Culturing Conditions

A Jurkat cell line expressing GFP upon NFAT activation was maintained in RPMI-1640 medium supplemented with 10% FBS, penicillin and streptomycin. K562 target cells were cultured in IMDM supplemented with 10% fetal bovine serum (FBS).

Effector and Target Cell Engineering with Lentivirus

Pantropic VSV-G pseudotyped lentivirus was produced from Lenti-X 293T cells (Clontech Laboratories #632180) co-transfected with a pHR'SIN:CSW transgene expression vector, viral packaging plasmids pCMVdR8.91 and pMD2.G using Lipofectamine LTX (Life Technologies #15338). Infection medium supernatant was collected 48 hours after transfection and used directly for transduction.

Jurkat and K562 cells were split 1-2 days in advance to ensure that cultures would be in log phase at the time of transduction. Transduced Jurkat and K562 cells were cultured for at least 7 days before experiments were conducted. Expression levels of CARs encoded in the lentiviral constructs were quantified by detecting either fluorophore-conjugated antibodies or fluorescent reporter proteins using a flow cytometer.

Quantitation of IL-2 Production

Jurkat CD4+ T cells expressing CARs were mixed with cognate or non-cognate K562 target cells at a 1:2 effector:target ratio. The rapalog A/C Heterodimerizer (Clontech Laboratories #635055) were serially diluted in medium and added to reaction mixtures. After 20-24 hours of incubation, medium supernatants were collected and analyzed with BD OptEIA Human IL-2 ELISA Set (BD Biosciences #555190).

Results

Figure 19D:
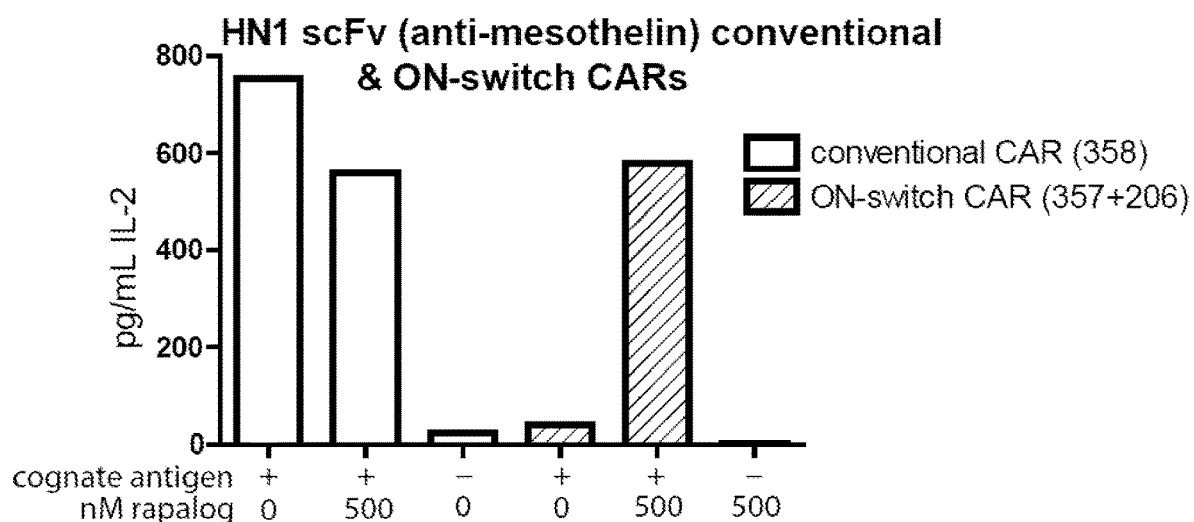
Figure 19E:
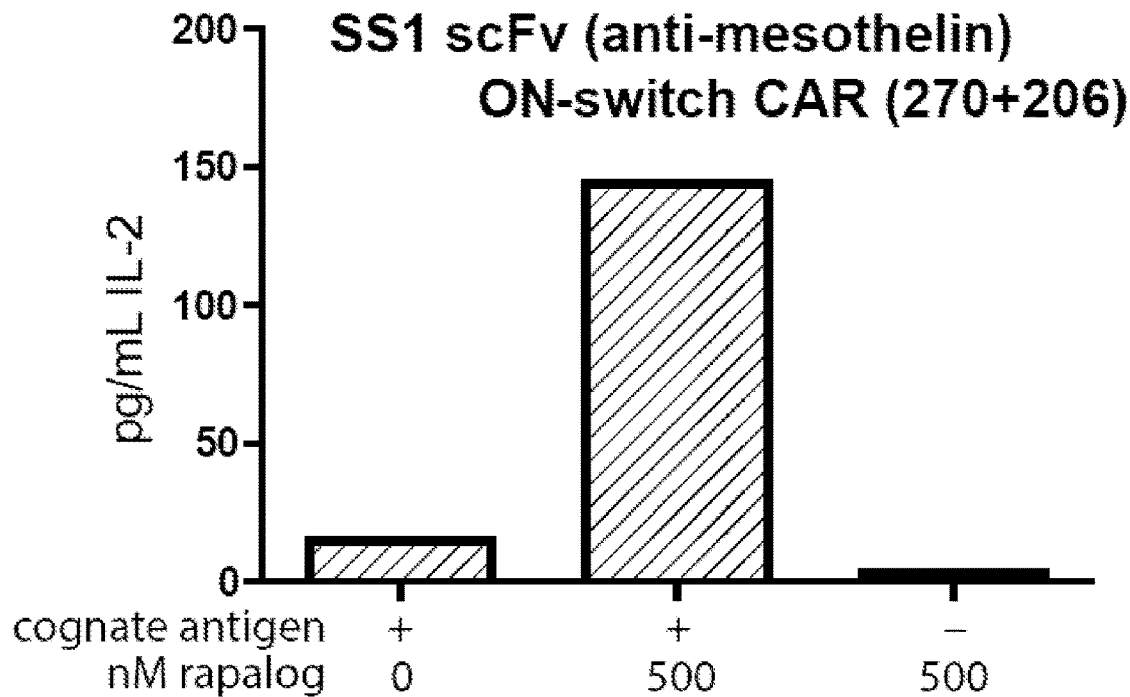
Figure 19F:
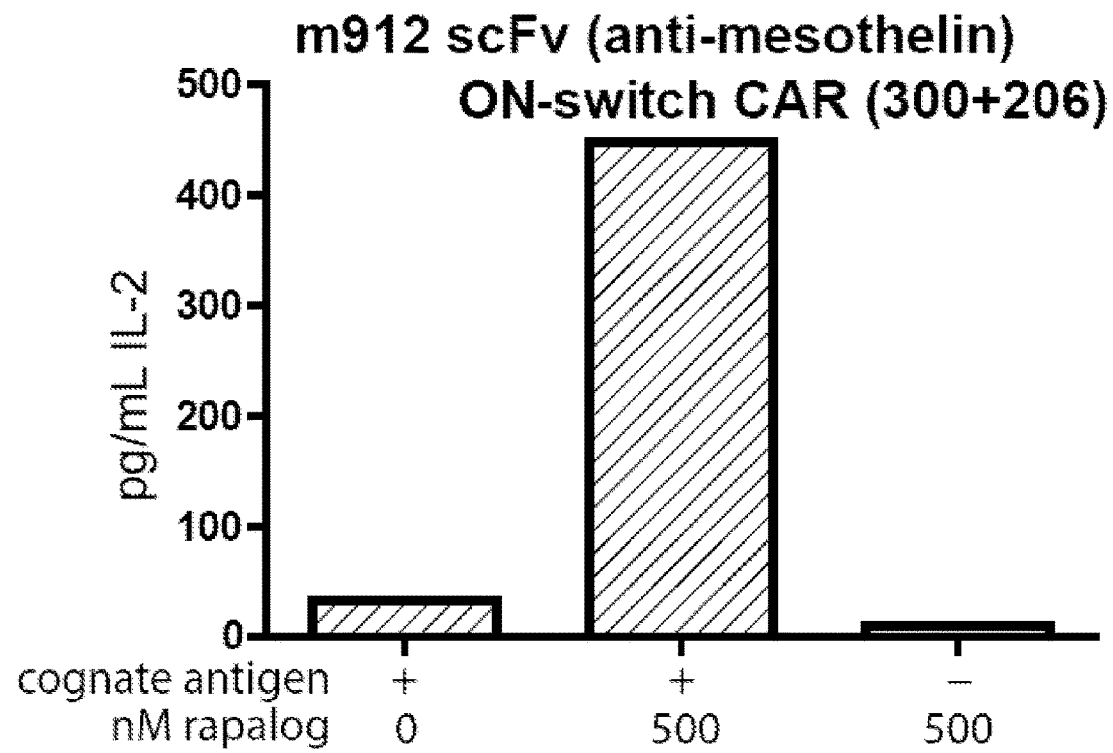
Figure 19G:
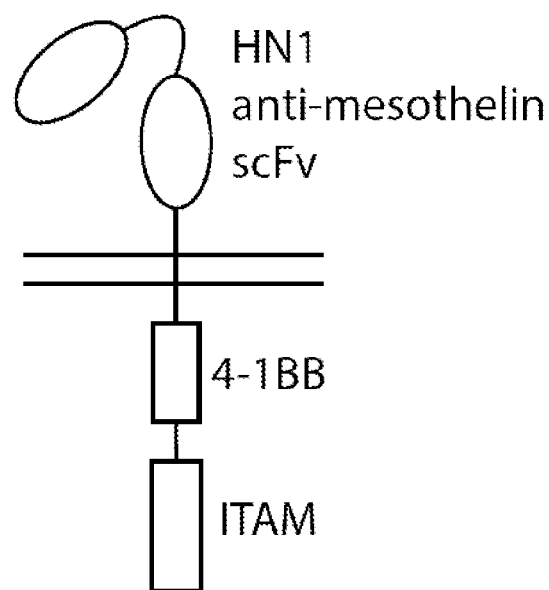

IL-2 production elicited by the anti-mesothelin CAR constructs was assessed. The data are presented in FIG. 19D-F.

FIG. 19. IL-2 production triggered by HN1 scFv (FIG. 19D), SS1 scFv (FIG. 19E), and m912 scFv (FIG. 19F) On-switch CAR variants. IL-2 production by a conventional CAR (FIG. 19G, construct #358) was measured and included for comparison to On-switch CARs (FIG. 19D). Effector=human CD4+ Jurkat T cells engineered with CARs. Target=K562 cell lines with or without the cognate mesothelin antigen. Amounts of secreted IL-2 by effector cells were quantified by enzyme-linked immunosorbent assay (ELISA).

Example 3: Gibberellic Acid as a Dimerizer of On-Switch CARs

Materials and Methods

Figure 20A:
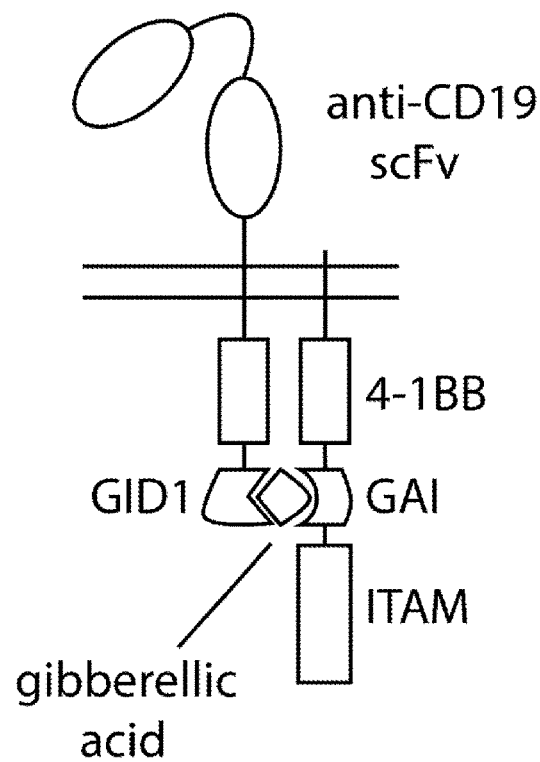
FIGS. 20A-C depict IL-2 production triggered by an On-switch CAR variant with a gibberellic acid responsive dimerization pair.

FIG. 20A summarizes the molecular structure of the subject gibberellic acid dimerizer CAR. The antigen binding portion comprises the anti-human CD19 scFv. The intracellular portion comprises two 4-1BB co-stimulatory domains, a GID1 and GAI dimerizer-binding pair, and an ITAM intracellular signaling domain. All membrane-anchored polypeptides are di-sulfide bonded homo-dimers.

Generation of CAR Constructs

Sequences encoding the gibberellic acid dimerizer CAR were cloned from constructs. The anti-CD19 scFv was cloned from a plasmid. The human 4-1BB co-stimulation and CD3 zeta ITAM signaling chains were cloned from cDNAs supplied by Open Biosystems. GID1- and GAI-encoding sequences were cloned from Addgene plasmids. Standard molecular cloning techniques (polymerase chain reaction (PCR), restriction digestion, ligation, etc.) were applied to generate lentiviral expression plasmids.

Effector and Target Cell Culturing Conditions

A Jurkat cell line expressing GFP upon NFAT activation was maintained in RPMI-1640 medium supplemented with 10% FBS, penicillin and streptomycin. K562 target cells were cultured in IMDM supplemented with 10% fetal bovine serum (FBS).

Effector and Target Cell Engineering with Lentivirus

Pantropic VSV-G pseudotyped lentivirus was produced from Lenti-X 293T cells (Clontech Laboratories #632180) co-transfected with a pHR'SIN:CSW transgene expression vector, viral packaging plasmids pCMVdR8.91 and pMD2.G using Lipofectamine LTX (Life Technologies #15338). Infection medium supernatant was collected 48 hours after transfection and used directly for transduction.

Jurkat and K562 cells were split 1-2 days in advance to ensure that cultures would be in log phase at the time of transduction. Transduced Jurkat and K562 cells were cultured for at least 7 days before experiments were conducted. Expression levels of CARs encoded in the lentiviral constructs were quantified by detecting either fluorophore-conjugated antibodies or fluorescent reporter proteins using a flow cytometer.

Quantitation of IL-2 Production

Jurkat CD4+ T cells expressing CARs were mixed with cognate or non-cognate K562 target cells at a 1:2 effector:target ratio. The gibberellic acid-3 acetoxymethyl ester (gibberrelic acid-3 AM) pre-dissolved in ethanol (Toronto Research Chemicals #G377500) was diluted in growth medium and added to reaction mixtures. Gibberellic acid (gibberellic acid-3 AM) was used at 10 mM. After 20-24 hours of incubation, medium supernatants were collected and analyzed with BD OptEIA Human IL-2 ELISA Set (BD Biosciences #555190).

Results

IL-2 production elicited by the gibberellic acid dimerizer CAR construct was assessed. The data are presented in FIG. 20.

Figure 20B:
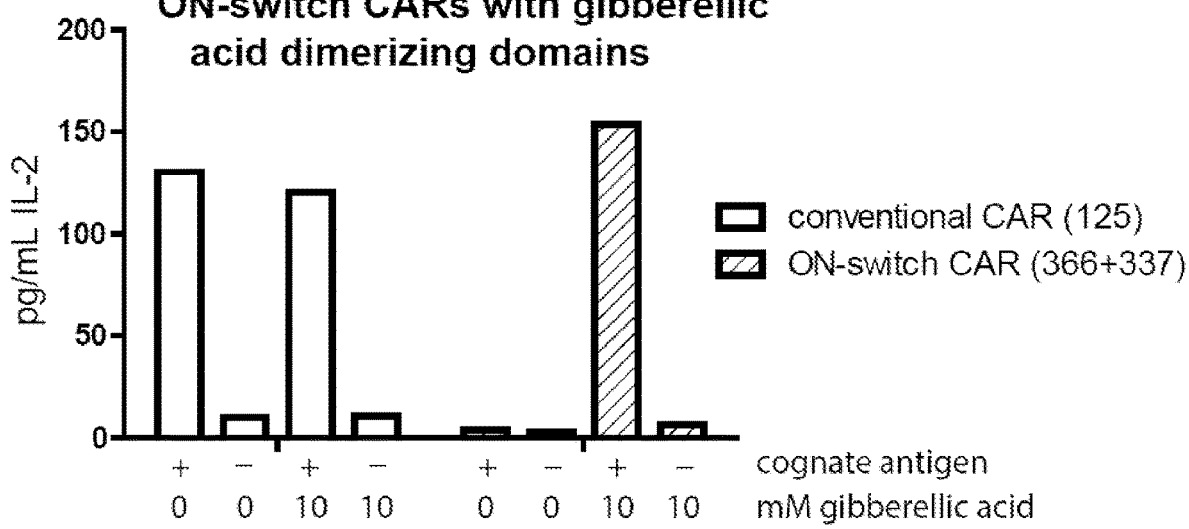
Figure 20C:
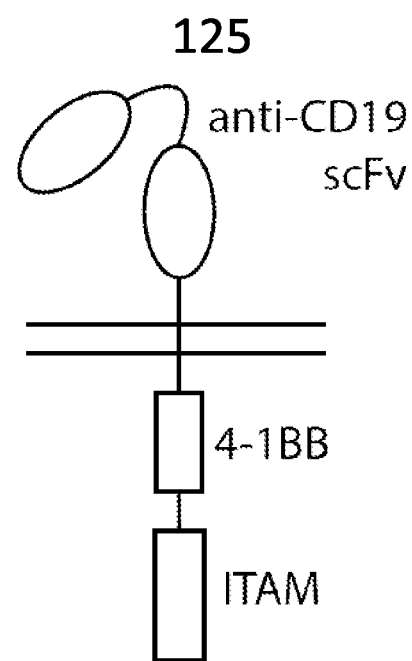

FIG. 20. IL-2 production triggered by gibberellic acid dimerizer CAR variant (FIG. 20B). IL-2 production by a conventional CAR (FIG. 20C, construct "125") was measured and included for comparison to On-switch CAR. Effector=human CD4+ Jurkat T cells engineered with CARs. Target=K562 cell lines with or without the cognate CD19 antigen. Amounts of secreted IL-2 by effector cells were quantified by enzyme-linked immunosorbent assay (ELISA).

Example 4: On-Switch CARs with Various Co-Stimulatory Domains

Materials and Methods

Figure 21A:
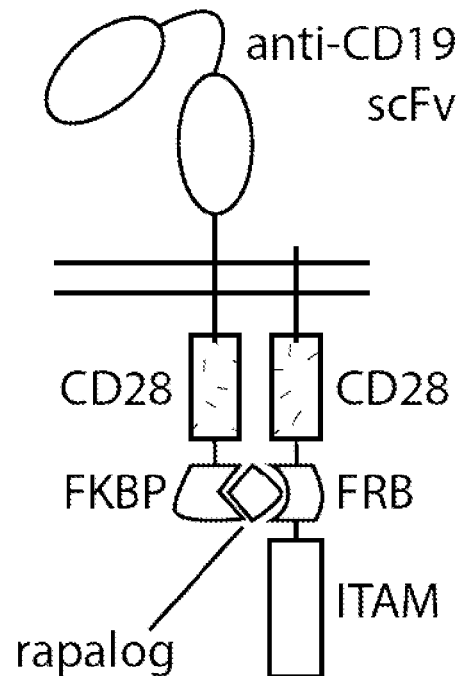
FIGS. 21A-D depict exemplary On-switch CARs and conventional CARs with various co-stimulatory domains.
Figure 21B:
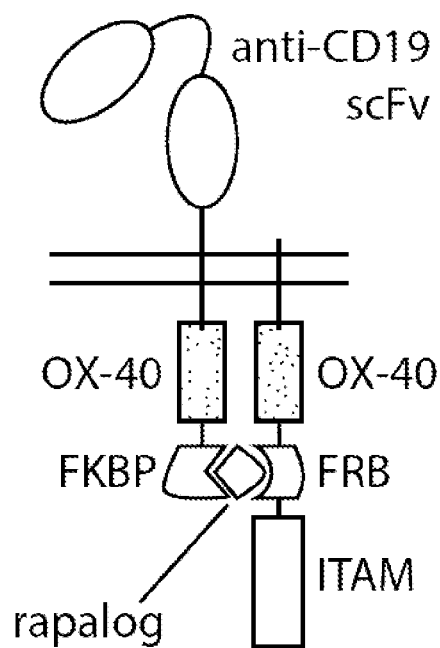

A number of chimeric antigen receptor constructs were made essentially as described for Example 1, except various other co-stimulatory domains were exchanged for the 4-1BB co-stimulatory domains. FIGS. 21A and 21B summarize the molecular structure of the CARs described here.

Generation of CAR Constructs

Sequences encoding the anti-human CD19 scFv were cloned from a plasmid. The human CD3 zeta ITAM signaling chain and the human co-stimulatory domains CD28 and OX-40 encoding sequences were cloned from cDNAs supplied by Open Biosystems. FKBP- and FRB-encoding sequences were cloned from plasmids from Addgene.

Standard molecular cloning techniques (polymerase chain reaction (PCR), restriction digestion, ligation, etc.) were applied to generate lentiviral expression plasmids.

Testing of CAR Constructs

Figure 21C:
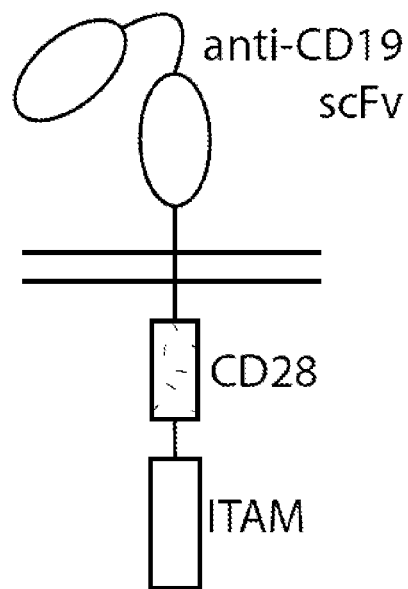
Figure 21D:
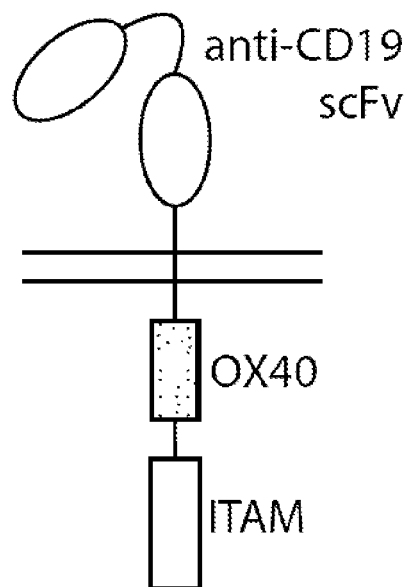

Effector and target cells are cultured and transfected according to Example 1 using the on-switch CAR CD28 and OX-40 co-stimulatory domain containing constructs described (FIG. 21A-B, constructs "365+367" and "399+400", respectively) and corresponding conventional CAR controls (FIG. 21C-D, constructs "366" and "398", respectively). IL-2 production, NFAT activity assays, and flow cytometry-based assays can also be performed with the CD28 co-stimulatory domain containing construct and OX-40 co-stimulatory domain containing construct as described for Example 1. Alternatively, subunits of on-switch CAR CD28 and OX-40 co-stimulatory domain containing constructs can be paired with subunits of constructs from Example 1 (e.g., "197+367", "365+206," "197+400", "399+206," etc.).

Example 5: In Vivo Assessment of On-Switch CAR

An On-switch CAR can be assessed for its ability to mediate in vivo killing of a target tumor cell. In vivo tumor cell killing elicited by injection of T cells expressing the ON-switch CAR is assessed. Tumor cell lines that have been confirmed in vitro to express the cognate antigen and can be killed by $CD8^+$ T cells expressing the corresponding CAR are used. Tumor cells engineered to express either the firefly or Renilla luciferase to enable bio-luminescence imaging to quantify tumor burden in vivo can be used. Tumor cells are injected into immunocompromised mice (e.g., 6~10 week old female NOD scid gamma (NSG) mice) either subcutaneously for subcutaneous tumor models or intravenously for systemic tumor models. The method of tumor implantation and the optimal number of tumor cells to implant can be based on conditions optimal for the tumor cell line used. Tumor burden can be monitored twice a week by bio-luminescence imaging and by caliper measurement when applicable. As soon as tumor burden is detectable, 0.5~2.5× $10^7$ total T cells (1:1 $CD4^+:CD8^+$) expressing the ON-switch CAR are intravenously injected into mice to begin treatment. A dimerizing small molecule drug (e.g., rapalog) is administered intraperitoneally in a vehicle formulation. On-switch CAR-expressing T cells can be injected repeatedly during the experiment to enhance the anti-tumor effect. Interleukin-2 (IL-2) can be administered to enhance the anti-tumor effect.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for activating a T lymphocyte, comprising: contacting:
   (a) a T lymphocyte expressing a heterodimeric, conditionally active chimeric antigen receptor (CAR) comprising:
      (i) a first polypeptide comprising:
         a first member of a specific binding pair;
         a first member of a dimerization pair; and
         a transmembrane domain between the first member of the specific binding pair and the first member of the dimerization pair; and
      (ii) a second polypeptide comprising:
         a second member of the dimerization pair; and
         an immunoreceptor tyrosine-based activation motif (ITAM);
   with:
   (b) a dimerization agent that dimerizes the first and second members of the dimerization pair; and
   (c) a target cell that comprises a cell surface antigen to which the first member of the specific binding pair binds;
   wherein binding of the first polypeptide to the antigen on the surface of the target cell in the presence of the dimerization agent results in signal transduction via the ITAM of the second polypeptide and activation of the T lymphocyte.

2. The method of claim 1, wherein the method is done in vitro by incubating the T lymphocyte in a growth medium that comprises the dimerization agent and the target cell.

3. The method of claim 1, wherein the method is done in vivo by administering the T lymphocyte and the dimerization agent to a subject that comprises the target cell.

4. The method of claim 3, wherein the target cell is a cancer cell and the antigen is a marker for the cancer.

5. The method of claim 1, wherein the first member of the specific binding pair of (a) (i) is an antibody or antibody fragment.

6. The method of claim 1, wherein the first member of the specific binding pair is a single-chain Fv (scFv), VHH or VH antibody.

7. The method of claim 1, wherein the ITAM is an ITAM of DAP12, FCER1 gamma, CD3 delta, CD3 epsilon, CD3 gamma, CD3 zeta or CD79 alpha.

8. The method of claim 1, wherein the first and second members of the dimerization pair homodimerize in the presence of the dimerization agent.

9. The method of claim 1, wherein the first and second members of the dimerization pair heterodimerize in the presence of the dimerization agent.

10. The method of claim 1, wherein the dimerization agent is a rapalog.

11. The method of claim 1, wherein the first and second members of the dimerization pair are selected from:
   a) FK506 binding protein (FKBP) and FKBP;
   b) FKBP and calcineurin catalytic subunit A (CnA);
   c) FKBP and cyclophilin;
   d) FKBP and FKBP-rapamycin associated protein (FRB);
   e) gyrase B (GyrB) and GyrB;
   f) dihydrofolate reductase (DHFR) and DHFR;
   g) DmrB and DmrB;
   h) PYL and ABI;
   i) Cry2 and CIP;
   j) GAI and GID1.

12. The method of claim 1, wherein the first polypeptide comprises a hinge region between the first member of the specific binding pair and the transmembrane domain.

13. The method of claim 1, wherein the second polypeptide of (a) (ii) comprises transmembrane domain.

14. The method of claim 1, wherein the first polypeptide and/or the second polypeptide comprises a co-stimulatory domain.

15. The method of claim 14, wherein the costimulatory domain is selected from the costimulatory domains of 4-1BB (CD137), CD28, ICOS, BTLA, OX-40, CD27, CD30, GITR, HVEM, DAP10, DAP12, and CD28.

16. The method of claim 1, wherein the first and second polypeptides each comprise a co-stimulatory domain.

17. The method of claim 16, wherein the costimulatory domains are independently selected from the costimulatory domains of 4-1BB (CD137), CD28, ICOS, BTLA, OX-40, CD27, CD30, GITR, HVEM, DAP10, DAP12, and CD28.

18. The method of claim 1, wherein:
the second polypeptide comprises a transmembrane domain;
the first and second members of the dimerization pair are FKBP and FRB; and
the first and second polypeptide domains each comprise a co-stimulatory domain.

* * * * *